(12) United States Patent
Chin et al.

(10) Patent No.: US 12,286,657 B2
(45) Date of Patent: Apr. 29, 2025

(54) METHODS AND COMPOSITIONS

(71) Applicant: United Kingdom Research and Innovation, Swindon (GB)

(72) Inventors: Jason Chin, Cambridgeshire (GB); Nicolas Huguenin-Dezot, Basel (CH); Mohan Mahesh, Cambridgeshire (GB); Shan Tang, Cambridgeshire (GB); Duy P. Nguyen, Cambridgeshire (GB)

(73) Assignee: United Kingdom Research and Innovation, Swindon (GB)

( * ) Notice: Subject to any disclaimer, the term of this patent is extended or adjusted under 35 U.S.C. 154(b) by 780 days.

(21) Appl. No.: 17/288,798

(22) PCT Filed: Oct. 24, 2019

(86) PCT No.: PCT/GB2019/053023
§ 371 (c)(1),
(2) Date: Apr. 26, 2021

(87) PCT Pub. No.: WO2020/084307
PCT Pub. Date: Apr. 30, 2020

(65) Prior Publication Data
US 2022/0010296 A1    Jan. 13, 2022

(30) Foreign Application Priority Data

Oct. 26, 2018 (GB) ..................... 1817444

(51) Int. Cl.
*C12N 9/00* (2006.01)
*C07D 317/62* (2006.01)
*C12N 9/50* (2006.01)

(52) U.S. Cl.
CPC ............. *C12N 9/93* (2013.01); *C07D 317/62* (2013.01); *C12N 9/506* (2013.01); *C12Y 304/22069* (2013.01); *C12Y 601/01026* (2013.01); *C07K 2319/60* (2013.01)

(58) Field of Classification Search
CPC .......... C12N 9/93; C12N 9/506; C12N 9/104; C07D 317/62; C12Y 304/22069; C12Y 601/01026; C07K 2319/60; C07K 11/02; Y02A 50/30; A61K 38/00; C12P 21/02; C12Q 1/37
See application file for complete search history.

(56) References Cited

U.S. PATENT DOCUMENTS

| | | | |
|---|---|---|---|
| 7,829,659 B2 | 11/2010 | Grabstein et al. | |
| 9,868,956 B2 | 1/2018 | Nguyen et al. | |
| 9,968,690 B2 | 5/2018 | Chin et al. | |
| 10,738,339 B2 | 8/2020 | Chin et al. | |
| 10,774,039 B2 | 9/2020 | Elliott | |
| 11,622,993 B2 * | 4/2023 | Ptacin | C07K 14/55 424/85.2 |
| 11,667,933 B2 | 6/2023 | Fredens et al. | |
| 11,732,001 B2 | 8/2023 | Chin et al. | |

(Continued)

FOREIGN PATENT DOCUMENTS

| | | |
|---|---|---|
| CA | 2885796 A1 | 3/2014 |
| CN | 101076598 A | 11/2007 |

(Continued)

OTHER PUBLICATIONS

Baumann et al., Orthogonal Protein Translation Using Pyrrolysyl-tRNA Synthetases for Single and Multiple-Noncanonical Amino Acid Mutagenesis. Adv. Biochem Eng Biotechnol., DOI: 10.1007/1010_2016_37, 2016, Springer International Publishing Switzerland 2016, pp. 1-19. (Year: 2016).*

(Continued)

*Primary Examiner* — Ganapathirama Raghu
(74) *Attorney, Agent, or Firm* — Clark & Elbing LLP

(57) ABSTRACT

The invention relates to genetic incorporation of 2,3-diamino propionic acid (DAP) into polypeptides, to unnatural amino acids comprising DAP, to a tRNA synthetase for charging tRNA with unnatural amino acids comprising DAP, and to methods of using the resulting polypeptides, for example in capturing substrates and/or intermediates in enzymatic reactions. The invention also relates to compounds of formula (I) or (II):

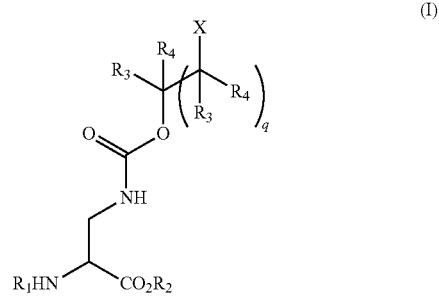

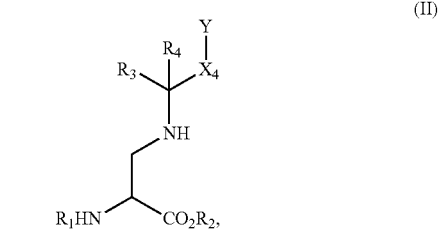

or salts, solvates, tautomers, isomers or mixtures thereof.

16 Claims, 34 Drawing Sheets
Specification includes a Sequence Listing.

(56) References Cited

U.S. PATENT DOCUMENTS

| | | | |
|---|---|---|---|
| 2009/0068738 | A1 | 3/2009 | Bertozzi et al. |
| 2011/0027829 | A1 | 2/2011 | Neumann et al. |
| 2012/0077186 | A1 | 3/2012 | Skach et al. |
| 2012/0077948 | A1 | 3/2012 | Nguyen et al. |
| 2013/0066063 | A1 | 3/2013 | Berry et al. |
| 2013/0137763 | A1 | 5/2013 | Van Delft et al. |
| 2015/0005481 | A1 | 1/2015 | Chin et al. |
| 2015/0148525 | A1 | 5/2015 | Chin et al. |
| 2015/0259721 | A1 | 9/2015 | Grabstein et al. |
| 2017/0015623 | A1 | 1/2017 | Elliot |
| 2017/0356023 | A1 | 12/2017 | Chin et al. |
| 2020/0271658 | A1 | 5/2020 | Chin et al. |
| 2022/0282241 | A1 | 9/2022 | Fredens et al. |
| 2023/0340013 | A1 | 10/2023 | Chin et al. |

FOREIGN PATENT DOCUMENTS

| | | | |
|---|---|---|---|
| CN | 104203971 | A | 12/2014 |
| CN | 105026574 | A | 11/2015 |
| EP | 1911840 | A1 | 4/2008 |
| EP | 2192185 | A1 | 2/2010 |
| JP | 2007-514447 | A | 6/2007 |
| WO | WO 2005/003294 | A2 | 1/2005 |
| WO | WO 2006/034332 | A2 | 3/2006 |
| WO | WO 2006/110182 | A2 | 10/2006 |
| WO | WO 2007/090198 | A2 | 8/2007 |
| WO | WO 2008/134761 | A2 | 11/2008 |
| WO | WO 2009/056803 | A1 | 5/2009 |
| WO | WO 2010/139948 | A2 | 12/2010 |
| WO | WO 2011/039518 | A2 | 4/2011 |
| WO | WO 2011/039519 | A2 | 4/2011 |
| WO | WO 2011/130616 | A1 | 10/2011 |
| WO | WO 2011/136645 | A1 | 11/2011 |
| WO | WO 2011/156686 | A2 | 12/2011 |
| WO | WO 2012/104422 | A1 | 8/2012 |
| WO | WO 2012/175924 | A2 | 12/2012 |
| WO | WO 2013/108044 | A2 | 7/2013 |
| WO | WO 2013/171485 | A1 | 11/2013 |
| WO | WO 2014/036492 | A1 | 3/2014 |
| WO | WO 2014/044872 | A1 | 3/2014 |
| WO | WO 2015/136265 | A1 | 9/2015 |
| WO | WO 2016/066995 | A1 | 5/2016 |
| WO | WO 2020/084307 | A1 | 4/2020 |
| WO | WO-2022248061 | A1 | 12/2022 |

OTHER PUBLICATIONS

Guo et al., Polyspecific pyrrolysyl-tRNA synthetases from directed evolution. PNAS., 2014, vol. 111(47): 16724-16729. (Year: 2014).*
Herrera-Guzman K., Enzyme-Free Ubiquitin Ligation From Native Chemical Ligation and Spin Labeling To Dimerization By Inter-Ubiquitin Mimicking Linkages and PH-Dependent Conformational Switch. PhD., Thesis, Univ. of Maryland, 2016, pp. 1-152. (Year: 2016).*
Jiang et al., Studies of the Pyrrolysyl-TRNA Synthetase. PhD., Thesis, The Ohio State University 2013, pp. 1-169. (Year: 2013).*
Serfling et al., Designer tRNAs for efficient incorporation of non-canonical amino acids by the pyrrolysine system in mammalian cells. Nuc. Acids Res., 2018, vol. 46(1), pp. 1-10. (Year: 2018).*
Turcattii et al., Probing the Structure and Function of the Tachykinin Neurokinin-2 Receptor through Biosynthetic Incorporation of Fluorescent Amino Acids at Specific Sites. The J. Biol. Chem., 1996, vol. 271(33): 19991-19998. (Year: 1996).*
Volkwein et al., A Versatile Toolbox for the Control of Protein Levels Using Nϵ-Acetyl-L-lysine Dependent Amber Suppression. ACS Synth. Biol., 2017, vol. 6: 1892-1902. (Year: 2017).*
Ambrogelly et al., "Pyrrolysine is not hardwired for cotranslational insertion at UAG codons," Proc. Natl. Acad. Sci. USA (2007); 104(9): 3141-3146.
Kiick,et al., "Incorporation of azides into recombinant proteins for chemoselective modification by the Staudinger ligation," Proc. Natl. Acad. Sci. USA (2002); 99(1): 19-24.

Polycarpo, et al., "An aminoacyl-tRNA synthetase that specifically activates pyrrolysine," Proc. Natl. Acad. Sci. USA (2004); 101(34): 12450-12454.
Xie and Schultz, "Adding amino acid to the genetic repertoire", Current Opinion in Chemical Biology (2005); 9: 548-554.
International Search Report for International Application No. PCT/GB2019/053023, mailed Mar. 31, 2020 (6 pages).
International Preliminary Report on Patentability for International Application No. PCT/GB2019/053023, issued Apr. 27, 2021 (12 pages).
English Translation of the Office Action for Japanese Patent Application No. 2021-521504, mailed Oct. 23, 2023 (6 pages).
[Author Unknown] ThermoFisher Scientific, Amine-Reactive Crosslinker Chemistry, Thermo Fisher Scientific, ThermoFisher. com, attached as pdf, 8 pages (Apr. 18, 2012). (cited in U.S. Appl. No. 14/401,803 by the Examiner as having a published date of Apr. 18, 2012).
Agard, et al., "A Strain-Promoted [3+2] Azide-Alkyne Cycloaddition for Covalent Modification of Biomolecules in Living Systems". J. Am. Chem. Soc. (2004); vol. 126: pp. 15046-15047.
Aggarwal, Anup, et al. "Development of a novel lead that targets M. tuberculosis polyketide synthase 13." Cell 170.2 (2017): 249-259.
Akey, David L., et al. "Structural basis for macrolactonization by the pikromycin thioesterase." Nature Chemical Biology 2.10 (2006): 537-542.
Alonzo, Diego A., et al. "Characterization of cereulide synthetase, a toxin-producing macromolecular machine." PloS one 10.6 (2015): e0128569, 19pgs.
Argyropoulos, Panos, et al. "Towards a characterization of the structural determinants of specificity in the macrocyclizing thioesterase for deoxyerythronolide B biosynthesis." Biochimica et Biophysica Acta (BBA)-General Subjects 1860.3 (2016): 486-497.
Baker, Austin S., et al. "Optical control of protein function through unnatural amino acid mutagenesis and other optogenetic approaches." ACS Chemical Biology 9.7 (2014): 1398-1407.
Barker, et al. "Tetrazine-Norbornene Click Reactions to Functionalize Degradable Polymers Derived from Lactide". Macromol, Rapid Commun. (2011); 32(17), pp. 1362-1366.
Berge, Stephen M., et al. "Pharmaceutical salts." Journal of Pharmaceutical Sciences (1977), 66(1), 1-19.
Bianco, et al. "Expanding the genetic code of *Drosophila melanogaster*" Nature Chemical Biology (Sep. 2012); 8(9); pp. 748-750.
Blackman, et al. "Tetrazine Ligation: Fast Bioconjugation Based on Inverse-Electron-Demand Diels-Alder Reactivity" J. Am. Chem. Soc., 2008, vol. 130, pp. 13518-13519.
Blight, et al. "Direct charging of tRNAcua with pyrrolysine in vitro and in vivo" NATURE, vol. 43, Sep. 16, 2004, pp. 333-335.
Bruner, Steven D., et al. "Structural basis for the cyclization of the lipopeptide antibiotic surfactin by the thioesterase domain SrfTE." Structure 10.3 (2002): 301-310.
Bulygin, et al., "Three distinct peptides from the N domain of translation termination factor eRF1 surround stop codon in the ribosome" RNA (2010), 16: 1902-1914.
Canalle, et al., "Clickable Enzyme-linked Immunosorbent Assay". BioMacromolecules (2011); vol. 12: 3692-3697.
Cappadocia, Laurent, et al. "Ubiquitin-like protein conjugation: structures, chemistry, and mechanism." Chemical Reviews 118.3 (2018): 889-918.
Chen, et al., "Clicking 1,2,4,5-tetrazine and cyclooctynes with tunable reaction rates", Chem. Commun,. vol. 48:1736-1738 (online Nov. 24, 2011).
Chin, "Reprogramming the genetic code" EMBO Journal, vol. 30:2312-2324 (2011).
Chin, Jason W. "Expanding and reprogramming the genetic code of cells and animals." Annual Review of Biochemistry 83 (2014): 379-408.
Cleary, Jennifer A., et al. "Quantifying tetrahedral adduct formation and stabilization in the cysteine and the serine proteases." Biochimica et Biophysica Acta (BBA)-Proteins and Proteomics 1854.10 (2015): 1382-1391.
Cravatt, Benjamin F., et al. "Activity-based protein profiling: from enzyme chemistry to proteomic chemistry." Annu. Rev. Biochem. 77 (2008): 383-414.

(56) References Cited

OTHER PUBLICATIONS

Davis et al., "Designer proteins: applications of genetic code expansion in cell biology", Nature Reviews Molecular Cell Biology (Mar. 2012); vol. 13: 168-182.
Devaraj, et al. "Tetrazine-Based Cycloadditions: Application to Pretargeted Live Cell Imaging" Bioconjugate Chem. (2008); 19(12); pp. 2297-2299.
Di Cera, Enrico. "Serine proteases." IUBMB Life 61.5 (2009): 510-515.
Dommerholt, et al., "Readily Accessible Bicyclononynes for Bioorthogonal Labeling and Three-Dimensional Imaging of Living Cells", Angew. Chem. Int. Ed. (Dec. 3, 2010); vol. 49:9422-9425.
Drake, Eric J., et al. "Structures of two distinct conformations of holo-non-ribosomal peptide synthetases." Nature 529.7585 (2016): 235-238.
Ekici, Özlem Doğan, et al. "Unconventional serine proteases: variations on the catalytic Ser/His/Asp triad configuration." Protein Science 17.12 (2008): 2023-2037.
Elliott, Thomas et al. "Proteome labeling and protein identification in specific tissues and at specific developmental stages in an animal" Nature Biotechnology (2014), vol. 32, No. 5, pp. 465-472.
Faure, Sophie, et al. "Asymmetric intramolecular [2 +2] photocycloadditions: alpha- and beta-hydroxy acids as chiral tether groups". The Journal of Organic Chemistry. 67.4 (2002); 1061-1070.
Fekner, et al., "A Pyrrolysine Analogue for Protein Click Chemistry". Angew Chem Int Ed Engl. (2009); 48(9): 1633-1635.
Frueh, Dominique P., et al. "Dynamic thiolation-thioesterase structure of a non-ribosomal peptide synthetase." Nature 454.7206 (2008): 903-906.
Gaston, et al. "The complete biosynthesis of the genetically encoded amino acid pyrrolysine from lysine" Nature, vol. 471, No. 7340, Mar. 31, 2011, pp. 647-650.
Gavalda, Sabine, et al. "The polyketide synthase Pks13 catalyzes a novel mechanism of lipid transfer in mycobacteria." Chemistry & Biology 21.12 (2014): 1660-1669.
Gehret, Jennifer J., et al. "Terminal alkene formation by the thioesterase of curacin A biosynthesis: structure of a decarboxylating thioesterase." Journal of Biological Chemistry 286.16 (2011): 14445-14454.
Giraldes, John W., et al. "Structural and mechanistic insights into polyketide macrolactonization from polyketide-based affinity labels." Nature Chemical Biology 2.10 (2006): 531-536.
Guntaka, Naga Sandhya, et al. "Structure and functional analysis of ClbQ, an unusual intermediate-releasing thioesterase from the colibactin biosynthetic pathway." ACS Chemical Biology 12.10 (2017): 2598-2608.
Hao, et al A readily synthesized cyclic pyrrolysine analogue for site-specific protein "click labeling" Chem. Commun. (2011); 47: 4502-4504.
Hay, R. W., et al. "Interaction of DL-2, 3-diaminopropionic acid and its methyl ester with metal ions. Part II. Hydrolysis kinetics." Journal of the Chemical Society, Dalton Transactions 1 (1973): 56-61.
Hedstrom, Lizbeth. "Serine protease mechanism and specificity." Chemical Reviews 102.12 (2002): 4501-4524.
Holliday, Gemma L., et al. "Understanding the functional roles of amino acid residues in enzyme catalysis." Journal of Molecular Biology 390.3 (2009): 560-577.
Horsman, Mark E., et al. "Polyketide synthase and non-ribosomal peptide synthetase thioesterase selectivity: logic gate or a victim of fate ?. " Natural Product Reports 33.2 (2016): 183-202.
Hoyer, Katharina M., et al. "The iterative gramicidin s thioesterase catalyzes peptide ligation and cyclization." Chemistry & Biology 14.1 (2007): 13-22.
Huguenin-Dezol, et al., "Trapping biosynthetic acyl-enzyme intermediates with encoded 2, 3-diaminopropionic acid". Nature (Jan. 2019); 565(7737): 112-117.
Ilegems, Erwin, et al. "Downregulation cif eRFl by RNA interference increases mis-acylated tRNA suppression efficiency in human cells" Protein Engineering, Design & Selection, vol. 17, No. 12, pp. 821-827, 2004.

International Preliminary Report on Patentability for International Application No. PCT/GB2013/050121 mailed Jul. 22, 2014, 11 pages.
International Preliminary Report on Patentability in International Application No. PCT/GB2010/001083, dated Dec. 6, 2011, 9 pages.
International Preliminary Report on Patentability in International Application No. PCT/GB2013/051249, dated Nov. 18, 2014, 9 pages.
International Preliminary Report on Patentability in International Application No. PCT/GB2015/050694, dated Sep. 14, 2016, 8 pages.
International Preliminary Report on Patentability in International Application No. PCT/GB2015/053141 dated Feb. 3, 2017, 17 pages.
International Search Report and Written Opinion for International Application No. PCT/GB2013/050121 mailed Oct. 9, 2013, 20 pages.
International Search Report and Written Opinion in International Application No. PCT/GB2010/001083, dated Mar. 28, 2011, 16 pages.
International Search Report and Written Opinion in International Application No. PCT/GB2013/051249, dated Oct. 14, 2013, 15 pages.
International Search Report and Written Opinion in International Application No. PCT/GB2015/050694, mailed May 22, 2015, 12 pages.
International Search Report and Written Opinion in International Application No. PCT/GB2015/053141 mailed Feb. 2, 2016, 12 pages.
Jaitzig, Jennifer, et al. "Reconstituted biosynthesis of the nonribosomal macrolactone antibiotic valinomycin in Escherichia coli." ACS Synthetic Biology 3.7 (2014): 432-438.
Kaya, et al. "A Genetically Encoded Norbornene Amino Acid for the Mild and Selective Modification of Proteins in a Copper-Free Click Reaction" Angew. Chem. Int. Ed. (2012); 571(18), pp. 4466-4469.
Koglin, Alexander, et al. "Structural basis for the selectivity of the external thioesterase of the surfactin synthetase." Nature 454.7206 (2008): 907-911.
Koglin, et al., "Facile and Selective Nanoscale Labeling of Peptides in Solution by Using Photolabile Protecting Groups", J. Med. Chem. (2003); vol. 46:4369-4372.
Kolosov, et al., "Invariant amino acids essential for decoding function of polypeptide release factor eRF1", Nucleic Acids Research (2005); vol. 33, No. 19; pp. 6418-6425.
Korman, Tyler Paz, et al. "Structure and function of an iterative polyketide synthase thioesterase domain catalyzing Claisen cyclization in aflatoxin biosynthesis." Proceedings of the National Academy of Sciences 107.14 (2010): 6246-6251.
Kryuchkova, P., "Two-step model of stop codon recognition by eukaryotic release factor eRF1", Nucleic Acids Research (2013); vol. 41, No. 8, pp. 4573-4586.
Krzycki, et al. "The direct genetic encoding of pyrrolysine", Current Opinion in Microbiology, Current Biology Ltd, GB., vol. 8, No. 6, Dec. 1, 2005, pp. 706-712.
Lan, Yun, et al. "Incorporation of 2, 3-diaminopropionic acid in linear cationic amphipathic peptides produces pH sensitive vectors." Chembiochem: a European Journal of Chemical Biology 11.9 (2010): 1266.
Lang, K., et al. "Genetic Encoding of Bicyclononynes and trans-Cyclooctenes for Site-Specific Protein Labeling in Vitro and in Live Mammalian Cells via Rapid Fluorogenic Diels-Alder Reactions" J. Am. Chem. Soc. (2012); 134, pp. 10317-10320.
Lang, K., et al. "Genetically encoded norbornene directs site-specific cellular protein labelling via a rapid bioorthogonal reaction" Nature Chemistry (Apr. 2012); vol. 4(4); pp. 298-304.
Lekomtsev, S., et al., "Different modes of stop codon restriction by the Stylonychia and Paramecium eRF1 translation termination factors" PNAS (2007); vol. 104, No. 26; pp. 10824-10829.
Li, et al., "A Pyrrolysine Analogue for Site-Specific Protein Ubiquitination". Angew Chem Int Ed Engl. (2009); 48(48): 9184-9187.

(56) References Cited

OTHER PUBLICATIONS

Li, Jie, et al. "Palladium-triggered deprotection chemistry for protein activation in living cells." Nature Chemistry 6.4 (2014): 352-361.

Liu, Bin, et al. "Structural analyses on intermediates in serine protease catalysis." Journal of Biological Chemistry 281.33 (2006): 24024-24035.

Liu, Chang C., et al. "Adding new chemistries to the genetic code." Annual Review of Biochemistry 79 (2010): 413-444.

Liu, Ye, Tengfei Zheng, et al. "Structural basis for phosphopantetheinyl carrier domain interactions in the terminal module of nonribosomal peptide synthetases." Chemistry & Biology 18.11 (2011): 1482-1488.

Long, Jonathan Z., et al. "The metabolic serine hydrolases and their functions in mammalian physiology and disease." Chemical Reviews 111.10 (2011): 6022-6063.

Magarvey, Nathan A., et al. "Characterization of the cereulide NRPS α-hydroxy acid specifying modules: activation of α-keto acids and chiral reduction on the assembly line." Journal of the American Chemical Society 128.33 (2006): 10698-10699.

Malito, et al., Crystal structure of a Baeyer-Villiger monooxygenase, PNAS (Year: 2004); vol. 101 (36): 13157-13162.

May, Júrgen J., et al. "The dhb operon of bacillus subtilisEncodes the biosynthetic template for the catecholic siderophore 2, 3-dihydroxybenzoate-glycine-threonine trimeric ester bacillibactin." Journal of Biological Chemistry 276.10 (2001): 7209-7217.

Mayer, Scott C., et al. "Synthesis of new didemnin B analogs for investigations of structure/biological activity relationships." The Journal of Organic Chemistry 59.18 (1994): 5192-5205.

McGall, Glenn H., et al. "The efficiency of light-directed synthesis of DNA arrays on glass substrates." Journal of the American Chemical Society 119.22 (1997): 5081-5090.

Meeuwissen, et al., "Cofactor regeneration in polymersome nanoreactors: enzymatically catalysed Baeyer-Villiger reactions". J. Mater. Chem. (2011); vol. 21: 18923-18926 and pp. 1-14 of Supplemental Information (Sep. 12, 2011).

Morimoto, Jumpei, et al. "Flexizymes: their evolutionary history and the origin of catalytic function." Accounts of Chemical Research, (2011), 44(12), 1359-1368.

Mukai, et al., "Adding L-lysine derivatives to the genetic code of mammalian cells with engineered pyrrolysyl-tRNA synthetases", Biochemical and Biophysical Research Communications (Jul. 11, 2008); vol. 371, Issue 4, pp. 818-822.

Muñiz, A.A.A., "Structural and functional studies of cyclic depsipeptide biosynthesis", Thesis, McGill University, Canada, Apr. 1, 2019 (Apr. 1, 2019), pp. 1-211, XP055662394, Retrieved from the Internet: URL:http://digitool.library.mcgill.ca/R/-?func=dbin-jump-full&current base=GEN01&object_id=168964 [retrieved on Jan. 28, 2020].

Neumann, Heinz, et al. "Genetically encoding N ϵ-acetyllysine in recombinant proteins." Nature Chemical Biology 4.4 (2008): 232-234.

Ngo, Phong D., et al. "Serine protease catalysis: a computational study of tetrahedral intermediates and inhibitory adducts." The Journal of Physical Chemistry B 120.30 (2016): 7353-7359.

Nguyen, Duy P., et al. "Genetic encoding of photocaged cysteine allows photoactivation of TEV protease in live mammalian cells." Journal of the American Chemical Society, (2014), 136(6), 2240-2243.

Nguyen, Duy P., et al. "Genetically encoded 1, 2-aminothiols facilitate rapid and site-specific protein labeling via a bioorthogonal cyanobenzothiazole condensation." Journal of the American Chemical Society 133.30 (2011): 11418-11421.

Nguyen, et al., "Genetic Encoding and Labeling of Aliphatic Azides and Alkynes in Recombinant Proteins via a Pyrrolysyl-tRNA Synthetase/tRNACUA Pair and Click Chemistry". J Am Chem Soc. (Jul. 1, 2009); 131(25): 8720-8721.

Nozawa, et al., "Pyrrolysyl-tRNA synthetase:tRNAPyl structure reveals the molecular basis of orthogonality". Nature (Feb. 26, 2009); 457(7233): 1163-1167.

Nuemann, et al., "Genetically encoding N(epsilon)-acetyllysine in recombinant proteins", Nat Chem Biol. (Apr. 2008); 4(4): 232-234.

Otto, Hans-Hartwig, et al. "Cysteine proteases and their inhibitors." Chemical Reviews 97.1 (1997): 133-172.

Patterson, David M., et al., "Functionalized cyclopropenes as bioorthogonal chemical reporters." Journal of the American Chemical Society (2012); 134.45: 18638-18643.

PCT/GB2019/053023, International Preliminary Report on Patentability dated Apr. 27, 2021, 12 pages.

PCT/GB2019/053023, International Search Report and Written Opinion mailed Mar. 31, 2020, 17 pages.

PCT/GB2019/053023, Invitation to pay additional fees, mailed Feb. 7, 2020, 13 pages.

Pendrak, Israil, et al. "Synthesis and anti-HSV activity of methylenedioxy mappicine ketone analogs." The Journal of Organic Chemistry 60.9 (1995): 2912-2915.

Phan, Jason, et al. "Structural basis for the substrate specificity of tobacco etch virus protease." Journal of Biological Chemistry 277.52 (2002): 50564-50572.

Plass, et al., "Amino Acids for Diels-Alder Reactions in Living Cells" Angew. Chem. Int. Ed. (2012); 51(17), pp. 4166-4170.

Plechanovová, Anna, et al. "Structure of a RING E3 ligase and ubiquitin-loaded E2 primed for catalysis." Nature 489.7414 (2012): 115-120.

Prescher and Bertozzi, "Chemistry in living systems", Nature Chemical Biology (2005); vol. 1, No. 1, pp. 13-21.

Radzicka, Anna, et al. "Rates of uncatalyzed peptide bond hydrolysis in neutral solution and the transition state affinities of proteases." Journal of the American Chemical Society 118.26 (1996): 6105-6109.

Robbel, Lars, et al. "TioS T-TE-a prototypical thioesterase responsible for cyclodimerization of the quinoline-and quinoxaline-type class of chromodepsipeptides." The FEBS Journal 276.6 (2009): 1641-1653.

Rogerson, Daniel T., et al. "Efficient genetic encoding of phosphoserine and its nonhydrolyzable analog." Nature Chemical Biology 11.7 (2015): 496-503.

Sachdeva, Amit, et al. "Concerted, Rapid, Quantitative, and Site-Specific Dual Labeling of Proteins" Journal of the American Chemical Society (2014); 136, pp. 7785-7788.

Samel, Stefan A., et al. "The thioesterase domain of the fengycin biosynthesis cluster: a structural base for the macrocyclization of a non-ribosomal lipopeptide." Journal of Molecular Biology 359.4 (2006): 876-889.

Scaglione, Jamie B., et al. "Biochemical and structural characterization of the tautomycetin thioesterase: analysis of a stereoselective polyketide hydrolase." Angewandte Chemie International Edition 49.33 (2010): 5726-5730.

Schmied, Wolfgang H., et al. "Efficient Multisite Unnatural Amino Acid Incorporation in Mammalian Cells via Optimized Pyrrolysyl tRNA Synthetase/tRNA Expression and Engineered eRF1" Journal of the American Chemical Society (2014); 136, pp. 15577-15583.

Seit-Nebi, Alim, et al. "Conversion of omnipotent translation termination factor eRF1 into ciliate-like UGA-only unipotent eRF1" European Molecular Biology Organization (2002); vol. 3, No. 9; pp. 881-886.

Shaw-Reid, Cathryn A., et al. "Assembly line enzymology by multimodular nonribosomal peptide synthetases: the thioesterase domain of E. coli EntF catalyzes both elongation and cyclolactonization." Chemistry & Biology 6.6 (1999): 385-400.

Sletten and Bertozzi, "Bioorthogonal Chemistry: Fishing for Selectivity in a Sea of Functionality" Angew. Chem. Int. Ed. (2009); 48(38), pp. 6974-6998.

Strable, et al., "Unnatural Amino Acid Incorporation into Virus-Like Particles". Bioconjug Chem. (Apr. 2008); 19(4): 866-875. Epub Mar. 5, 2008.

Swatek, Kirby N., et al. "Ubiquitin modifications." Cell Research 26.4 (2016): 399-422.

(56) References Cited

OTHER PUBLICATIONS

Tanovic, Alan, et al. "Crystal structure of the termination module of a nonribosomal peptide synthetase." Science 321.5889 (2008): 659-663.

Trauger, John W., et al. "Cyclization of backbone-substituted peptides catalyzed by the thioesterase domain from the tyrocidine nonribosomal peptide synthetase." Biochemistry 40.24 (2001): 7092-7098.

Trauger, John W., et al. "Peptide cyclization catalysed by the thioesterase domain of tyrocidine synthetase." Nature 407.6801 (2000): 215-218.

Tsai, Shiou-Chuan, et al. "Crystal structure of the macrocycle-forming thioesterase domain of the erythromycin polyketide synthase: versatility from a unique substrate channel." Proceedings of the National Academy of Sciences 98.26 (2001): 14808-14813.

Tsai, Shiou-Chuan, et al. "Insights into channel architecture and substrate specificity from crystal structures of two macrocycle-forming thioesterases of modular polyketide synthases." Biochemistry 41.42 (2002): 12598-12606.

Tseng, Claire C., et al. "Characterization of the surfactin synthetase C-terminal thioesterase domain as a cyclic depsipeptide synthase." Biochemistry 41.45 (2002): 13350-13359.

Verma, Sonia, et al. "Cysteine proteases: modes of activation and future prospects as pharmacological targets." Frontiers in Pharmacology 7 (2016): 107.

Virdee, et al. "Traceless and Site-Specific Ubiquitination of Recombinant Proteins" J. Am. Chem. Soc., 2011, vol. 133, pp. 10708-10711.

Virdee, S., et al. "Semisynthetic Src SH2 domains demonstrate altered phosphopeptide specificity induced by incorporation of unnatural lysine derivatives." Chemistry & Biology. (2010), 17(3), 274-284.

Virdee, Satpal, et al. "Engineered diubiquitin synthesis reveals Lys29-isopeptide specificity of an OTU deubiquitinase." Nature Chemical Biology 6.10 (2010): 750-757.

Whicher, Jonathan R., et al. "Structure and function of the RedJ protein, a thioesterase from the prodiginine biosynthetic pathway in Streptomyces coelicolor." Journal of Biological Chemistry 286.25 (2011): 22558-22569.

Yanagisawa, et al, "Multistep engineering of pyrrolysyl-tRNA synthetase to genetically encode N(epsilon)-(oazidobenzyloxycarbonyl)lysine for site-specific protein modification", Chem & Biol. (Nov. 24, 2008); 15(11): 1187-1197.

Yang et al, "Live-Cell Imaging of Cyclopropene Tags with Fluorogenic Tetrazine Cycloadditions", Angew Chem Int Ed Engl. (Jul. 23, 2012); 51(30): 7476-7479.

Yang, Wei, et al. "Understanding the relative acyl-transfer reactivity of oxoesters and thioesters: computational analysis of transition state delocalization effects." Journal of the American Chemical Society 123.44 (2001): 11004-11009.

Yu and Lin, "Design of Spiro[2.3]hex-1-ene, a Genetically Encodable Double-Strained Alkene for Superfast Photoclick Chemistry" Journal of American Chemical Society (2014), 136, pp. 4153-4156, S1-S82.

Yu, Zhipeng, et al. "Genetically Encoded Cyclopropene Directs Rapid, Photoclick-Chemistry-Mediated Protein Labeling in Mammalian Cells" Angew. Chem. Int. Ed. 2012, 51, pp. 10600-10604.

Zeglis, et al., "Modular Strategy for the Construction of Radiometalated Antibodies for Positron Emission Tomography Based on Inverse Electron Demand Diels-Alder Click Chemistry" Bioconjugate Chem. (2011); 22(10), pp. 2048-2059.

Zhang, "Synthesis of Cyclopropene r-Amino Acids via Enantioselective Desymmetrization", Organic Letters (2006); vol. 8, No. 14, pp. 2965-2968.

Zhang, Michael Shaofei, et al. "Biosynthesis and genetic encoding of phosphothreonine through parallel selection and deep sequencing." Nature Methods 14.7 (2017): 729-736.

Zhou, Yongjun, et al. "Iterative mechanism of macrodiolide formation in the anticancer compound conglobatin." Chemistry & Biology 22.6 (2015): 745-754.

Zhou, Yongjun, et al. "Macrodiolide formation by the thioesterase of a modular polyketide synthase." Angewandte Chemie 127.17 (2015): 5321-5324.

\* cited by examiner

7 R₁=OH, R₂=SCH₂CH₂NHC(O)CH₃      8  R₁=H, R₂=SCH₂CH₂NHC(O)CH₃
9 R₁=OH, R₂=OH                                      10 R₁=H, R₂=OH

11 R₁=OH, R₂=SCH₂CH₂NHC(O)CH₃   12 R₁=H, R₂=SCH₂CH₂NHC(O)CH₃
13 R₁=OH, R₂=OH                                     14 R₁=H, R₂=OH

15 R₁=OH, R₂=SCH₂CH₂NHC(O)CH₃   16 R₁=H, R₂=SCH₂CH₂NHC(O)CH₃
17 R₁=OH, R₂=OH                                     18 R₁=H, R₂=OH

METHODS AND COMPOSITIONS

CROSS-REFERENCE TO RELATED APPLICATIONS

This application is a national phase filing under 35 U.S.C. § 371 of International PCT Application No. PCT/GB2019/053023, filed Oct. 24, 2019, which claims the benefit of priority to United Kingdom Application No. 1817444.1 filed on Oct. 26, 2018, each of which is hereby incorporated by reference in its entirety.

INCORPORATION BY REFERENCE OF SEQUENCE LISTING

The content of the text file submitted electronically herewith is incorporated herein by reference in its entirety: A computer readable format copy of the Sequence Listing (filename: LARC_008_N01US_SeqList_ST25.txt, date created: Apr. 23, 2021, file size: about 66 kilobytes).

FIELD OF THE INVENTION

The invention relates to genetic incorporation of 2,3-diamino propionic acid (DAP) into polypeptides, to unnatural amino acids comprising DAP, to a tRNA synthetase for charging tRNA with unnatural amino acids comprising DAP, and to methods of using the resulting polypeptides, for example in capturing substrates and/or intermediates in enzymatic reactions.

BACKGROUND

Many enzymes perform reactions that proceed through covalent intermediates bound to serine or cysteine sidechains in the enzyme active site[1]. The reaction of hydroxyl or sulfhydryl groups with carbonyl groups in substrates forms activated ester or thioester intermediates that are rapidly converted to products through further reactions with selected nucleophiles. Because the half-lives of thioesters and esters are commonly minutes to hours[8], it is challenging to isolate and characterize these important acyl-enzyme intermediates.

Strategies to stably capture these intermediates enable the identification of native substrates and the characterization of otherwise elusive intermediates and functional states. In known approaches, substrate analogues, bearing electrophilic replacements for the carbonyl group, can be used to capture analogues of acyl-enzyme intermediates[9-11]. In other known cases, mutations in an enzyme's active site may enable stabilization of its acyl-enzyme intermediates[12]. These approaches have provided valuable insight, but require the synthesis of substrate analogues and lead to non-native active sites or complexes with non-native substrates, which are drawbacks with these techniques. In the ubiquitin field, it has been possible to replace the key cysteine residues of E2's with lysine and make amide bonds to the C-terminus of ubiquitin; this has led to numerous insights into protein ubiquitination pathways[13,14]. However, this conjugation commonly requires elevated pH, and the resulting substitution is far from isosteric, which are drawbacks with this approach. Thus the strategy is unsuitable for application to most enzyme classes that proceed through acyl-enzyme intermediates in their reaction pathway, which is a problem in the art.

Acyl-enzyme intermediates—formed between sulfhydryl or hydroxyl sidechains of cysteine or serine residues in enzymes and carbonyl groups in substrates—are ubiquitous in diverse biological transformations, including those mediated by non-ribosomal peptide synthetases (NRPSs) and by proteases. These important thioester and ester intermediates are unstable, commonly having half-lives of minutes to hours, which makes their characterisation challenging. This is a problem in the art.

A polypeptide comprising 2,3-diamino propionic acid (DAP) has been disclosed in the prior art. Specifically, one or more polypeptides bearing DAP have been produced by solid phase synthesis/conjugation techniques in the prior art (see Virdee, S., Macmillan, D., & Waksman, G. (2010) Chemistry & Biology vol 17 pages 274-284 "Semisynthetic Src SH2 domains demonstrate altered phosphopeptide specificity induced by incorporation of unnatural lysine derivatives."). However, there are numerous problems with production of polypeptides comprising DAP by conventional solid phase synthesis/conjugation techniques. For example, it is extremely difficult or impossible to incorporate DAP into domains or motifs of greatest biological interest such as the active sites of enzymes using prior art techniques. This may be because the sites are not accessible for chemical conjugation, and/or because proteins made by solid phase synthesis require chemical refolding in order to attain the correct confirmation. As well as being laborious, this is also highly unreliable and unpredictable, and is very often unsuccessful. These are problems in the art.

SUMMARY

A key technical advance provided by the invention is a new way to produce polypeptides comprising 2,3-diamino propionic acid (DAP). This is especially useful in incorporating the DAP into locations which are difficult or impossible to modify in the prior art, such as incorporation into enzyme active site(s).

These methods are based on new unnatural amino acid(s) which serve for incorporation into polypeptide via naturally occurring translational machinery (e.g. the cell's own ribosomes). The methods also involve a new tRNA synthetase capable of charging an orthogonal tRNA with the new unnatural amino acid(s). Once the new unnatural amino acid(s) are incorporated into polypeptide they can be easily deprotected to leave DAP in the polypeptide backbone.

Thus the invention enables incorporation of DAP into a range of proteins, and/or into a range of locations within proteins, which are currently not possible using prior art techniques.

Thus in one aspect the invention provides an unnatural amino acid of formula (I) or (II):

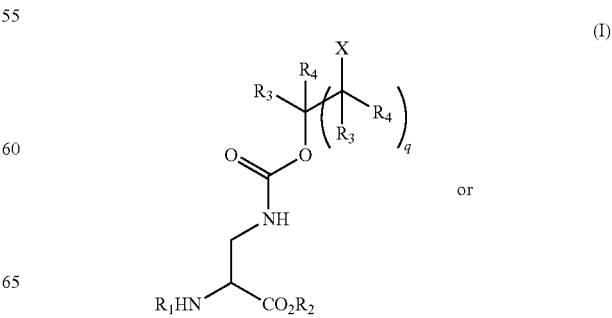

-continued

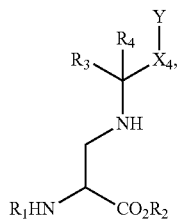
(II)

or salts, solvates, tautomers, isomers or mixtures thereof; wherein:
$R_1$ is H, an amino acid residue or a peptide;
$R_2$ is H, $C_{1-6}$ alkyl, $C_{1-6}$ haloalkyl or $C_{5-20}$ aryl.
q is 1, 2 or 3;
each $R_3$ or $R_4$ is independently selected from H, halo, $C_{1-6}$ alkyl, $C_{1-6}$ haloalkyl, $C_{5-20}$ aryl, $C_{3-20}$ heteroaryl, $OC_{1-6}$ alkyl, $SC_{1-6}$ alkyl, $NH(C_{1-6}$ alkyl) and $N(C_{1-6}$ alkyl)$_2$;
X is $X_1$—Y, S—S—$R_5$, Se—Se—$R_5$, O—NH—$R_5$, S—NH—$R_5$, Se—NH—$R_5$, $X_2$—$Y_1$, $X_3$—$Y_2$, $N_3$ or NH—S(O)$_2$—$Y_3$;
$X_1$ is S, Se, O, NH or N($C_{1-6}$ alkyl);
$X_2$ is S, Se or O;
$X_3$ is NH—C(O)—O;
$X_4$ is NH—C(O)—O, O, S or NH;
$R_5$ is selected from H, halo, $C_{1-6}$ alkyl, $C_{1-6}$ haloalkyl, $C_{5-20}$ aryl, $C_{3-20}$ heteroaryl, $OC_{1-6}$ alkyl, $NH(C_{1-6}$ alkyl), $N(C_{1-6}$ alkyl)$_2$, peptides, sugars, $C_{3-20}$ heterocyclyl and nucleic acids;
Y is a protecting group selected from:

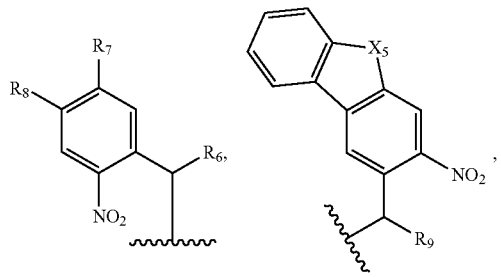

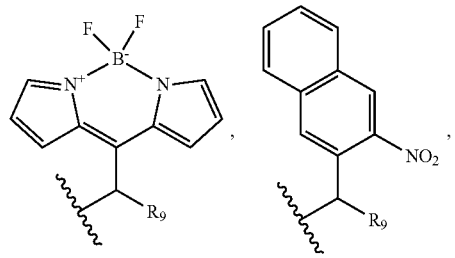

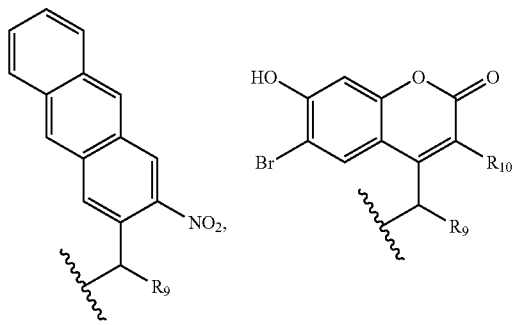

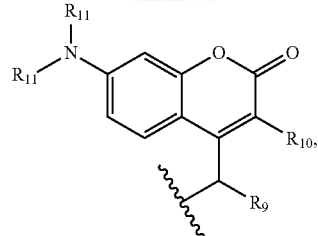

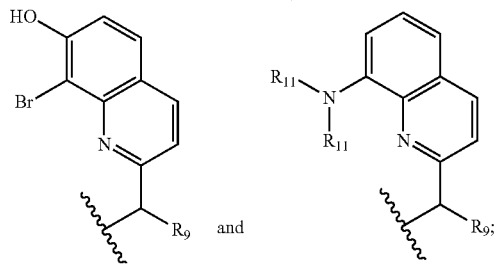

$R_6$ is selected from H, $C_{1-6}$ alkyl, $C_{1-6}$ haloalkyl, $CO_2H$, $CO_2R'$, $SO_2H$, $SO_2R'$, $C_{5-20}$ aryl, $C_{3-20}$ heteroaryl, NHC(O)R' and NHR';
$R_7$ and $R_8$ are independently selected from H, OH, O($C_{1-6}$ alkyl), O($C_{5-20}$ aryl) and O($C_{3-20}$ heteroaryl); or $R_7$ and $R_8$ are linked together to form an O—CH$_2$—O group;
each R' is independently selected from $C_{1-6}$ alkyl, $C_{1-6}$ haloalkyl and $C_{5-20}$ aryl;
$R_9$ is selected from H, $C_{1-6}$ alkyl, $C_{1-6}$ haloalkyl, $CO_2H$, $CO_2R'$, $SO_2H$, $SO_2R'$ and $C_{5-20}$ aryl;
$R_{10}$ is selected from H, $C_{1-6}$ alkyl and $C_{1-6}$ haloalkyl;
$R_{11}$ is selected from H, $C_{1-6}$ alkyl and $C_{1-6}$ haloalkyl;
$X_5$ is S, O, NH, N—C(O)—O—R', N—S(O)$_2$H, N—S(O)$_2$R' or NR';
$Y_1$ is a protecting group selected from

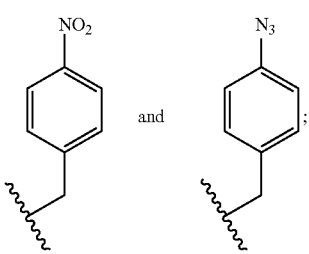 [SMILES: *Cc1ccc([N+](=O)[O-])cc1 ; *Cc1ccc(N=[N+]=[N-])cc1]

$Y_2$ is a protecting group selected from

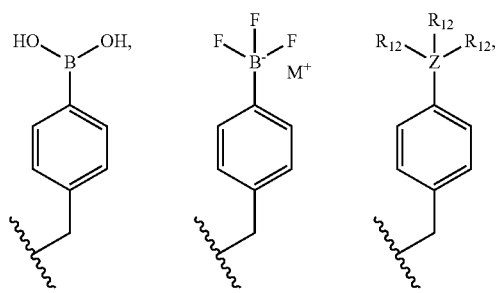

$M^+$ is $Li^+$, $Na^+$, $K^+$ or $N(R_{13})_4^+$;

Z is Si or Ge;

$R_{12}$ is $C_{1-6}$ alkyl or $C(O)$—$(C_{5-20}$ aryl);

$R_{13}$ is H, $C_{1-6}$ alkyl, allyl or $C_{5-20}$ aryl; and $Y_3$ is a protecting group

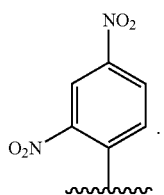

In one aspect the invention provides a polypeptide comprising an unnatural amino acid as described above wherein said unnatural amino acid is attached to said polypeptide via a peptide bond.

In one aspect, the invention relates to a method of preparing a polypeptide comprising DAP, the method comprising deprotecting a polypeptide as described above. Suitably said deprotecting comprises illumination at 365 nm, 35 mWcm$^{-2}$, for 1 minute.

In one aspect, the invention relates to a PylRS tRNA synthetase comprising the mutations Y271C, N311Q, Y349F and V366C. Suitably said PylRS tRNA synthetase is a *Methanosarcina barkeri* PylRS (MbPylRS) tRNA synthetase comprising said mutations.

In one aspect, the invention relates to a method of producing a polypeptide comprising 2,3-diamino propionic acid (DAP), said method comprising genetically incorporating an unnatural amino acid as described above into a polypeptide, and optionally deprotecting said unnatural amino acid to 2,3-diamino propionic acid (DAP).

Suitably producing the polypeptide comprises (i) providing a nucleic acid encoding the polypeptide which nucleic acid comprises an orthogonal codon encoding the unnatural amino acid according to any of claims 1 to 10;

(ii) translating said nucleic acid in the presence of an orthogonal tRNA synthetase/tRNA pair capable of recognising said orthogonal codon and incorporating said unnatural amino acid into the polypeptide chain.

Suitably said orthogonal codon comprises an amber codon (TAG), said tRNA comprises MbtRNA$_{CUA}$, and said tRNA synthetase comprises a MbPylRS synthetase having the mutations Y271C, N311Q, Y349F and V366C.

Suitably said unnatural amino acid comprises

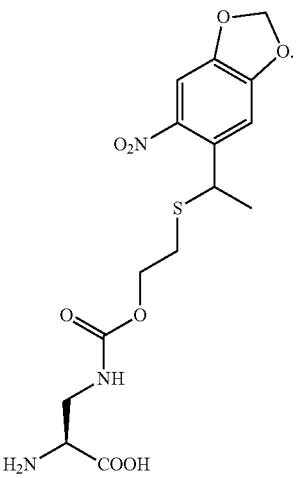 [SMILES: CC(SCCOC(=O)NC[C@H](N)C(=O)O)c1cc2c(cc1[N+](=O)[O-])OCO2]

In one aspect, the invention relates to a polypeptide as described above, or a method as described above, wherein said polypeptide is an enzyme, and wherein said unnatural amino acid is incorporated at a position corresponding to an amino acid residue within the active site of said enzyme.

In one aspect, the invention relates to a polypeptide as described above wherein said polypeptide is an enzyme, and wherein said enzyme is an EC 3.4 peptidase, an EC 3.4.22.44 peptidase, or an EC 2.3.2.23 E2 ubiquitin-conjugating enzyme, according to the International Nomenclature and Classification of Enzymes.

In one aspect, the invention relates to a polypeptide as described above which comprises one to twenty 2,3-diamino propionic acid (DAP) groups. Suitably said polypeptide comprises a single 2,3-diamino propionic acid (DAP) group.

In one aspect, the invention relates to a polypeptide as described above, or a method as described above, wherein said unnatural amino acid is incorporated at a position corresponding to a cysteine, serine or threonine residue in the wild type polypeptide, optionally at a position corresponding to a cysteine or serine residue in the wild type polypeptide.

In one aspect, the invention relates to use of an unnatural amino acid as described above in the production of a polypeptide comprising 2,3-diamino propionic acid (DAP). Suitably production of the polypeptide comprises performing a method as described above.

In one aspect, the invention relates to a method of capturing a substrate for an enzyme, the method comprising
 a) providing an enzyme comprising at least one 2,3-diamino propionic acid (DAP) group in its active site,
 b) contacting said enzyme with candidate substrate(s) for said enzyme, and
 c) incubating to allow reaction of said DAP group with said candidate substrate(s).

Suitably said substrate is a metabolite.

Suitably said enzyme is a peptidase or a ubiquitin-conjugating enzyme or a hydrolase or an enzyme forming carbon-sulphur bonds.

DETAILED DESCRIPTION

Here we disclose how genetically encoded 2,3-diaminopropionic acid enables structural insight into enzymatic reactions. In particular we exemplify this approach via acyl-thioesterase intermediates in the biosynthesis of valinomycin.

The invention enables a strategy for genetically directing the efficient incorporation of 2,3-diaminopropionic acid (DAP) into recombinant proteins produced in (for example) E. coli. We teach how to replace catalytic residues such as cysteine or serine residues with DAP. This enables the efficient capture of acyl-enzyme complexes that are linked through a stable amide bond.

The invention is demonstrated for example by elucidating the biosynthetic pathway by which the thioesterase domain of valinomycin synthetase (Vlm TE) facilitates both the sequential trimerisation of linear tetradepsipeptides to a dodecadepsipeptide and the subsequent cyclization of the dodecadepsipeptide to valinomycin. By trapping the first and last acyl-TE intermediates in the catalytic cycle of Vlm TE as DAP conjugates, using the invention provides structural insight into how conformational changes in the TE domains of NRPSs control the switch from oligomerisation to cyclisation of linear substrates. Strategies such as this enabled by the invention find application in facilitating the characterisation of diverse acyl-enzyme intermediates. Moreover, the invention finds application in enabling capture and identification of the native substrates for enzymes of unknown function.

In one aspect, the invention relates to a homogenous recombinant polypeptide as described above. Suitably said polypeptide is made by a method as described above.

In one aspect, the invention relates to a polypeptide produced according to the method(s) described herein. As well as being the product of those new methods, such a polypeptide has the technical feature of comprising an unnatural amino acid as described above, or comprising DAP.

Mutating has it normal meaning in the art and may refer to the substitution or truncation or deletion of the residue, motif or domain referred to. Mutation may be effected at the polypeptide level e.g. by synthesis of a polypeptide having the mutated sequence, or may be effected at the nucleotide level e.g. by making a nucleic acid encoding the mutated sequence, which nucleic acid may be subsequently translated to produce the mutated polypeptide. Where no amino acid is specified as the replacement amino acid for a given mutation site, suitably a randomisation of said site is used. As a default mutation, alanine (A) may be used. Suitably the mutations used at particular site(s) are as are set out herein.

A fragment is suitably at least 10 amino acids in length, suitably at least 25 amino acids, suitably at least 50 amino acids, suitably at least 100 amino acids, suitably at least 200 amino acids, suitably at least 250 amino acids, suitably at least 300 amino acids, suitably at least 313 amino acids, or suitably the majority of the polypeptide of interest.

The methods of the invention may be practiced in vivo or in vitro.

In one embodiment, suitably the methods of the invention are not applied to the human or animal body. Suitably the methods of the invention are in vitro methods. Suitably the methods do not require the presence of the human or animal body.

Suitably the methods are not methods of diagnosis or of surgery or of therapy of the human or animal body.

The term 'comprises' (comprise, comprising) should be understood to have its normal meaning in the art, i.e. that the stated feature or group of features is included, but that the term does not exclude any other stated feature or group of features from also being present.

DAP Incorporation

We hypothesized that selectively replacing catalytic cysteine or serine residues with an amino acid in which the sulfhydryl or hydroxyl group is replaced with an amino group (2,3-diaminopropionic acid (DAP, 1)) would allow trapping of acyl-enzyme intermediates linked via an amide bond (FIG. 1c). While the conjugate acid of the amine in a lysine sidechain has a pKa of 10.5, the pKa of the conjugate acid of the beta amino group of DAP is 9.4[15]. Moreover, when DAP is incorporated into a peptide, the pKa is substantially lowered by the electron withdrawing effect of the backbone amide: A single peptide bond to the carboxylate of DAP lowers the pKa of the conjugate acid of the beta amino group to 7.5[16], and a pKa of 6.3 was reported in longer peptides[16]. Thus, we anticipated that if DAP was used to replace Cys or Ser within the active sites of enzymes, a substantial fraction of the DAP sidechains would exist as the neutral amine at physiological pH. These amines would be available to act as nucleophiles, and may form amide bonds with the enzymes' substrates. The half-life of an amide in aqueous solution is of the order of 500 years[17], and we anticipated that the amide analogues of labile thioester and ester intermediates would be substantially stabilized, such that subsequent reactions with nucleophiles or solvent would not proceed or would be severely attenuated (FIG. 1c).

The secondary metabolite-producing megaenzymes non-ribosomal peptide synthetases (NRPSs) and polyketide synthases (PKSs) generate highly complex acyl-enzyme intermediates during their synthetic cycles. These molecular machines use thio-templated biosynthetic pathways to assemble small acyl molecules into a broad array of biologically active natural products, including clinical anticancer agents, antibiotics, antifungals, and immunosuppressants (Supplementary FIG. 1). Prior art attempts to unravel their detailed molecular function have been hampered by the challenge of characterising their multiple acyl-enzyme intermediates at high resolution. This challenge is exemplified with the thioesterase (TE) domains from NRPS pathways that oligomerise and cyclise linear peptidyl or depsipeptidyl substrates. These TE domains are involved in biosynthesis of the antibiotic gramicidin S[18], the emetic toxin cereulide[19, 20], the siderophores enterobactin and bacillibactin[21, 22], the anticancer conglobatin[23], the DNA bis-intercalator thiocoraline[24] and valinomycin, a potassium ionophore depsipeptide with antimicrobial, antitumoral and cytotoxic properties[20, 25]. They must first oligomerise their peptidyl intermediates up to, but not beyond, the number of copies found in the biologically active compound, and then catalyse the final release and cyclisation of the completed product. Furthermore, the required oligomerisations and cyclisations must be rapid enough for spontaneous hydrolysis not to cause substantial formation of free linear peptides, which cannot be re-incorporated into the synthetic cycle and thus are useless side products.

High-resolution structures of acyl-TE intermediates would provide mechanistic insight into how TEs control substrate fate and represent a substantial advance. A handful of high-resolution acyl-TE structures have been obtained, most notably with the polyketide pikromycin-forming TE and non-native substrate analogues[26]. These have helped identify the putative oxyanion hole and demonstrated the interaction of the "lid" element of the TE domain with the substrate. Structural studies of TE domains have been hampered by the combination of poor $K_d$ values for the small-molecule substrates[27], the multiple conformations of the peptidyl chain when bound to the TE domain[28, 29] and especially, the hydrolysis rates of acyl-TE intermediates[27, 29], which are high compared to the crystallographic time scale. These are problems with the prior art approaches.

The ability to access stable acyl-TE intermediates as provided by the invention is a significant benefit enabling the skilled worker to characterize the mechanism of TE domain selectivity in nonribosomal peptide biosynthesis as well as in polyketide and fatty acid biosynthesis.

As described in more detail below, the inventors have evolved an aminoacyl-tRNA synthetase/tRNA$_{CUA}$ pair incorporating an amino acid that can be post-translationally converted to DAP under mild conditions. We demonstrate use of this pair for the site-specific incorporation of DAP into recombinant proteins produced in E. coli. We demonstrate the efficient capture of acyl-enzyme intermediates for a cysteine protease and an NRPS TE domain. Valinomycin synthetase (Vlm), a 2-protein, 4-module NRPS, is proposed to alternatively link hydroxy acids (from in situ reduction of alpha-keto acids) and amino acids into a tetradepsipeptide intermediate, which the TE domain (Vlm TE) progressively trimerizes to a dodecadepsipeptide and then cyclizes to yield valinomycin[20, 25] (FIG. 2).

We demonstrate the invention used to elucidate the biosynthetic pathway for converting tetradepsipeptides to valinomycin. By replacing the catalytic serine in Vlm TE with DAP we demonstrate how to access stable deoxy-tetradepsipeptidyl-N-TE$_{DAP}$ and dodecadepsipeptidyl-TE$_{DAP}$ conjugates. Structural characterization of these conjugates provides insights into the first and last acyl-TE intermediates in the catalytic cycle of Vlm TE. Thus the invention finds application in investigating/revealing how the fate of substrates may be determined by conformational changes in the TE domains of NRPSs that oligomerise and cyclise linear precursors.

Suitably the polypeptide comprises a single DAP group and/or residue of unnatural amino acid as described above. This has the advantage of maintaining specificity for any further chemical modifications which might be directed at the DAP group/unnatural amino acid as described above, and/or specificity of capture when the DAP is present in the active site of an enzyme. For example when there is only a single DAP group/unnatural amino acid as described above in the polypeptide of interest then possible issues of partial modification/partial deprotection, or issues of reaction microenvironments varying between alternate DAP groups in the same polypeptide (which could lead to unequal reactivity between different DAP group(s) at different locations in the polypeptide) are advantageously avoided.

Suitably the polypeptide comprises two DAP groups; suitably the polypeptide comprises three DAP groups; suitably the polypeptide comprises four DAP groups; suitably the polypeptide comprises five DAP groups; suitably the polypeptide comprises ten DAP groups or even more, such as 15-20 DAP groups. Most suitably the polypeptide comprises one to five DAP groups. More suitably the polypeptide comprises one DAP group.

In principle multiple unnatural amino acid(s) as described above (either multiple copies of the same unnatural amino acid, or one or more copies of each of two or more different unnatural amino acids) could be incorporated by the same or by different orthogonal codons/orthogonal tRNA pairs. Suitably multiple unnatural amino acid(s) are incorporated by insertion/translation of multiple amber codons (together with a suitable orthogonal tRNA synthetase as described herein).

Novel Chemical Entities (NCE's)

Novel chemical entities (NCE's) are described herein using generic formulae in the conventional manner. There is described an unnatural amino acid of formula (I) or (II):

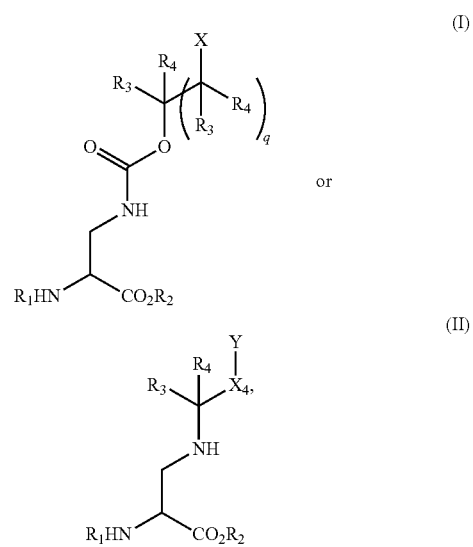

or salts, solvates, tautomers, isomers or mixtures thereof; wherein:

$R_1$ is H, an amino acid residue or a peptide;
$R_2$ is H, $C_{1-6}$ alkyl, $C_{1-6}$ haloalkyl or $C_{5-20}$ aryl.
q is 1, 2 or 3;
each $R_3$ or $R_4$ is independently selected from H, halo, $C_{1-6}$ alkyl, $C_{1-6}$ haloalkyl, $C_{5-20}$ aryl, $C_{3-20}$ heteroaryl, $OC_{1-6}$ alkyl, $SC_{1-6}$ alkyl, $NH(C_{1-6}$ alkyl) and $N(C_{1-6}$ alkyl)$_2$;
X is $X_1$—Y, S—S—$R_5$, Se—Se—$R_5$, O—NH—$R_5$, S—NH—$R_5$, Se—NH—$R_5$, $X_2$—$Y_1$, $X_3$—$Y_2$, $N_3$ or NH—S(O)$_2$—$Y_3$;
$X_1$ is S, Se, O, NH or N($C_{1-6}$ alkyl);
$X_2$ is S, Se or O;
$X_3$ is NH—C(O)—O;
$X_4$ is NH—C(O)—O, O, S or NH;
$R_5$ is selected from H, halo, $C_{1-6}$ alkyl, $C_{1-6}$ haloalkyl, $C_{5-20}$ aryl, $C_{3-20}$ heteroaryl, $OC_{1-6}$ alkyl, $NH(C_{1-6}$ alkyl), $N(C_{1-6}$ alkyl)$_2$, peptides, sugars, $C_{3-20}$ heterocyclyl and nucleic acids;
Y is a protecting group selected from:

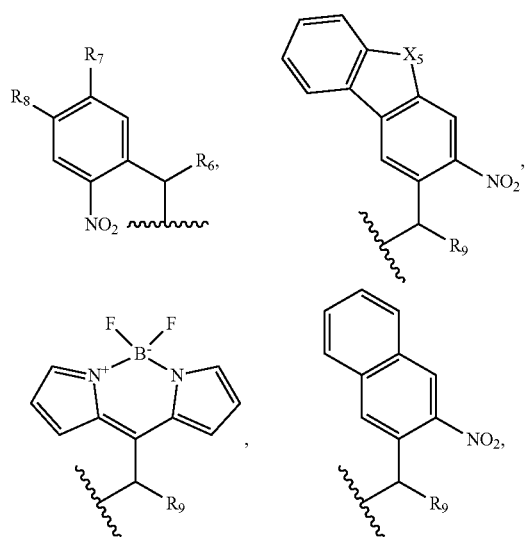

-continued

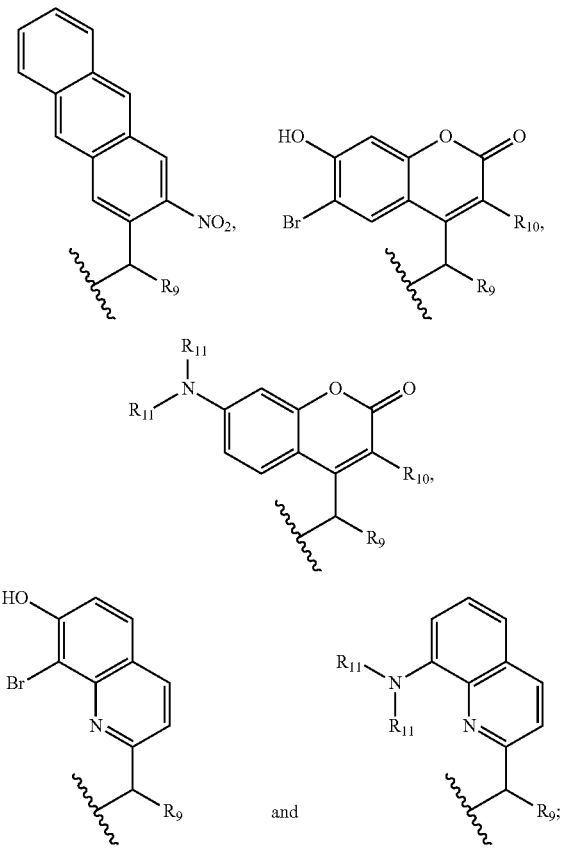

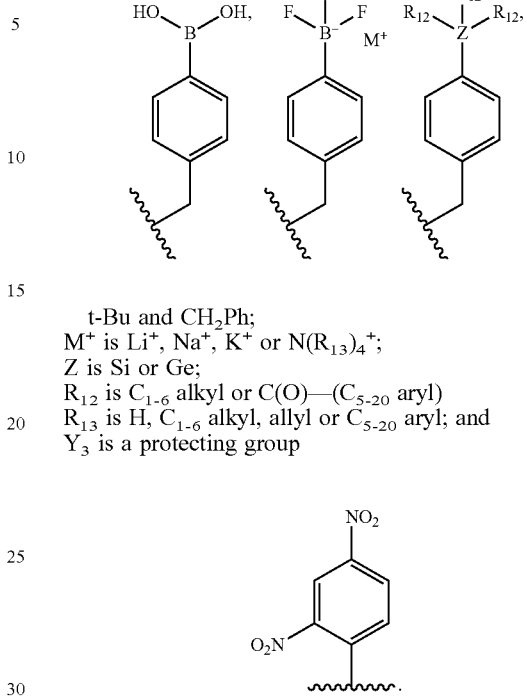

t-Bu and CH$_2$Ph;
M$^+$ is Li$^+$, Na$^+$, K$^+$ or N(R$_{13}$)$_4^+$;
Z is Si or Ge;
R$_{12}$ is C$_{1-6}$ alkyl or C(O)—(C$_{5-20}$ aryl)
R$_{13}$ is H, C$_{1-6}$ alkyl, allyl or C$_{5-20}$ aryl; and
Y$_3$ is a protecting group R$_6$ is selected from H, C$_{1-6}$ alkyl, C$_{1-6}$ haloalkyl, CO$_2$H, CO$_2$R', SO$_2$H, SO$_2$R', C$_{5-20}$ aryl, C$_{3-20}$ heteroaryl, NHC(O)R' and NHR';

R$_7$ and R$_8$ are independently selected from H, OH, O(C$_{1-6}$ alkyl), O(C$_{5-20}$ aryl) and O(C$_{3-20}$ heteroaryl); or R$_7$ and R$_8$ are linked together to form an O—CH$_2$—O group;

each R' is independently selected from C$_{1-6}$ alkyl, C$_{1-6}$ haloalkyl and C$_{5-20}$ aryl;

R$_9$ is selected from H, C$_{1-6}$ alkyl, C$_{1-6}$ haloalkyl, CO$_2$H, CO$_2$R' SO$_2$H, SO$_2$R' and C$_{5-20}$ aryl;

R$_{10}$ is selected from H, C$_{1-6}$ alkyl and C$_{1-6}$ haloalkyl;

R$_{11}$ is selected from H, C$_{1-6}$ alkyl and C$_{1-6}$ haloalkyl;

X$_5$ is S, O, NH, N—C(O)—O—R', N—S(O)$_2$H, N—S(O)$_2$R' or NR';

Y$_1$ is a protecting group selected from

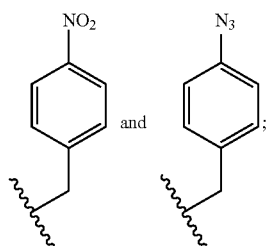 [SMILES: *Cc1ccc([N+](=O)[O-])cc1 ; *Cc1ccc(N=[N+]=[N-])cc1]

The term "or salts, solvates, tautomers, isomers or mixtures thereof" means that salt, solvate, tautomeric, isomeric forms of the shown structure are also included. Mixtures thereof means that mixture of these forms may be present, for example, the compounds of the invention may comprise a salt of a tautomeric form.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

As used herein, "solvate" refers to a complex of variable stoichiometry formed by a solute (e.g. formulas (I)-(II), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

"Independently selected" is used in the context of statement that, for example, "each R$_3$ and R$_4$ are independently selected from H, halo, C$_{1-6}$ alkyl, . . . " and means that each instance of the functional group, e.g. R$_3$, is selected from the listed options independently of any other instance of R$_3$ or R$_4$ in the compound. Hence, for example, H may be selected for the first instance of R$_3$ in the compound; methyl may be selected for the next instance of R$_3$ in the compound; and ethyl may be selected for the first instance of R$_4$ in the compound.

In this specification, C$_{1-6}$ alkyl: refers to straight chain and branched saturated hydrocarbon groups, generally having from 1 to 6 carbon atoms; more suitably a C$_{1-5}$ alkyl; more suitably a $C_{1-4}$ alkyl; more suitably a $C_{1-3}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

In this specification, "an amino acid residue" refers to an amino acid where either the amine or the carboxylic acid end of an amino acid has been replaced with a peptide bond.

$C_{5-20}$ aryl: refers to fully unsaturated monocyclic, bicyclic and polycyclic aromatic hydrocarbons having at least one aromatic ring and having a specified number of carbon atoms that comprise their ring members (e.g., $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Examples of aryl groups include phenyl, biphenyl, cyclobutabenzenyl, naphthalenyl, benzocycloheptenyl, azulenyl, biphenylenyl, anthracenyl, phenanthrenyl, naphthacenyl, pyrenyl, groups derived from cycloheptatriene cation, and the like. Examples of aryl groups which comprise fused rings, at least one of which is an aromatic ring, include, but are not limited to, groups derived from indanyl, indenyl, isoindenyl, tetralinyl, acenaphthenyl, fluorenyl, phenalenyl, acephenanthrenyl and aceanthrenyl.

"Halo" or "halogen": refers to —F, —Cl, —Br or —I.

"$C_{1-6}$ haloalkyl": refers to a group derived from a $C_{1-6}$ alkyl group where 1 or more of the hydrogen atoms have been replaced with halo atoms. Suitably, the $C_{1-6}$ haloalkyl is $CH_2F$, $CHF_2$, $CF_3$, $CH_2Cl$, $CHCl_2$ or $CCl_3$.

"$C_{3-20}$ Heteroaryl": refers to unsaturated monocyclic, bicyclic or polycylic aromatic groups comprising from 3 to 20 ring atoms, whether carbon or heteroatoms, of which from 1 to 10 are ring heteroatoms. Suitably, each ring has from 3 to 7 ring atoms and from 1 to 4 ring heteroatoms. Suitably each ring heteroatom is independently selected from nitrogen, oxygen, and sulfur. The bicyclic and polycyclic may include any bicyclic or polycyclic group in which any of the above-listed monocyclic heterocycles are fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:
$N_1$: pyrrole, pyridine;
$O_1$: furan;
$S_1$: thiophene;
$N_1O_1$: oxazole, isoxazole, isoxazine;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2$: imidazole, pyrazole, pyridazine, pyrimidine (e.g., cytosine, thymine, uracil), pyrazine;
$N_3$: triazole, triazine; and,
$N_4$: tetrazole.

Examples of heteroaryl which comprise fused rings, include, but are not limited to, those derived from:
$O_1$: benzofuran, isobenzofuran, chromene, isochromene, chroman, isochroman, dibenzofuran, xanthene;
$N_1$: indole, isoindole, indolizine, isoindoline, quinoline, isoquinoline, quinolizine, carbazole, acridine, phenanthridine;
$S_1$: benzothiofuran, dibenzothiophene, thioxanthene;

$N_1O_1$: benzoxazole, benzisoxazole, benzoxazine, phenoxazine;
$N_1S_1$: benzothiazole, phenothiazine;
$O_1S_1$: phenoxathiin;
$N_2$: benzimidazole, indazole, benzodiazine, pyridopyridine, quinoxaline, quinazoline, cinnoline, phthalazine, naphthyridine, benzodiazepine, carboline, perimidine, pyridoindole, phenazine, phenanthroline, phenazine;
$O_2$: benzodioxole, benzodioxan, oxanthrene;
$S_2$: thianthrene
$N_2O_1$: benzofurazan;
$N_2S_1$: benzothiadiazole
$N_3$: benzotriazole
$N_4$: purine (e.g., adenine, guanine), pteridine;

"$C_{3-20}$ heterocyclyl": refers to saturated or partially unsaturated monocyclic, bicyclic or polycyclic groups having ring atoms composed of 3 to 20 ring atoms, whether carbon atoms or heteroatoms, of which from 1 to 10 are ring heteroatoms. Suitably, each ring has from 3 to 7 ring atoms and from 1 to 4 ring heteroatoms (e.g., suitably $C_{3-5}$ heterocyclyl refers to a heterocyclyl group having 3 to 5 ring atoms and 1 to 4 heteroatoms as ring members). The ring heteroatoms are independently selected from nitrogen, oxygen, and sulphur.

As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:
$N_1$: aziridine, azetidine, pyrrolidine, pyrroline, 2H-pyrrole or 3H-pyrrole, piperidine, dihydropyridine, tetrahydropyridine, azepine;
$O_1$: oxirane, oxetane, tetrahydrofuran, dihydrofuran, tetrahydropyran, dihydropyran, pyran, oxepin;
$S_1$: thiirane, thietane, tetrahydrothiophene, tetrahydrothiopyran, thiepane;
$O_2$: dioxoiane, dioxane, and dioxepane;
$O_3$: trioxane;
$N_2$: imidazoiidine, pyrazolidine, imidazoline, pyrazoline, piperazine:
$N_1O_1$: tetrahydrooxazole, dihydrooxazole, tetrahydroisoxazole, dihydroisoxazole, morpholine, tetrahydrooxazine, dihydrooxazine, oxazine;
$N_1S_1$: thiazoline, thiazolidine, thiomorpholine;
$N_2O_1$: oxadiazine;
$O_1S_1$: oxathiole and oxathiane (thioxane); and
$N_1O_1S_1$: oxathiazine.

Examples of substituted monocyclic heterocyclyl groups include those derived from saccharides, in cyclic form, for example, furanoses, such as arabinofuranose, lyxofuranose, ribofuranose, and xylofuranse, and pyranoses, such as aliopyranose, altropyranose, glucopyranose, mannopyranose, gulopyranose, idopyranose, galactopyranose, and talopyranose.

The term "peptide" as used herein refers to a linear molecule comprising multiple amino acid residues that are combined with each other by peptide bonds.

Protecting groups are groups that are introduced into a molecule by chemical modification of a functional group to temporarily mask the characteristic chemistry of a functional group to prevent it from interfering with another reaction. A protecting group that can be removed by a photolytic reaction (i.e. is capable of being removed/is removable/can be deprotected by a photolytic reaction) is a group that can be removed by radiant energy such as light. Protecting groups are described in Wuts, P. G. M. and Greene, T. W., Protective Groups in Organic Synthesis, 4*th* Edition, Wiley-Interscience, 2007, and in P. Kocienski, *Protective Groups*, 3rd Edition (2005).

A "sugar" substituent represents a monosaccharide or polysaccharide where a H from a hydroxyl group of the sugar has been replaced with a bond attaching the sugar substituent to the rest of the compound of formula (I) or (II). Suitably, the sugar is a monosacchride. Suitably, the sugar is glucose, mannose or galactose.

Suitably, the protecting group is photolabile and so can be deprotected at wavelengths $\lambda_{max}$ greater than 300 nm. These are wavelengths that are non-detrimental to biological systems.

In one aspect, suitably, the unnatural amino acid of formula (I) or (II) is:

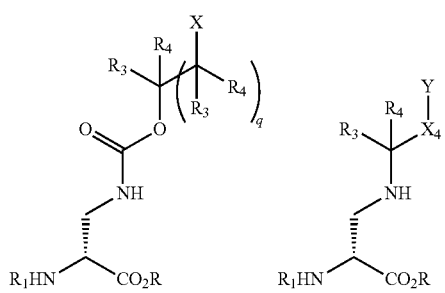

or salts, solvates, tautomers, isomers or mixtures thereof. Hence, in this aspect, the unnatural amino acid of formula (I) or (II) is in the D-form.

More suitably, the unnatural amino acid of formula (I) or (II) is:

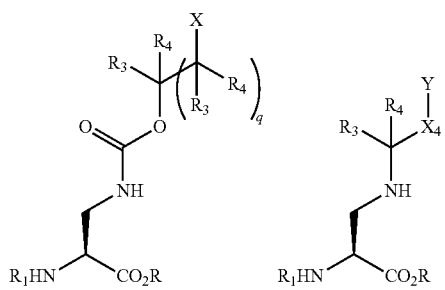

or salts, solvates, tautomers, isomers or mixtures thereof. Hence, in this more suitable aspect, the unnatural amino acid of formula (I) or (II) is in the L-form.

Suitably, the unnatural amino acid of formula (I) or (II) is:

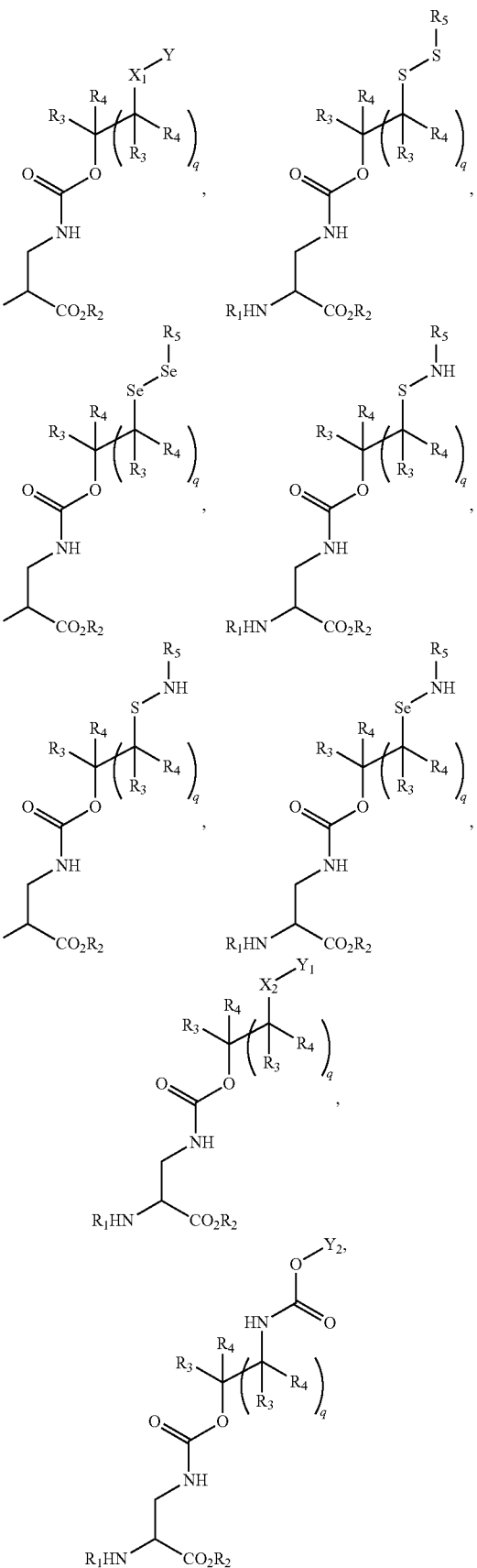

-continued

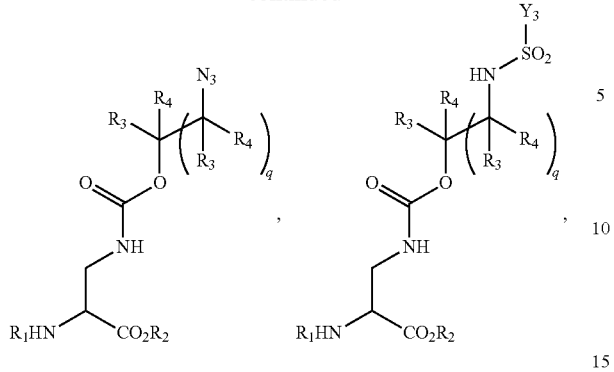

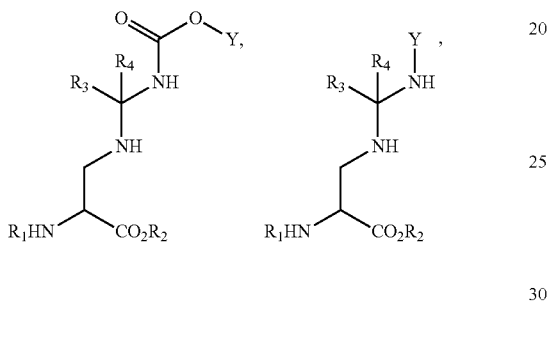

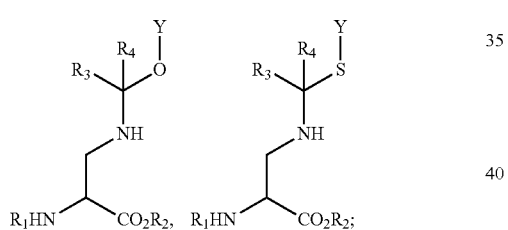

or salts, solvates, tautomers, isomers or mixtures thereof.
Suitably, the above unnatural amino acids formula (I) or (II) are in the D-form. More suitably, the above unnatural amino acids formula (I) or (II) are in the L-form.

More suitably, the unnatural amino acid of formula (I) or (II) is:

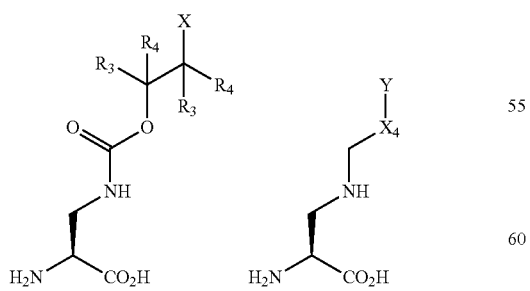

or salts, solvates, tautomers, isomers or mixtures thereof.
Suitably, the unnatural amino acid is an unnatural amino acid of formula (I) or salts, solvates, tautomers, isomers or mixtures thereof.

Suitably, the unnatural amino acid of formula (I) has the following formula:

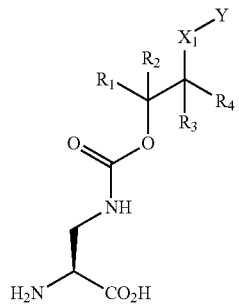

or salts, solvates, tautomers, isomers or mixtures thereof.
Suitably, the unnatural amino acid of formula (I) has the following formula:

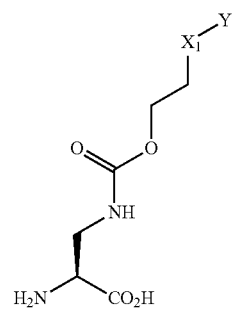

or salts, solvates, tautomers, isomers or mixtures thereof.
Suitably, the unnatural amino acid of formula (I) has the following formula:

or salts, solvates, tautomers, isomers or mixtures thereof.
Suitably, X is $X_1$—Y, S—S—$R_5$, O—NH—$R_5$, S—NH—$R_5$, $X_2$—$Y_1$, $X_3$—$Y_2$, $N_3$ or NH—$S(O)_2$—$Y_3$.
Suitably, X is $X_1$—Y, $X_2$—$Y_1$, $X_3$—$Y_2$, $N_3$ or NH—$S(O)_2$—$Y_3$. More suitably, X is $X_1$—Y.
Suitably, $X_1$ is S, Se, O, NH, $N(CH_3)$ or $N(CH_2CH_3)$. More suitably, $X_1$ is S or O. More suitably, $X_1$ is S.

Suitably, $X_2$ is S or O. Suitably, $X_2$ is S

Suitably, $X_4$ is NH—C(O)—O, O, S or NH. Suitably, $X_4$ is NH—C(O)—O.

Suitably, $X_5$ is S, O, NH, N—C(O)—O—$CH_3$, N—C(O)—O—$CH_2CH_3$, N—C(O)—O-Ph, N—S(O)$_2$$CH_3$, N—S(O)$_2$$CH_2CH_3$, N—$CH_3$, N—$CH_2CH_3$ or N-Ph. More suitably, $X_5$ is S, O, NH or N—$CH_3$.

$R_1$ is H, an amino acid residue or a peptide. Suitably, $R_1$ is H or a proteinogenic amino acid residue. Most suitably, $R_1$ is H.

Suitably, $R_2$ is H, $C_{1-6}$ alkyl, $C_{1-6}$ haloalkyl or phenyl. More suitably, $R_2$ is H, $CH_3$, $CH_2CH_3$, $CF_3$ or phenyl. More suitably, $R_2$ is H.

Suitably, q is 1 or 2. More suitably, q is 1.

Suitably, each $R_3$ and $R_4$ is independently selected from H, F, Cl, Br, $CH_3$, $CH_2CH_3$, $CF_3$, Ph, pyridyl, pyrrolyl, imidazolyl, $OCH_3$, $OCH_2CH_3$, $SCH_3$, $SCH_2CH_3$, NH($CH_3$), NH($CH_2CH_3$), N($CH_3$)$_2$ and N($CH_2CH_3$)$_2$.

Suitably, each $R_3$ is H, $CH_3$, $CH_2CH_3$, $CF_3$, Ph, $OCH_3$ or $OCH_2CH_3$. More suitably, each $R_3$ is H.

Suitably, each $R_4$ is H, $CH_3$, $CH_2CH_3$, $CF_3$, Ph, $OCH_3$ or $OCH_2CH_3$. More suitably, each $R_4$ is H.

Suitably, $R_5$ is selected from H, halo, $C_{1-6}$ alkyl, $C_{1-6}$ haloalkyl, $C_{5-20}$ aryl, $C_{3-20}$ heteroaryl, $OC_{1-6}$ alkyl, NH($C_{1-6}$ alkyl) and N($C_{1-6}$ alkyl)$_2$.

More suitably, $R_5$ is H, F, Cl, Br, $CH_3$, $CH_2CH_3$, $CF_3$, Ph, pyridyl, pyrrolyl, imidazolyl, $OCH_3$, $OCH_2CH_3$, $SCH_3$, $SCH_2CH_3$, NH($CH_3$), NH($CH_2CH_3$), N($CH_3$)$_2$ or N($CH_2CH_3$)$_2$.

When $R_6$ or $R_9$ is a substituent other than H, then protecting group Y comprises a stereocenter at the carbon to which the $R_6$ or $R_9$ is attached. Suitably, Y is a racemic mixture, or has (R)-configuration or (S)-configuration for the stereocenter at the carbon to which $R_6$ or $R_9$ is attached.

In some aspects, more suitably, Y has (R)-configuration for the stereocenter at the carbon to which $R_6$ or $R_9$ is attached.

In some aspects, more suitably, Y has (S)-configuration for the stereocenter at the carbon to which $R_6$ or $R_9$ is attached.

Suitably, the compound of formula (I) or (II) or salts, solvates, tautomers, isomers or mixtures thereof, comprises a group Y.

Suitably, Y is:

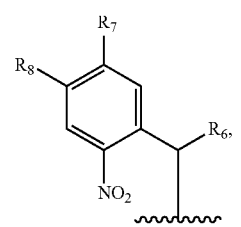
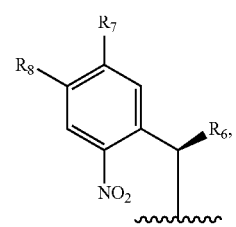
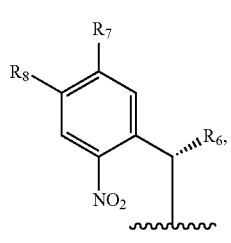
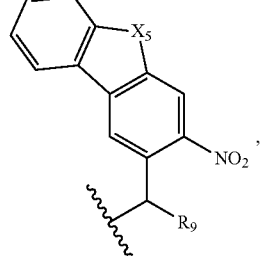
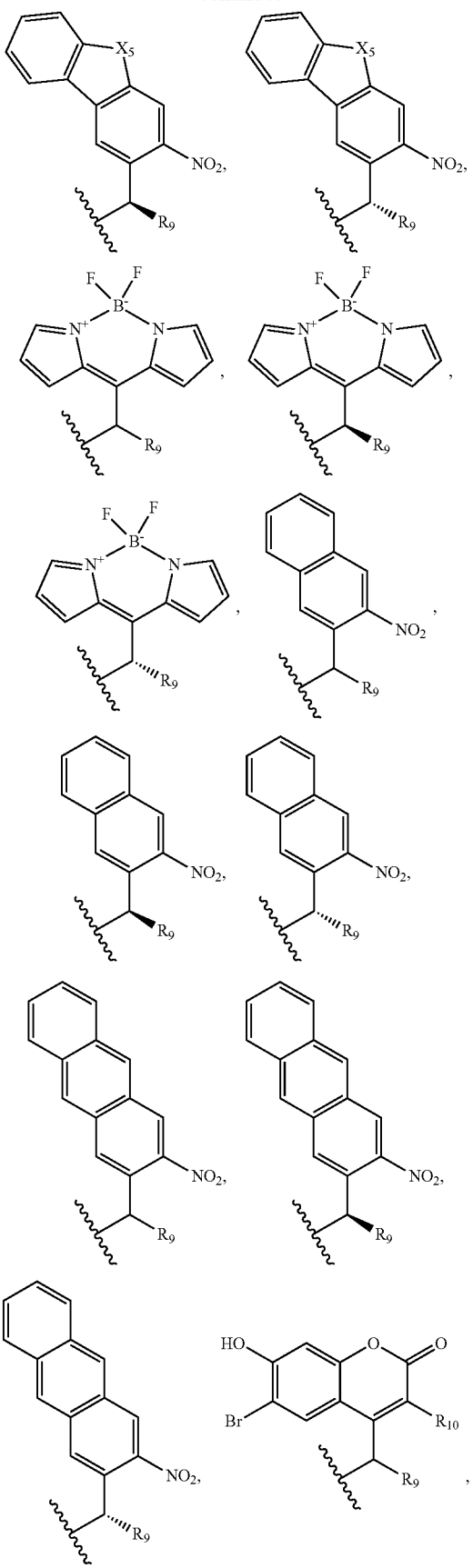

-continued

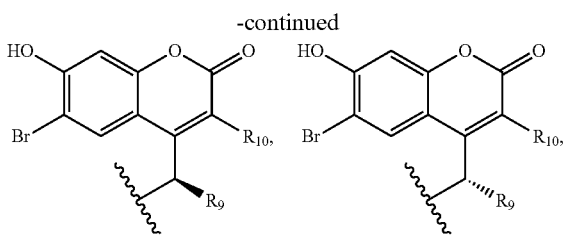

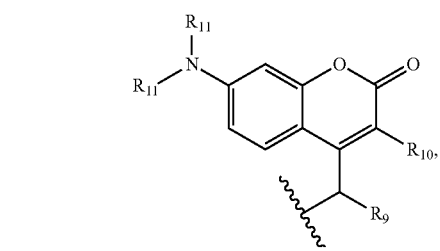

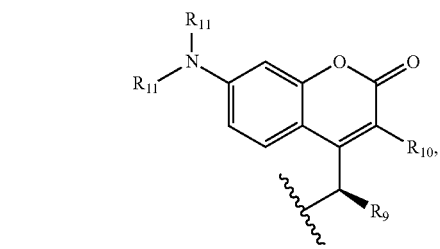

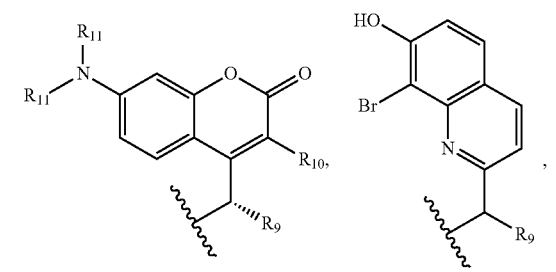

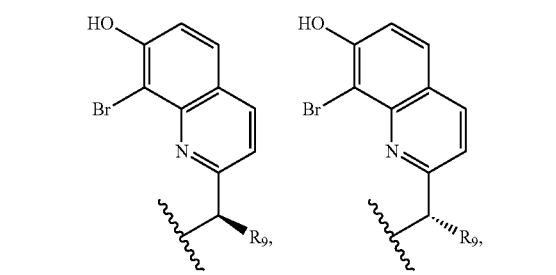

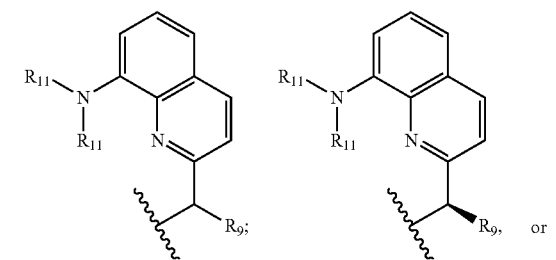

-continued

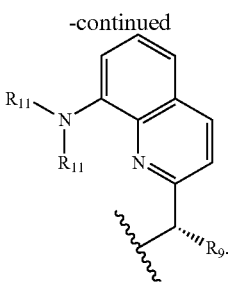

More suitably, the unnatural amino acid comprises a group Y that is:

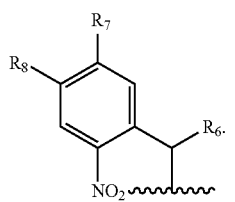

More suitably, the unnatural amino acid comprises a group Y that is:

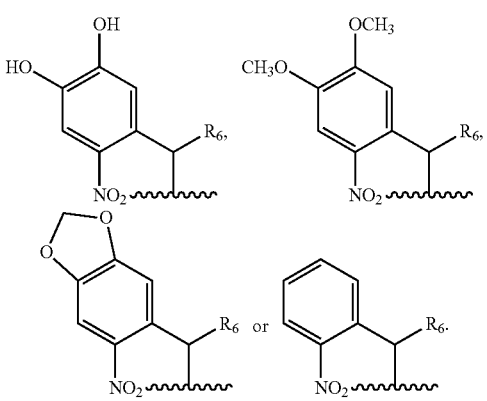

Suitably, $R_6$ is selected from H, $CH_3$, $CH_2CH_3$, $CF_3$, $CO_2H$, $CO_2CH_3$, $CO_2CH_2CH_3$ and Ph.

More suitably, $R_6$ is $CH_3$.

Suitably, $R_7$ and $R_8$ are independently selected from H, OH, $OCH_3$, $OCH_2CH_3$ and O-Ph; or $R_7$ and $R_8$ are linked together to form an O—$CH_2$—O group.

In some aspects, more suitably, $R_7$ and $R_8$ are the same. Suitably, $R_7$ and $R_8$ are H, OH, $OCH_3$ or $OCH_2CH_3$; or $R_7$ and $R_8$ are linked together to form an O—$CH_2$—O group.

More suitably, $R_7$ and $R_8$ are linked together to form an O—$CH_2$—O group.

Suitably, each R' is independently selected from H, $CH_3$, $CH_2CH_3$, $CF_3$ and Ph.

Suitably, $R_9$ is selected from H, $CH_3$, $CH_2CH_3$, $CF_3$, $CO_2H$, $CO_2CH_3$, $CO_2CH_2CH_3$ and Ph.

Suitably, $R_9$ is selected from H, $CH_3$, $CH_2CH_3$ and $CF_3$.
Suitably, $R_{10}$ is selected from H, $CH_3$, $CH_2CH_3$ and $CF_3$.
Suitably, $R_{11}$ is selected from H, $CH_3$, $CH_2CH_3$ and $CF_3$.
Suitably, in one aspect $M^+$ is $Li^+$, $Na^+$ or $K^+$.

In one aspect, $M^+$ is $Li^+$. In an alternative aspect, $M^+$ is $Na^+$. In an alternative aspect, $M^+$ is $N(R_{13})_4^+$. In a more suitable aspect, $M^+$ is $K^+$.

In one aspect, Z is Si.

In an alternative aspect, Z is Ge.

Suitably, $R_{12}$ is $CH_3$, $CH_2CH_3$ or $C(O)$-(Ph).

In one aspect, suitably $R_{13}$ is $C_{1-6}$ alkyl, allyl or $C_{5-20}$ aryl. In an alternative aspect, suitably, $R_{13}$ is H, $CH_3$ or $CH_2CH_3$ or allyl. Suitably, $R_{13}$ is $CH_3$ or $CH_2CH_3$.

More suitably, Y is:

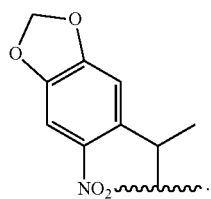 [SMILES: *C(C)c1cc2c(cc1[N+](=O)[O-])OCO2]

In some aspects, Y is:

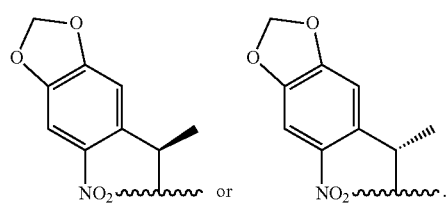 [SMILES: *[C@H](C)c1cc2c(cc1[N+](=O)[O-])OCO2 ; *[C@@H](C)c1cc2c(cc1[N+](=O)[O-])OCO2]

In one embodiment, the compound of formula (I) or (II) is

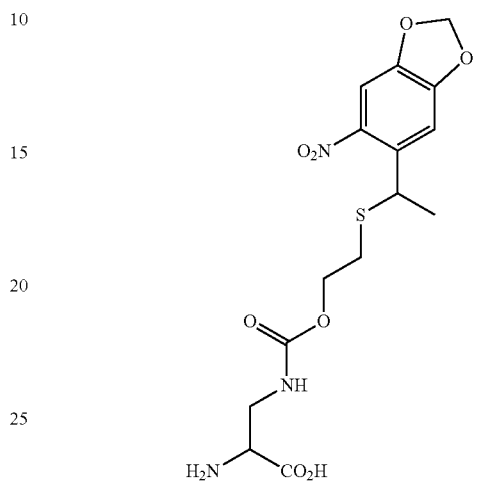

or salts, solvates, tautomers, isomers or mixtures thereof.

A highly suitable embodiment is presented as:

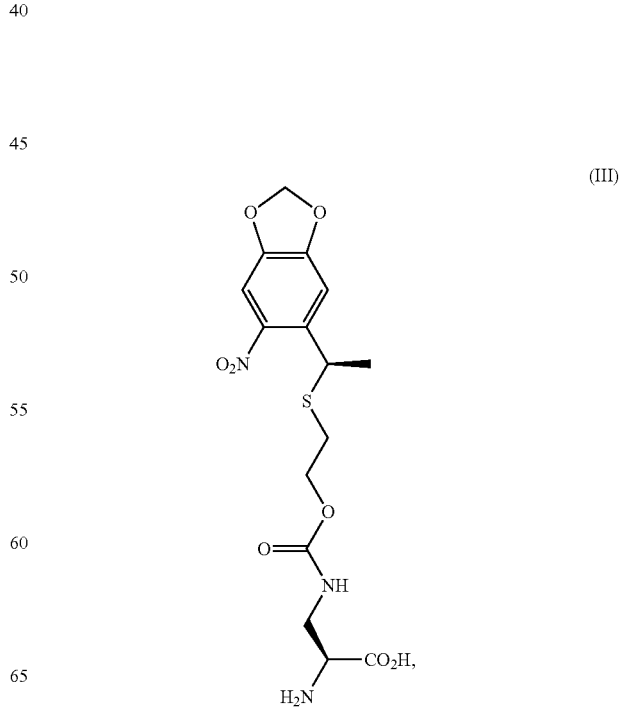

or salts, solvates, tautomers, isomers or mixtures thereof.

This embodiment is sometimes referred to as '6', or as 'Compound 6', or as 'DAP 5' herein; each of these designations refers to the same chemical structure as shown above.

In one aspect, more suitably, the unnatural amino acid is:

(III)

-continued (IV)
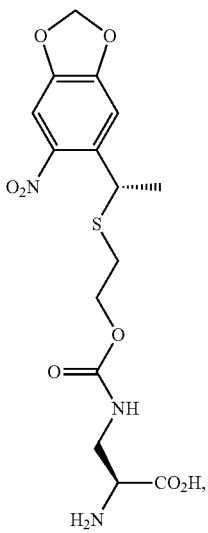

(V)
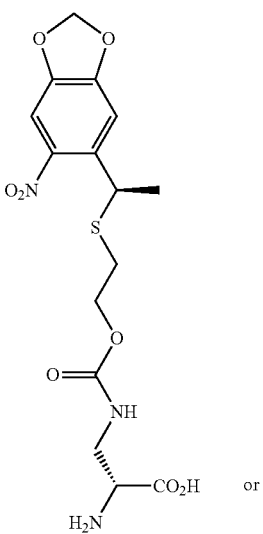
or (VI)
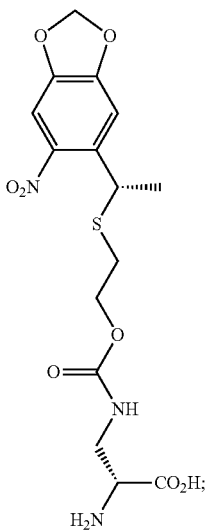

or salts, solvates, tautomers, isomers or mixtures thereof.

More suitably, the unnatural amino acid is a compound of formula (III) or (IV) or salts, solvates, tautomers, isomers or mixtures thereof. In one aspect, the unnatural amino acid is a compound of formula (III) or salts, solvates, tautomers, isomers or mixtures thereof. In another aspect, the unnatural amino acid is a compound of formula (IV) or salts, solvates, tautomers, isomers or mixtures thereof.

In one aspect, one or more of the compounds 2, 3, 4 or 5 of FIG. 3 may be used in an in vitro translation system using, the synthetase as described above, or for example the synthetase described in Nguyen, D. P. et al. (2014) [J. Am. Chem. Soc., 2014, 136 (6), pp 2240-2243] i.e. synthetase "PCC1RS" which is MbPylRS with the mutations N311M, C313Q, V366G, W382N, R85H. This PCC1RS synthetase did incorporate very similar unnatural amino acids (photocaged cysteines) and the inventors assert that it would accept the protected versions of DAP, which only differ from them by 1 atom (or two with the hydrogen atom). Another technique would consist in loading the tRNAs with so-called "flexizymes" that can virtually load any tRNA with any amino acid (e.g. see Morimoto et al., 2011, Acc. Chem Res. 44). They then could be used in an in vitro system. Without wishing to be bound by theory, the inventors believe that analogues compounds 2, 3, 4 or 5 of FIG. 3 do not work in cells because they cannot enter the cells.

Other Forms

Unless otherwise specified, included in the above are the well known ionic, salt or solvate forms of these substituents. For example, a reference to carboxylic acid (—COOH) also includes the anionic (carboxylate) form (—COO—), a salt or solvate thereof.

Similarly, a reference to an amino group includes the protonated form (—N$^+$HR$^1$R$^2$), a salt or solvate of the amino group, for example, a hydrochloride salt. Similarly, a reference to a hydroxyl group also includes the anionic form (—O—), a salt or solvate thereof.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

A reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, amide/imino alcohol —NH—C(=O)—/—N=C(—OH)—; or keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{11}$C, $^{12}$C, $^{13}$C, and $^{14}$C; O may be in any isotopic form, including $^{16}$O and $^{18}$O; and the like. For example, compound 6 may be the $^{13}$C and $^{15}$N isotopically labelled or the $^{18}$O isotopically labelled compound as shown below:

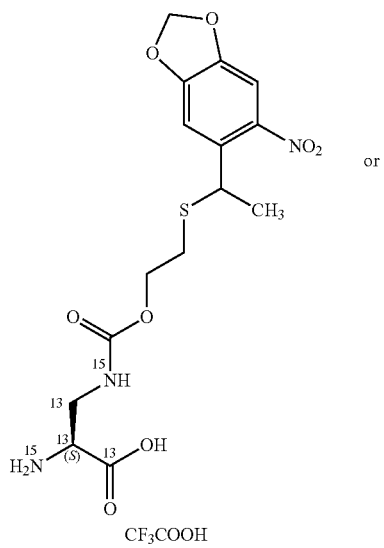

CF$_3$COOH

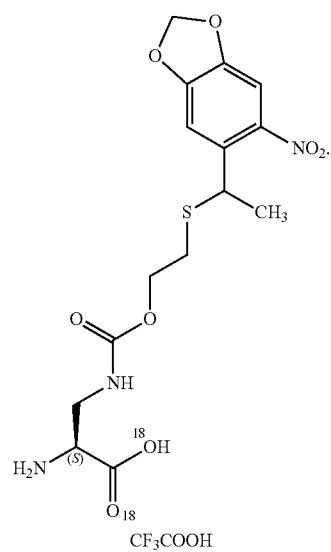

CF$_3$COOH

Unless otherwise specified, a reference to a particular compound includes all such isomeric forms, including (wholly or partially) racemic and other mixtures thereof. An example of otherwise specified bond is the CH group in DAP which is shown below with a specified stereochemistry:

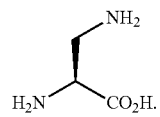

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

In some embodiments, the compound of formula (I) or (II) or salts, solvates, tautomers, isomers or mixtures thereof, comprises pharmaceutically acceptable salts of the compounds of formula (I) or (II).

Compounds of formula (I) or (II), which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —NH$_2$ may be —NH$_3$+), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, sulphurous acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO—), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium (Na$^+$) potassium (K$^+$), magnesium (Mg$^{2+}$), calcium (Ca$^{2+}$), zinc (Zn$^{2+}$), and aluminum (Al$^{3+}$). Examples of suitable organic cations include, but are not limited to, ammonium ion (i.e. $NH_4^+$) and substituted ammonium ions (e.g. $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of formula (I) or (II) with an appropriate acid or base to give the desired salt. One may also react a precursor of the compound of formula (I) or (II) with an acid or base to remove an acid- or base-labile protecting group or to open a lactone or lactam group of the precursor. Additionally, one may convert a salt of the compound of formula (I) or (II) to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Genetic Incorporation

For production of polypeptide according to the invention by genetic incorporation, said genetic incorporation preferably uses an orthogonal or expanded genetic code, in which one or more specific orthogonal codons have been allocated to encode the unnatural amino acid of interest so that it can be genetically incorporated by using an orthogonal tRNA synthetase/tRNA pair. The orthogonal tRNA synthetase/tRNA pair can in principle be any such pair capable of charging the tRNA with the unnatural amino acid of interest and capable of incorporating that unnatural amino acid of interest into the polypeptide chain in response to the orthogonal codon.

The orthogonal codon may be the orthogonal codon amber, ochre, opal or a quadruplet codon. The codon simply has to correspond to the orthogonal tRNA which will be used to carry the unnatural amino acid of interest. Most suitably the orthogonal codon is amber.

It should be noted that many of the specific examples shown herein have used the amber codon and the corresponding tRNA/tRNA synthetase. As noted above, these may be varied. Alternatively, in order to use other codons without going to the trouble of using or selecting alternative tRNA/tRNA synthetase pairs capable of working with the unnatural amino acid of interest, the anticodon region of the tRNA may simply be swapped for the desired anticodon region for the codon of choice. The anticodon region is not involved in the charging or incorporation functions of the tRNA nor recognition by the tRNA synthetase so such swaps are entirely within the ambit of the skilled operator. Thus in some embodiments the anticodon region of the tRNA used in the invention such as $MbtRNA_{CUA}$ or $MmtRNA_{CUA}$ may be exchanged i.e. a chimeric $tRNA_{CUA}$ may be used such that the anticodon region is swapped to recognise an alternate codon so that the unnatural amino acid of interest may be incorporated in response to a different orthogonal codon as discussed herein including ochre, opal or a quadruplet codon, and the nucleic acid encoding the polypeptide into which the unnatural amino acid of interest is to be incorporated is correspondingly mutated to introduce the cognate codon at the point of incorporation of the unnatural amino acid of interest. Most suitably the orthogonal codon is amber.

Thus alternative orthogonal tRNA synthetase/tRNA pairs may be used if desired, provided the desired charging activity is retained.

The *Methanosarcina barkeri* PylT gene encodes the $MbtRNA_{CUA}$ tRNA (i.e. $MbtRNA^{Pyl}_{CUA}$). Suitably the $tRNA_{CUA}$ sequence is as below:

```
tRNAcua
MbPylT (strain MS, from Genbank
accession number AY064401)
                                        (SEQ ID NO: 1)
gggaacctgatcatgtagatcgaatggactctaaat ccgttcagccgggttagattcccgggtttccgcca
```

There are two variants of this tRNA which may be used. One starts with ggg (as above), the other starts with gga (as below):

```
tRNAcua "gga" variant
MbPylT (strain MS, from Genbank
accession number AY064401)
                                        (SEQ ID NO: 2)
ggaaacctgatcatgtagatcgaatggactctaaat ccgttcagccgggttagattcccgggtttccgcca
```

There are no substantial differences between these two variants.

The *Methanosarcina barkeri* PylS gene encodes the MbPylRS tRNA synthetase protein.

tRNA Synthetases

If required, the person skilled in the art may adapt MbPylRS tRNA synthetase protein by mutating it so as to optimise for the particular unnatural amino acid to be used. The need for mutation (if any) depends on the particular unnatural amino acid used. An example where the MbPylRS tRNA synthetase may need to be mutated is when the particular unnatural amino acid used is not processed by the MbPylRS tRNA synthetase protein.

In the present invention the inventors invested significant intellectual effort into the creation of the novel synthetase DAPRS. See example 3 in particular. Suitably the synthetase of the invention comprises C at 271, Q at 311, F at 349 and C at 366 (i.e. Y271C, N311Q, Y349F and V366C with reference to MbPylRS) or the equivalent positions if using a different starting synthetase sequence/backbone synthetase sequence from another species.

Exemplary Sequence of Novel Synthetase DAPRS:
DAPRS (Mutated Residues are Underlined):

```
                                        (SEQ ID NO: 3)
MDKKPLDVLISATGLWMSRTGTLHKIKHHEVSRSK

IYIEMACGDHLVVNNSRSCRTARAFRHHKYRKTCK

RCRVSDEDINNFLTRSTESKNSVKVRVVSAPKVKK

AMPKSVSRAPKPLENSVSAKASTNTSRSVPSPAKS

TPNSSVPASAPAPSLTRSQLDRVEALLSPEDKISL

NMAKPFRELEPELVTRRKNDFQRLYTNDREDYLGK

LERDITKFFVDRGFLEIKSPILIPAEYVERMGINN

DTELSKQIFRVDKNLCLRPMLAPTLCNYLRKLDRI

LPGPIKIFEVGPCYRKESDGKEHLEEFTMVQFCQM

GSGCTRENLEALIKEFLDYLEIDFEIVGDSCMVFG

DTLDIMHGDLELSSACVGPVSLDREWGIDKPWIGA

GFGLERLLKVMHGFKNIKRASRSESYYNGISTNL
```

Preferably the orthogonal synthetase/tRNA pair are *Methanosarcina barkeri* MS pyrrolysine tRNA synthetase (MbPylRS) and its cognate amber suppressor tRNA (MbtRNA$_{CUA}$) (i.e. MbtRNA$^{Pyl}_{CUA}$), wherein said MbPylRS comprises the mutations explained herein which are important to its activity i.e. that the MbPylRS comprises C at 271, Q at 311, F at 349 and C at 366 (i.e. Y271C, N311Q, Y349F and V366C).

The tRNA synthetase of the invention may be varied. Although specific tRNA synthetase sequences may have been used in the examples, the invention is not intended to be confined only to those examples.

In principle any tRNA synthetase which provides the same tRNA charging (aminoacylation) function can be employed in the invention.

For example the tRNA synthetase may be from any suitable species such as from archea, for example from *Methanosarcina barkeri* MS; *Methanosarcina barkeri* str. Fusaro; *Methanosarcina mazei* G01; *Methanosarcina acetivorans* C2A; *Methanosarcina thermophila*; or *Methanococcoides burtonii*. Alternatively the tRNA synthetase may be from bacteria, for example from *Desulfitobacterium hafniense* DCB-2; *Desulfitobacterium hafniense* Y51; *Desulfitobacterium hafniense* PCP1; *Desulfotomaculum acetoxidans* DSM 771.

Exemplary sequences from these organisms are the publically available sequences. The following examples are provided as exemplary sequences for pyrrolysine tRNA synthetases:

```
>M. barkeriMS/1-419/
Methanosarcina barkeri MS
VERSION Q6WRH6.1 GI: 74501411
                                        (SEQ ID NO: 4)
MDKKPLDVLISATGLWMSRTGTLHKIKHHEVSRSK

IYIEMACGDHLVVNNSRSCRTARAFRHHKYRKTCK

RCRVSDEDINNFLTRSTESKNSVKVRVVSAPKVKK

AMPKSVSRAPKPLENSVSAKASTNTSRSVPSPAKS

TPNSSVPASAPAPSLTRSQLDRVEALLSPEDKISL

NMAKPFRELEPELVTRRKNDFQRLYTNDREDYLGK

LERDITKFFVDRGFLEIKSPILIPAEYVERMGINN

DTELSKQIFRVDKNLCLRPMLAPTLYNYLRKLDRI

LPGPIKIFEVGPCYRKESDGKEHLEEFTMVNFCQM

GSGCTRENLEALIKEFLDYLEIDFEIVGDSCMVYG

DTLDIMHGDLELSSAVVGPVSLDREWGIDKPWIGA

GFGLERLLKVMHGFKNIKRASRSESYYNGISTNL

>M. barkeriF/1-419/
Methanosarcina barkeri str. Fusaro
VERSION YP_304395.1 GI: 73668380
                                        (SEQ ID NO: 5)
MDKKPLDVLISATGLWMSRTGTLHKIKHYEVSRSK

IYIEMACGDHLVVNNSRSCRTARAFRHHKYRKTCK

RCRVSDEDINNFLTRSTEGKTSVKVKVVSAPKVKK

AMPKSVSRAPKPLENPVSAKASTDTSRSVPSPAKS

TPNSPVPTSAPAPSLTRSQLDRVEALLSPEDKISL

NIAKPFRELESELVTRRKNDFQRLYTNDREDYLGK

LERDITKFFVDRDFLEIKSPILIPAEYVERMGINN

DTELSKQIFRVDKNLCLRPMLAPTLYNYLRKLDRI

LPDPIKIFEVGPCYRKESDGKEHLEEFTMVNFCQM

GSGCTRENLESLIKEFLDYLEIDFEIVGDSCMVYG

DTLDIMHGDLELSSAVVGPVPLDREWGIDKPWIGA

GFGLERLLKVMHGFKNIKRASRSESYYNGISTNL

>M. mazei/1-454
Methanosarcina mazei Go1
VERSION NP_633469.1 GI: 21227547
                                        (SEQ ID NO: 6)
MDKKPLNTLISATGLWMSRTGTIHKIKHHEVSRSK

IYIEMACGDHLVVNNSRSSRTARALRHHKYRKTCK

RCRVSDEDLNKFLTKANEDQTSVKVKVVSAPTRTK

KAMPKSVARAPKPLENTEAAQAQPSGSKFSPAIPV

STQESVSVPASVSTSISSISTGATASALVKGNTNP

ITSMSAPVQASAPALTKSQTDRLEVLLNPKDEISL

NSGKPFRELESELLSRRKKDLQQIYAEERENYLGK

LEREITRFFVDRGFLEIKSPILIPLEYIERMGIDN
```

-continued

DTELSKQIFRVDKNFCLRPMLAPNLYNYLRKLDRA

LPDPIKIFEIGPCYRKESDGKEHLEEFTMLNFCQM

GSGCTRENLESIITDFLNHLGIDFKIVGDSCMVYG

DTLDVMHGDLELSSAVVGPIPLDREWGIDKPWIGA

GFGLERLLKVKHDFKNIKRAARSESYYNGISTNL

>M. acetivorans/1-443
Methanosarcina acetivorans C2A
VERSION NP_615128.2 GI: 161484944
(SEQ ID NO: 7)
MDKKPLDTLISATGLWMSRTGMIHKIKHHEVSRSK

IYYIEMACGERLVVNNSRSSRTARALRHHKYRKTCR

HCRVSDEDINNFLTKTSEEKTTVKVKVVSAPRVRK

AMPKSVARAPKPLEATAQVPLSGSKPAPATPVSAP

AQAPAPSTGSASATSASAQRMANSAAAPAAPVPTS

APALTKGQLDRLEGLLSPKDEISLDSEKPFRELES

ELLSRRKKDLKRIYAEERENYLGKLEREITKFFVD

RGFLEIKSPILIPAEYVERMGINSDTELSKQVFRI

DKNFCLRPMLAPNLYNYLRKLDRALPDPIKIFEIG

PCYRKESDGKEHLEEFTMLNFCQMGSGCTRENLEA

IITEFLNHLGIDFEIIGDSCMVYGNTLDVMHDDLE

LSSAVVGPVPLDREWGIDKPWIGAGFGLERLLKVM

HGFKNIKRAARSESYYNGISTNL

>M.thermophila/1-478
Methanosarcina thermophila,
VERSION DQ017250.1 GI: 67773308
(SEQ ID NO: 8)
MDKKPLNTLISATGLIVMSRTGKLHKIRHHEVSKR

KIYIEMECGERLVVNNSRSCRAARALRHHKYRKIC

KHCRVSDEDLNKFLTRTNEDKSNAKVTVVSAPKIR

KVMPKSVARTPKPLENTAPVQTLPSESQPAMPISA

STTAPASTSTTAPAPASTTAPAPASTTAPASASTT

ISTSAMPASTSAQGTTKFNYISGGFPRPIPVQASA

PALTKSQIDRLQGLLSPKDEISLDSGTPFRKLESE

LLSRRRKDLKQIYAEEREHYLGKLEREITKFFVDR

GFLEIKSPILIPMEYIERMGIDNDKELSKQIFRVD

NNFCLRPMLAPNLYNYLRKLNRALPDPIKIFEIGP

CYRKESDGKEHLEEFTMLNFCQMGSGCTRENLEAI

IKDFLDYLGIDFEIVGDSCMVYGDTLDVMHGDLEL

SSAVVGPVPMDRDWGINKPWIGAGFGLERLLKVMH

NFKNIKRASRSESYYNGISTNL

>M.burtonii/1-416
Methanococcoides burtonii DSM 6242,
VERSION YP_566710.1 GI: 91774018
(SEQ ID NO: 9)
MEKQLLDVLVELNGVWLSRSGLLHGIRNFEITTKH

IHIETDCGARETVRNSRSSRSARSLRHNKYRKPCK

-continued

RCRPADEQIDRFVKKTFKEKRQTVSVFSSPKKHVP

KKPKVAVIKSFSISTPSPKEASVSNSIPTPSISVV

KDEVKVPEVKYTPSQIERLKTLMSPDDKIPIQDEL

PEFKVLEKELIQRRRDDLKKMYEEDREDRLGKLER

DITEFFVDRGFLEIKSPIMIPFEYIERMGIDKDDH

LNKQIFRVDESMCLRPMLAPCLYNYLRKLDKVLPD

PIRIFEIGPCYRKESDGSSHLEEFTMVNFCQMGSG

CTRENMEALIDEFLEHLGIEYEIEADNCMVYGDTI

DIMHGDLELSSAVVGPIPLDREWGVNKPWMGAGFG

LERLLKVRHNYTNIRRASRSELYYNGINTNL

>D. hafniense_DCB-2/1-279
Desulfitobacterium hafniense DCB-2
VERSION YP_002461289.1 GI: 219670854
(SEQ ID NO: 10)
MSSFWTKVQYQRLKELNASGEQLEMGFSDALSRDR

AFQGIEHQLMSQGKRHLEQLRTVKHRPALLELEEG

LAKALHQQGFVQVVTPTIITKSALAKMTIGEDHPL

FSQVFWLDGKKCLRPMLAPNLYTLWRELERLWDKP

IRIFEIGTCYRKESQGAQHLNEFTMLNLTELGTPL

EERHQRLEDMARWVLEAAGIREFELVTESSVVYGD

TVDVMKGDLELASGAMGPHFLDEKWEIVDPWVGLG

FGLERLLMIREGTQHVQSMARSLSYLDGVRLNIN

>D. hafniense_Y51/1-312
Desulfitobacterium hafniense Y51
VERSION YP_521192.1 GI: 89897705
(SEQ ID NO: 11)
MDRIDHTDSKFVQAGETPVLPATFMFLTRRDPPLS

SFWTKVQYQRLKELNASGEQLEMGFSDALSRDRAF

QGIEHQLMSQGKRHLEQLRTVKHRPALLELEEGLA

KALHQQGFVQVVTPTIITKSALAKMTIGEDHPLFS

QVFWLDGKKCLRPMLAPNLYTLWRELERLWDKPIR

IFEIGTCYRKESQGAQHLNEFTMLNLTELGTPLEE

RHQRLEDMARWVLEAAGIREFELVTESSVVYGDTV

DVMKGDLELASGAMGPHFLDEKWEIVDPWVGLGFG

LERLLMIREGTQHVQSMARSLSYLDGVRLNIN

>D. hafniensePCP1/1-288
Desulfitobacterium hafniense
VERSION AY692340.1 GI: 53771772
(SEQ ID NO: 12)
MFLTRRDPPLSSFWTKVQYQRLKELNASGEQLEMG

FSDALSRDRAFQGIEHQLMSQGKRHLEQLRTVKHR

PALLELEEKLAKALHQQGFVQVVTPTIITKSALAK

MTIGEDHPLFSQVFWLDGKKCLRPMLAPNLYTLWR

ELERLWDKPIRIFEIGTCYRKESQGAQHLNEFTML

NLTELGTPLEERHQRLEDMARWVLEAAGIREFELV

-continued

TESSVVYGDTVDVMKGDLELASGAMGPHFLDEKWE

IFDPWVGLGFGLERLLMIREGTQHVQSMARSLSYL

DGVRLNIN

>D. acetoxidans/1-277
Desulfotomaculum acetoxidans DSM 771
VERSION YP 003189614.i GI: 258513392
(SEQ ID NO: 13)
MSFLWTVSQQKRLSELNASEEEKNMSFSSTSDREA

AYKRVEMRLINESKQRLNKLRHETRPAICALENRL

AAALRGAGFVQVATPVILSKKLLGKMTITDEHALF

SQVFWIEENKCLRPMLAPNLYYILKDLLRLWEKPV

RIFEIGSCFRKESQGSNHLNEFTMLNLVEWGLPEE

QRQKRISELAKLVMDETGIDEYHLEHAESVVYGET

VDVMHRDIELGSGALGPHFLDGRWGVVGPWVGIGF

GLERLLMVEQGGQNVRSMGKSLTYLDGVRLNI

When the particular tRNA charging (aminoacylation) function has been provided by mutating the tRNA synthetase, then it may not be appropriate to simply use another wild-type tRNA synthetase sequence, for example one selected from the above. In this scenario, it will be important to preserve the same tRNA charging (aminoacylation) function. This is accomplished by transferring the mutation(s) in the exemplary tRNA synthetase into an alternate tRNA synthetase backbone, such as one selected from the above.

In this way it should be possible to transfer selected mutations to corresponding tRNA synthetase sequences such as corresponding pylS sequences from other organisms beyond exemplary *M. barkeri* and/or *M. mazei* sequences.

Target tRNA synthetase proteins/backbones, may be selected by alignment to known tRNA synthetases such as exemplary *M. barkeri* and/or *M. mazei* sequences.

This subject is now illustrated by reference to the pylS (pyrrolysine tRNA synthetase) sequences but the principles apply equally to the particular tRNA synthetase of interest.

For example, an alignment of all PylS sequences may be prepared. These can have a low overall % sequence identity. Thus it is important to study the sequence such as by aligning the sequence to known tRNA synthetases (rather than simply to use a low sequence identity score) to ensure that the sequence being used is indeed a tRNA synthetase.

Thus suitably when sequence identity is being considered, suitably it is considered across the sequences of the examples of tRNA synthetases as above. Suitably the % identity may be as defined from an alignment of the above sequences.

It may be useful to focus on the catalytic region. The aim of this is to provide a tRNA catalytic region from which a high % identity can be defined to capture/identify backbone scaffolds suitable for accepting mutations transplanted in order to produce the same tRNA charging (aminoacylation) function, for example new or unnatural amino acid recognition.

Thus suitably when sequence identity is being considered, suitably it is considered across the catalytic region. Suitably the % identity may be as defined from the catalytic region.

'Transferring' or 'transplanting' mutations onto an alternate tRNA synthetase backbone can be accomplished by site directed mutagenesis of a nucleotide sequence encoding the tRNA synthetase backbone. This technique is well known in the art. Essentially the backbone pylS sequence is selected (for example using the active site alignment discussed above) and the selected mutations are transferred to (i.e. made in) the corresponding/homologous positions.

When particular amino acid residues are referred to using numeric addresses, unless otherwise apparent, the numbering is taken using MbPylRS (*Methanosarcina barkeri* pyrrolysyl-tRNA synthetase) amino acid sequence as the reference sequence (i.e. as encoded by the publicly available wild type *Methanosarcina barkeri* PylS gene Accession number Q46E77):

(SEQ ID NO: 14)
MDKKPLDVLI SATGLWMSRT GTLHKIKHYE VSRSKIYIEM

ACGDHLVVNN SRSCRTARAF RHHKYRKTCK RCRVSDEDIN

NFLTRSTEGK TSVKVKVVSA PKVKKAMPKS VSRAPKPLEN

PVSAKASTDT SRSVPSPAKS TPNSPVPTSA PAPSLTRSQL

DRVEALLSPE DKISLNIAKP FRELESELVT RRKNDFQRLY

TNDREDYLGK LERDITKFFV DRDFLEIKSP ILIPAEYVER

MGINNDTELS KQIFRVDKNL CLRPMLAPTL YNYLRKLDRI

LPDPIKIFEV GPCYRKESDG KEHLEEFTMV NFCQMGSGCT

RENLESLIKE FLDYLEIDFE IVGDSCMVYG DTLDIMHGDL

ELSSAVVGPV PLDREWGIDK PWIGAGFGLE RLLKVMHGFK

NIKRASRSES YYNGISTNL

This is to be used as is well understood in the art to locate the residue of interest. This is not always a strict counting exercise—attention must be paid to the context or alignment. For example, if the protein of interest is of a slightly different length, then location of the correct residue in that sequence corresponding to (for example) L266 may require the sequences to be aligned and the equivalent or corresponding residue picked, rather than simply taking the 266th residue of the sequence of interest. This is well within the ambit of the skilled reader.

Notation for mutations used herein is the standard in the art. For example L266M means that the amino acid corresponding to L at position 266 of the wild type sequence is replaced with M.

The amino acid which is introduced is the most important information in this notation.

For example if the 'L266M' mutation is transplanted onto another synthetase starting sequence (backbone sequence), it is possible that this alternate starting sequence may not have 'L' at position 266 (or at the position corresponding to L266 of the reference sequence as explained above). However, in this case it is important that the correct amino acid corresponding to L266 of the reference sequence is identified in the synthetase starting sequence (backbone sequence) of interest, and that this residue (whatever it may be) is changed to M. Thus 'L266M' may be understood as 'X266M' when transplanting onto alternate backbone/starting sequences.

With reference to the exemplary DAPRS synthetase described herein, the mutations would be noted as Y271C, N311Q, Y349F and V366C compared to the M.b. reference sequence (see above), or could be understood as X271C, X311Q, X349F and X366C if transplanting onto a backbone having different amino acid(s) at those positions in the starting sequence.

The transplantation of mutations between alternate tRNA backbones is now illustrated with reference to exemplary *M. barkeri* and *M. mazei* sequences, but the same principles apply equally to transplantation onto or from other backbones.

For example Mb AcKRS is an engineered synthetase for the incorporation of AcK

Parental protein/backbone: *M. barkeri* PylS

Mutations: L266V, L270I, Y271F, L274A, C317F

Mb PCKRS: engineered synthetase for the incorporation of PCK

Parental protein/backbone: *M. barkeri* PylS

Mutations: M241F, A267S, Y271C, L274M

Synthetases with the same substrate specificities can be obtained by transplanting these mutations into *M. mazei* PylS. Thus the following synthetases may be generated by transplantation of the mutations from the Mb backbone onto the Mm tRNA backbone: Mm AcKRS introducing mutations L301V, L305I, Y306F, L309A, C348F into *M. mazei* PylS, and Mm PCKRS introducing mutations M276F, A302S, Y306C, L309M into *M. mazei* PylS.

Full length sequences of these exemplary transplanted mutation synthetases are given below.

```
>Mb_PylS/1-419
                                    (SEQ ID NO: 15)
MDKKPLDVLISATGLWMSRTGTLHKIKHHEVSRSK

IYIEMACGDHLVVNNSRSCRTARAFRHHKYRKTCK

RCRVSDEDINNFLTRSTESKNSVKVRVVSAPKVKK

AMPKSVSRAPKPLENSVSAKASTNTSRSVPSPAKS

TPNSSVPASAPAPSLTRSQLDRVEALLSPEDKISL

NMAKPFRELEPELVTRRKNDFQRLYTNDREDYLGK

LERDITKFFVDRGFLEIKSPILIPAEYVERMGINN

DTELSKQIFRVDKNLCLRPMLAPTLYNYLRKLDRI

LPGPIKIFEVGPCYRKESDGKEHLEEFTMVNFCQM

GSGCTRENLEALIKEFLDYLEIDFEIVGDSCMVYG

DTLDIMHGDLELSSAVVGPVSLDREWGIDKPWIGA

GFGLERLLKVMHGFKNIKRASRSESYYNGISTNL

>Mb_AcKRS/1-419
                                    (SEQ ID NO: 16)
MDKKPLDVLISATGLWMSRTGTLHKIKHHEVSRSK

IYIEMACGDHLVVNNSRSCRTARAFRHHKYRKTCK

RCRVSGEDINNFLTRSTESKNSVKVRVVSAPKVKK

AMPKSVSRAPKPLENSVSAKASTNTSRSVPSPAKS

TPNSSVPASAPAPSLTRSQLDRVEALLSPEDKISL

NMAKPFRELEPELVTRRKNDFQRLYTNDREDYLGK

LERDITKFFVDRGFLEIKSPILIPAEYVERMGINN

DTELSKQIFRVDKNLCLRPMVAPTIFNYARKLDRI

LPGPIKIFEVGPCYRKESDGKEHLEEFTMVNFFQM

GSGCTRENLEALIKEFLDYLEIDFEIVGDSCMVYG

DTLDIMHGDLELSSAVVGPVSLDREWGIDKPWIGA

GFGLERLLKVMHGFKNIKRASRSESYYNGISTNL

>Mb_PCKRS/1-419
                                    (SEQ ID NO: 17)
MDKKPLDVLISATGLWMSRTGTLHKIKHHEVSRSK

IYIEMACGDHLVVNNSRSCRTARAFRHHKYRKTCK

RCRVSDEDINNFLTRSTESKNSVKVRVVSAPKVKK

AMPKSVSRAPKPLENSVSAKASTNTSRSVPSPAKS

TPNSSVPASAPAPSLTRSQLDRVEALLSPEDKISL

NMAKPFRELEPELVTRRKNDFQRLYTNDREDYLGK

LERDITKFFVDRGFLEIKSPILIPAEYVERFGINN

DTELSKQIFRVDKNLCLRPMLSPTLCNYMRKLDRI

LPGPIKIFEVGPCYRKESDGKEHLEEFTMVNFCQM

GSGCTRENLEALIKEFLDYLEIDFEIVGDSCMVYG

DTLDIMHGDLELSSAVVGPVSLDREWGIDKPWIGA

GFGLERLLKVMHGFKNIKRASRSESYYNGISTNL

>Mm_PylS/1-454
                                    (SEQ ID NO: 18)
MDKKPLNTLISATGLWMSRTGTIHKIKHHEVSRSK

IYIEMACGDHLVVNNSRSSRTARALRHHKYRKTCK

RCRVSDEDLNKFLTKANEDQTSVKVKVVSAPTRTK

KAMPKSVARAPKPLENTEAAQAQPSGSKFSPAIPV

STQESVSVPASVSTSISSISTGATASALVKGNTNP

ITSMSAPVQASAPALTKSQTDRLEVLLNPKDEISL

NSGKPFRELESELLSRRKKDLQQIYAEERENYLGK

LEREITRFFVDRGFLEIKSPILIPLEYIERMGIDN

DTELSKQIFRVDKNFCLRPMLAPNLYNYLRKLDRA

LPDPIKIFEIGPCYRKESDGKEHLEEFTMLNFCQM

GSGCTRENLESIITDFLNHLGIDFKIVGDSCMVYG

DTLDVMHGDLELSSAVVGPIPLDREWGIDKPWIGA

GFGLERLLKVKHDFKNIKRAARSESYYNGISTNL

>Mm_AcKRS/1-454
                                    (SEQ ID NO: 19)
MDKKPLNTLISATGLWMSRTGTIHKIKHHEVSRSK

IYIEMACGDHLVVNNSRSSRTARALRHHKYRKTCK

RCRVSDEDLNKFLTKANEDQTSVKVKVVSAPTRTK

KAMPKSVARAPKPLENTEAAQAQPSGSKFSPAIPV

STQESVSVPASVSTSISSISTGATASALVKGNTNP

ITSMSAPVQASAPALTKSQTDRLEVLLNPKDEISL

NSGKPFRELESELLSRRKKDLQQIYAEERENYLGK

LEREITRFFVDRGFLEIKSPILIPLEYIERMGIDN

DTELSKQIFRVDKNFCLRPMVAPNIFNYARKLDRA

LPDPIKIFEIGPCYRKESDGKEHLEEFTMLNFFQM

GSGCTRENLESIITDFLNHLGIDFKIVGDSCMVYG
```

```
DTLDVMHGDLELSSAVVGPIPLDREWGIDKPWIGA

GFGLERLLKVKHDFKNIKRAARSESYYNGISTNL

>Mm_PCKRS/1-454
                                    (SEQ ID NO: 20)
MDKKPLNTLISATGLWMSRTGTIHKIKHHEVSRSK

IYIEMACGDHLVVNNSRSSRTARALRHHKYRKTCK

RCRVSDEDLNKFLTKANEDQTSVKVKVVSAPTRTK

KAMPKSVARAPKPLENTEAAQAQPSGSKFSPAIPV

STQESVSVPASVSTSISSISTGATASALVKGNTNP

ITSMSAPVQASAPALTKSQTDRLEVLLNPKDEISL

NSGKPFRELESELLSRRKKDLQQIYAEERENYLGK

LEREITRFFVDRGFLEIKSPILIPLEYIERFGIDN

DTELSKQIFRVDKNFCLRPMLSPNLCNYMRKLDRA

LPDPIKIFEIGPCYRKESDGKEHLEEFTMLNFCQM

GSGCTRENLESIITDFLNHLGIDFKIVGDSCMVYG

DTLDVMHGDLELSSAVVGPIPLDREWGIDKPWIGA

GFGLERLLKVKHDFKNIKRAARSESYYNGISTNL
```

The same principle applies equally to other mutations and/or to other backbones.

Transplanted polypeptides produced in this manner should advantageously be tested to ensure that the desired function/substrate specificities have been preserved.

In one embodiment, the tRNA may be from one species such as *Methanosarcina barkeri*, and the tRNA synthetase may be from another species such as *Methanosarcina mazei*. In another embodiment, tRNA may be from a first species such as *Methanosarcina mazei* and the tRNA synthetase may from a second species such as *Methanosarcina barkeri*. When an orthogonal pair comprises tRNA and tRNA synthetase from different species, it is always with the proviso that the orthogonal pair work effectively together i.e. that the tRNA synthetase will effectively amino acylate the tRNA of the amino acid of interest.

Most suitably, orthogonal pairs comprise the tRNA and a tRNA synthetase from the same species.

The properties of the tRNA synthetase and particular mutations helpful for its activity are discussed separately below.

Chimeric tRNA synthetases may be produced provided that the charging/acylation part of the tRNA synthetase molecule is based on or derived from Pyl tRNA synthetase. In other words, the anti-codon part of the tRNA molecule may be varied according to operator choice, for example to direct tRNA in recognising an alternate codon such as a sense codon, a quadruplet codon, an amber codon or another "stop" codon. However, the functional acylation/charging part of the tRNA molecule should be conserved in order to preserve the charging activity useful with the unnatural amino acids as described above.

Either of the *Methanosarcina barkeri* and *Methanosarcina mazei* tRNAs are suitable. In any case these tRNAs differ by only one nucleotide. This one nucleotide difference has no impact on their activity. Therefore, either tRNA is equally applicable in the present invention.

The tRNA used may be varied such as mutated. In all cases, any such variants or mutants of the Pyl tRNA should always retain the capacity to interact productively with the tRNA synthetase used to charge the tRNA with the unnatural amino acid(s) as described above.

tRNA Synthetase

*Methanosarcina barkeri* and *Methanosarcina mazei* species pyrrolysine tRNA synthetases are suitable, provided they comprise mutations as described herein helpful for charging tRNA with the unnatural amino acid(s) as described above.

Incorporation of Unnatural Amino Acids by Peptide Bond

It will be apparent that the direct product of incorporating an unnatural amino acid as described herein into a polypeptide will be a polypeptide comprising a residue of said unnatural amino acid joined into the polypeptide backbone by a peptide bond. This means that in a strict sense the polypeptide will not comprise exactly the unnatural amino acid referred to, but will rather comprise a residue of it having undergone a condensation reaction as the amino acid group of the unnatural amino acid referred to reacts with its adjacent amino acid residue in the polypeptide chain, resulting in peptide bond based incorporation of a residue of the unnatural amino acid referred to plus one molecule of $H_2O$ which is liberated. References to "incorporation of unnatural amino acid X into the polypeptide chain" or "polypeptide comprising unnatural amino acid X" should be interpreted accordingly. This is entirely conventional nomenclature in the art, for example when an amino acid such as valine is incorporated into a polypeptide chain, the polypeptide chain is described as comprising valine whereas in fact it comprises an amino acid residue of valine which has been joined into the polypeptide chain by reaction its amino acid group and formation of a peptide bond and liberation of one $H_2O$ molecule as noted above.

In one aspect the invention relates to a polypeptide comprising an unnatural amino acid as described above.

In one aspect the invention relates to a polypeptide comprising an unnatural amino acid as described above wherein said unnatural amino acid is attached to said polypeptide via a peptide bond.

In one aspect the invention relates to a polypeptide comprising an unnatural amino acid as described above wherein said unnatural amino acid is joined to said polypeptide via a peptide bond.

In one aspect the invention relates to a polypeptide comprising an unnatural amino acid as described above incorporated by or via a peptide bond.

In one aspect the invention relates to a polypeptide comprising a residue of an unnatural amino acid as described above incorporated by or via a peptide bond.

In this specification, "unnatural amino acids' refers to amino acids that are not naturally encoded or found in the genetic code of any organism. Thus, unnatural amino acids are compounds containing amine and carboxylic acid functional groups and a side chain but which are not any of the proteinogenic amino acids used by translational machinery to assemble proteins.

Similarly, exemplary unnatural amino acids disclosed herein may be referred to as 'unnatural amino acids comprising DAP' or 'amino acids comprising DAP' or similar.

Clearly in the strictest sense of IUPAC nomenclature conventions, DAP has two NH2 groups whereas the unnatural amino acids discussed have a single NH2 group, the other NH2 group having lost a H atom and being instead bonded via the corresponding N atom to the rest of the amino acid side chain. Notwithstanding this, references to 'unnatural amino acid comprising DAP' or 'amino acid comprising DAP' are used herein as is common in the art and may refer to one or any of compounds 2, 3, 4, 5 and 6, each of which has the H2N—C—(COOH)—C—N(H)—R moiety (i.e. 'comprising DAP').

Host Cells, Vectors, Protein Production

Polynucleotides encoding the polypeptide of interest for the method described above can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*.

Preferably, a polynucleotide of the invention in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

Vectors of the invention may be transformed or transfected into a suitable host cell as described to provide for expression of a protein of the invention. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid. Vectors may be used, for example, to transfect or transform a host cell. Control sequences operably linked to sequences encoding the protein of the invention include promoters/enhancers and other expression regulation signals. These control sequences may be selected to be compatible with the host cell for which the expression vector is designed to be used in. The term promoter is well-known in the art and encompasses nucleic acid regions ranging in size and complexity from minimal promoters to promoters including upstream elements and enhancers.

Another aspect of the invention is a method, such as an in vitro method, of incorporating the unnatural amino acid(s) comprising DAP genetically and site-specifically into the protein of choice, suitably in a host cell. One advantage of incorporating genetically by said method is that it obviates the need to deliver the proteins comprising DAP into a cell once formed, since in this embodiment they may be synthesised directly in the target cell. The method comprises the following steps:
 (i) introducing, or replacing a specific codon with, an orthogonal codon such as an amber codon at the desired site in the nucleotide sequence encoding the protein,
 (ii) introducing an expression system of orthogonal tRNA synthetase/tRNA pair in the cell, such as a DAPRS tRNA synthetase/tRNA pair,
 growing the cells in a medium with the unnatural amino acid(s) comprising DAP according to the invention.

Step (i) entails or replacing a specific codon with an orthogonal codon such as an amber codon at the desired site in the genetic sequence of the protein. This can be achieved by simply introducing a construct, such as a plasmid, with the nucleotide sequence encoding the protein, wherein the site where the unnatural amino acid(s) comprising DAP is desired to be introduced/replaced is altered to comprise an orthogonal codon such as an amber codon. This is well within the person skilled in the art's ability and examples of such are given herein.

Step (ii) requires an orthogonal expression system to specifically incorporate the unnatural amino acid(s) comprising DAP at the desired location (e.g. the amber codon). Thus a specific orthogonal tRNA synthetase such as an orthogonal DAPRS-tRNA synthetase and a specific corresponding orthogonal tRNA pair which are together capable of charging said tRNA with the unnatural amino acid(s) comprising DAP are required. Examples of these are provided herein.

Protein Expression and Purification

Host cells comprising polynucleotides of the invention may be used to express proteins of the invention.

Suitable host cells include bacteria such as *E. coli*, or certain eukaryotic cells.

For eukaryotic cells, many UAAs using the PylS/PylT system have been shown to work in eukaryotic cells (the closest example is Nguyen, D. P. et al. (2014) [J. Am. Chem. Soc., 2014, 136 (6), pp 2240-2243] for the photocaged cysteines; this document is incorporated herein by reference for the teachings of operation in eukaryotic cells.

The eukaryotic cell may be any suitable eukaryotic cell such as an insect cell (e.g. Sf9 insect cells), a mammalian cell such as a mouse cell or a human cell.

Suitably the eukaryotic cell is a mammalian cell. Suitably the mammalian cell is a HEK293 cell such as a HEK293T cell.

In one embodiment suitably the eukaryotic cell, mammalian cell, HEK293 cell or HEK293T cell is in vitro. In this embodiment suitably the cell is not an in vivo cell.

Suitably the host cell is a bacterial cell. Suitably the host cell is *E. coli*. Suitably the host cell is an *E. coli* cell. Suitably the *E. coli* cell is a BL21 DE3 *E. coli* cell.

In one aspect, the invention relates to a method of producing a polypeptide comprising 2,3-diamino propionic acid (DAP) as described above, wherein said method is carried out inside a live cell.

Suitably said method comprises genetically incorporating an unnatural amino acid as described above into a polypeptide, and optionally deprotecting said unnatural amino acid to 2,3-diamino propionic acid (DAP).

Suitably said live cell comprises an *E. coli* cell such as a BL21 DE3 *E. coli* cell.

Suitably said live cell comprises a mammalian cell such as a HEK293T cell.

Host cells may be cultured under suitable conditions which allow expression of the proteins of the invention. Expression of the proteins of the invention may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

HEK293T (Human Embryonic Kidney with large T antigen) cells are widely available such as ATCC® CRL-3216 from LGC Standards, Queens Road, Teddington, Middlesex, TW11 oLY, UK. HEK293T cells may be cultured as is known in the art, for example in Dulbecco's modified eagle medium (DMEM) with appropriate supplementation as required.

BL21 DE3 *E. coli* cells are widely available such as C2527I or C2527H from New England Biolabs New England Biolabs, 240 County Road, Ipswich, MA 01938-2732, USA. These can be cultured according to the supplier's instructions, as is well known in the art.

Proteins of the invention can be extracted from host cells by a variety of techniques known in the art, including enzymatic, chemical and/or osmotic lysis and physical disruption.

Proteins of the invention can be purified by standard techniques known in the art such as preparative chromatography, affinity purification or any other suitable technique.

Target Site for Incorporation

Suitably the DAP and/or unnatural amino acid as described above is incorporated at a position corresponding to a cysteine, serine or threonine residue in the wild type polypeptide, optionally at a position corresponding to a cysteine or serine residue in the wild type polypeptide, most suitably at a position corresponding to a cysteine residue in the wild type polypeptide.

More suitably the DAP and/or unnatural amino acid as described above is incorporated at a position corresponding to a catalytic cysteine, catalytic serine or catalytic threonine residue in the wild type polypeptide, optionally at a position corresponding to a catalytic cysteine or catalytic serine residue in the wild type polypeptide, most suitably at a position corresponding to a catalytic cysteine residue in the wild type polypeptide.

Enzymes

The invention finds particular application in modification of active site(s) of enzymes by incorporation of DAP. Suitably the DAP or unnatural amino acid described herein is incorporated at a position corresponding to an amino acid within the active site of the wild-type enzyme. Suitably the DAP or unnatural amino acid described herein is incorporated at a position corresponding to a catalytic amino acid within the active site of the wild-type enzyme.

Suitably the polypeptide is an enzyme. Suitably the enzyme which generates ester or thioester intermediate(s). Suitably the polypeptide of the invention is an enzyme which follows this general mechanism; more suitably the polypeptide may be a serine hydrolase (which are coded for by 1% of the genes in the human genome); suitably the enzyme may be a protease, peptidase, amidase, deubiquitinase, lipase, cholinesterase, thioesterase, phospholipase, glycan hydrolase[2-4], cysteine protease (such as a caspase), or an enzyme involved in ubiquitination and/or SUMOylation (such as E1's, E2's or certain families of E3's)[5-7].

More suitably the DAP or unnatural amino acid described herein is incorporated into an enzyme such as a protease.

With reference to the International Nomenclature and Classification of Enzymes system (as prepared and updated by the Nomenclature Committee of the International Union of Biochemistry and Molecular Biology (NC-IUBMB) in consultation with the IUPAC-IUBMB Joint Commission on Biochemical Nomenclature (JCBN)), suitably the DAP or unnatural amino acid described herein is incorporated into an enzyme from one or more enzymes from the classification groups:

| Enzyme Subclass | Name | Especially suitable Sub-Subclass(es) | Name(s) | Comments/ Preferred species or source |
|---|---|---|---|---|
| EC 3.4 | Peptidases (Acting on peptide bonds) | EC 3.4.22.44 | Nuclear-inclusion-a endopeptidase; Potyvirus NIa protease | Tobacco Etch Virus (TEV) Active site includes Cys-151 |
| EC 2.3.2 | Aminoacyl-transferases (e.g. ubiquitin-conjugating enzymes) | EC 2.3.2.23 | E2 ubiquitin-conjugating enzyme | Catalytic center is located at Cys-87. UBE2L3. Uniprot P68036 |
| EC 3 (except 3.8 [acting on halide bonds] and 3.9 [acting on phosphorus-nitrogen bonds] where DAP use is less of advantage) | hydrolases | EC 3.4.21.- | Serine protease SplD | SplD active site includes Ser-156 |
| EC 6.2 | Forming Carbon-Sulphur Bonds | EC 6.2.1.45 | Ubiquitin-like modifier-activating enzyme 1 | UBA1 active site includes Cys 517 |

INDUSTRIAL APPLICATION

The invention provides, among other things, a new way to produce polypeptides comprising 2,3-diamino propionic acid (DAP). This has a range of industrial applications, for example exploiting its reactive properties to covalently trap molecules of interest such as substrates for enzymes being studied. This also enables dissection of metabolic pathways through similar approaches enabled by incorporating the DAP into the heart of the enzyme active site. Applications also include study/capture of small molecule drugs so as to identify how they are modified/metabolised by enzymes, and/or to identify their protein target(s).

Structural characterisation of proteins often represents the starting point for many drug discovery projects. Since DAP can be used in any protein catalysing reactions that proceed through covalent intermediates bound to serine or cysteine sidechains in the enzyme active site, it has a wide application potential. DAP can be used to structurally characterise these covalent intermediate. In addition to that, DAP also allows the identification of new substrates for these enzymes, which again may represent the starting point to new drug development strategies

Further Applications

Our technique allows to site-specifically incorporate DAP into recombinant protein. DAP can be used in any protein catalysing reaction that proceeds through covalent intermediates bound to serine or cysteine sidechains in the enzyme active site. DAP can be used to structurally characterise these covalent intermediates but also allows to identify new substrates for these enzymes.

We have evolved an aminoacyl-tRNA synthetase/tRNA$_{CUA}$ pair incorporating an amino acid (DAP5) that can be post-translationally converted to DAP under mild conditions. This allows us to site-specifically incorporate of DAP into recombinant proteins produced in E. coli. This allows us to efficiently capture acyl-enzyme intermediates.

In one embodiment the invention provides an amino acid (DAP5), which gets incorporated in protein with the use of a mutant of the pyrrolysine tRNA synthetase, which has been evolved to load its cognate tRNA with DAP5 (DAPRS). This allows synthesising recombinant proteins with site-specifically incorporated DAP5, which can be deprotected to DAP under mild conditions.

Suitably illumination to deprotect is for less than one minute, suitably for about one minute, suitably for one minute, suitably for at least one minute. Suitably illumination to deprotect is for 1 millisecond to 120 seconds, more suitably for 1 millisecond to 60 seconds. Most suitably illumination to deprotect is for one minute.

Suitably the protein is subsequently incubated after illumination, at any temperature above freezing. Incubation is the second stage of deprotection. The time it takes to go to completion depends on the protein in which DAP is incorporated. In the examples the sample was incubated for 1 to 2 h after illumination.

In one aspect the invention relates to a method of capturing a substrate for an enzyme.

Suitable substrates are those for which thioester or ester intermediate bonds are created by action of the enzyme on said substrate (N.B. the substrate does not contain an ester or a thioester—suitably the substrate comprises a chemical structure such that these moieties are created during catalysis). Suitably these bonds are created after, or as a result of, nucleophilic attack of the enzyme on its substrate. In case of a substitution of the active site residue by DAP according to the present invention, the created bond is an amide bond (discussed in more detail below).

Suitably said substrate is captured as a stable amide analogue.

Suitably said substrate may be an analogue of the naturally occurring substrate, Suitably said enzyme is a cysteine protease or a thioesterase.

Suitably said enzyme acts through one or more acyl-enzyme intermediates, more suitably through one or more cysteine- or serine-bound acyl-enzyme intermediates.

In one embodiment the invention may be used to look at the intermediate enzyme-substrate complexes that are formed with the addition of a small molecule (drug). This enables to elucidate how the drug disrupts this enzyme-substrate interaction during different complex formations. Thus if the small molecule is a substrate for the enzyme, this is a useful application of the invention. As long as DAP replaces any nucleophilic (catalytic) residue, suitably cysteine and/or serine, it will trap any substrate.

The invention finds application in researching insights into biosynthetic acyl-enzyme intermediates via encoded 2,3-diaminopropionic acid.

Further particular and preferred aspects are set out in the accompanying independent and dependent claims. Features of the dependent claims may be combined with features of the independent claims as appropriate, and in combinations other than those explicitly set out in the claims.

Where an apparatus feature is described as being operable to provide a function, it will be appreciated that this includes an apparatus feature which provides that function or which is adapted or configured to provide that function.

BRIEF DESCRIPTION OF THE DRAWINGS

Embodiments of the present invention will now be described further, with reference to the accompanying drawings, in which.

a, b, Active site serine or cysteine nucleophiles react with carbonyl groups to form tetrahedral intermediates (not shown) that collapse to the acyl enzyme intermediates by loss of R$_1$—XH, (where X is commonly NH, O, S). Attack of the acyl-enzyme intermediate by nucleophilic R$_3$ (commonly hydroxyls, amines or thiols) releases the bound substrate fragment and regenerates the enzyme. c, Replacement of cysteine or serine with 2,3-diaminoproprionic acid (DAP) may create enzymes that proceed to a first acyl-enzyme intermediate that is resistant to cleavage.

Figure 1:
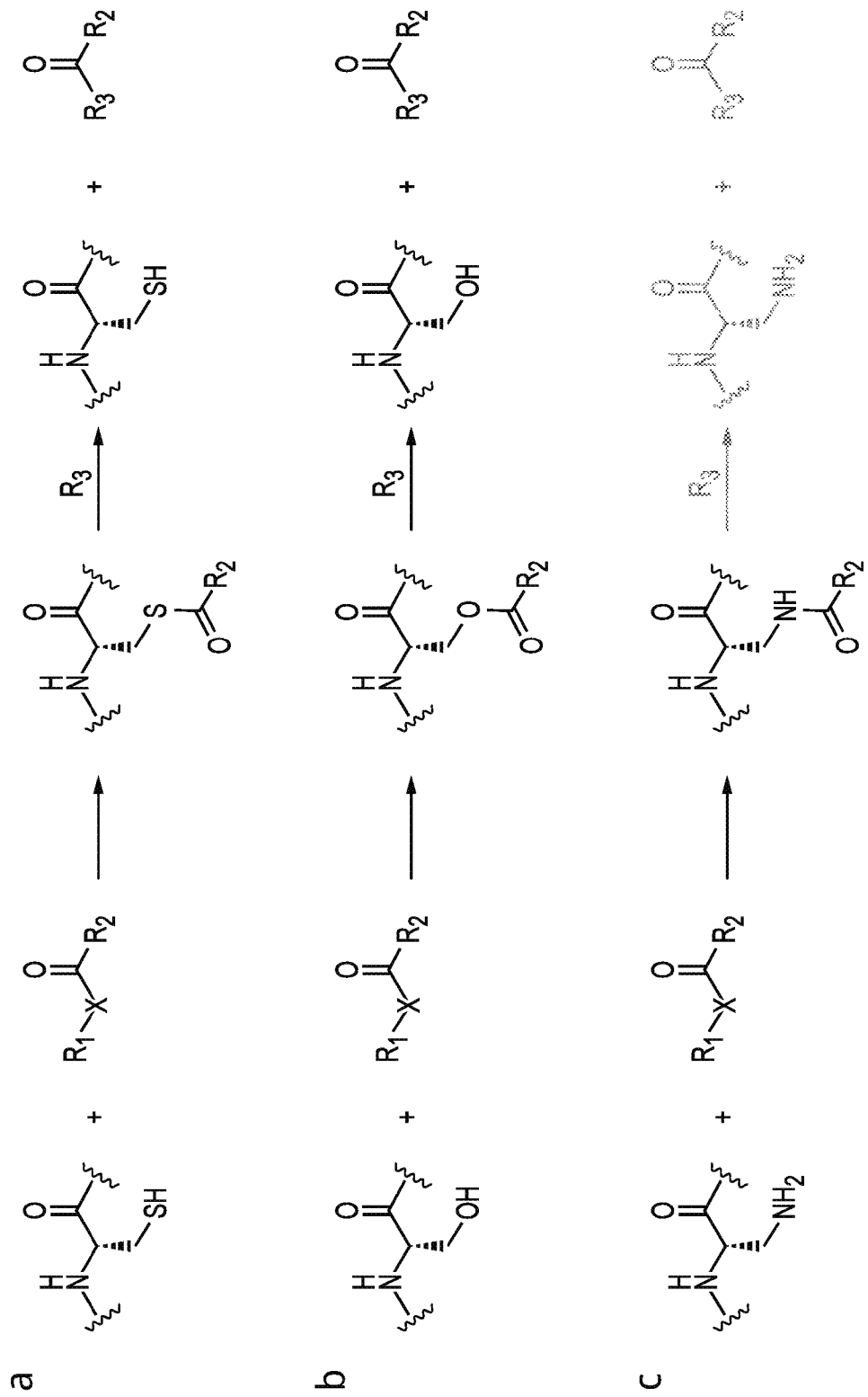
FIG. 1 shows general mechanism of enzymes with cysteine and serine nucleophiles in the active site that proceed through acyl-enzyme intermediates.
Figure 2:
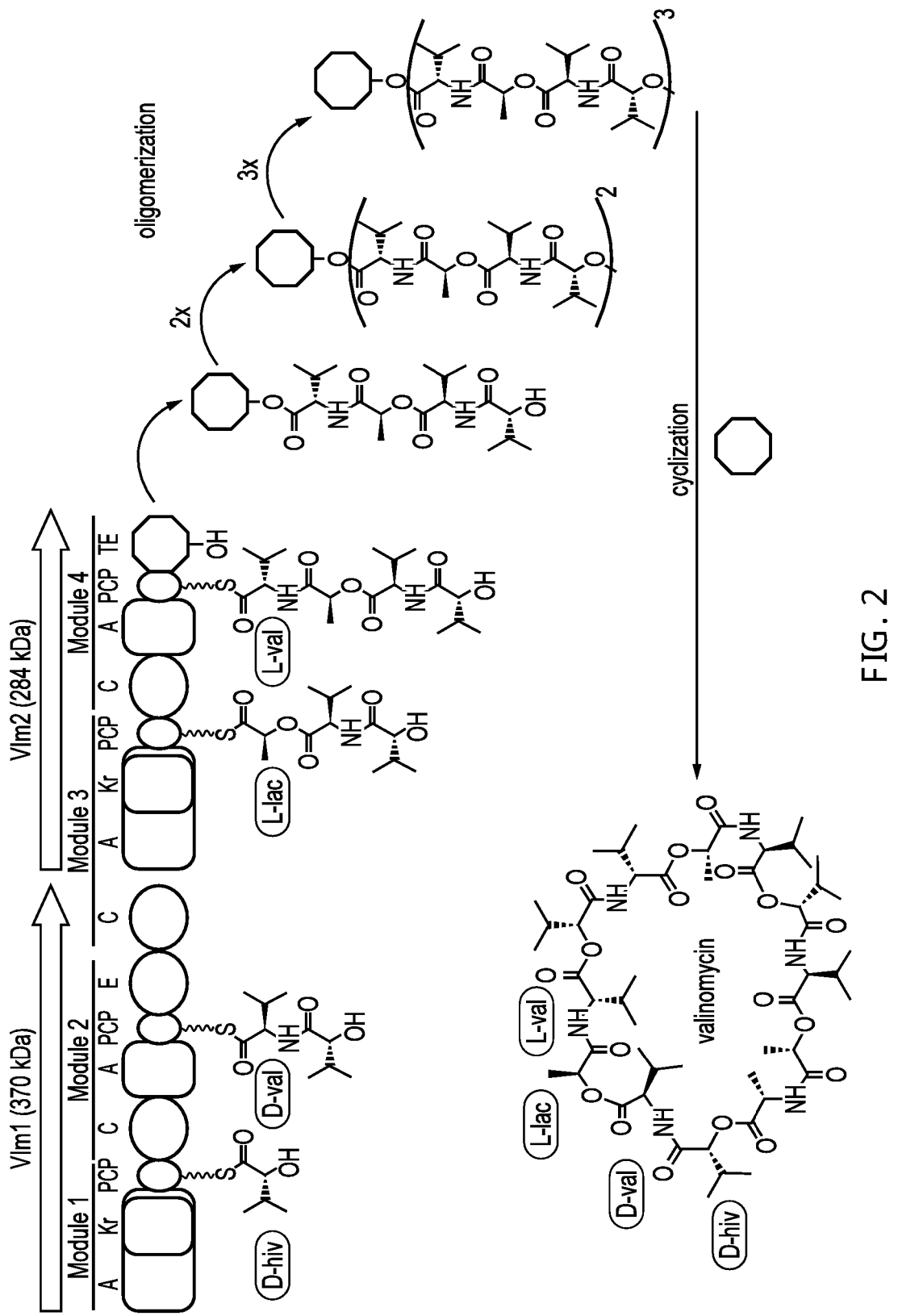

FIG. 2 shows valinomycin synthetase and the proposed biosynthesis of valinomycin. Valinomycin synthetase subunits Vlm1 and Vlm2 condense D-α-hydroxyisovaleric acid (D-α-hiv), D-valine (D-val), L-lactic acid (L-lac), and L-valine (L-val) in a sequential manner to form the tetradepsipeptidyl (D-hiv-D-val-L-lac-L-val) intermediate. D-α-hiv and L-lac arise from the selection and ketoreduction of their precursor ketoacids by the specialized modules 1 and 3, which include ketoreductase (KR) domains. The tetradepsipeptidyl intermediate is oligomerized to an octadepsipeptidyl intermediate and then dodecadepsipeptidyl intermediate, which is cyclized by the terminal thioesterase (TE) domain, producing valinomycin. A: adenylation domain, PCP: peptidyl carrier protein domain; C: condensation domain. See Supplementary FIG. 1 for a synthetic cycle of a canonical NRPS.

Figure 3:
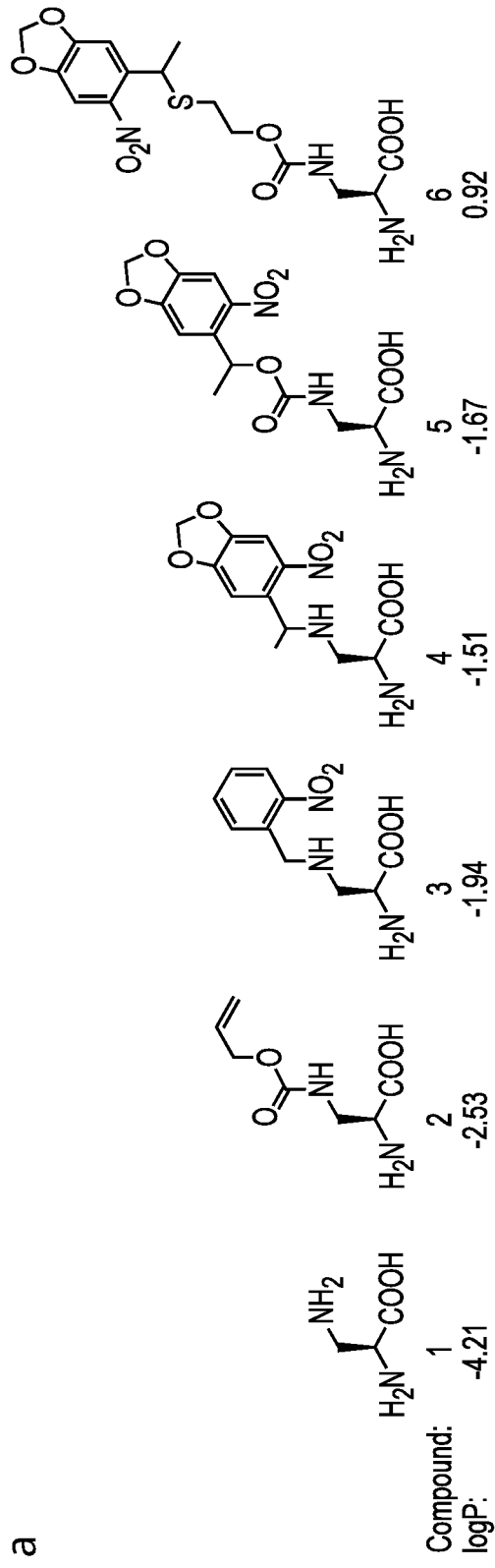
Figure 3:
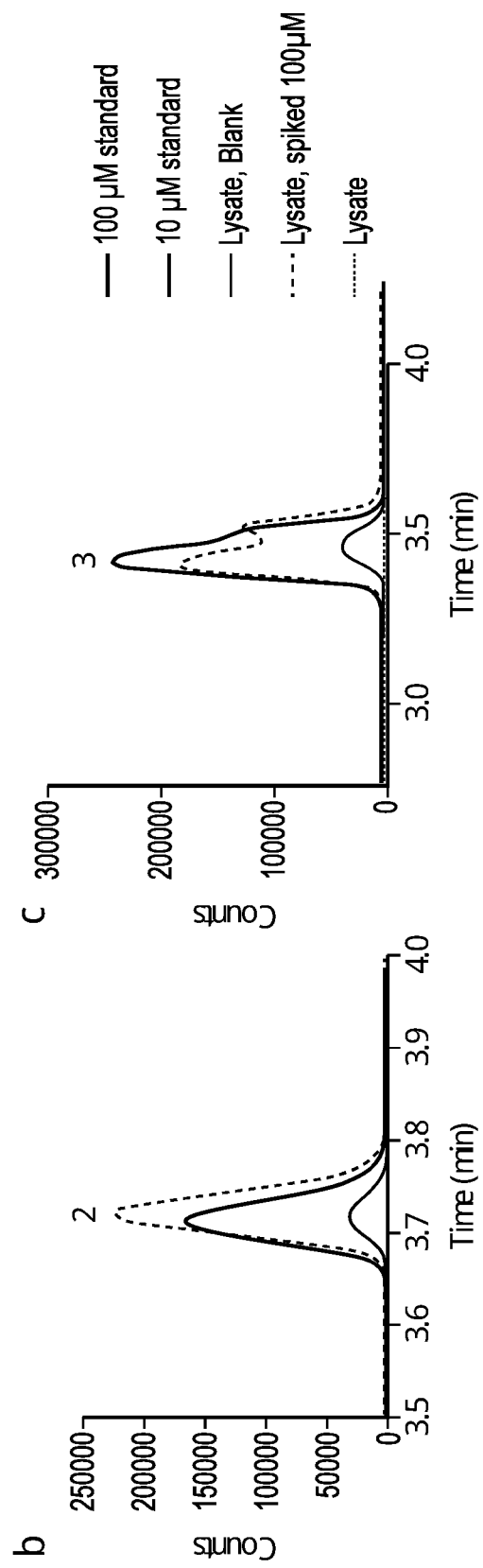
Figure 3:
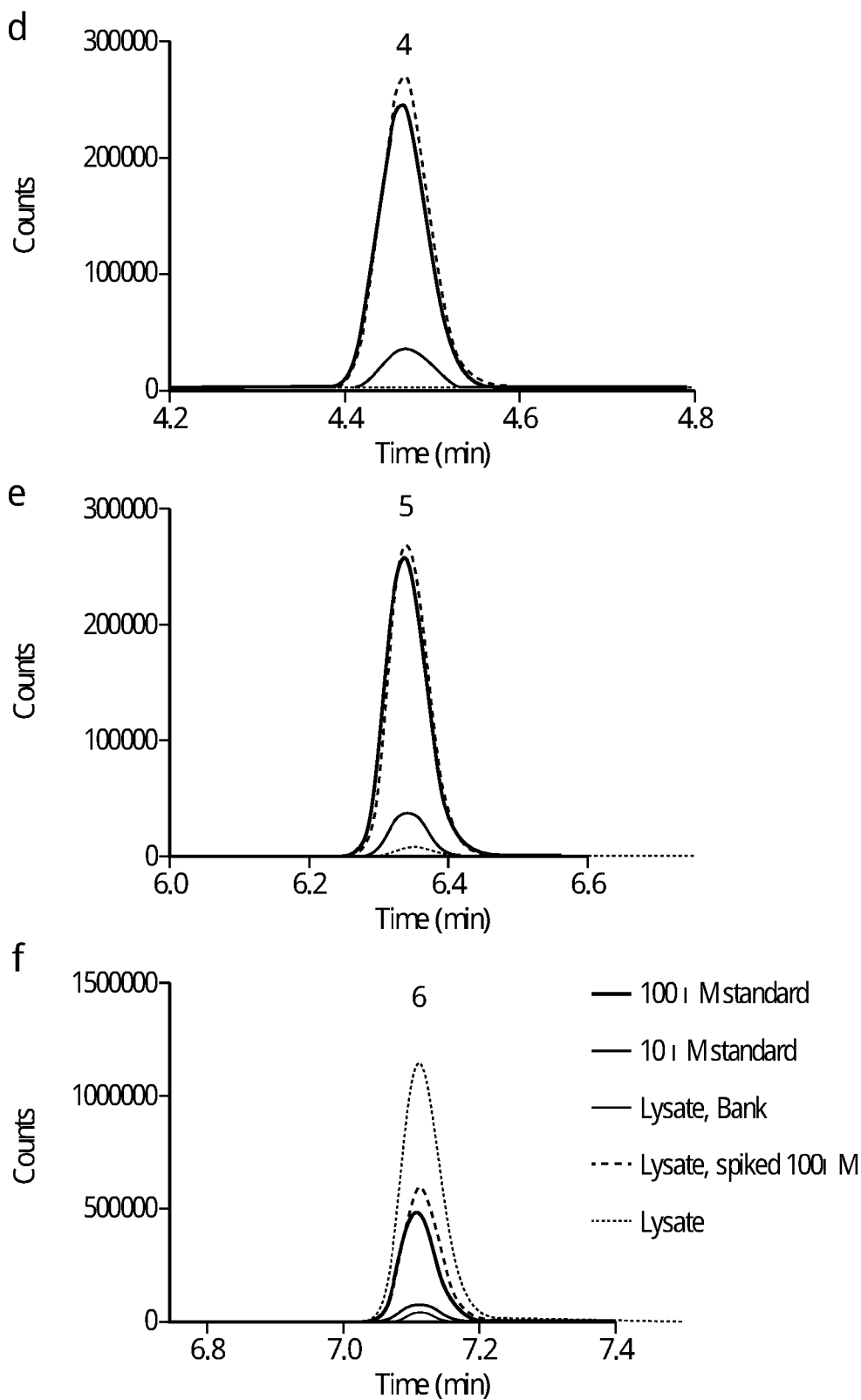
Figure 3:
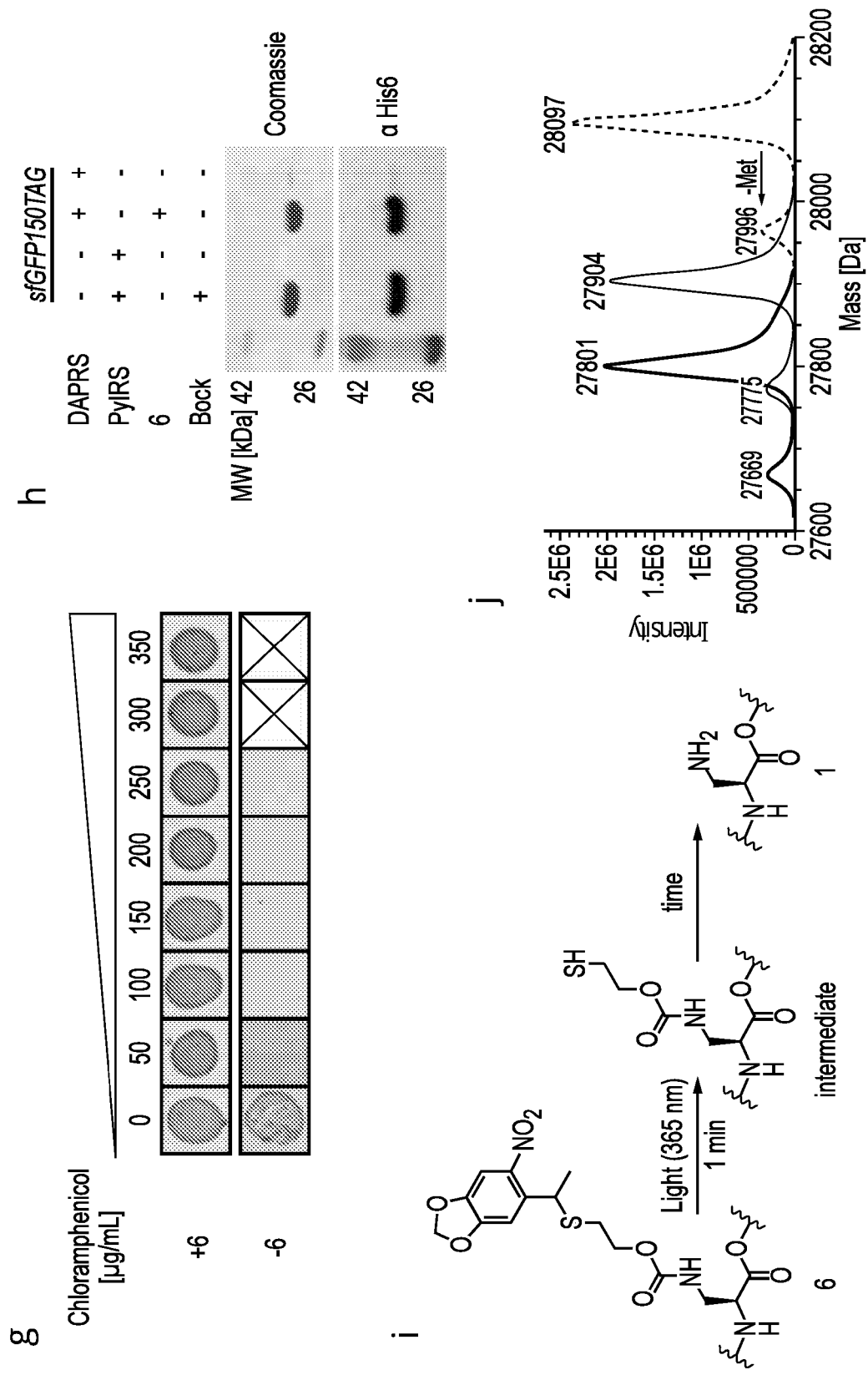

FIG. 3 shows genetically directing DAP incorporation in recombinant proteins. a, Structure of DAP and the protected versions investigated herein. 1: 2,3-diaminopropionic acid (DAP). 2: (S)-3-(((allyloxy)carbonyl)amino)-2-aminopropanoic acid. 3: (S)-2-amino-3-((2-nitrobenzyl)amino)propanoic acid 4: (2S)-2-amino-3-((1-(6-nitrobenzo[d][1,3]dioxol-5-yl)ethyl)amino)propanoic acid 5: (2S)-2-amino-3-(((1-(6-nitrobenzo[d][1,3]dioxol-5-yl)ethoxy)carbonyl)amino)propanoic acid 6: (2S)-2-amino-3-(((2-((1-(6-nitrobenzo[d][1,3]dioxol-5-yl)ethyl)thio)ethoxy)carbonyl)amino)propanoic acid. b-f, Determining the intracellular concentration of compounds 2-6 by an LC-MS assay, performed on extracts. The dark-blue trace represents a 100 µM standard for each compound. The light-blue trace represents a 10 µM standard for each compound. The red trace results from cells grown in the absence of the compound. The brown trace results from cells grown in the absence of the compound, but spiked with the compound to 10 PM. The green trace results from cells grown in the presence of 1 mM compound. g, Phenotyping of the DAPRS/tRNA$_{CUA}$ pair. Cells containing the DAPRS/tRNA$_{CUA}$ pair and cat (112TAG) were plated in the presence or absence of 6 on the indicated concentrations of chloramphenicol. h, Expression of sfGFP containing either 6 or BocK at position 150. Following expression and purification, equal volumes of protein solution were loaded on an SDS-PAGE gel and coomassie stained (top gel) or analysed by western blot with an α-His antibody (bottom gel). i, Encoded 6 was deprotected with UV-light, leading to an intermediate (in red), which spontaneously fragments to reveal DAP. j, The deprotection of 6 in sfGFP was followed by ESI-MS analysis. Green trace: Purified sfGFP containing 6 at position 150: Expected mass: 28096.27 Da; Observed: 28097.21 Da. Red trace: sfGFP containing 6 following illumination to convert 6 to the intermediate: Expected mass: 27902.22 Da; Observed: 27904.14 Da. Blue trace: sfGFP containing 6 following illumination (to convert 6 to the intermediate) and further incubation to convert the intermediate to DAP (i): Expected mass: 27798.23 Da; Observed: 27800.88 Da. Each trace also displays the mass of a protein adduct resulting from the spontaneous loss of the N-terminal methionine.

Figure 4A:
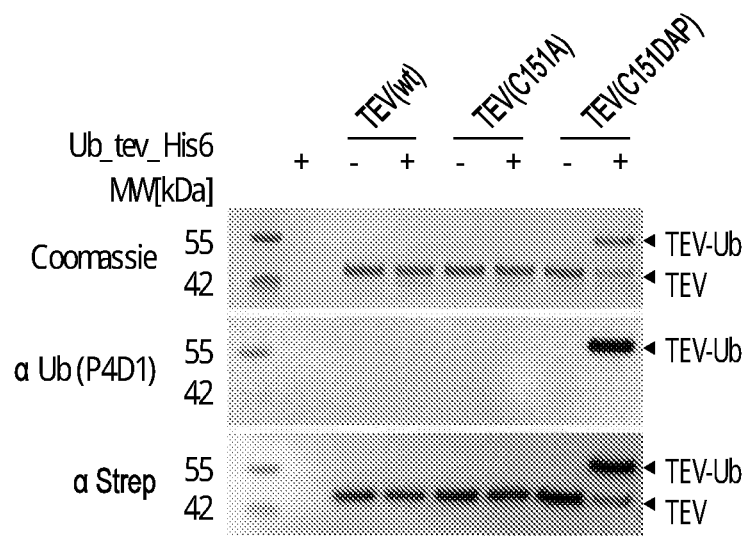
Figure 4A:
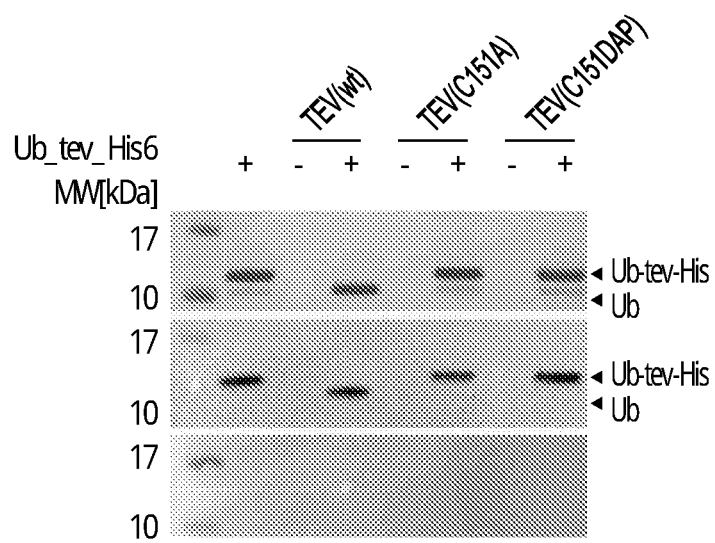
Figure 4B:
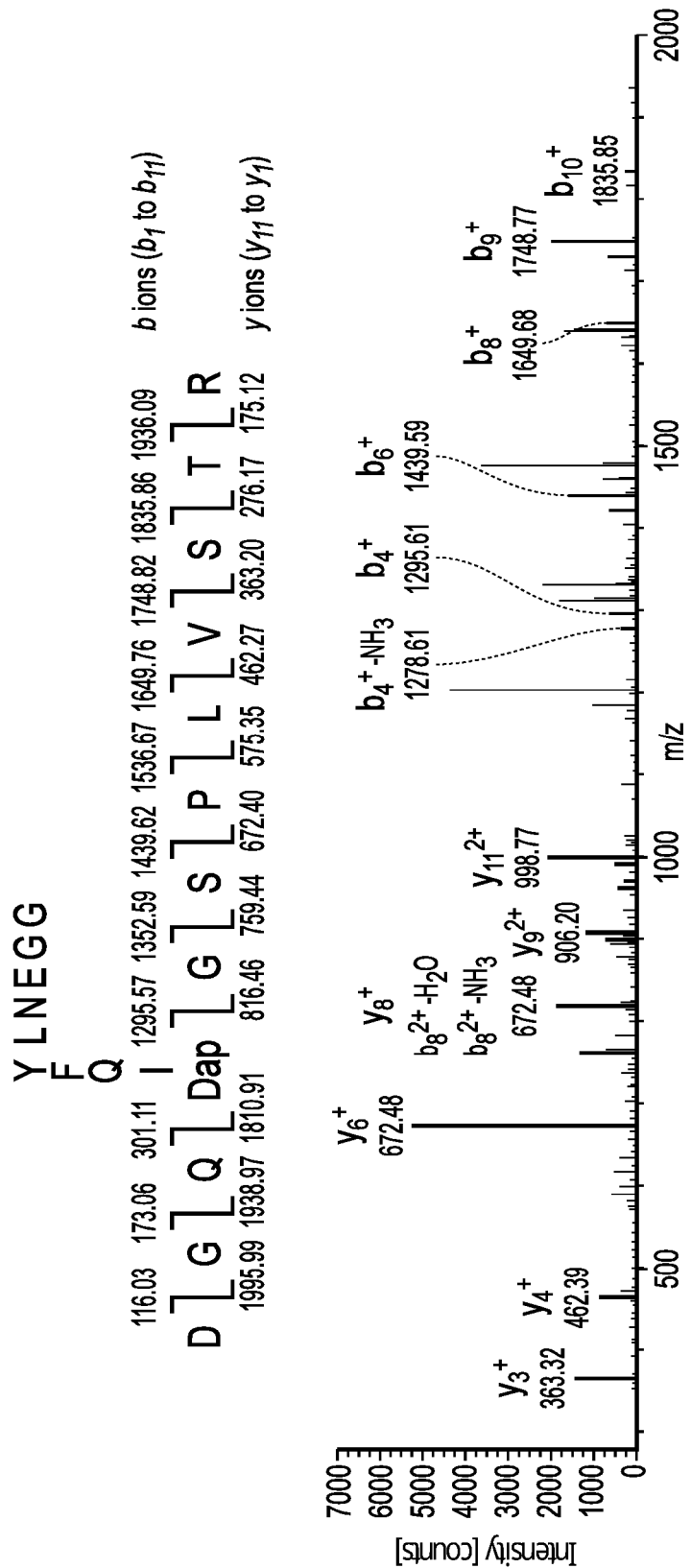

FIG. 4 shows stably trapping acyl-enzyme intermediates with TEV(C151DAP). a, The indicated variants of TEV protease were incubated with Ub-tev-His. The use of TEV (wt) results in cleavage of the TEV cleavage sequence. The use of TEV(C151A) results in minimal cleavage. The presence of DAP in the active site of TEV results in the presence of a new band in the coomassie gel, representing the isopeptide-linked TEV(C151DAP)-Ub complex (left). αUb and αStrep western blots of the reactions confirm the identity of the complex (TEV constructs contain a Strep tag). b, Tandem mass spectrometry of isopeptide-linked TEV (C151DAP)-Ub complex. Tandem mass spectrometry unambiguously identifies the DAP modification at the desired site and the expected tev-Gly-Gly modification on the residue, consistent with Ub trapping on DAP.

Figure 5:
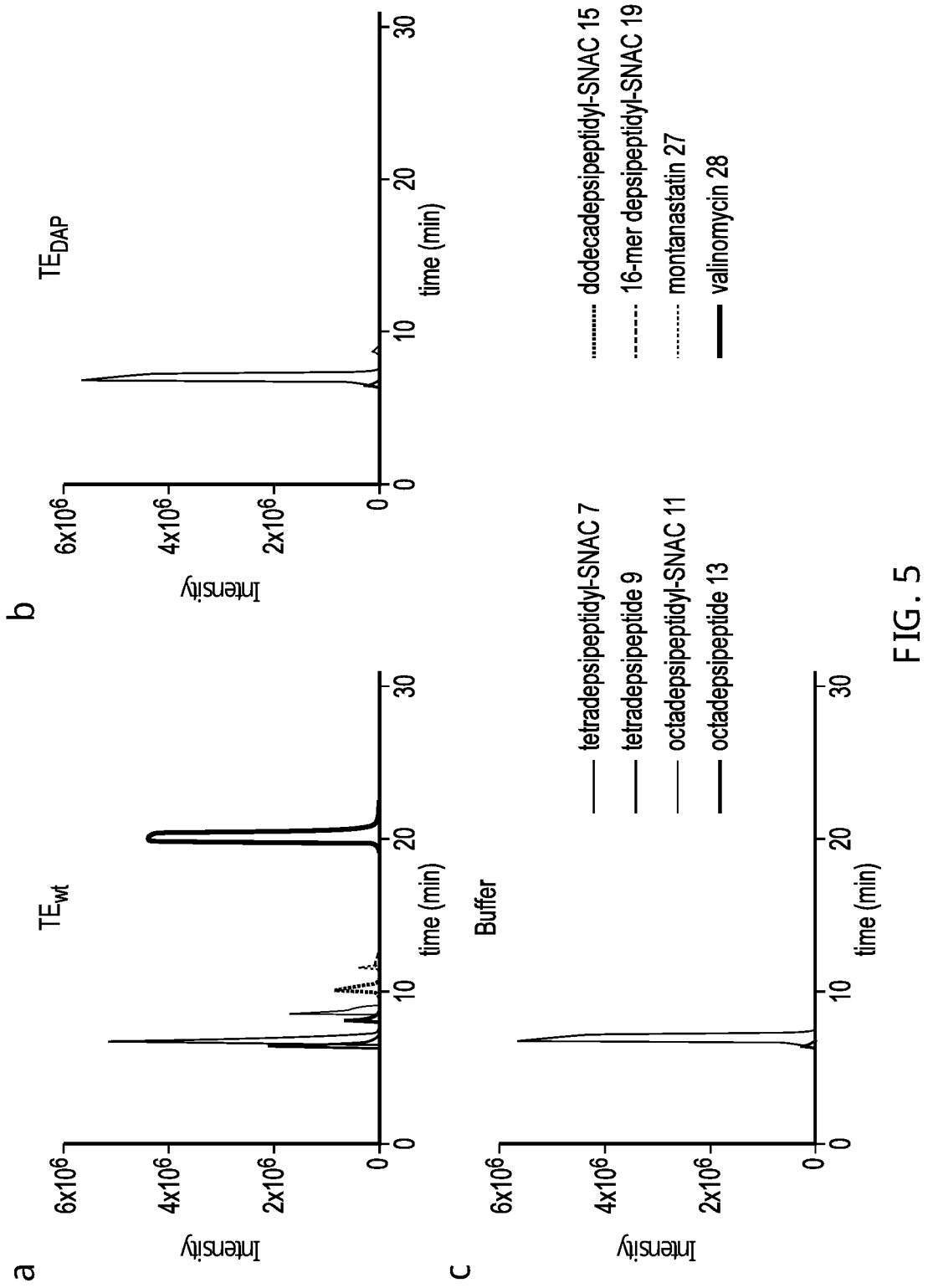

FIG. 5 shows small molecule products made by Vlm TE from tetradepsipeptidyl-SNAC delineate the oligomerization pathway.

Extracted ion chromatograms (EICs) from HR-LC-ESI-MS of reactions of tetradepsipeptidyl-SNAC 7 (1.7 mM) and Vlm TE (6.5 µM). a, TE$_{wt}$ produces valinomycin as its major product. The presence of octadepsipeptidyl-SNAC 11, dodecadepsipeptidyl-SNAC 15 and 16-mer depsipeptidyl-SNAC 19 confirm the oligomerization scenario in Supplementary FIG. 10b. b, TE$_{DAP}$ produces a small amount of octadepsipeptidyl-SNAC 11. c, The control reaction without enzyme shows a small amount tetradepsipeptide 9, likely from uncatalyzed hydrolysis of the thioester in solution. See Supplementary Table 2 for accurate mass analysis and deviations from calculated m/z values of each compound.

Figure 6:
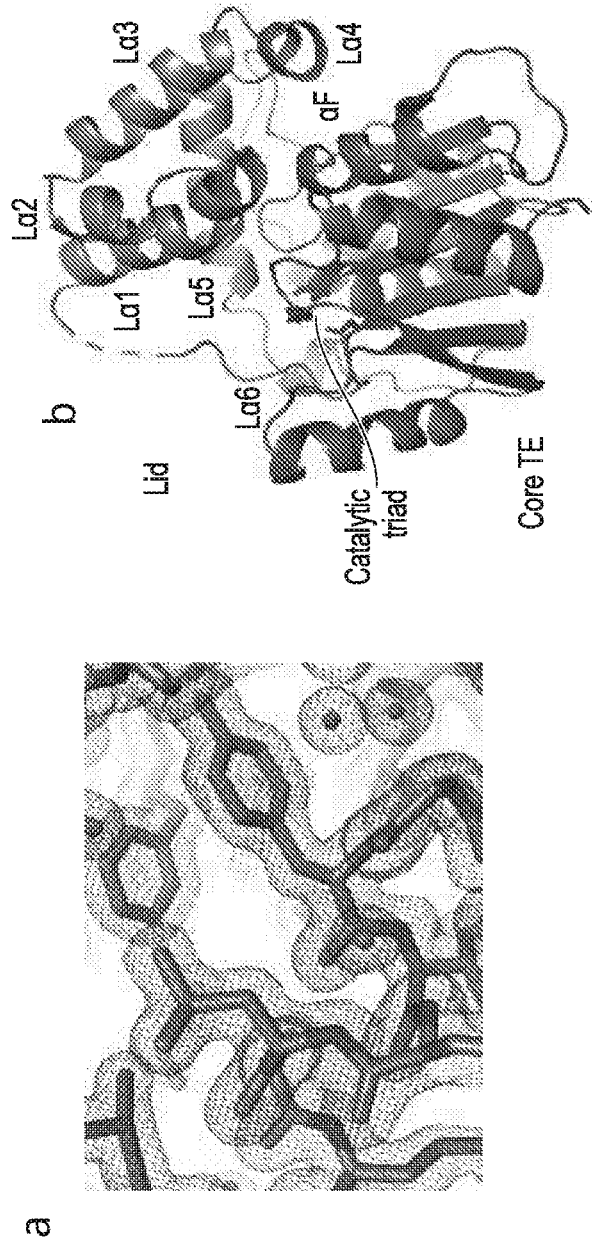
Figure 6:
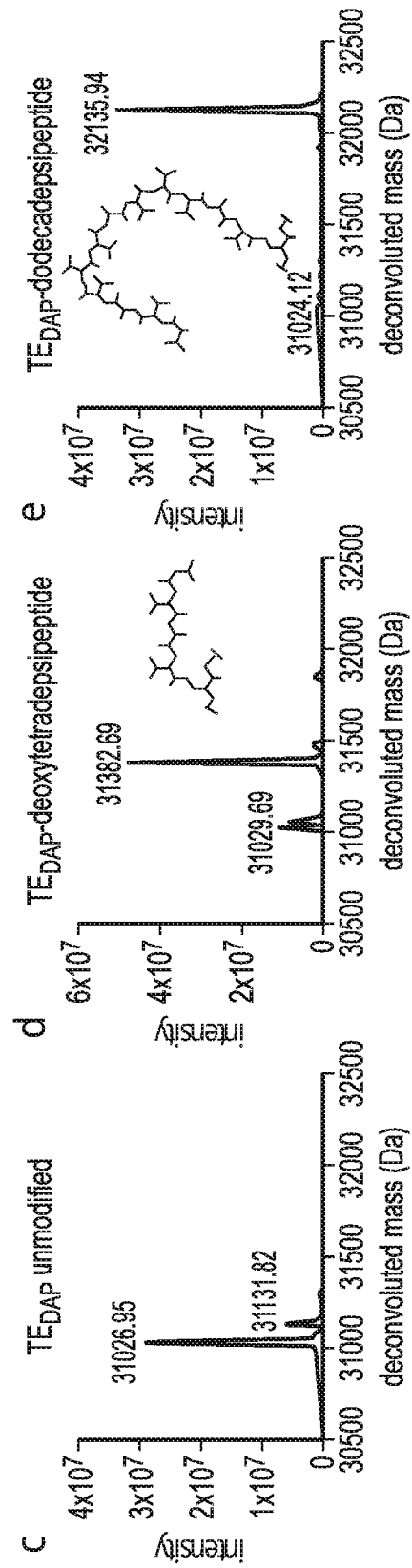
Figure 6:
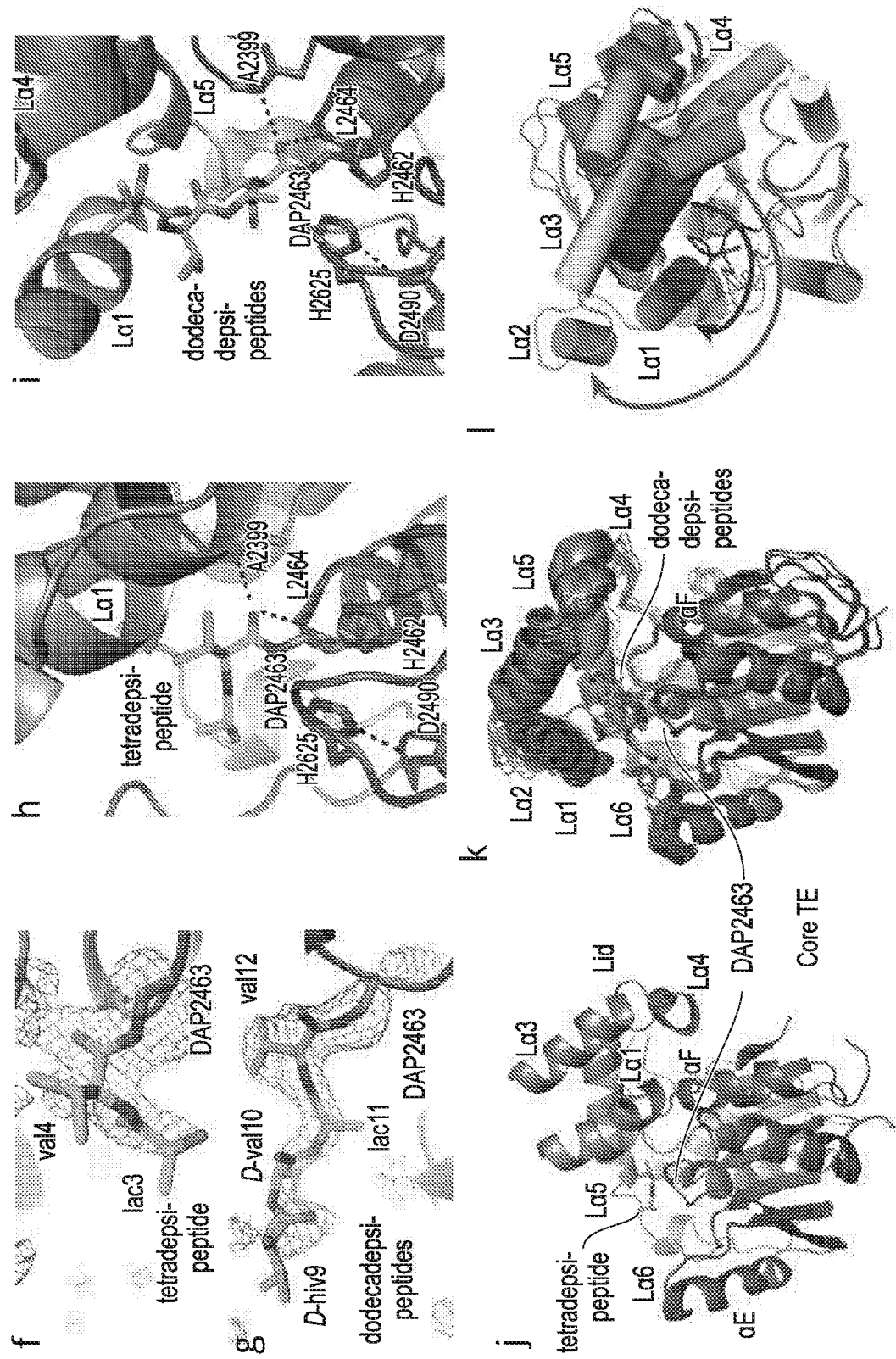

FIG. 6 shows crystal structures of complexes of TE$_{DAP}$. a, Representative electron density for TE$_{wt}$ (2mFo-DFc map contoured at 1.0 σ). b, The structure of TE$_{wt}$. The lid (grey) is nearly completely ordered but has higher B factors than the core of the protein. Deconvoluted mass spectra of c, TE$_{DAP}$. d, TE$_{DAP}$ incubated with deoxy-tetradepsipeptidyl-SNAC 8. e, TE$_{DAP}$ incubated with valinomycin. f and g, Unbiased mFo-DFc electron density map (green mesh, 2.5 σ) for depsipeptide residues of tetradepsipeptidyl-TE$_{DAP}$ (f) and dodecadepsipeptidyl-TE$_{DAP}$ (g). An amide bond links diaminopropionic acid (DAP, brown sticks) and depsipeptide residues (cyan sticks). h and i, The active site of tetradepsipeptidyl-TE$_{DAP}$ (h) and dodecadepsipeptidyl-TE$_{DAP}$ (i) complexes. The carbonyl oxygen of the amide formed by DAP and val4 (h) or val12 (i) is positioned close to the oxyanion hole formed by the main chain amine of A2399 and L2464. The catalytic triad residues H2625 and D2490 are shown in sticks. j, The lid of tetradepsipeptidyl-TE$_{DAP}$ is in a similar position to that seen in TE$_{wt}$ while k, all crystallographically independent molecules of the dodecadepsipeptidyl-TE$_{DAP}$ (from P1 and H3 space group structures) are in a set of similar conformations, distinct from that seen in TE$_{wt}$. l, An illustration of the substantial conformational change in lid helixes Lα1-Lα4 between structures of tetradepsipeptidyl-TE$_{DAP}$ and dodecadepsipeptidyl-TE$_{DAP}$. The mobile helices are shown in colours of progressively higher wavelengths for clarity.

Figure 7:
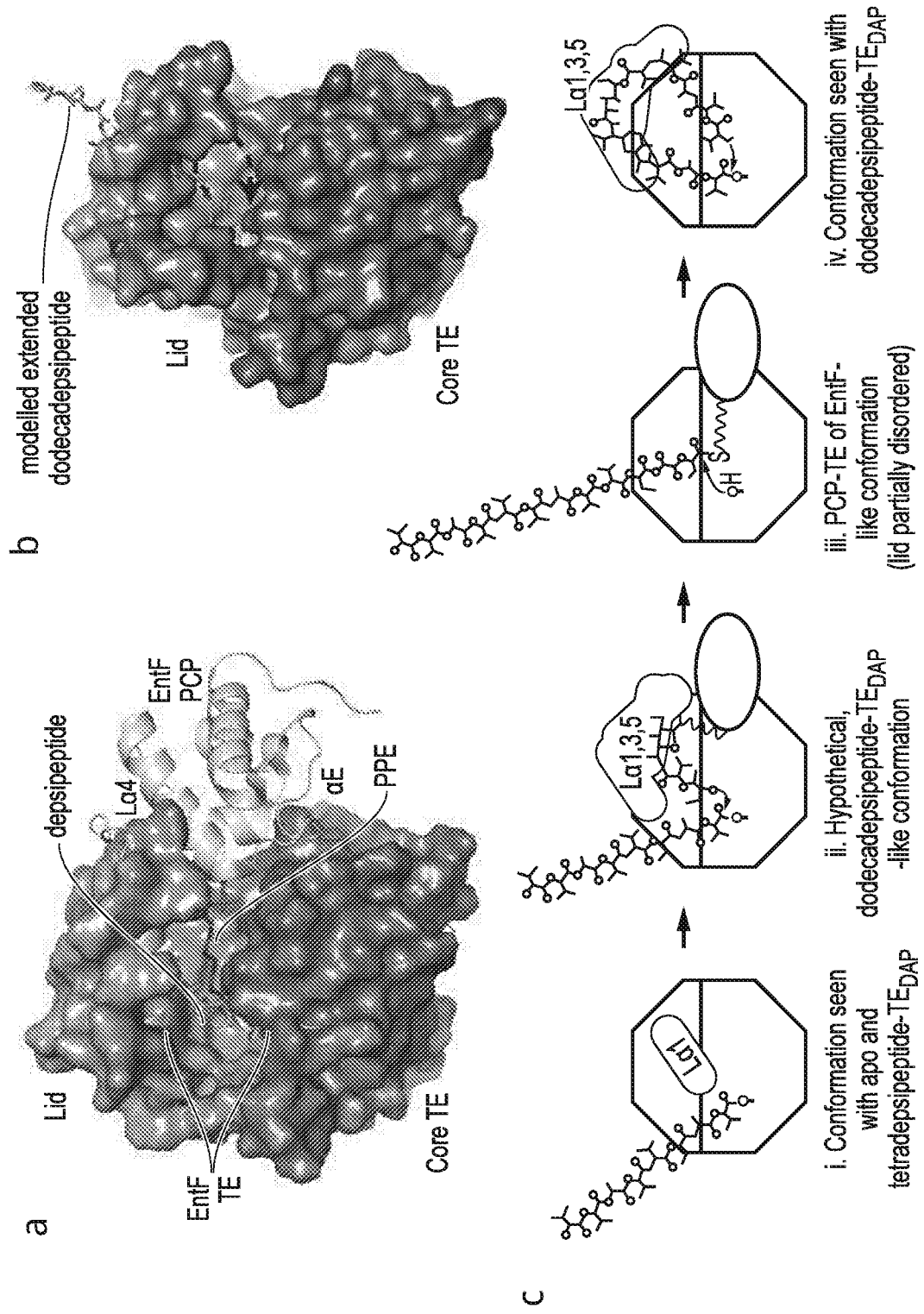

FIG. 7 shows modelling of PCP domain interaction with the TE domain and putative pathway.

a, Superimposition of dodecadepsipeptidyl-TE$_{DAP}$ with the structure of EntF PCP-TE didomain[46] shows the path of the PPE moiety to the active site. b, The lid sterically prevents the dodecadepsipeptide from extending out in a linear fashion, and favours curling back through this steric block and largely hydrophobic, non-specific interactions between lid and dodecadepsipeptide. c, Hypothetical pathway for oligomerization and cyclization, starting from octadepsipeptidyl-TE. i, The position of Lα1 in observed apo/tetradepsipeptide conformation promotes an extended peptide conformation. ii, The tetradepsipeptidyl-PCP accepts the octadepsipeptide onto its terminal hydroxyl, perhaps using a dodecadepsipeptide-like lid conformation which could accommodate the ~30 Å tetradepsipeptidyl-PPE bound to the PCP domain and guide it towards the active site. iii, The PCP domain presents the thioester for transfer back to the Ser2463. iv, Finally, the lid conformation observed in the dodecadepsipeptide-TE$_{DAP}$ structures could help curl the dodecadepsipeptide back towards Ser2463 for cyclization.

Figure 8:
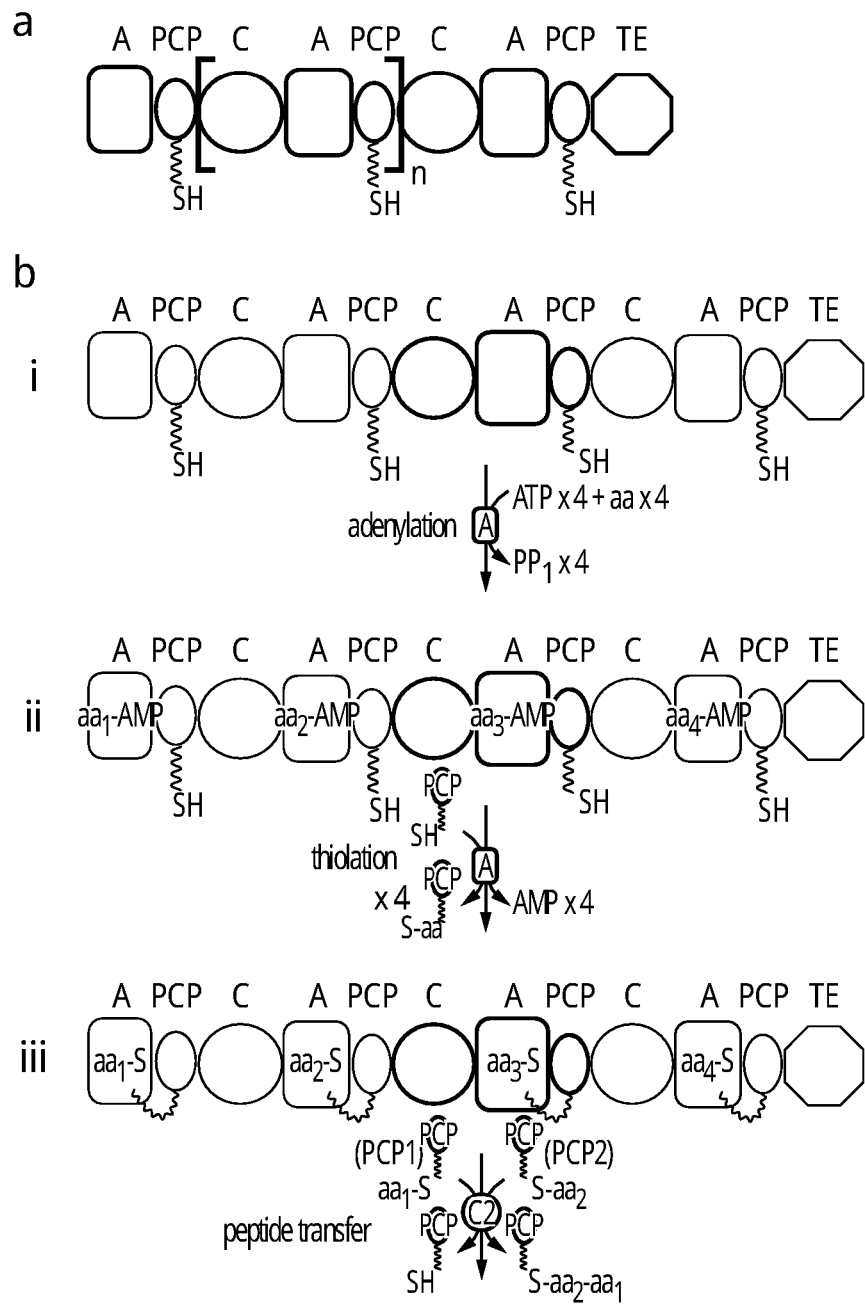
Figure 8:
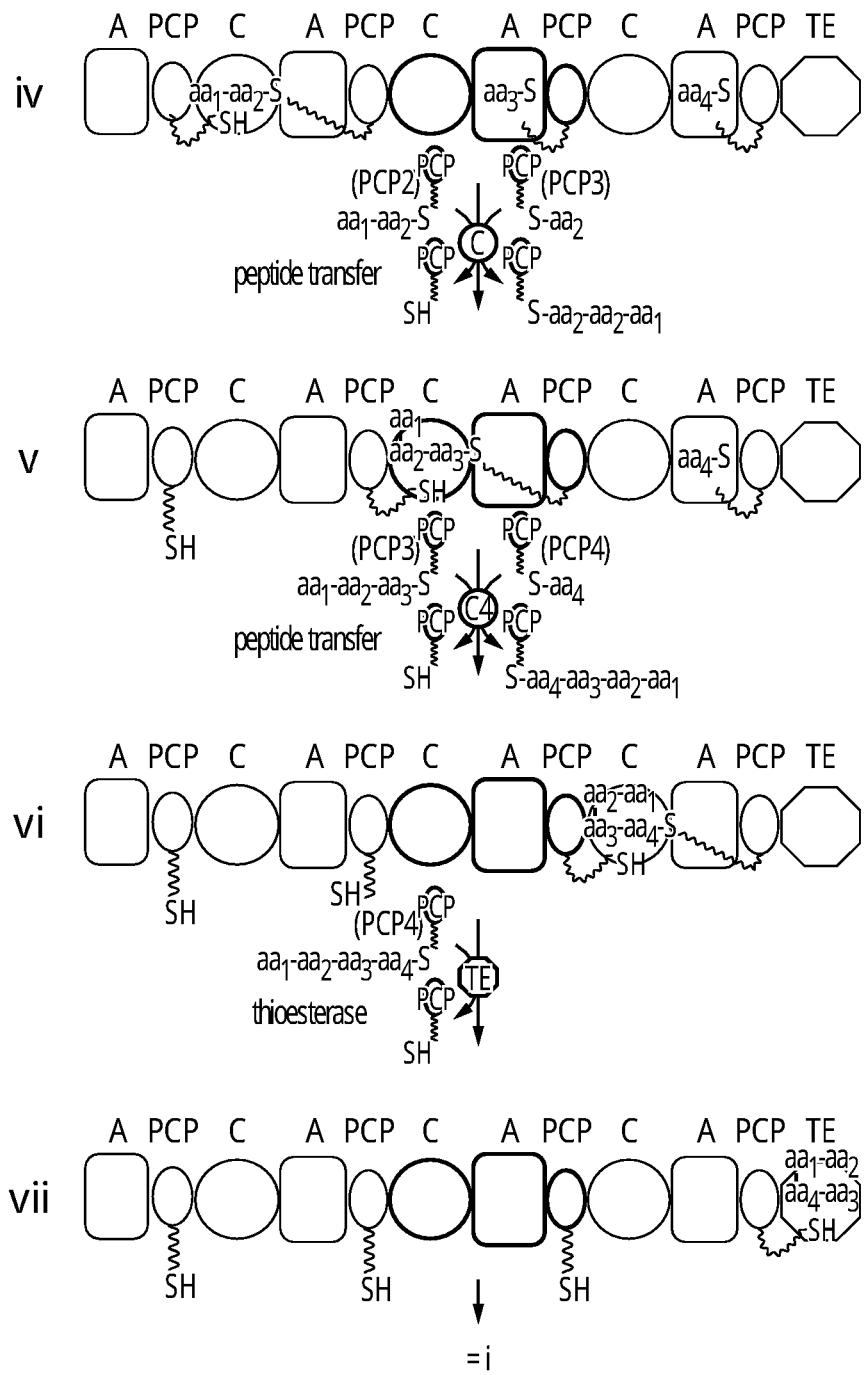
Figure 9:
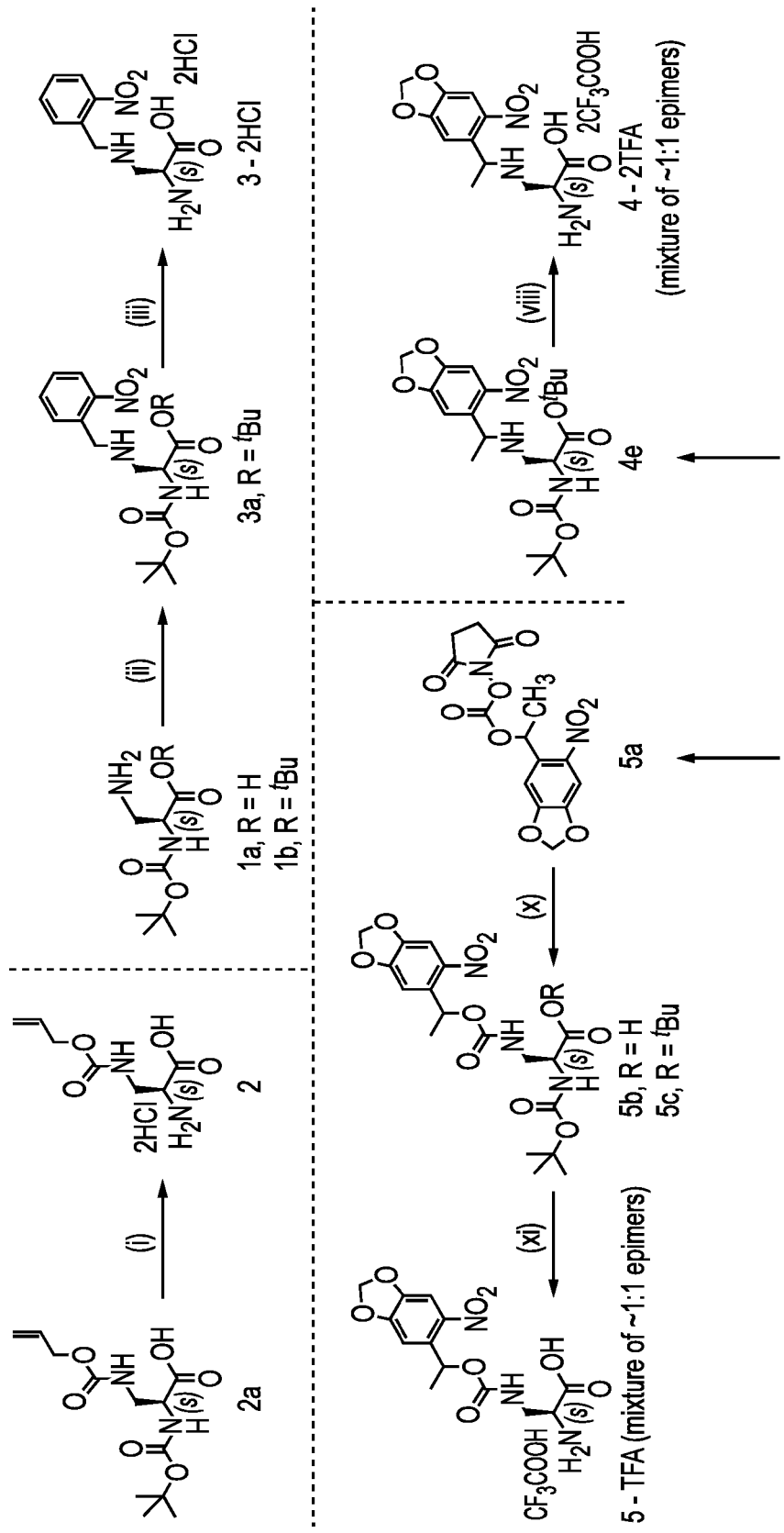
Figure 9:
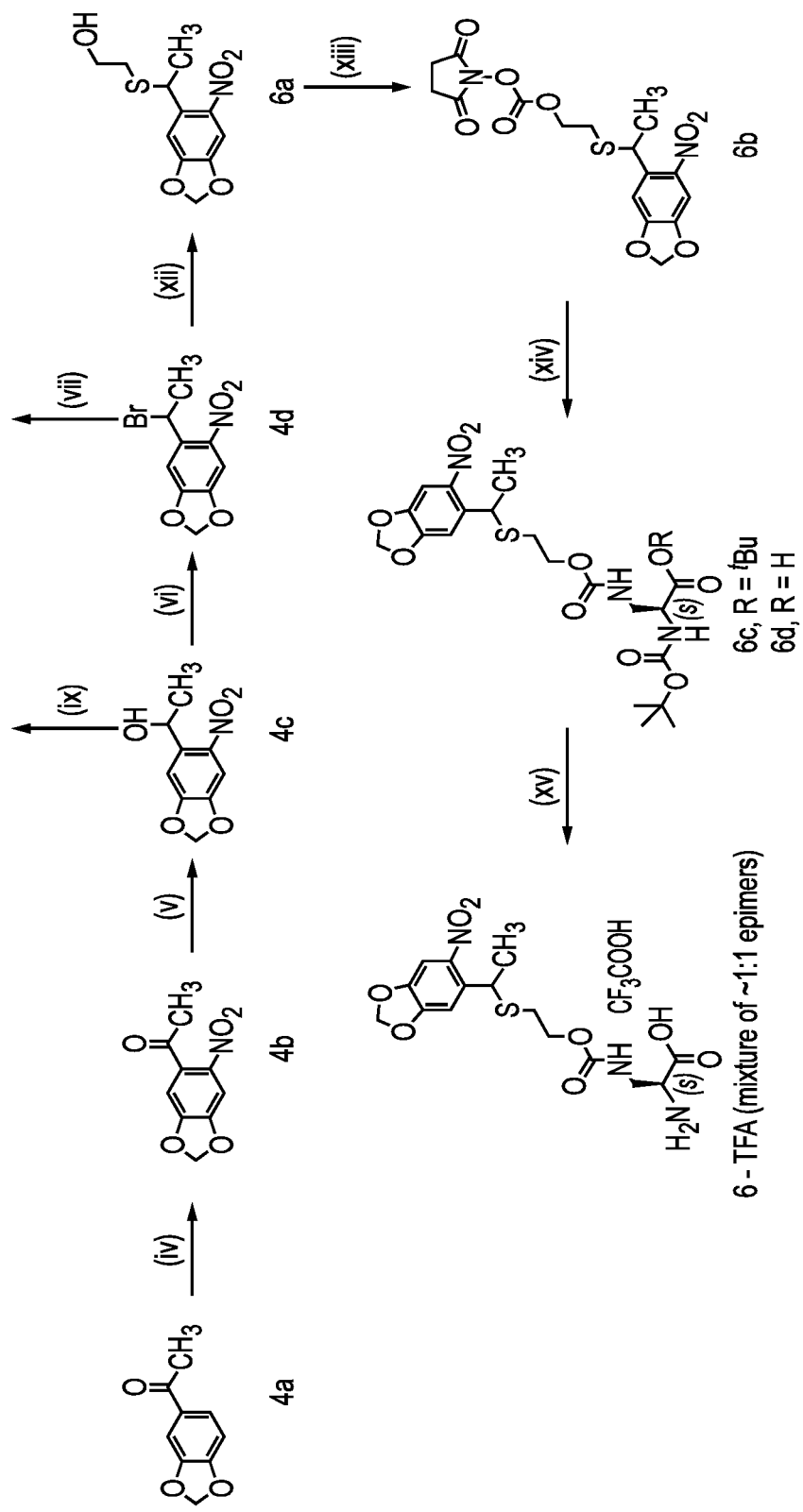
Figure 10:
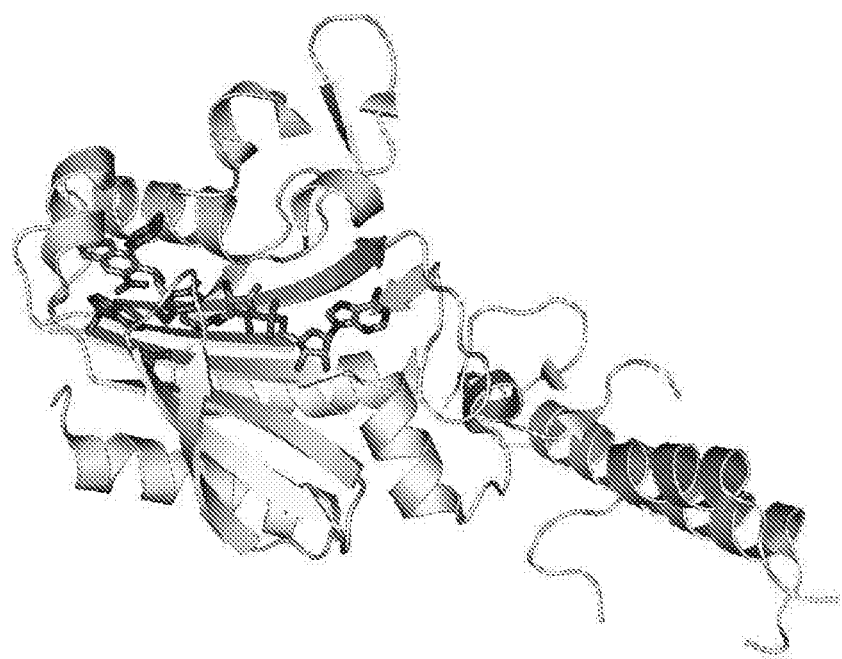
Figure 10:
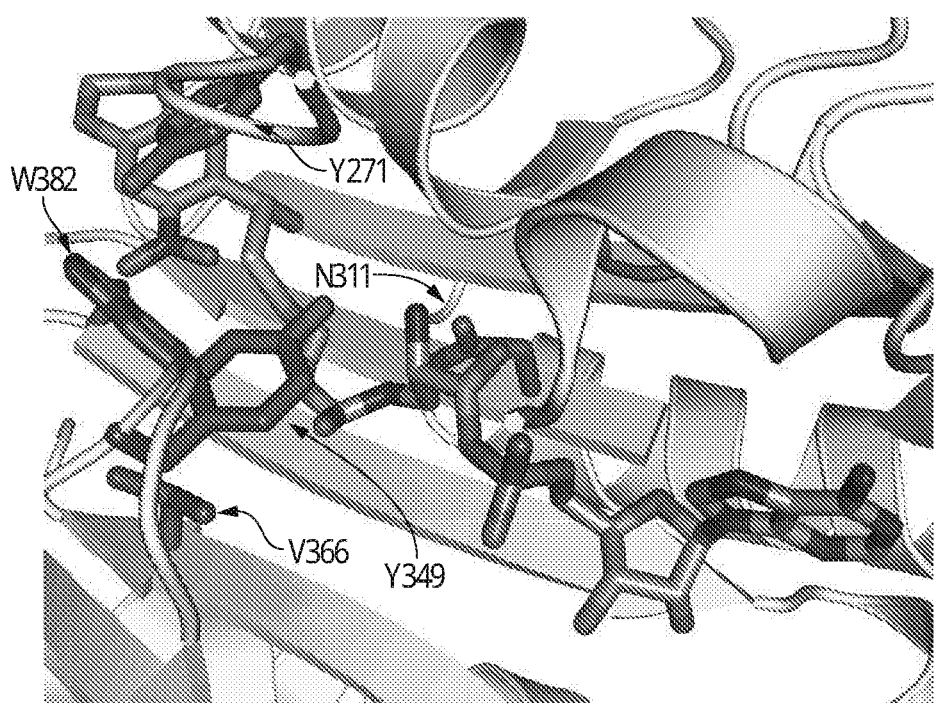
Figure 11:
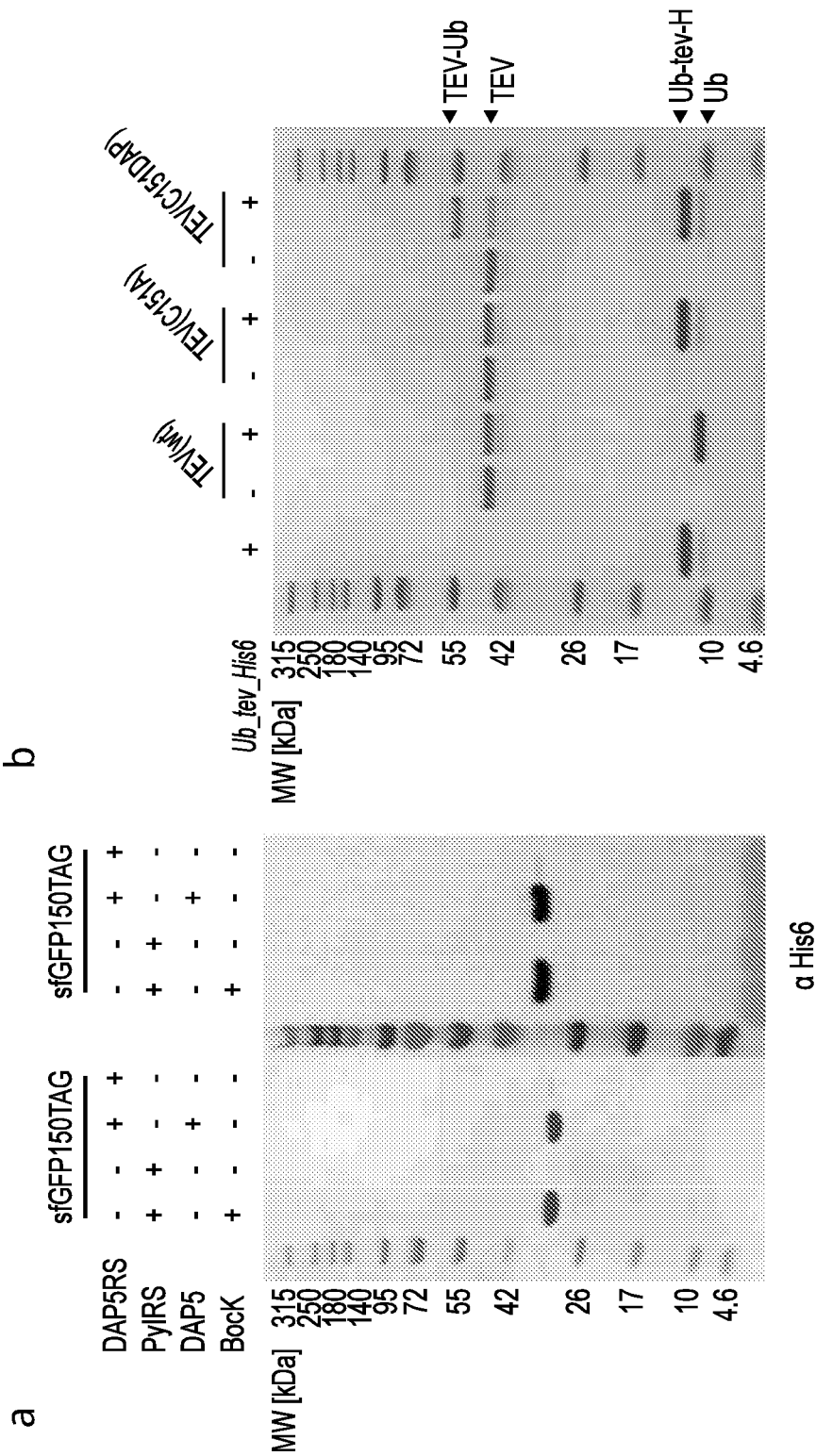
Figure 11:
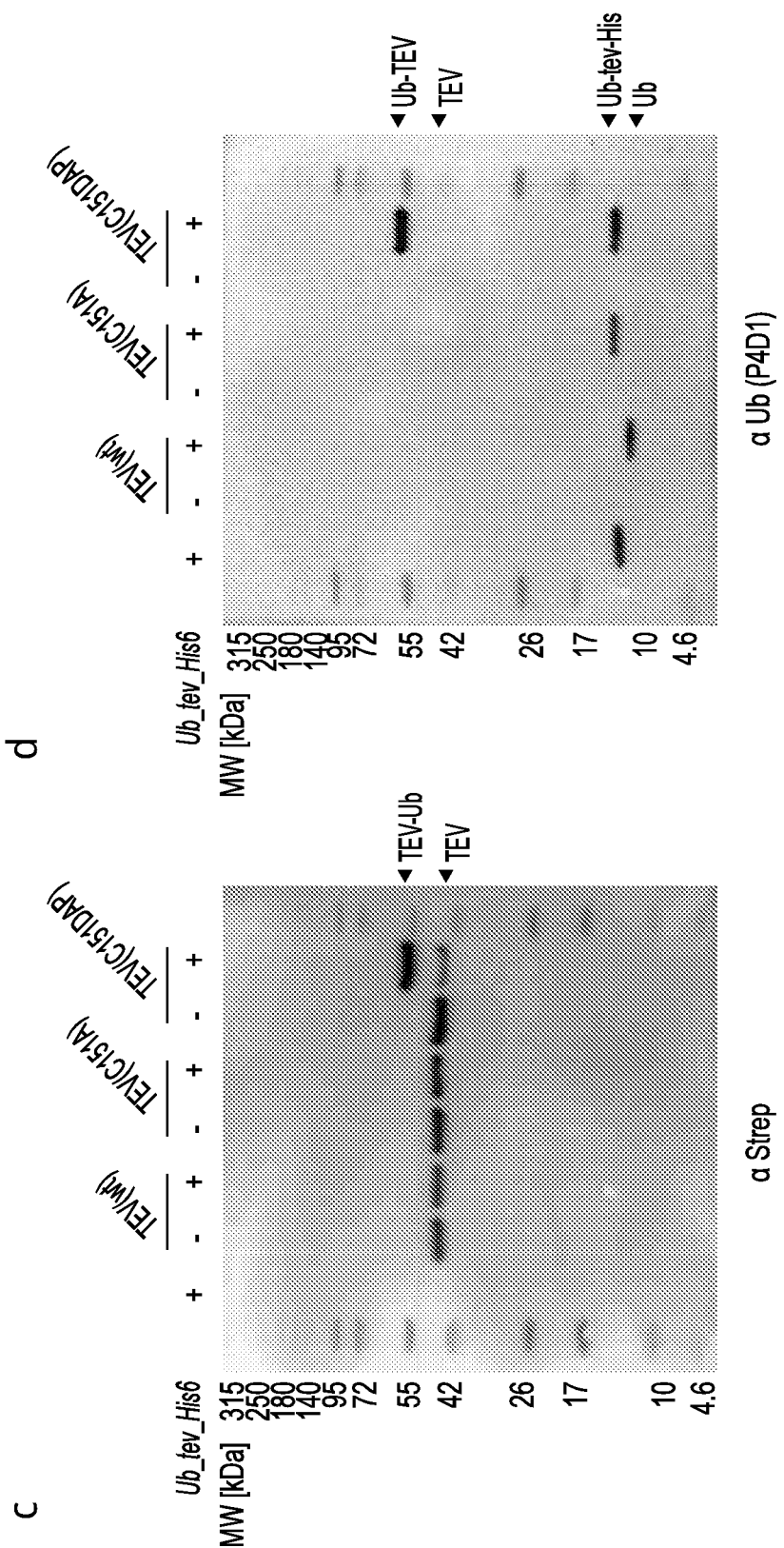
Figure 12:
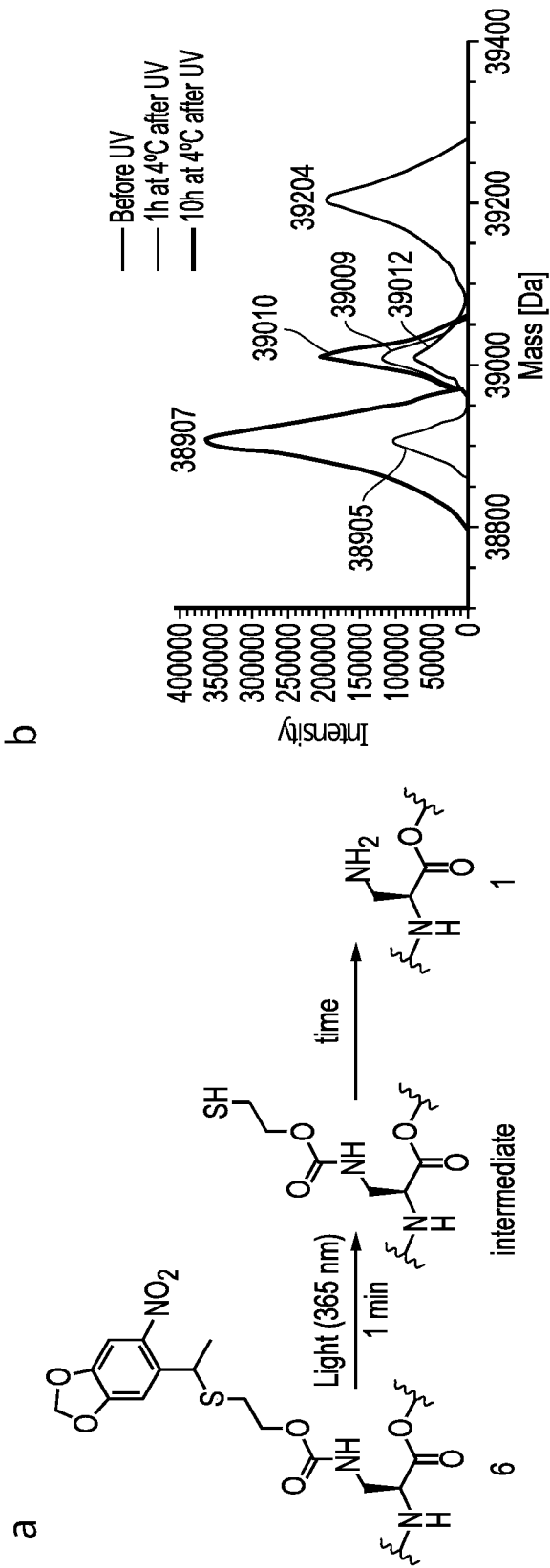
Figure 13:
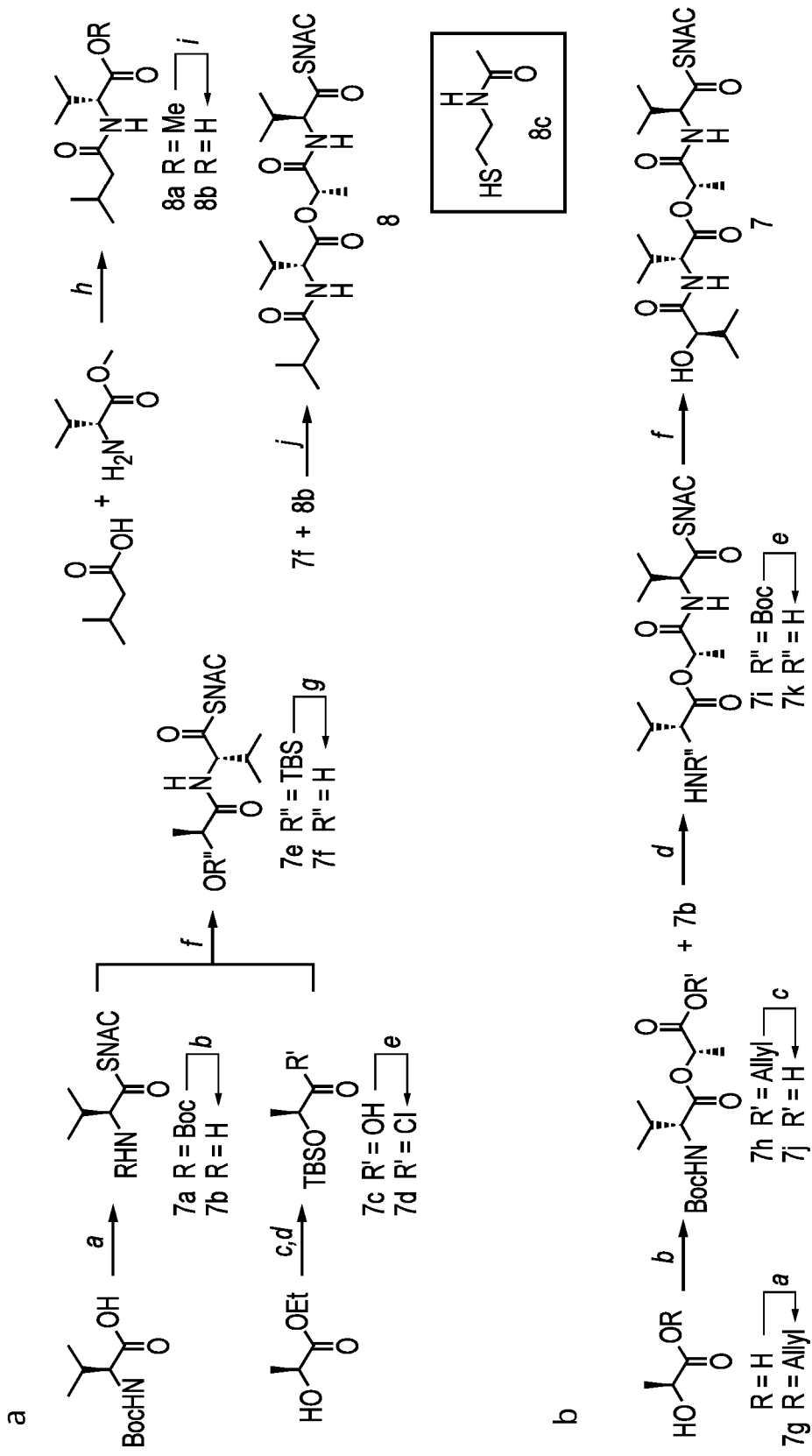
Figure 13:
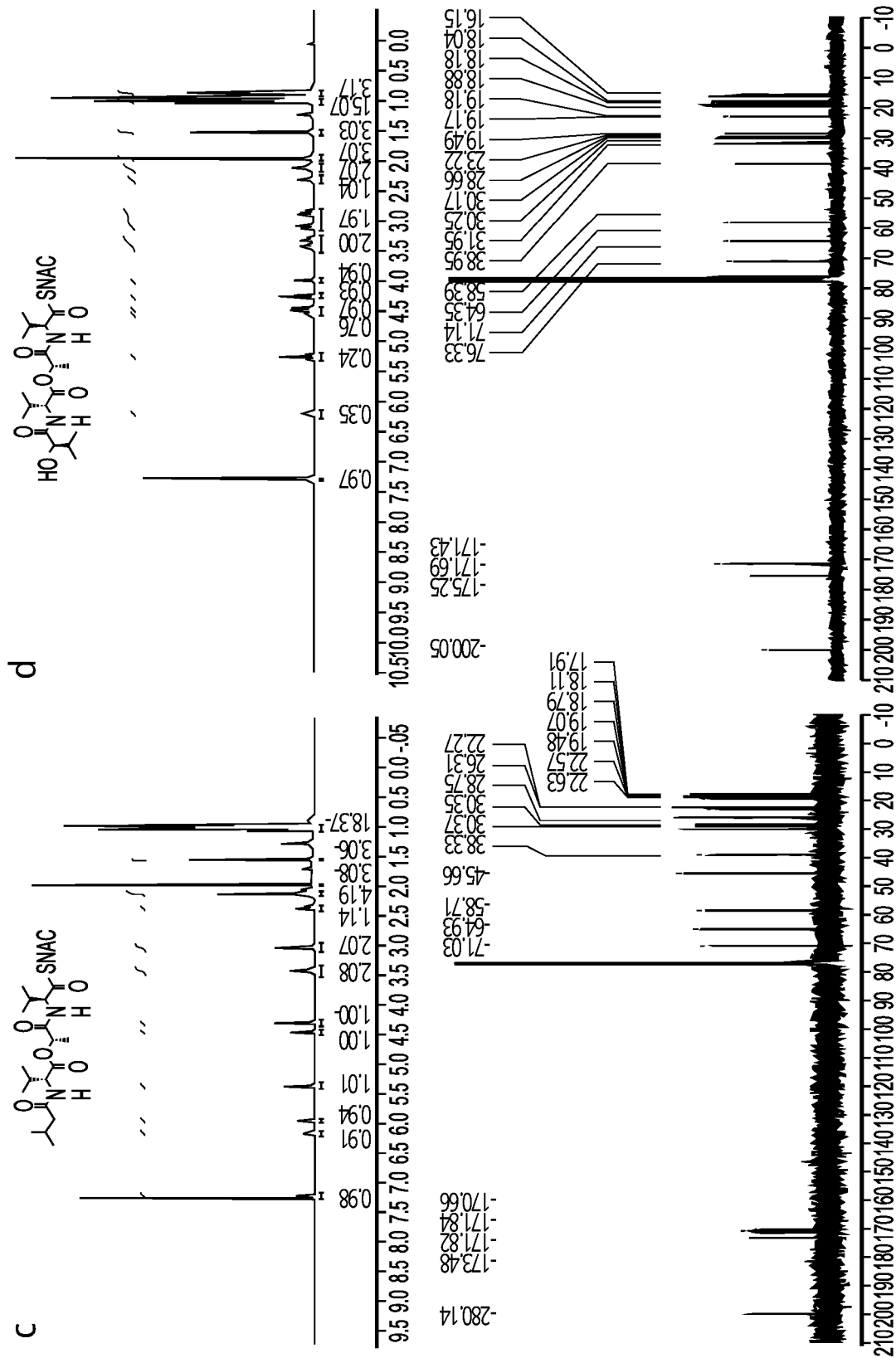
Figure 14:
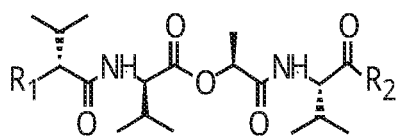
Figure 14:
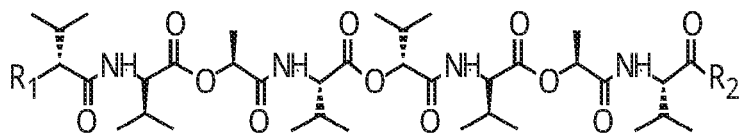
Figure 14:
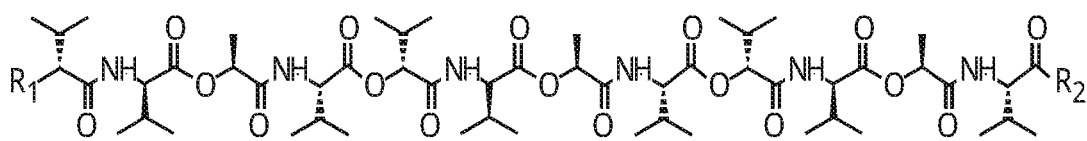
Figure 14:
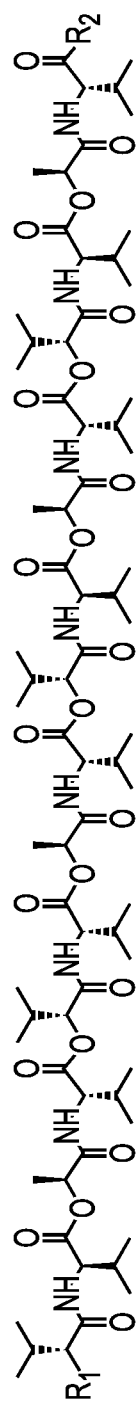
Figure 14:
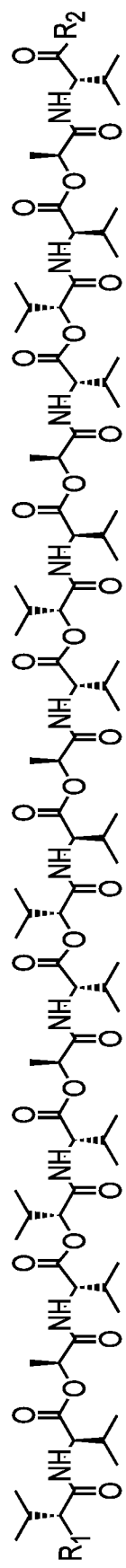
Figure 14:
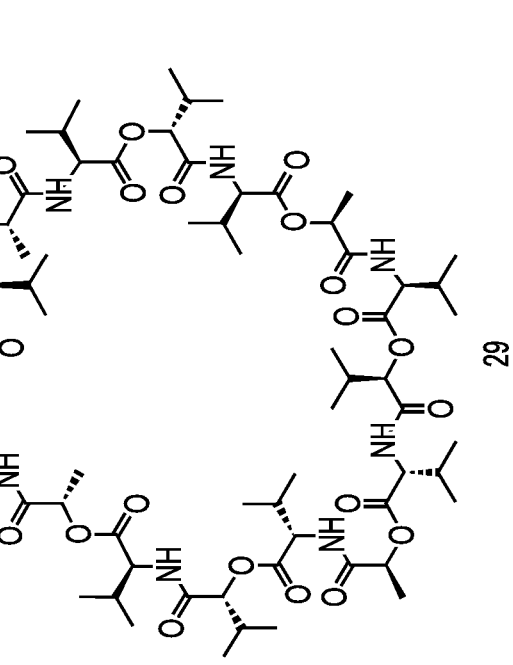
Figure 14:
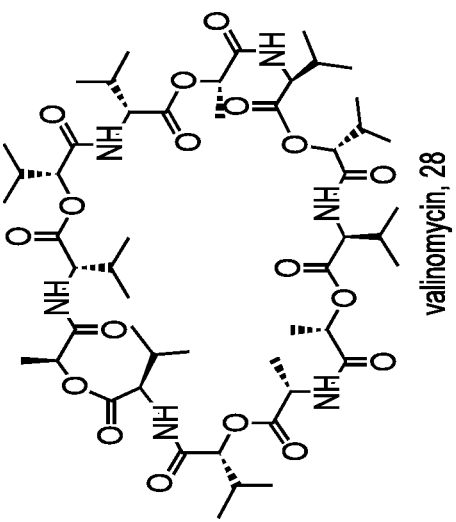
Figure 15:
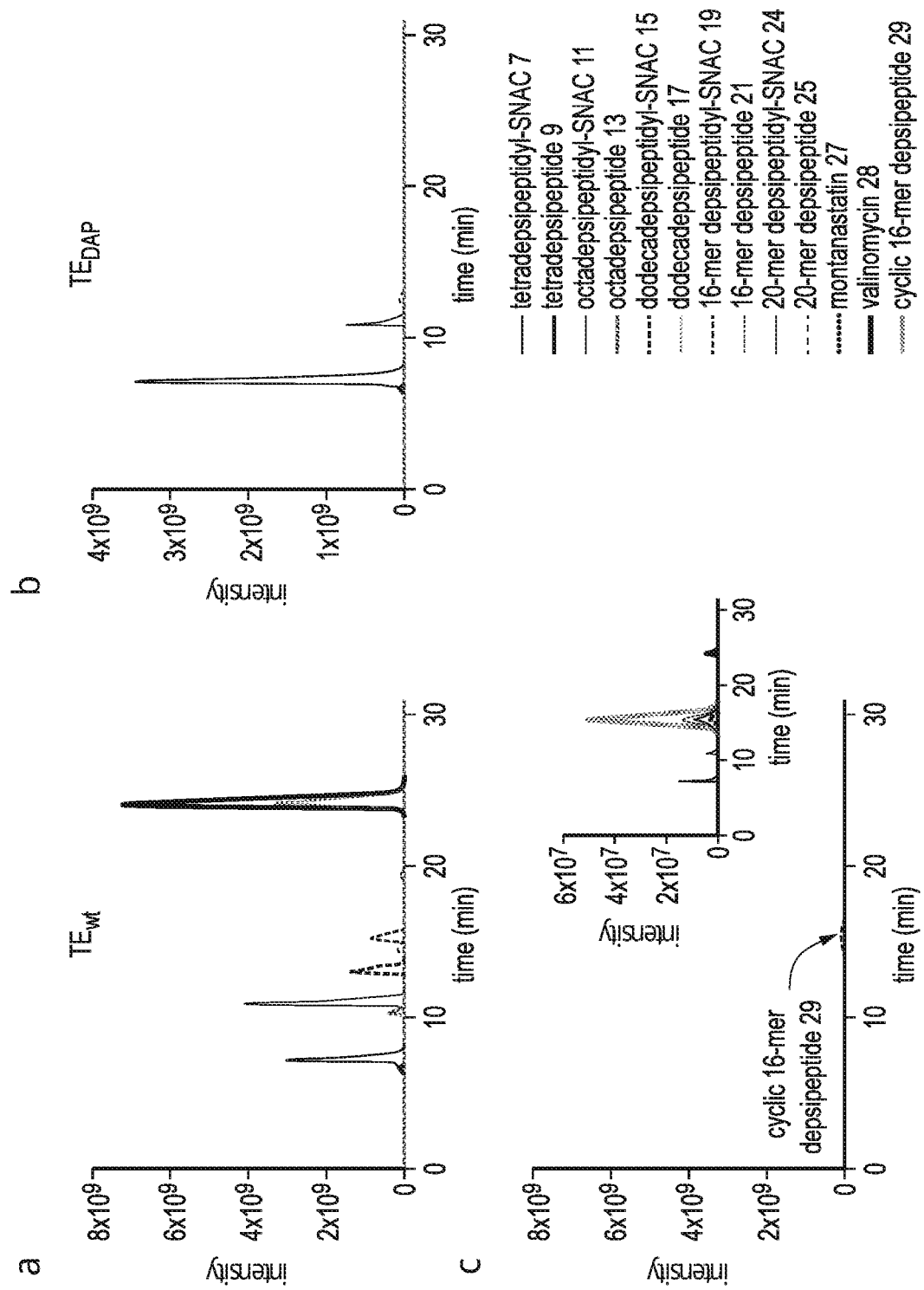
Figure 16:
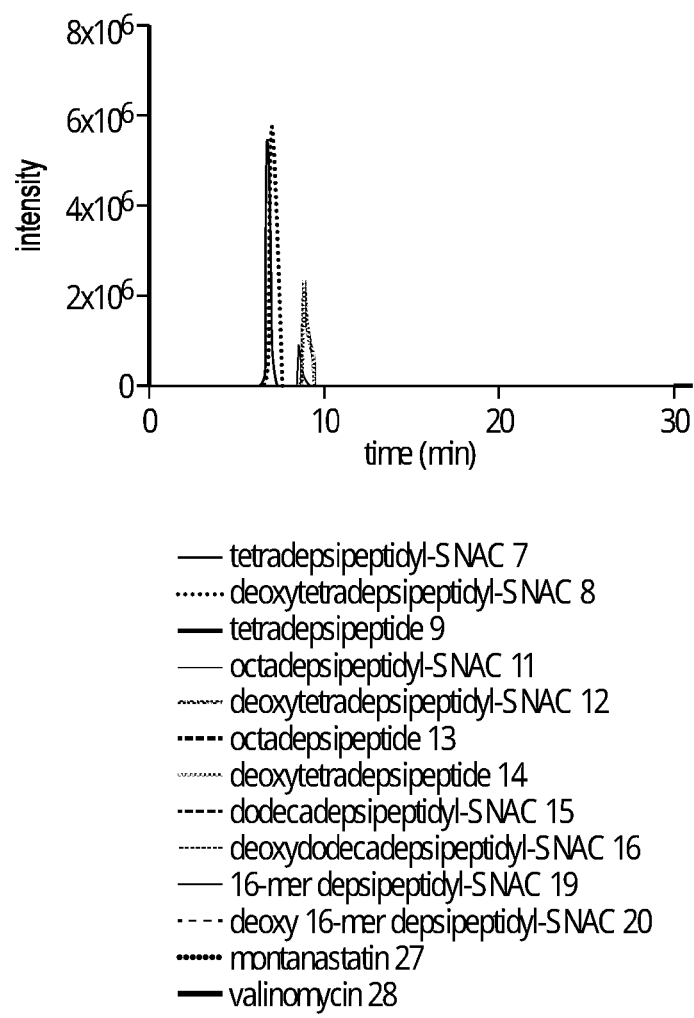
Figure 17:
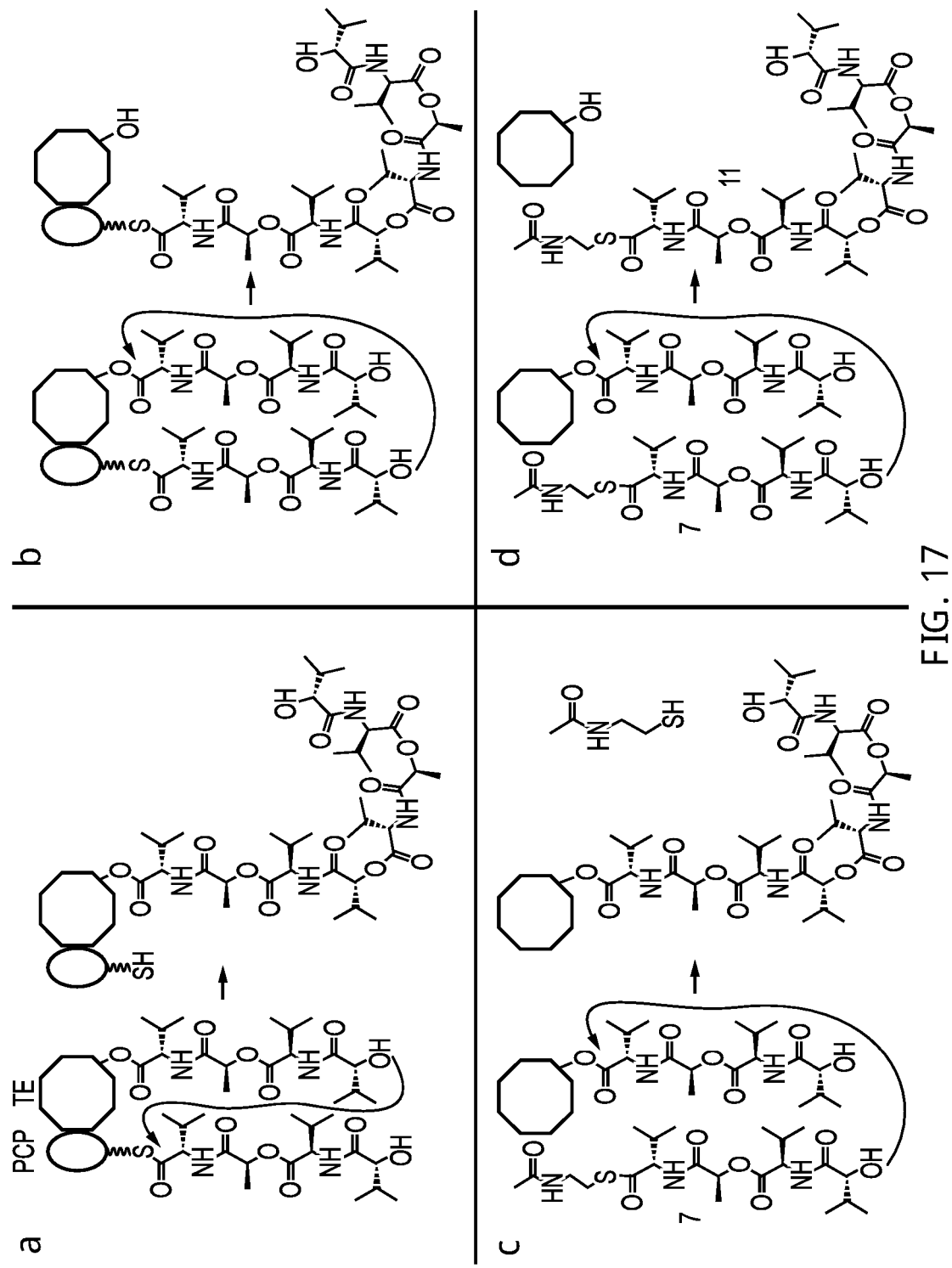
Figure 18:
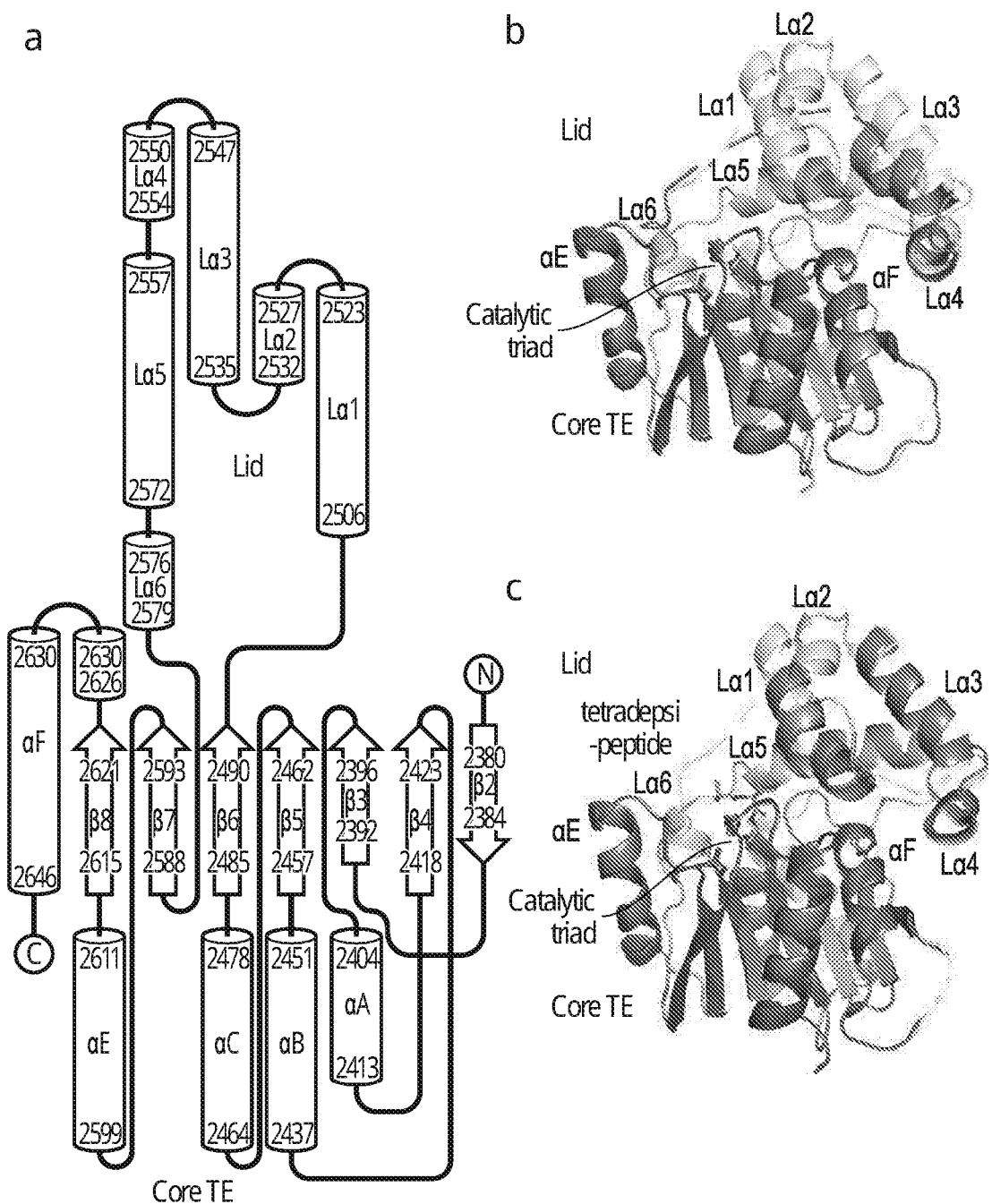

FIG. 8 shows supplementary FIG. 1.
FIG. 9 shows supplementary FIG. 2.
FIG. 10 shows supplementary FIG. 3.
FIG. 11 shows supplementary FIG. 4.
FIG. 12 shows supplementary FIG. 5.
FIG. 13 shows supplementary FIG. 6.
FIG. 14 shows supplementary FIG. 7.
FIG. 15 shows supplementary FIG. 8.
FIG. 16 shows supplementary FIG. 9.
FIG. 17 shows supplementary FIG. 10.
FIG. 18 shows supplementary FIG. 11.

Figure 19:
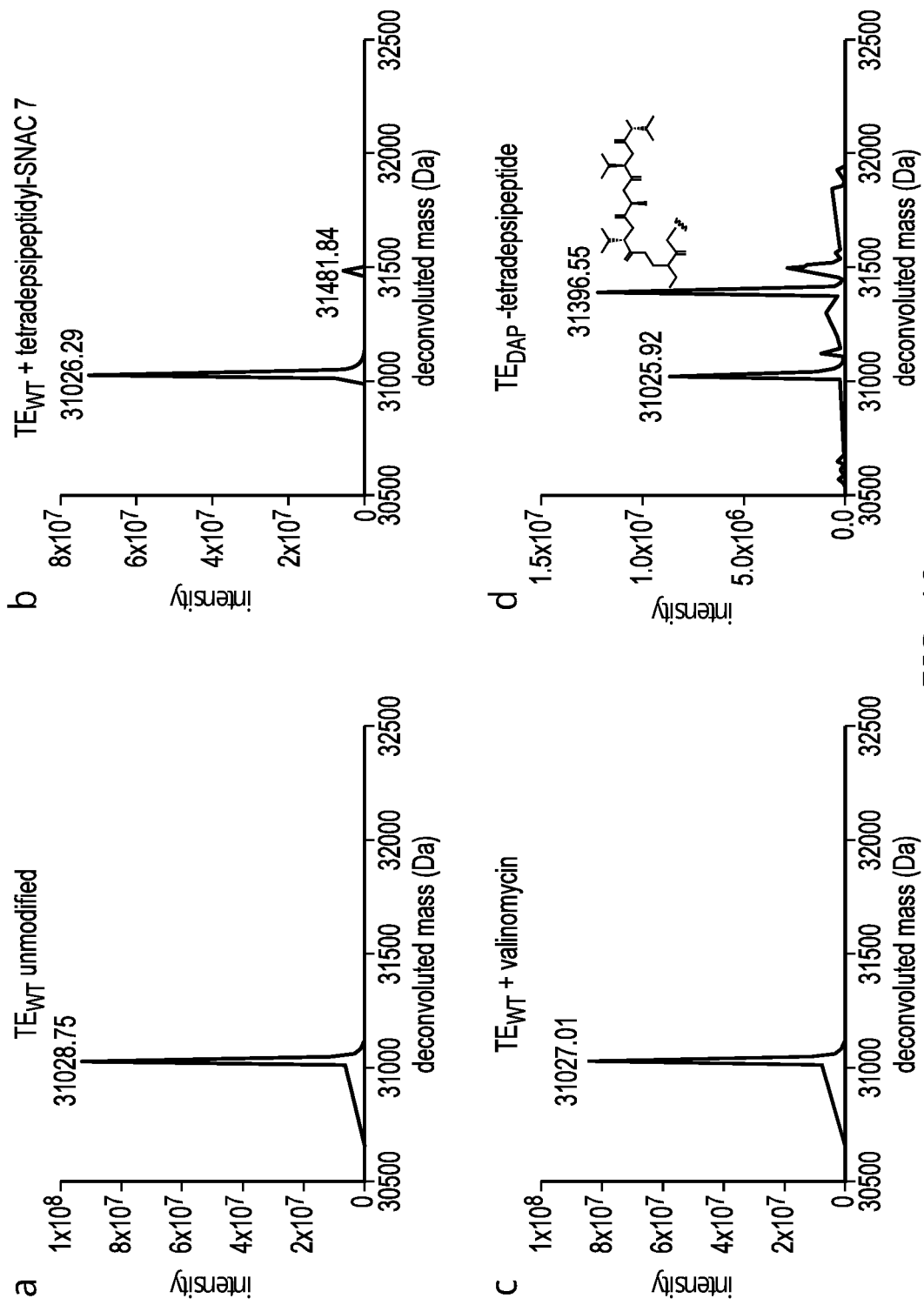
Figure 20:
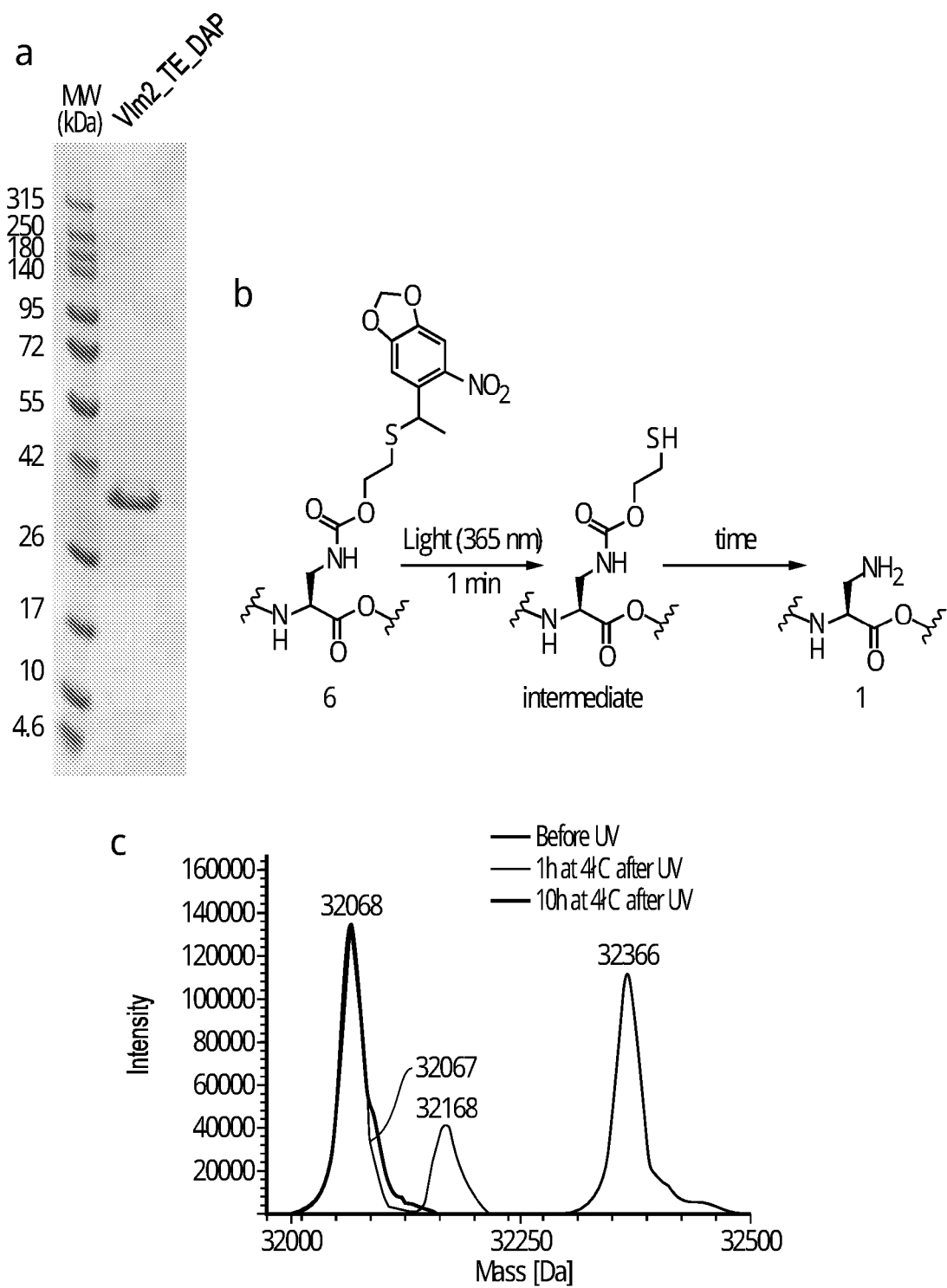
Figure 21:
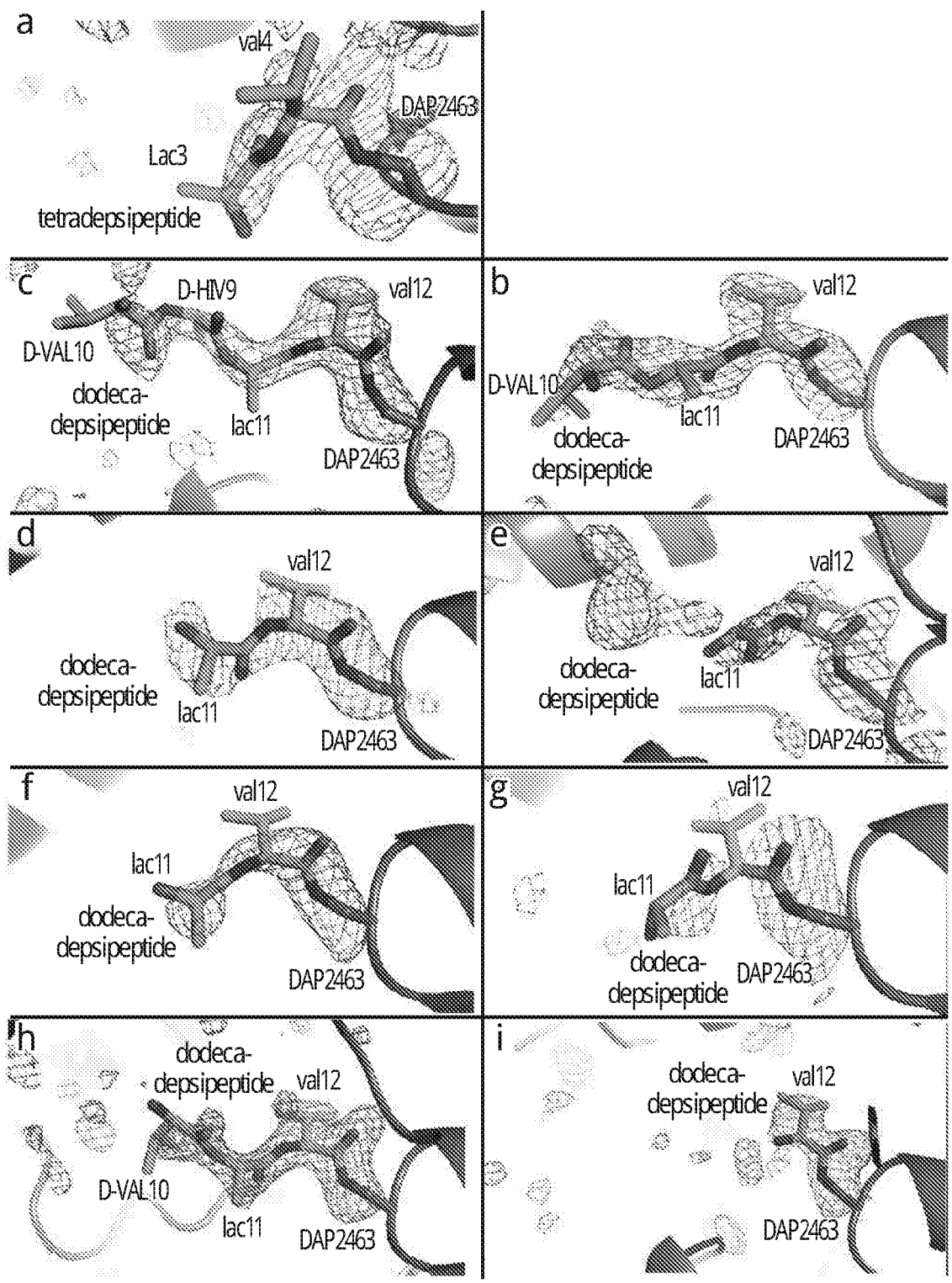
Figure 22:
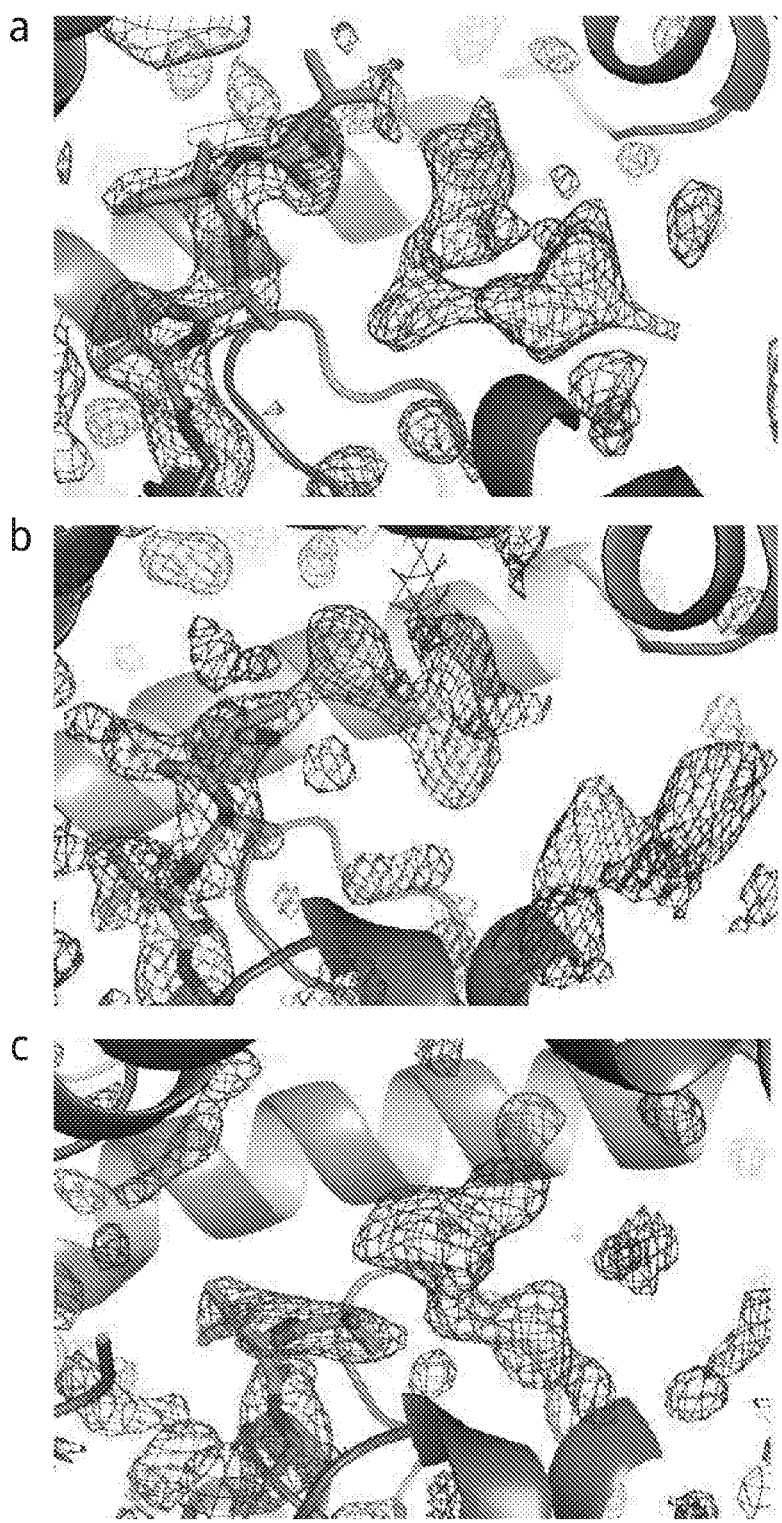
Figure 23:
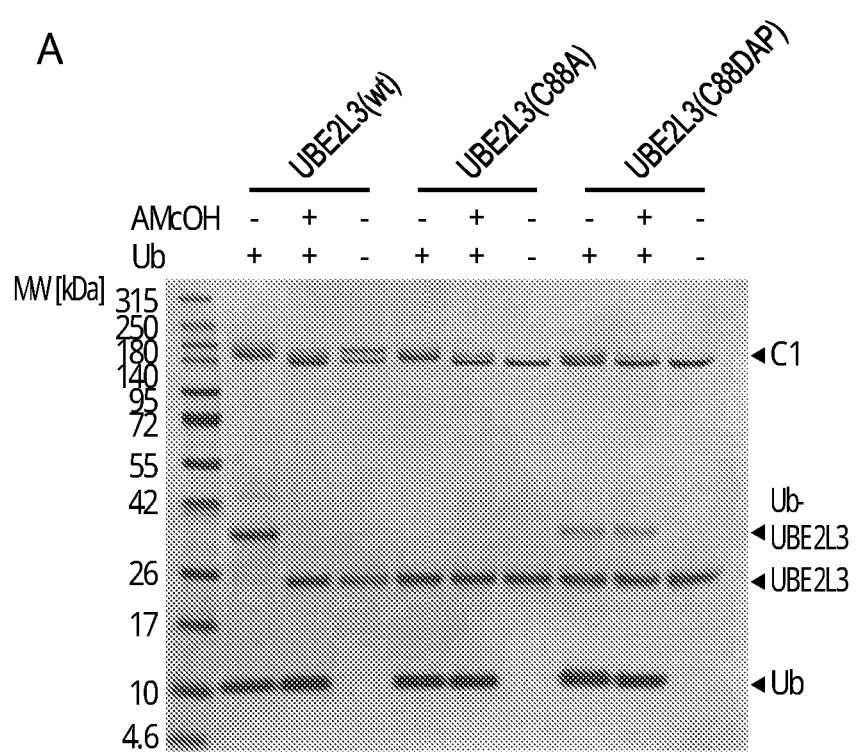
Figure 23:
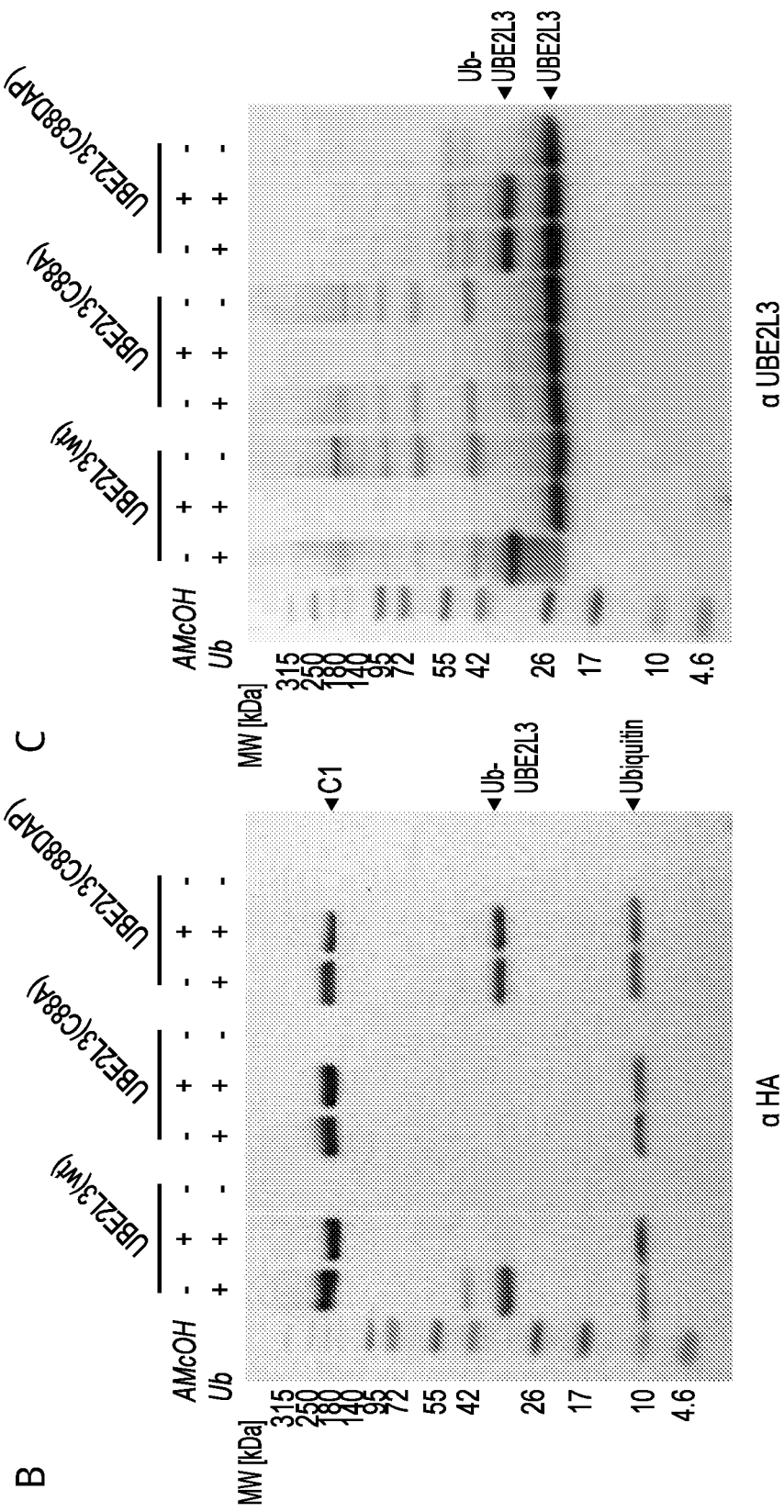
Figure 24:
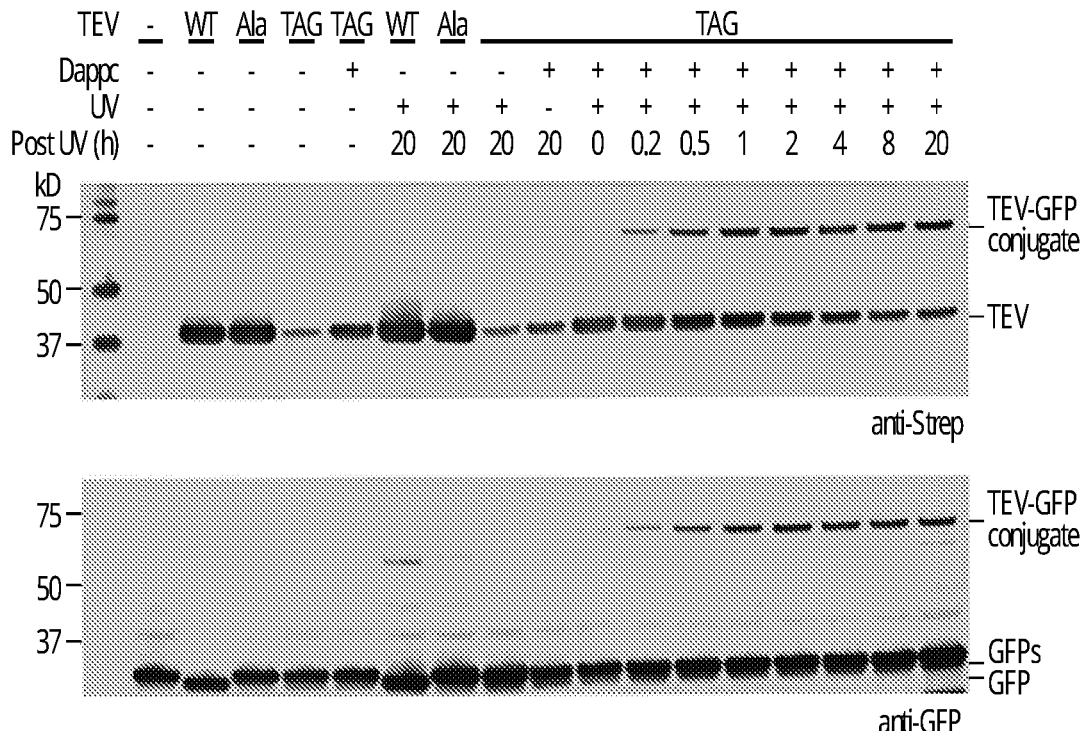
Figure 25:
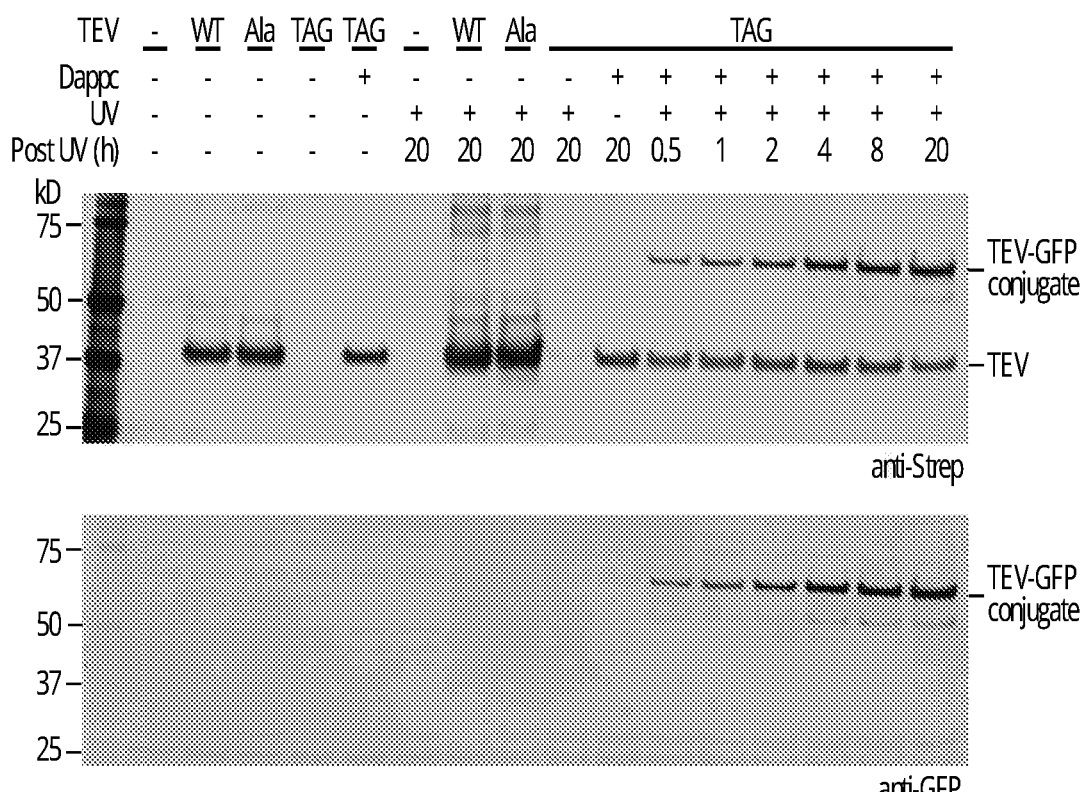

FIG. 19 shows supplementary FIG. 12.
FIG. 20 shows supplementary FIG. 13.
FIG. 21 shows supplementary FIG. 14.
FIG. 22 shows supplementary FIG. 15.
FIG. 23 shows photographs. Ubiquitination test with UBE2L3(C86DAP). A: Coomassie staining of a ubiquitination reaction with either UBE2L3(wt), UBE2L3(C86A) or UBE2L3(C86DAP), in the presence or absence of Ub and ß-mercaptoethanol. αHA (B) and αUBE2L3(111-125) (C) western-blots of ubiquitination reactions with either UBE2L3(wt), UBE2L3(C86A) or UBE2L3(C86DAP), in the presence or absence of Ub and ß-mercaptoethanol. Ub-UBE2L3: Thioester-linked (UBE2L3[wt]) or isopeptidelinked (UBE2L3[C86DAP]) E2-Ub complex. The complex formed between UBE2L3(C86DAP) and Ub is not sensitive to the presence of ß-mercaptoethanol, unlike the complex between UBE2L3(wt) and Ub, with is reduced in the presence of ß-mercaptoethanol
FIG. 24 shows photographs.
FIG. 25 shows photographs.

EXAMPLES: GENETICALLY ENCODING DAP DERIVATIVES IN RECOMBINANT PROTEINS

Example 1

The inventors reasoned that the structural similarity of DAP to cysteine and serine, which are constitutively present in the cell, suggests that it may be challenging to discover an aminoacyl-tRNA synthetase that selectively incorporates DAP. We therefore designed and synthesized (FIG. 3a, Supplementary FIG. 2) four protected versions of DAP (compounds 2-5). We anticipated that the discovery of aminoacyl-tRNA synthetase-tRNA$_{CUA}$ pairs for these amino acids would enable their site-specific incorporation into proteins, and that post-translational deprotection of the encoded amino acids, via transition metal catalysis[30] (2) or light[31] (3-5), would reveal DAP.

Compounds 3 and 4 contain a conservative SH to NH$_2$ substitution relative to photocaged cysteine derivatives that we have previously incorporated into proteins using the PCC1RS/tRNA$_{CUA}$ and PCC2RS/tRNA$_{CUA}$ pairs, respectively[32]. (These pairs were derived from the pyrrolysyl-tRNA synthetase/tRNA$_{CUA}$ pair). This similarity suggested that these pairs might direct the incorporation of 3 or 4 in response to the amber codon. However, we found that these pairs did not function to suppress amber codons in reporter genes when cells were provided with 3 or 4 and the relevant pair.

In an effort to discover orthogonal aminoacyl-tRNA synthetases that incorporate amino acids 2-5, we interrogated five variant libraries (Susan1, Susan2[32], Susan4, PylS fwd[33] and D3 (Supplementary Table 1)) of the MbPylRS/tRNA$_{CUA}$ pair. These libraries randomize residues in the active site of the synthetase, and were previously generated to enable ncAA incorporation. The Susan2 library has previously been used to discover synthetases for photocaged derivatives of cysteine[32]. We subjected each library to two rounds of serial positive selections in the presence of each ncAA and one round of negative selections in the absence of ncAA[34-36]. However, we did not discover a synthetase/tRNA pair for compounds 2-5 from these selections.

Examination of the predicted log P values for compounds 2-5 revealed that they are quite hydrophilic; prompting us to examine whether they enter cells. Using an LC-MS based amino acid uptake assay[37] we did not detect substantial quantities of amino acids 2-5 in cells, and our data suggest that the intracellular concentrations of compounds 2-5 are substantially below 10 µM (FIG. 3b-e). These observations suggest that compounds 2-5 are not efficiently taken up by E. coli, or they are metabolized; this may explain why it was not possible to select synthetases for incorporating these amino acids in vivo.

Example 2: Preferred Unnatural Amino Acid Comprising DAP

To address the challenge of encoding a protected version of DAP, the inventors designed and synthesized amino acid 6 (Supplementary FIG. 2), which we anticipated could be post-translationally deprotected to reveal the sidechain amine. This amino acid has a more favourable predicted log P value than amino acids 1-5, and we found that the addition of 1 mM 6 to cell media led to an intracellular concentration of approximately 2 mM (FIG. 3f). Thus, in contrast to amino acids 2-5, amino acid 6 can accumulate in E. coli at millimolar concentrations.

Example 3: Creation of DAP tRNA Synthetase ('DAPRS')

In light of the failure of numerous earlier approaches, the inventors devised and created a completely new library, DAPRSlib, in which positions to be randomised were carefully chosen based on a model of 6 in the active site of PylRS (Supplementary FIG. 3 and Supplementary Table 1).

As a result of this intellectual exercise, decisions were made that five positions (Y271; N311; Y349; V366; W382) were randomised to all twenty canonical amino acids, leading to a theoretical library diversity of 3.4×10$^7$ different sequences. We subjected DAPRSlib to three rounds of serial positive and negative selection[34] in the presence and absence of 6. Following this selection, we screened 96 clones in cells containing a cat(112TAG) reporter.

We obtained a single clone that conferred high levels of chloramphenicol resistance in the presence of 6 and minimal chloramphenicol resistance in the absence of 6 (FIG. 3g).

The selected synthetase contains four active-site mutations (Y271C, N311Q, Y349F and V366C) with respect to MbPylRS.

(It may be noted that the library contained randomised 5 positions but only 4 mutations are present in DAPRS—the 5th position is wild-type (i.e. W382) in DAPRS.)

Example 4: Incorporation of Unnatural Amino Acid Comprising DAP into a Polypeptide To further characterize the genetically directed, site-specific incorporation of 6 into a protein, superfolder green fluorescent protein (sfGFP) containing an amber stop codon (TAG) at position 150 (sfGFP(150TAG)His6) was expressed in the presence of DAPRS/tRNA$^{Pyl}_{CUA}$ and 1 mM 6, and purified by Ni-NTA affinity chromatography (FIG. 3h and Supplementary FIG. 4a). As a benchmark, the same gene was expressed in the presence of PylRS/tRNA$^{Pyl}_{CUA}$ and 1 mM of N$^\varepsilon$-tert-butyloxycarbonyl-lysine (BocK), which is known to lead to efficient amber suppression[38].

The yield of GFP incorporating 6 (GFP(6)), was comparable to that for BocK incorporation, demonstrating the efficiency of the DAPRS/tRNA$^{Pyl}_{CUA}$ pair. Electrospray ionization mass spectrometry (ESI-MS) confirms that the DAPRS/tRNA$^{Pyl}_{CUA}$ pair directs the incorporation of 6 into proteins in response to the amber codon (FIG. 3i, j).

Example 5: Deprotection of Amino Acid Comprising DAP

Here we demonstrate deprotection of the amino acid comprising DAP, leaving the DAP group in the polypeptide backbone, thereby resulting in a polypeptide comprising DAP.

We anticipated that illumination of proteins incorporating amino acid 6 with 365 nm light would reveal a sulfhydryl group containing intermediate, that may undergo further reactions that lead to DAP (either through 5 exo-trig cyclization of the sulfhydryl group onto the carbonyl of the carbamate and collapse of the resulting tetrahedral intermediate to release the amino group, or through formation of the episulfide and carbon dioxide to release the amino group). Indeed, illumination of GFP(6) (365 nm, 35 mWcm$^{-2}$, 1 min) led to complete deprotection of 6 to the expected sulfhydryl (FIG. 3$i, j$). Subsequent incubation of the protein at 37° C., led to complete deprotection of the desired amino group, revealing amino acid 1 in GFP (FIG. 3$i, j$).

Example 6: Stably Trapping a Cysteine Protease Acyl-Enzyme Intermediate

Cysteine proteases like the tobacco etch virus (TEV) protease commonly contain a Cys-His-Asp catalytic triad and generate a thioester intermediate upon treatment with their cognate substrates[5, 39]. We thus aimed to replace the active site cysteine of the TEV protease with DAP and trap the acyl-enzyme intermediate. *E. coli* provided with 0.1 mM 6 and expressing His6-Lipoyl-TEV(151TAG)-Strep, and the DAPRS/tRNA$^{Pyl}_{CUA}$ pair were used to produce TEV$_{Cys151 6}$ protease, in which 6 replaces the catalytic cysteine in the active site. The protein was purified by tandem affinity chromatography with a yield of ~0.1 mg per litre of culture, and ESI-MS confirmed the incorporation of 6 at the genetically encoded site. Photodeprotection quantitatively converted encoded 6 to the sulfhydryl intermediate, and approximately 70% of the protein was subsequently completely deprotected to reveal amino acid 1 at position 151 of TEV (TEV$_{DAP}$), as judged by ESI-MS (Supplementary FIG. 5).

To demonstrate that replacing the catalytic cysteine with DAP enables the capture of a covalent protease-substrate intermediate, we incubated TEV$_{DAP}$ with a model substrate, Ub-tev-His6 (in which the TEV cleavage site (tev) is flanked by ubiquitin and the hexahistidine tag) and resolved the protein species by SDS-PAGE. We observed the formation of a new band that migrated more slowly than TEV$_{DAP}$, and did not observe free ubiquitin, which would have been generated by cleavage of the tev site (FIG. 4$a$ and Supplementary FIG. 4). Western blots show that the new band contains both TEV and ubiquitin (FIG. 4$a$). Control experiments confirm that wild-type TEV cleaves Ub-tev-His6 to the more rapidly migrating Ub, and that TEV(C151A) does not cleave Ub-tev-His6 (FIG. 4$a$). These experiments demonstrate that the Cys151DAP substitution is essential for formation of the slower mobility band that contains TEV and Ub, and that Ub is not released from the TEV$_{DAP}$ mutant. Tryptic MS/MS of the slower mobility band identifies the isopeptide linkage between DAP and Ub, confirming formation of the TEV$_{DAP}$-Ub (FIG. 4$b$). Therefore, the substitution of the catalytic cysteine in TEV with DAP enables the creation of a protease that goes through the first step of the protease cycle: nucleophilic attack on the substrate carbonyl to form the first tetrahedral intermediate. This intermediate collapses, releasing the C-terminal fragment of the substrate and leaving the N-terminal fragment of the substrate covalently attached to the protease, through a stable amide bond that is not subject to hydrolysis.

Example 7: Activity and Synthetic Pathway of Vlm TE

To gain insight into TE domain function and to prepare it for use with the DAP incorporation system, we cloned and expressed Vlm TE, and purified the resulting Vlm TE (TE$_{wt}$, wild type) protein for biochemical and structural studies. The native substrate of TE domains is the peptide intermediate linked by thioester to the phosphopantetheine-PCP (peptidyl-PCP). In NRPS TE domains, including those from gramicidin S, surfactin and fengycin synthetases[18, 27, 28], the PCP-linked substrates can be mimicked by a small molecule in which the peptide intermediate is linked by a thioester to N-acetylcysteine (peptidyl-SNAC). We synthesized the SNAC derivative of the native peptide, D-hiv-D-val-L-lac-L-val-SNAC (tetradepsipeptidyl-SNAC 7, Supplementary FIG. 6 and Supplementary FIG. 7), and found that its incubation with Vlm TE$_{wt}$ led to production of valinomycin (FIG. 5, Supplementary FIG. 8, 9 and Supplementary Table 2). This demonstrates that Vlm TE$_{wt}$ can use tetradepsipeptidyl-SNAC 7 to complete all stages of its catalytic cycle: oligomerization of the tetradepsipeptide intermediate to octadepsipeptide, oligomerization of octadepsipeptide to dodecadepsipeptide, and cyclization of dodecadepsipeptide to release valinomycin.

The synthetic intermediates detected in valinomycin synthesis reveal the oligomerization pathway catalyzed by Vlm TE$_{wt}$, differentiating between two possible pathways (Supplementary Figure to)[18, 40]. Vlm TE$_{wt}$ could potentially oligomerize D-hiv-D-val-L-lac-L-val moieties by ester bond formation between the distal hydroxyl of D-hiv in tetradepsipeptidyl-O-TE and the carbonyl of L-val from tetradepsipeptidyl-S-PCP ("forward transfer"), or else by ester bond formation between the distal hydroxyl of D-hiv in tetradepsipeptidyl-S-PCP and the carbonyl of L-val from tetradepsipeptidyl-O-TE ("reverse transfer", so called because the octadepsipeptide would later be transferred again to the TE domain). The LC-MS of reactions of valinomycin synthesis from tetradepsipeptidyl-SNAC 7 showed signal for masses corresponding to octadepsipeptidyl-SNAC 11 and dodecadepsipeptidyl-SNAC 15, intermediates that are produced only in the "reverse transfer" oligomerization pathway (Supplementary FIG. 7 and Supplementary Figure to). Consistently, experiments using a mixture of tetradepsipeptidyl-SNAC 7 and tetradepsipeptidyl-SNAC missing the terminal hydroxyl (deoxy-tetradepsipeptidyl-SNAC 8), showed peaks for deoxy-octadepsipeptidyl-SNAC 12 and deoxy-dodecadepsipeptidyl-SNAC 16 (Supplementary FIG. 9). That oligomerizing-cyclizing depsipeptide synthetases use an analogous pathway to the more canonical gramicidin S synthetase[18, 40] suggests that all oligomerizing-cyclizing NRPS's (or PKS's[41]) will use this synthetic scheme. Lastly, the valinomycin synthesis assay also shows small peaks corresponding to the 16-mer depsipeptidyl-SNAC 19, the 20-mer depsipeptidyl-SNAC 23 and the cyclic 16-mer depsipeptide 29, indicating that the Vlm TE domain has somewhat more flexibility in final product than previously thought (FIG. 5 and Supplementary FIG. 8).

Example 8: Visualizing Key Intermediates in TE Domain-Mediated Valinomycin Synthesis We next obtained and optimized crystallization conditions for robust and repeatable growth of TE$_{wt}$, and determined its structure (FIG. 6, Supplementary FIG. 11, and Supplementary Table 3). Vlm TE adopts the a/P hydrolase fold typical of type I TE domains, with a canonical Ser-His-Asp catalytic triad of Ser2463, His2625 and Asp2490[42] covered by the TE "lid". The lid is a structural element known to be mobile, suggested to play roles in TE domain function which vary from substrate positioning to exclusion of solvent[27, 43, 44]. Although composition can vary substantially, a typical lid is composed of ~50 residues and ~2-4 helices. The Vlm TE lid region is ~88 residues (~2494-2582), and is composed of an extended loop, three helices (L$\alpha$1-3) which are seen here as a bundle, a short, 5-residue helix (L$\alpha$4), a long helix (L$\alpha$5) and another short helix (L$\alpha$6) (FIG. 6b). We obtained two structures of $TE_{wt}$ which differ only in the lid region. In one structure, the lid is nearly completely ordered, although the B factors are markedly higher for the region including L$\alpha$1-4, which makes almost no contact with the rest of the domain (Supplementary FIG. 11b). In the second $TE_{wt}$ structure, L$\alpha$4-5 have similar positions to those observed in the first structure, whereas L$\alpha$3 is rotated 10° towards the active site and L$\alpha$1-2 are too disordered to model.

Incubation of Vlm TE with depsipeptidyl-SNAC molecules did not yield stable conjugates (Supplementary FIG. 12a-c and Supplementary Table 4), and several attempts to soak $TE_{wt}$ crystals with depsipeptidyl-SNAC molecules failed to reveal interpretable ligand electron density in the active site or conformational changes in the surrounding area. Other groups have reported similar setbacks when attempting to visualize acyl-enzyme complexes from SNAC molecules (Supplementary Table 6)[27, 29]. We conclude that acyl-intermediates in Vlm TE-mediated synthesis of valinomycin rapidly hydrolyse, and thus, as expected, it will be exceptionally challenging to use wild type Vlm TE to visualize biosynthetic intermediates through crystallography.

To enable the visualization of acyl-enzyme complexes of Vlm TE, we produced Vlm TE in which the active site serine 2463 was replaced by DAP ($TE_{DAP}$). Expression of Vlm2TE (2463TAG) in *E. coli* containing a DAPRS/tRNA$_{CUA}$ pair and supplemented with 0.1 mM 6 enabled the purification of Vlm TE in which serine 2463 is replaced by 6, with a yield of ~0.1-0.5 mg per litre of culture. Deprotection of 6 led to quantitative production of $TE_{DAP}$ (FIG. 6c and Supplementary FIG. 13).

To provide insight into the first acyl-TE intermediate in the catalytic cycle of Vlm TE, we captured a tetradepsipeptidyl-N-$TE_{DAP}$ conjugate. Incubation of $TE_{DAP}$ with tetradepsipeptidyl-SNAC 7 led to production of a stable depsipeptidyl-$TE_{DAP}$ intermediate at >60% yield (Supplementary FIG. 12d and Supplementary Table 4), and we did not observe valinomycin synthesis. However, remarkably, a small amount of octadepsipeptidyl-SNAC 11 was observed (FIG. 5b and Supplementary FIG. 8b). The octadepsipeptidyl-SNAC 11 is likely formed by $TE_{DAP}$-catalyzed attack of the hydroxyl group of the tetradepsipeptidyl-SNAC 7 on tetradepsipeptidyl-N-$TE_{DAP}$, indicating that $TE_{DAP}$ has the power to successfully catalyze the attack of a hydroxyl on an amide. This reaction is evidently much slower than the more isoenergetic ester-for-ester reaction, as only a small amount of octadepsipeptidyl-SNAC 11 was formed. The attack of a hydroxyl on an amide is analogous to the first reaction employed by related serine proteases[45], in which the substrate peptide backbone is cleaved from the ester-linked acyl-enzyme intermediate. However, it is surprising that this TE domain, which did not evolve to perform this reaction, was capable of catalysing it.

We hypothesized that $TE_{DAP}$-catalyzed attack of the hydroxyl group of the tetradepsipeptidyl-SNAC 7 on the tetradepsipeptidyl-N-$TE_{DAP}$ conjugate might contribute to the observed non-quantitative yield of the conjugate. Therefore, we optimized conditions for conjugating deoxy-tetradepsipeptidyl-SNAC 8 with $TE_{DAP}$, which produced (~70%) the deoxy-depsipeptidyl-$TE_{DAP}$ conjugate (FIG. 6d and Supplementary Table 4).

To determine the structure of the deoxy-tetradepsipeptidyl-N-$TE_{DAP}$ conjugate, we incubated pre-formed $TE_{DAP}$ crystals with the deoxy-tetradepsipeptidyl-SNAC 8 substrate analogue. The resulting electron density shows somewhat weak, but unambiguous density for an amide bond between residue DAP2463 and L-val4 of the deoxy-tetradepsipeptide (FIG. 6f, h). The carbonyl oxygen of the L-val4 position is close to backbone amides of residues Ala2399 and Leu2464, the putative oxyanion hole[28]. There is also density for the next residue, L-lac3, but it is insufficient to reliably model the adjacent D-val2 and D-hiv1 as the deoxy-tetradepsipeptide arcs out, indicative of flexibility. The deoxy-tetradepsipeptide does not make any interactions with the lid, which is in a conformation nearly identical to that in the first $TE_{wt}$ structure (Supplementary FIG. 11b).

Next, we focussed on gaining insight into the last acyl-TE intermediate in the catalytic cycle of Vlm TE by capturing a dodecadepsipeptidyl-N-$TE_{DAP}$ conjugate. We reasoned that incubation of valinomycin and $TE_{DAP}$ might lead to dodecadepsipeptidyl-N-$TE_{DAP}$ through a reaction analogous to the reverse of cyclisation, and that this conjugate would be thermodynamically favoured by virtue of the amide bond. Indeed, under optimized conditions we observed dodecadepsipeptidyl-N-$TE_{DAP}$ conjugate formation in ~65-100% yield (FIG. 6e and Supplementary Table 4). Crystallization trials with dodecadepsipeptidyl-$TE_{DAP}$ produced crystals in similar conditions to those of $TE_{wt}$, but with a different morphology and belonging to two different space groups (H3 and P1, with 2 and 6 molecules per asymmetric unit, respectively) (Supplementary Table 3).

All eight crystallographically independent molecules of dodecadepsipeptidyl-$TE_{DAP}$ showed some density for the dodecadepsipeptide. Molecules P1_A-F and H3_A-B show strong density for 4, 3, 2, 2, 2, 2, 3 and 1 dodecadepsipeptide residues respectively (Supplementary FIG. 14). Additional weaker density is present in some molecules which could accommodate up to the full 12 residues (Supplementary FIG. 15), and in others weaker density suggests multiple conformations for the distal residues, but it was not possible to definitively model into this density. The modelled depsipeptides all follow a similar trajectory away from the active site DAP. There is no consistent interaction between the depsipeptide beyond the L-val residue attached to DAP and the TE domain (FIG. 6g, i). Rather, each depsipeptide makes different contacts with the lid. The lid forms a semi-sphere-like pocket/steric barrier made up of helices L$\alpha$1, 3, 4 and 5, and the strand N-terminal to L$\alpha$1. The lid of each crystallographically independent molecule of dodecadepsipeptidyl-$TE_{DAP}$ is in a similar but non-identical position, and the loops between lid helices are disordered in most of the molecule (FIG. 6k). This again highlights the mobility of the lid and explains why the conformation and extent of order of the dodecadepsipeptidyl differ between molecules (FIG. 6k). The semi-sphere-like barrier occurs only because of a major rearrangement of the lid in the dodecadepsipeptidyl-$TE_{DAP}$ structures with respect to the conformation of the lid seen in both the apo and tetradepsipeptidyl-bound structures of Vlm TE (FIG. 6l).

Comparing the position of the Vlm TE lid in the apo/tetradepsipeptide-bound structures with the position of the lid in the dodecadepsipeptide-bound structures demonstrates and emphasizes its extreme mobility. To transition from one lid conformation to the other, helices Lα5-6 maintain their position, Lα3-4 rotate ~45° and translocate ~13 Å, Lα2 translocates ~25 Å, and Lα1 shortens, translocates ~13 Å, and rotates >90° in the opposite direction to Lα3-4 (FIG. 6l, Supplementary Animation 1, 2). This dramatic re-arrangement means the lid helices of Vlm TE pack together in a markedly different manner in the apo/tetradepsipeptidyl-bound structure and in dodecadepsipeptidyl-bound conformations.

The distinct lid conformations directly influence the possible location of the depsipeptide. In the apo/tetradepsipeptide-bound conformation of the lid, the C-terminus of helix Lα1 comes within 10 Å of Ser/DAP2463, leading the tetradepsipeptide to extend towards the TE core helix αE. In the dodecadepsipeptide-bound conformations of the lid, the loop adjacent to Lα1 blocks the location occupied by the tetradepsipeptide in the tetradepsipeptide-bound structure. Moreover, in the dodecadepsipeptide-bound structure the N-terminus of Lα1 forms part of the semi-sphere-like pocket, which likely helps curl the dodecadepsipeptide back towards Ser/DAP2463 during the cyclization step.

The models and structure factors for the crystal structures are deposited in at the Protein Data Bank with accession numbers 6ECB, 6ECC, 6ECD, 6ECE and 6ECF.

Methods

General Synthetic Procedures.

All reagents were purchased from Sigma-Aldrich with the following exceptions: L-lactic acid was purchased from Fisher Scientific, EDC was purchased from Oakwood Chemicals (Estill, SC) at the highest available purity and used without further purification. Valinomycin was purchased from Sigma-Aldrich and BioShop Canada. All solvents were purchased from Fisher Scientific. All reactions were conducted using dry solvents under an argon atmosphere unless otherwise noted. NMR spectroscopy was performed with a Bruker AVANCE II, operating at 400 MHz for $^1$H spectra, and 100 MHz for $^{13}$C spectra and a Bruker AVANCE 300, operating at 300 MHz for $^1$H spectra, and 75 MHz for $^{13}$C spectra. High-resolution mass spectroscopy (HRMS) was conducted on a Micromass Q-TOF I for ESI measurements (John L. Holmes Mass Spectroscopy Facility).

Abbreviations: M=Molarity; conc.=concentrated; mol=moles; mmol=millimoles; °C.=degree Celcius; eq.=equivalents; h=hour; min=minutes; r.t.=room temperature; cat.=catalytic, aq.=aqueous; Su=succinimidyl; DIPEA=diisopropylethylamine; atm=atmosphere, Boc=tert-butoxycarbonyl; $^t$Bu=tert-butyl; Et=ethyl; Ph=phenyl; TFA=trifluoroacetic acid; THF=tetrahydrofuran; LC-MS=liquid chromatography-mass spectrometry; ELS=evaporative light scattering.

Synthesis of Amino Acids

The general synthetic scheme for preparation of amino acids is shown below, the reagents and conditions used are as follows:

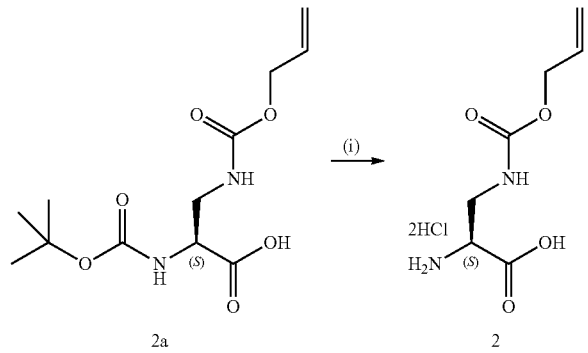

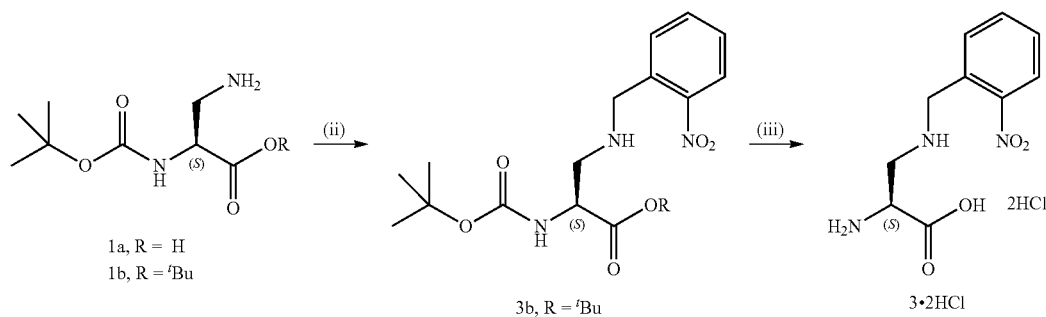

-continued

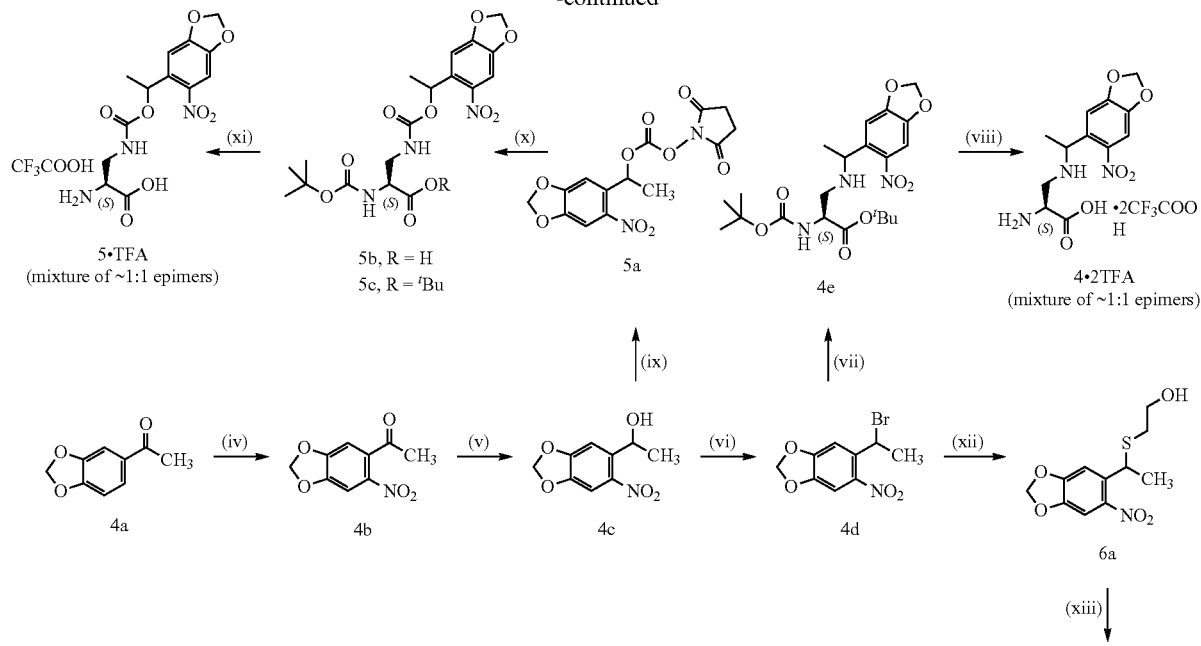

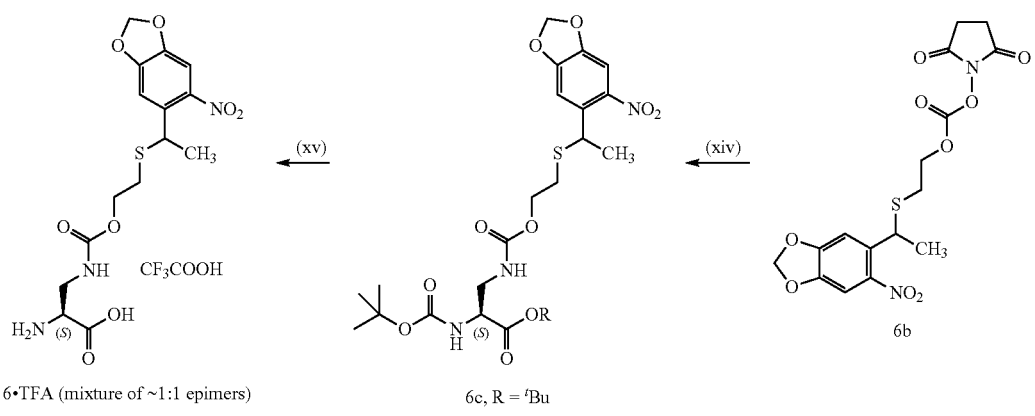

Reagents and Conditions: (i) 2a (10.0 mmol), HCl (4M in 1,4-dioxane) (8.0 eq.), Et₃SiH (2 eq.), r.t., 1 h, 90% (2); (ii) 1b (19.2 mmol), 2-nitrobenzyl bromide (1.2 eq.), DIPEA (2.0 eq.), dry THF, r.t., 10 h, 67% (3a); (iii) 3a (11.6 mmol), HCl (4M in 1,4-dioxane) (8.62 eq.), Et₃SiH (2.7 eq.), r.t., 24 h, 99% (3•2HCl); (iv) 4a (20.0 mmol) in glacial CH₃COOH (1.563M), dropwise addition to conc. HNO₃ (70%), 0° C., 1 h of dropwise addition, then 40° C., 2.5 h, 58% (4b); (v) 4b (209.0 mmol), NaBH₄ (0.9 eq.), portion-wise addition (8 × 15 min), r.t., CH₃OH → C₂H₅OH → CH₂Cl₂ (44:29:27), then 4 h (total time = 6 h), r.t., 99% (4c); (vi) 4c (75.0 mmol), PBr₃ (0.4 eq., dropwise addition), dry CH₂Cl₂, 0° C., then dry pyridine (cat.), 0° C., 15 min, then r.t., 1.5 h, 89% (4d); (vii) Boc-L-Dap-O'Bu 1b (15.0 mmol), 13 (1.2 eq.), DIPEA (3.0 eq., dry THF, r.t., 64 h 82% (4e); (viii) 4e (9.49 mmol) TFA (20.64 eq.), Et₃SiH (6.60 eq.), dry CH₂Cl₂, 73% (4•2CF₃COOH); (ix) 4c (100.0 mmol), Su₂O (1.5 eq.), DIPEA (3.0 eq.), dry CH₃CN, r.t., 16 h, 92% (5a); (x) Method 1: Boc-L-Dap-O'Bu 1b (14.05 mmol), 5a (1.2 eq.), DIPEA (3.0 eq.), dry CH₂Cl₂/dry THF (2:1), r.t. 20 h, 94% (5c); Method 2: 5a (12.5 mmol), Boc-L-Dap-OH 1a (1.25 eq.), DIPEA (3.0 eq.), dry THF/dry CH₃CN (9:1), r.t., 24 h, 99% (5b); (xi) 5b (9.2 mmol), TFA (21.3 eq.), dry CH₂Cl₂, r.t., 99% (5•CF₃COOH); (xii) 4d (21.0 mmol), 2-mercaptoethanol (1.05 eq.), 1,4-dioxane (degassed), aq. NaOH (0.5 M in degassed H₂O, 1.0 eq.), r.t., 12 h, dark, argon atm., 95% (6a); (xiii) 6a (61.0 mmol), Su₂O (1.4 eq.), dry DIPEA (4.0 eq.), dry CH₃CN, r.t., dark, argon atm., 14 h, quant. conv. (6b); (xiv) Method 1: 6b (18.0 mmol) Boc-L-Dap-O'Bu•HCl 1b (1.6 eq.), dry DIPEA (3.0 eq.), dry CH₃CN, r.t., 10 h, dark, argon atm., 94% (6c); Method 2: 6b (60.0 mmol), Boc-L-Dap-OH•HCl 1a (1.1 eq.), dry DIPEA (4.0 eq.), dry CH₃CN, r.t., 14 h dark, argon atm., 96% (6d); (xv) Method 1: 6c (12.066 mmol), TFA (21.647 eq.), dry Et₃SiH (10.378 eq.), dry CH₂Cl₂, r.t., dark 24 h, monitored by LC-MS instrument (reverse phase, H₂O — CH₃CN as mobile phase), product purified by trituration (CH₃OH/Et₂O), 64% (6•TFA); Method 2: 6d (57.626 mmol), TFA (9.065 eq.), dry Et₃SiH (2.173 eq.), dry CH₂Cl₂, r.t., dark, 5 h, monitored by LC-MS instrument (reverse phase, H₂O — CH₃CN as mobile phase), if reaction was incomplete it was left stirring longer with additional TFA (up to 2 eq.), product purified by trituration (dry CH₃OH/Et₂O), 63% (6•TFA);

(S)-3-{[(Allyloxy)carbonyl]amino}-2-aminopropanoic acid (2)

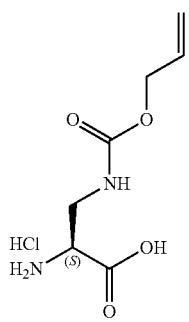

Chemical Formula: C₇H₁₂N₂O₄·HCl
Exact Mass: 188.07971 (without HCl)
Molecular Weight: 224.64100 (with HCl)

Boc-Dap(Alloc)-OH 2a (4.325 g, 15.0 mmol, 1.0 eq., procured from Bachem Ltd.) was loaded onto a dry 250 mL single-necked round-bottomed flask and dissolved in HCl (4M in 1,4-dioxane, 60.0 mL, 240.0 mmol, 16.0 eq.). Dry Et₃SiH (10.0 mL, 62.6075 mmol, 4.174 eq.) was added to the solution at r.t. and a faint white precipitate appeared immediately, which intensified with time upon stirring at r.t. under a nitrogen atmosphere. After 24 h, an intense white precipitate was observed and the reaction was judged to be complete by LC-MS analysis (C18 reverse phase column, H₂O—CH₃CN as mobile phase, gradient). The mixture was then evaporated under reduced pressure and the product was dissolved in dry CH₃OH (100 mL) followed by evaporation to dryness under reduced pressure. This was repeated thrice to remove bulk of 1,4-dioxane by azeotropic evaporation. The residue was re-dissolved in dry CH₃OH (10 mL) and triturated with dry Et₂O (500 mL) to precipitate the product. This was filtered and washed with further Et₂O (2×125 mL) and dried in high vacuum (<0.1 mbar) overnight to obtain (S)-3-{[(allyloxy)carbonyl]amino}-2-aminopropanoic acid HCl salt 2 as a bright white powder (3.03 g, 90%); ¹H NMR (400.13 MHz, DMSO-d₆) δ 3.42-3.56 (m, 2H), 4.48 (d, J=5.3 Hz, 2H), 5.15-5.36 (m, 2H), 5.80-5.98 (m, 1H), 7.44-7.60 (m, 1H), 8.24-8.70 (broad s, 3H); ¹³C NMR (100.61 MHz, DMSO-d₆) δ 40.4 (CH₂), 52.4 (CH), 64.7 (CH₂), 117.2 (CH₂), 133.4 (CH), 156.2 (C), 169.1 (C); MS (ESI+) m/z (rel intensity) 189 [(M+H)⁺, 100], 134 (4), 81 (9); HRMS (ESI+) m/z calc'd for C₇H₁₃O₄N₂ [M+H]⁺: 189.0870. found 189.0866 (Δ=−2.19 ppm)

tert-Butyl (S)-2-[(tert-butoxycarbonyl)amino]-3-[(2-nitrobenzyl)amino]propanoate (3a)

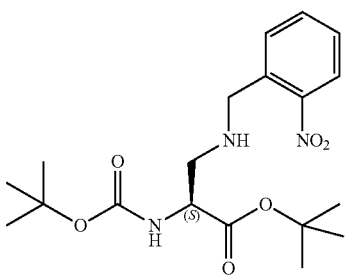

Chemical Formula: C₁₉H₂₉N₃O₆
Exact Mass: 395.20564
Molecular Weight: 395.45600

Boc-L-Dap-O^tBu·HCl 1b (5.0 g, 19.206 mmol, 1.0 eq.) was loaded into a dry 500 mL 2-neck round-bottomed flask and dry THF (75 mL) was added to it, followed by dry DIPEA (6.69 mL, 38.412 mmol, 2.0 eq.). The contents were left stirring under an argon atmosphere at 0° C. 2-nitrobenzyl bromide (4.979 g, 23.048 mmol, 1.2 eq.) was loaded on to a separate 250 mL dry single-neck round bottomed flask, dissolved in dry THF (125 mL), and the resulting solution then transferred to the main flask containing Boc-L-Dap-O^tBu by cannula under a positive pressure of argon over 5 min at 0° C. The mixture was then warmed to r.t. and left stirring at r.t. for 10 h. The reaction mixture was then concentrated under reduced pressure and the crude mixture extracted with EtOAc (200 mL) and washed with brine solution (3×250 mL). The organic layer was separated, dried over anhydrous Na₂SO₄, filtered and evaporated to dryness to obtain a brown viscous oil. Product was purified by flash chromatography on SiO₂ (gradient; eluent: EtOAc/n-hexane=1:9-1:4) to obtain the desired product, tert-butyl (S)-2-[(tert-butoxycarbonyl)amino]-3-[(2-nitrobenzyl)amino]propanoate 3a as a faint yellow viscous oil (5.05 g, 67%): R_f=0.27 (SiO₂ plate, EtOAc/n-hexane=1:4); ¹H NMR (400.13 MHz, CDCl₃ with TMS as internal standard) δ 1.44 (s, 9H), 1.46 (s, 9H), 2.85-3.40 (m, 2H), 4.02 (d, J=14.5 Hz, 1H), 4.07 (d, J=14.5 Hz, 1H), 4.22-4.35 (m, 1H), 5.20-5.55 (m, 1H), 7.41 (ddd, J=8.4, 8.4, 2.0 Hz, 1H), 7.50-7.67 (m, 2H), 7.94 (d, J=8.0 Hz, 1H); ¹³C NMR (100.61 MHz, CDCl₃ with TMS as internal standard) δ 28.1 (CH₃), 28.5 (CH₃), 50.7 (CH₂), 50.9 (CH₂), 54.4 (CH), 79.9 (C), 82.3 (C), 124.9 (CH), 128.2 (CH), 131.3 (CH), 133.3 (CH), 135.5 (C), 149.2 (C), 155.7 (C), 170.9 (C).

(S)-2-Amino-3-[(2-nitrobenzyl)amino]propanoic acid 3

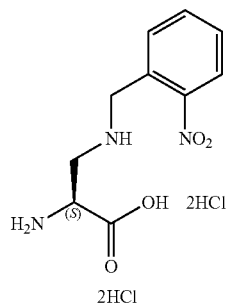

2HCl
Chemical Formula: $C_{10}H_{13}N_3O_4 \cdot 2HCl$
Exact Mass: 239.09061
Molecular Weight: 312.14700 (as 2HCl salt)

A 100 mL dry single necked round-bottomed flask was charged with tert-butyl (S)-2-[(tert-butoxycarbonyl)amino]-3-[(2-nitrobenzyl)amino]propanoate 3a (4.59 g, 11.607 mmol, 1.0 eq.). HCl (25 mL, 4 M in 1,4-dioxane, 100.0 mmol, 8.615 eq.) was added, followed by dry $Et_3SiH$ (5.0 mL, 31.304 mmol, 2.697 eq.). The contents were stirred in the dark under an argon atmosphere. The progress of the reaction was periodically monitored by TLC analysis ($SiO_2$ plate, EtOAc/n-hexane=3:7). After 48 h, an intense white precipitate was formed and the reaction was judged to be complete by TLC and LC-MS analysis (C18 reverse phase column, $H_2O$—$CH_3CN$ as mobile phase, gradient). The contents were evaporated to dryness under reduced pressure. Remaining 1,4-dioxane was removed by azeotropic evaporation 3× dry $CH_3OH$ (25 mL). The contents were then re-dissolved in dry $CH_3OH$ (25 mL), cooled to 0° C., triturated with dry $Et_2O$ (400 mL) and vigorously stirred in the dark at room temperature to obtain an intense precipitate. The precipitate was filtered, washed with further dry $Et_2O$ (150 mL), followed by dry n-hexane (50 mL), and then evaporated to dryness under high vacuum (<0.1 mbar) for 14 h in dark to obtain the desired product, (S)-2-amino-3-[(2-nitrobenzyl)amino]propanoic acid HCl salt 3, as an off-white powder (3.575 g, 99%): $^1$H NMR (400.13 MHz, $CD_3OD$) δ3.68 (dd, J=13.2, 5.6 Hz, 1H), 3.81 (dd, J=13.2, 7.7 Hz, 1H); 4.48 (dd, J=7.7, 5.6 Hz, 1H), 4.65 (d, J=13.2 Hz, 1H), 4.69 (d, J=13.2 Hz, 1H), 7.74-7.82 (m, 1H), 7.84-7.95 (m, 2H), 8.30 (app. d, J=8.1 Hz, 1H); $^{13}$C NMR (100.61 MHz, $CD_3OD$) δ 47.8 ($CH_2$), 50.2 (CH), 50.7 ($CH_2$), 127.1 (CH), 127.3 (C), 132.8 (CH), 135.3 (CH), 136.0 (CH), 150.3 (C), 169.0 (C); MS (ESI+, LC-MS) m/z (rel intensity) 240 [(M+H)+, 100%].

4',5'-Methylenedioxy-2'-nitroacetophenone (4b)

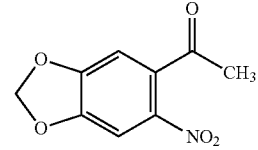

Chemical Formula: $C_9H_7NO_5$
Exact Mass: 209.03242
Molecular Weight: 209.15700

Following a slightly modified procedure described by McGall et al.[50], a solution of 3',4'-(methylenedioxy)acetophenone 4a (16.416 g, 0.1 mol) in glacial $CH_3COOH$ (64 mL) was added drop-wise to a 2 litre three-necked round-bottomed flask containing conc. $HNO_3$ (136 mL, 70% strength) at 0° C. over 1 h. The reaction mixture was maintained at 0° C. during addition and for a further 1 h with stirring under an argon atmosphere. The mixture was then warmed to 40° C. and stirred for additional 2.5 h. Finally, the mixture was cooled to r.t. and poured slowly into crushed ice (1 litre) in a beaker. A yellow precipitate appeared which was stirred for 15 min and then filtered. The yellow solid was washed with water (3×200 mL) and dried in vacuum. The crude yellow solid was then purified by recrystallization (THF/n-hexane) and then by flash chromatography on $SiO_2$ [eluent: $CH_2Cl_2$/n-hexane (1:1) to 100% $CH_2Cl_2$] to obtain 4',5'-methylenedioxy-2'-nitroacetophenone[32,50,51] 4b as yellow crystals (12.141 g, 58%): $R_f$=0.52 ($CH_2Cl_2$); m.p. 122.8-124.0° C.($^{51}$ m.p. 112° C.); $^1$H NMR (400.13 MHz, $CDCl_3$) δ 2.45 (s, 3H), 6.16 (s, 2H), 6.71 (s, 1H), 7.48 (s, 1H); $^{13}$C NMR (100.61 MHz, $CDCl_3$) δ 30.2 ($CH_3$), 103.8 ($CH_2$), 104.8 (CH), 106.2 (CH), 135.1 (C), 140.1 (C), 148.9 (C), 152.8 (C), 199.3 (C); IR ($CH_2Cl_2$) $v_{max}$ 2980, 1708, 1525, 1506, 1484, 1424, 1362, 1338, 1271, 1152, 1038, 932, 875, 819 cm$^{-1}$; MS (ESI+) m/z (rel intensity) 232 [(M+Na)+, 10%], 210 (2), 209 (7), 194 (100), 171 (45), 130 (32), 111 (9).

(R,S)-1-[4',5'-(Methylenedioxy)-2'-nitrophenyl]ethanol (4c)

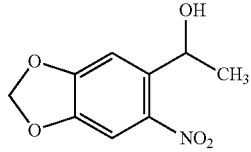

Chemical Formula: $C_9H_9NO_5$
Exact Mass: 211.04807
Molecular Weight: 211.17300

4',5'-Methylenedioxy-2'-nitroacetophenone 4b (43.714 g, 0.209 mol, 1.0 eq.) was suspended in $CH_2Cl_2$ (400 mL), $CH_3OH$ (650 mL) and absolute $CH_3CH_2OH$ (425 mL) in a 2 litre, single-necked, round-bottomed flask. The mixture was sonicated for 10 min at r.t. to dissolve the majority of the yellow solid. $NaBH_4$ granules (7.116 g, 0.188 mol, 0.9 eq.) were added in 8 portions (each 0.890 g) to the yellow suspension every 15 min (total time=2 h addition) at 15° C., NOTE: effervescence appeared as NaBH$_4$ dissolved and the reaction mixture became a homogeneous yellow solution. After the addition was complete, the reaction mixture was stirred at r.t. for a further 4 h. After this time the reaction was judged complete by TLC analysis (SiO$_2$, TLC eluent: 100% CH$_2$Cl$_2$), and the reaction quenched by addition of dry acetone (100 mL) stirring at r.t. for a further 2 h. The mixture was then evaporated to dryness under reduced pressure to obtain a yellow solid. The solid was subsequently re-dissolved in CH$_2$Cl$_2$ (800 mL) and washed sequentially with saturated aq. NH$_4$Cl solution (3×500 mL) and finally with saturated aq. NaCl solution (6×800 mL) The organic layer was separated, dried over anhydrous Na$_2$SO$_4$, filtered, and evaporated to dryness in high vacuum to obtain (R,S)-1-[4', 5'-(methylenedioxy)-2'-nitrophenyl]ethanol[32,50] 4c as a yellow solid (43.563 g, 99%): R$_f$=0.19 (CH$_2$Cl$_2$); m.p. 76.5-77.5° C.; $^1$H NMR (400.13 MHz, CDCl$_3$) δ 1.50 (d, J=6.3 Hz, 3H), 2.54 (d, J=3.0 Hz, 1H), 5.42 (qd, J=6.3, 3.0 Hz, 2H), 6.096 (app. d, $^2$J$_{HH}$=3.5 Hz, 1H, diastereotopic OCH$_2$O), 6.104 (app. d, $^2$J$_{HH}$=3.5 Hz, 1H, diastereotopic OCH$_2$O), 7.24 (s, 1H), 7.42 (s, 1H); $^{13}$C NMR (100.61 MHz, CDCl$_3$) δ 24.3 (CH$_3$), 65.8 (CH), 103.1 (CH$_2$), 105.2 (CH), 106.4 (CH), 139.2 (C), 141.5 (C), 147.0 (C), 152.5 (C); IR (CH$_2$Cl$_2$) ν$_{max}$ 3649, 2980, 2889, 2360, 2343, 1521, 1506, 1482, 1393, 1340, 1253, 1135, 1090, 1038, 934, 819 cm$^{-1}$; MS (ESI+) m/z (rel intensity) 234 [(M+Na)$^+$, 1%], 194 [(M−OH)$^+$, 100], 130 (20); HRMS (ESI+) m/z calc'd for C$_9$H$_9$NO$_5$ [M+Na]$^+$: 234.0373. found 234.0364 (Δ=−3.95 ppm).

(R,S)-1-Bromo-1-[4',5'-(methylenedioxy)-2'-nitrophenyl]ethane (4d)

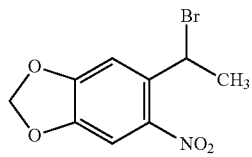

Chemical Formula: C$_9$H$_8$BrNO$_4$
Exact Mass: 272.96367
Molecular Weight: 274.07000

A 1 litre, 3-necked round-bottomed flask was dried in vacuo for 15 min at >100° C. using a heat gun and purged with dry argon gas and allowed to cool to room temperature. To this was added (R,S)-1-[4',5'-(methylenedioxy)-2'-nitrophenyl]ethanol, 4c (15.838 g, 75.0 mmol, 1.0 eq.). 4c was dissolved in dry CH$_2$Cl$_2$ (375 mL, sonication required for complete solubility), cooled to 0° C. under an argon atmosphere, and the round-bottomed flask was wrapped with aluminium foil to shield it from light. After 20 min, PBr$_3$ (2.82 mL, 30.0 mmol, 0.4 eq.) was added dropwise for 10 min using a syringe pump at 0° C., followed by addition of dry pyridine (0.5 mL). The yellow reaction mixture was stirred at 0° C. for 15 min, then brought to r.t. and stirred continuously for 1.5 h. The reaction was judged to be complete by TLC analysis (SiO$_2$, TLC eluent: 100% CH$_2$Cl$_2$), cooled to 0° C., quenched by the addition of dry CH$_3$OH (15 mL), warmed to r.t. and stirred for 30 min under an argon atmosphere. After the quenching was complete, the reaction mixture was evaporated to dryness under reduced pressure using a rotary evaporator. The resulting yellow gum was dissolved in CH$_2$Cl$_2$ (300 mL) and saturated aq. NaHCO$_3$ solution (300 mL). The contents were loaded into a separating funnel, the aqueous phase was discarded and the organic phase was washed sequentially with further saturated aq. NaHCO$_3$ solution (1×300 mL) and saturated aq. NaCl solution (3×300 mL). The organic layer was separated, dried over anhydrous Na$_2$SO$_4$, filtered and evaporated to dryness to obtain a yellow solid. The crude product was purified by flash chromatography on SiO$_2$ [eluent: CH$_2$Cl$_2$/n-hexane (1:1), then 100% CH$_2$Cl$_2$] to obtain a pure sample of (R,S)-1-bromo-1-[4',5'-(methylenedioxy)-2'-nitrophenyl]ethane[32] 4d (18.330 g, 89%) as shining yellow crystals. The sample was stored in a freezer at −20° C. in a dry atmosphere and in the dark for several months without any significant decomposition: R$_f$=0.17 (CH$_2$Cl$_2$/n-hexane, 1:4); m.p. 76.1-77.8° C.; $^1$H NMR (400.13 MHz, CDCl$_3$) δ 2.04 (d, J=6.8 Hz, 3H), 5.89 (q, J=6.8 Hz, 1H), 6.13 (s, 2H), 7.27 (s, 1H), 7.35 (s, 1H); $^{13}$C NMR (100.61 MHz, CDCl$_3$) δ 27.6 (CH$_3$), 42.9 (CH), 103.3 (CH$_2$), 105.1 (CH), 108.8 (CH), 134.8 (C), 141.6 (C), 147.7 (C), 152.1 (C); IR (CH$_2$Cl$_2$) ν$_{max}$ 2981, 2970, 2930, 1615, 1504, 1481, 1420, 1395, 1385, 1328, 1305, 1257, 1156, 1141, 1057, 1028, 1014, 957, 925, 872, 815, 752, 730, 719, 698 cm$^{-1}$; HRMS (ESI+) m/z calc'd for C$_9$H$_8$$^{79}$BrNO$_4$ [M+Na]$^+$: 295.9529. found 295.9519 (Δ=−3.45 ppm).

tert-Butyl (2S)-2-[(tert-butoxycarbonyl)amino]-3-{[1-(6-nitrobenzo[d][1,3]dioxol-5-yl)ethyl]amino}propanoate (4e)

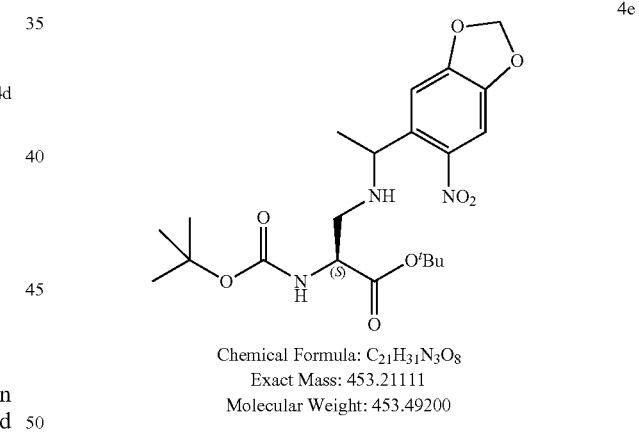

Chemical Formula: C$_{21}$H$_{31}$N$_3$O$_8$
Exact Mass: 453.21111
Molecular Weight: 453.49200

Boc-L-Dap-O$^t$Bu·HCl 1b (6.233 g, 21.0 mmol, 1.1 eq.) was suspended in dry THF (275 mL) in a dry 1 litre 3-neck round-bottomed flask and dry DIPEA (9.98 mL, 57.273 mmol, 3.0 eq.) was added. The contents were stirred for 10 min at r.t. under a nitrogen atmosphere. The flask was wrapped with aluminium foil and the contents were kept in the dark. (R,S)-1-bromo-1-[4',5'-(methylenedioxy)-2'-nitrophenyl]ethane 4d (5.232 g, 19.091 mmol, 1.0 eq.) was then added to the reaction mixture. The homogeneous yellow solution and was left stirring in the dark at r.t. under a nitrogen atmosphere for a period of 68 h. The reaction was judged to be complete by TLC analysis (SiO$_2$ plate; CH$_2$Cl$_2$/n-hexane=3:7) and evaporated to dryness under reduced pressure to obtain a dark brown oil. The crude reaction oil was dissolved in CH$_2$Cl$_2$ (250 mL) and washed with saturated brine solution (3×500 mL). The organic layer was separated, dried over anhydrous Na$_2$SO$_4$, filtered and evaporated to dryness to obtain a dark brown viscous oil. This was then purified by flash chromatography on SiO$_2$ (gradient; eluent: 100% CH$_2$Cl$_2$, then CH$_2$Cl$_2$/CH$_3$OH/NEt$_3$=94:5:1) to afford the desired product, tert-butyl (2S)-2-[(tert-butoxycarbonyl)amino]-3-{[1-(6-nitrobenzo[d][1,3]dioxol-5-yl)ethyl]amino}propanoate 4e, as a yellow-brown sticky gum (7.49 g, 87%): R$_f$=0.13 (SiO$_2$ plate, CH$_2$Cl$_2$); $^1$H NMR (400.13 MHz, CDCl$_3$ with TMS as internal standard) δ 1.34 and 1.36 (2×d, J=3.6 and 3.6 Hz, 3H), 1.42 and 1.450 (2×s, 9H), 1.454 and 1.47 (2×s, 9H), 2.54-2.74 (m, 1H), 2.75-2.89 (m, 1H), 4.03-4.27 (m, 1H), 4.28-4.53 (m, 1H), 5.15-5.43 (m, 1H), 6.05-6.10 (m, 2H), 7.21 (app. broad s, 1H), 7.345 and 7.352 (2×s, 1H); $^{13}$C NMR (100.61 MHz, CDCl$_3$ with TMS as internal standard) δ (mixture of diastereoisomers) 23.9 (CH$_3$), 24.0 (CH$_3$), 28.12 (CH$_3$), 28.15 (CH$_3$), 28.41 (CH$_3$), 28.46 (CH$_3$), 49.3 (CH$_2$), 49.4 (CH$_2$), 53.1 (CH), 53.2 (CH), 54.3 (CH), 54.5 (CH), 79.9 (C), 80.1 (C), 82.3 (C), 82.4 (C), 102.8 (2×CH$_2$), 105.2 (2×CH), 106.77 (CH), 106.83 (CH), 138.1 (C), 143.30 (C), 143.37 (C), 146.7 (C), 152.1 (C), 152.2 (C), 155.5 (C), 155.6 (C), 170.7 (C), 170.8 (C); MS (ESI+) m/z (rel intensity) 454 [(M+H)$^+$, 86%], 301 (70), 261 (100), 205 (7), 203 (10), 186 (7), 147 (10); HRMS (ESI+) m/z calc'd for C$_{21}$H$_{32}$O$_8$N$_3$ [M+H]$^+$: 454.2184. found 454.2201 (Δ=3.65 ppm).

(2S)-2-Amino-3-{[i-(6-nitrobenzo[d][1,3]dioxol-5-yl)ethyl]amino}propanoic acid (4)

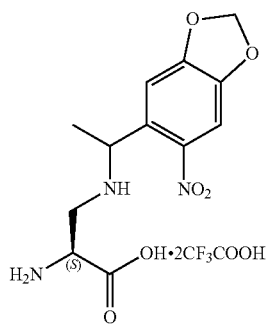

2TFA (mixture of ~1:1 epimers)
Chemical Formula: C$_{21}$H$_{15}$N$_3$O$_6$·2CF$_3$COOH
Exact Mass: 297.09609
Molecular Weight: 525.31342 (as disalt of CF$_3$COOH)

tert-Butyl (2S)-2-[(tert-butoxycarbonyl)amino]-3-{[1-(6-nitrobenzo[d][1,3]dioxol-5-yl) ethyl]amino}propanoate 4e (4.303 g, 9.489 mmol, 1.0 eq.) was dissolved in dry CH$_2$Cl2 (30 mL) in a dry 250 mL round-bottomed flask wrapped with aluminium foil to exclude light. Freshly distilled CF$_3$COOH (15 mL, 195.887 mmol, 20.644 eq.) was added and the yellow solution turned brown. Dry Et$_3$SiH (10.0 mL, 62.608 mmol, 6.598 eq.) was added and the reaction mixture stirred at r.t. in the dark. The reaction was periodically monitored by LC-MS analysis. After 48 h, the reaction was judged to be complete by LC-MS analysis (C18 reverse phase column, H$_2$O—CH$_3$CN as mobile phase, gradient), and the mixture then evaporated to dryness to obtain a dark brown gum. The gum was dissolved in anhydrous CH$_3$OH (10 mL) and cooled to 0° C. under an argon atmosphere in a dry 2 L round-bottomed flask. This was triturated by addition of dry Et$_2$O (900 mL) at 0° C. and then stirred vigorously at r.t. for 1 h to obtain a pale-yellow precipitate. The precipitate was filtered, washed with additional dry Et$_2$O (2×200 mL), followed by n-hexane (150 mL). The pale yellow powder was transferred to a 100 mL round-bottomed flask and dried in high vacuum (<0.1 mbar) for 40 h in the dark. (2S)-2-Amino-3-{[1-(6-nitrobenzo[d][1,3]dioxol-5-yl)ethyl]amino}propanoic acid 4 was obtained as a free-flowing pale yellow powder (3.646 g, 73%). The product is a salt of CF$_3$COOH and a ~1:1 mixture of epimers. The product was stored under argon in the dark at −20° C.: $^1$H NMR (400.13 MHz, DMSO-d$_6$ with TMS as internal standard) δ 1.36 and 1.38 (2×d, J=3.8 and 3.8 Hz, 3H), 2.65-2.95 and 2.96-3.20 (2×m, 1H), 3.07-3.25 (m, 1H), 3.60-3.70 (m, 1H), 3.71-3.85 and 4.18-4.44 (2×m, 1H), 6.21 and 6.23 (2×d, J=3.5 and 2.9 Hz, 2H), 7.41 and 7.42 (2×s, 1H), 7.52 and 7.53 (2×s, 1H); $^{13}$C NMR (100.61 MHz, DMSO-d$_6$ with TMS as internal standard) δ (mixture of diastereoisomers) 22.6 (CH$_3$), 22.7 (CH$_3$), 38.5 (CH$_2$), 45.8 (CH$_2$), 51.6 (CH), 51.8 (CH), 52.3 (CH), 52.6 (CH), 103.2 (CH$_2$), 103.3 (CH$_2$), 104.5 (CH), 104.6 (CH), 106.4 (CH), 106.6 (CH), 117.1 (C, q, $^1J_{C-F}$=299.0 Hz), 135.4 (C), 135.6 (C), 142.96 (C), 143.01 (C), 146.61 (C), 146.66 (C), 151.93 (C), 151.96 (C), 158.56 (C, q, $^2J_{C-F}$=31.5 Hz), 168.7 (2×C), 169.6 (2×C); MS (ESI+) m/z (rel intensity) 298 [(M+H)$^+$, 100%], 261 (10), 225 (10), 211 (4), 147 (12), 144 (9), 134 (6), 105 (9), 82 (31); HRMS (ESI+) m/z calc'd for C$_{12}$H$_{16}$O$_6$N$_3$ [M+H]$^+$: 298.1034. found 298.1039 (Δ=1.74 ppm).

2,5-Dioxopyrrolidin-1-yl (1-(6-nitrobenzo[d][1,3]dioxol-5-yl)ethyl) carbonate (5a)

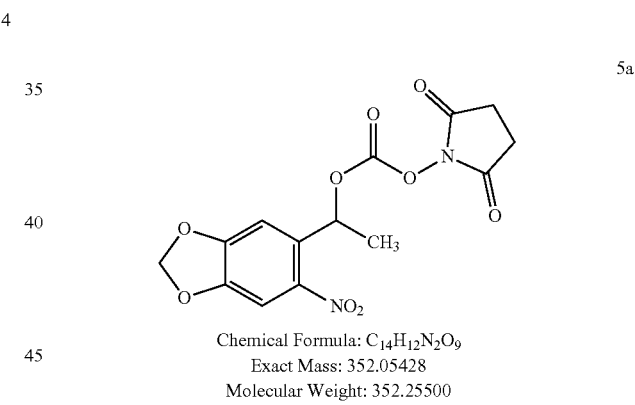

Chemical Formula: C$_{14}$H$_{12}$N$_2$O$_9$
Exact Mass: 352.05428
Molecular Weight: 352.25500

(R,S)-1-[4',5'-(Methylenedioxy)-2'-nitrophenyl]ethanol 4c (42.234 g, 200.0 mmol, 1.0 eq.) was charged onto a dry 2 litre 3-neck round-bottomed flask and dissolved in dry CH$_3$CN (1 L). Dry DIPEA (104.5 mL, 600.0 mmol, 3.0 eq.) was added to the solution, followed by N,N-disuccinimidyl carbonate (80.896 g of 95% purity, 300 mmol, 1.5 eq.). The flask was wrapped with aluminium foil to keep the contents in the dark. The yellow heterogeneous reaction mixture was stirred at r.t. under an argon atmosphere in the dark. After 16 h, the reaction mixture was homogeneous and reaction was judged to be complete by TLC analysis (SiO$_2$ plate, CH$_3$CN/CH$_2$Cl$_2$=1:19). The yellow reaction mixture was then adsorbed on to Biotage® Isolute HM-N sorbent and dried under reduced pressure. This was then quickly subjected to flash chromatography on SiO$_2$ [eluent: CH$_2$Cl$_2$, then CH$_3$CN/CH$_2$Cl$_2$=1:19] in the dark to obtain the desired product, 2,5-dioxopyrrolidin-1-yl-(1-(6-nitrobenzo[d][1,3]dioxol-5-yl)ethyl) carbonate 5a as yellow crystalline needles (65-051 g, 92%) [NOTE: The flash column must be performed quickly to avoid decomposition of the product on prolonged exposure to $SiO_2$]. The product 5a was used for the subsequent step immediately. It can be stored in the dark at −20° C. in a freezer: $R_f$=0.6 ($SiO_2$ plate, $CH_3CN/CH_2Cl_2$=1:19); $^1$H NMR (400.13 MHz, $CDCl_3$ with TMS as internal standard) δ 1.75 (d, J=6.4 Hz, 3H), 2.81 (s, 4H), 6.15 (d, J=3.0 Hz, 2H), 6.42 (q, J=6.4 Hz, 1H), 7.11 (s, 1H), 7.51 (s, 1H); $^{13}$C NMR (100.61 MHz, $CDCl_3$ with TMS as internal standard) δ 22.2 ($CH_3$), 25.6 ($CH_2$), 76.4 (CH), 103.5 ($CH_2$), 105.5 (CH), 105.8 (CH), 133.1 (C), 141.6 (C), 148.0 (C), 150.7 (C), 153.0 (C), 168.6 (C).

(2S)-2-[(tert-Butoxycarbonyl)amino]-3-({[i-(6-nitrobenzo[d][1,3]dioxol-5-yl)ethoxy]carbonyl}-amino)propanoic acid (5b)

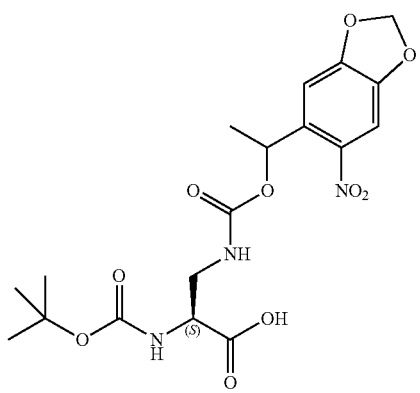

Chemical Formula: $C_{18}H_{23}N_3O_{10}$
Exact Mass: 441.13834
Molecular Weight: 441.39300

Boc-L-Dap-OH 1a (2.553 g, 12.5 mmol, 1.25 eq.) was suspended in dry THF (180 mL) and dry $CH_3CN$ (20 mL) in a dry 1 litre single-necked round-bottomed flask wrapped with aluminium foil to exclude light. Dry DIPEA (5.23 mL, 30.0 mmol, 3.0 eq.) was added to the mixture and the contents were stirred for 20 min at r.t. under an argon atmosphere, after which 2,5-dioxopyrrolidin-1-yl-(1-(6-nitrobenzo[d][1,3]dioxol-5-yl)ethyl) carbonate 5a (3.523 g, 10.0 mmol, 1.0 eq.) was added. The heterogeneous mixture was stirred at r.t. under an argon atmosphere in the dark and the progress of the reaction was periodically monitored by LC-MS analysis. After a few hours the heterogeneous mixture started to be a homogeneous yellow solution. After 24 h, the reaction was judged to be complete and the contents were adsorbed onto Biotage® Isolute HM-N sorbent and dried under reduced pressure. This was then quickly subjected to flash chromatography on $SiO_2$ [eluent: $CH_2Cl_2$, then $CH_2Cl_2/CH_3OH/CH_3COOH$=94:5:1] in the dark to obtain the desired product, (2S)-2-[(tert-butoxy-carbonyl)amino]-3-({[1-(6-nitrobenzo[d][1,3]dioxol-5-yl)ethoxy]carbonyl}amino) propanoic acid 5b as a brown-yellow gum. This was subjected to azeotropic evaporation using $CH_2Cl_2$/cyclohexane (1:1) under reduced pressure to remove residual $CH_3COOH$ from the product 5b. The product was dried in high vacuum to obtain a pure sample of 5b as a yellow solid (4.360 g, 99%) and a ~1:1 mixture of epimers; $R_f$=0.41 ($SiO_2$ plate, $CH_2Cl_2/CH_3OH/CH_3COOH$=94:5:1); MS (ESI−, LC-MS) m/z (rel intensity) 440 [(M−H)−, 100%].

(2S)-2-Amino-3-({[i-(6-nitrobenzo[d][1,3]dioxol-5-yl)ethoxy]carbonyl}-amino)propanoic acid (5)

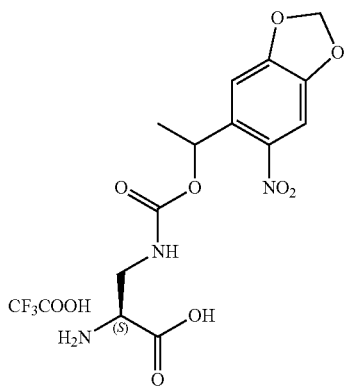

TFA (mixture of~1:1 epimers)
Chemical Formula: $C_{13}H_{15}N_3O_8$·$CF_3COOH$
Exact Mass: 341.08591
Molecular Weight: 455.29921(with TFA)

Freshly distilled $CF_3COOH$ (15 mL, 195.894 mmol, 21.293 eq.) was added to a solution of (2S)-2-[(tert-butoxycarbonyl)amino]-3-({[1-(6-nitrobenzo[d][1,3]dioxol-5-yl)-ethoxy]carbonyl}amino)propanoic acid 5b (4.061 g, 9.2 mmol, 1.0 eq.) in dry $CH_2Cl2$ (50 mL) in a dry 1 L single-necked round-bottomed flask wrapped with aluminium foil. Upon addition of $CF_3COOH$ the yellow solution turned to dark brown, the reaction was stirred at r.t. in the dark and monitored by TLC analysis. After 2 h, the reaction was judged to be complete by both TLC ($SiO_2$ plate; $CH_2Cl_2/CH_3OH/CH_3COOH$=94:5:1) and LC-MS analysis (C18 reverse phase column, $H_2O$—$CH_3CN$ as mobile phase, gradient). The reaction mixture was evaporated to dryness under reduced pressure to obtain a dark brown gum. The gum was dissolved in dry $CH_3OH$ (5 mL), cooled to 0° C. and triturated with dry $Et_2O$ (0.9 L) to obtain a pale yellow precipitate. The mixture was left stirring vigorously in the dark under an atmosphere of argon at r.t. The pale yellow precipitate was then filtered and washed with $Et_2O$ (2×100 mL) and dry hexane (50 mL). This was dried in vacuo (<0.1 mbar) for 2 days in the dark to obtain the desired (2S)-2-amino-3-({[1-(6-nitrobenzo[d][1,3]dioxol-5-yl)ethoxy]carbonyl}-amino)propanoic acid TFA salt 5 as a fine, pale yellow powder (4.132 g, 99%) and a ~1:1 mixture of epimers as observed by $^1$H and $^{13}$C NMR spectroscopic analysis: $^1$H NMR (400.13 MHz, $CD_3OD$) d1-57 (d, J=6.2 Hz, 3H), 2.68 (s, 2H), 3.41-3.58 (m, 1H), 3.59-3.74 (m, 1H), 3.78-4.15 (m, 1H), 6.14 (s, 2H), 6.22 (q, J=6.2 Hz, 1H), 7.12 (app. d, J=5.2 Hz, 1H), 7.47 (s, 1H); $^{13}$C NMR (100.61 MHz, $CD_3OD$) δ 22.4 ($CH_3$), 22.5 ($CH_3$), 42.1 ($CH_2$), 42.3 ($CH_2$), 55.6 (CH), 55.9 (CH), 70.4 (2×CH), 104.8 (2×$CH_2$), 105.7 (2×CH), 106.7 (CH), 106.9 (CH), 118.2 (C, q, $^1J_{C-F}$=292.6 Hz), 136.8 (C), 137.1 (C), 142.8 (C), 142.9 (C), 148.8 (C), 154.0 (C), 158.5 (C), 158.6 (C), 163.1 (C, q, $^2J_{C-F}$=34.4 Hz), 170.9 (2×C), 174.9 (2×C); MS (ESI+) m/z (rel intensity) 342 [(M+H)+, 100%], 311 (10), 233 (5), 189 (9), 130 (19); HRMS (ESI+) m/z calc'd for $C_{13}H_{16}O_8N_3$ [M+H]+: 342.0932. found 342.0923 (Δ=−2.63 ppm).

2-{[1-(6-Nitrobenzo[d][1,3]dioxol-5-yl)ethyl]thio}ethan-1-ol (6a)

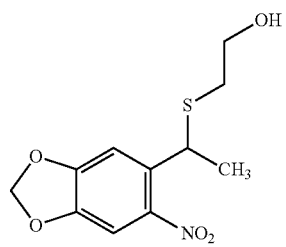

6a

Chemical Formula: $C_{11}H_{13}NO_5S$
Exact Mass: 271.05144
Molecular Weight: 271.28700

A freshly prepared solution of NaOH (0.5 M, 8 g in 40 mL of deionized $H_2O$, 20.0 mmol, 1 eq.) was loaded onto a 500 mL round 3-necked round-bottomed flask and the solution was degassed by bubbling through a stream of argon gas at r.t. After 30 min, mercaptoethanol (1.47 mL, 21.0 mmol, 1.05 eq.) was added to the flask and degassing was continued for a further 15 min. Separately, freshly (R,S)-1-bromo-1-[4',5'-(methylenedioxy)-2'-nitrophenyl]ethane 13 (5.481 g, 20.0 mmol, 1.0 eq) was dissolved in 1,4-dioxane (20 mL) in a 100 mL round-bottomed flask wrapped with aluminium foil and degassed by bubbling a stream of argon gas for 15 min in the dark. The degassed solution of 13 in 1,4-dioxane was transferred onto the flask containing aq. NaOH and mercaptoethanol solution, dropwise, for a period of 90 min at r.t. using a cannula under a positive pressure of argon gas. A yellow precipitate formed, which was then dissolved by addition of degassed 1,4-dioxane (60 mL), followed by sonication for 30 min until a homogenous clear yellow solution was obtained. The contents were then left stirring for 12 h at r.t. in the dark under an argon atmosphere, after which time the reaction was judged to be complete by TLC and LC-MS analysis (C18 reverse phase column, $H_2O$—$CH_3CN$ as mobile phase, gradient). The mixture was then evaporated under reduced pressure to remove the volatile organic components. The yellow aqueous content was then extracted with EtOAc (2×175 mL) and the combined organic phase was washed with saturated $NH_4Cl$ solution (1×500 mL), followed by brine solution (3×500 mL). The organic layer was then separated, dried over anhydrous $Na_2SO_4$, filtered and evaporated to dryness to obtain a yellow oil. The product was purified by flash chromatography on $SiO_2$ (eluent: EtOAc/n-hexane=3:7) in the dark to obtain 2-{[1-(6-nitrobenzo[d][1,3]dioxol-5-yl)ethyl]thio}ethan-1-ol 6a as a sticky yellow oil (5.179 g, 95%): $R_f$=0.33 ($SiO_2$ plate, EtOAc/n-hexane=3:7); $^1$H NMR (400.13 MHz, $CDCl_3$) δ 1.55 (d, J=7.0 Hz, 3H), 1.96 (t, J=5.9 Hz, 1H), 2.44-2.65 (m, 2H), 3.52-3.74 (m, 2H), 4.78 (q, J=7.0 Hz, 1H), 6.10 (dd, J=3.8, 1.0 Hz, 2H), 7.27 (s, 1H), 7.28 (s, 1H); $^{13}$C NMR (100.61 MHz, $CDCl_3$) δ 23.2 ($CH_3$), 34.9 ($CH_2$), 38.4 (CH), 60.9 ($CH_2$), 103.1 ($CH_2$), 104.8 (CH), 108.0 (CH), 136.1 (C), 143.3 (C), 146.9 (C), 152.0 (C); IR (neat) $ν_{max}$ 3393, 2980, 1617, 1518, 1503, 1480, 1418, 1375, 1332, 1252, 1156, 1031, 928, 872, 817, 759; m/z (ESI-, LC-MS) 270.1 [(M-H)$^-$, 100%].

2,5-Dioxopyrrolidin-1-yl-(2-{[i-(6-nitrobenzo[d][1,3]dioxol-5-yl)ethyl]thio}ethyl) carbonate (6b)

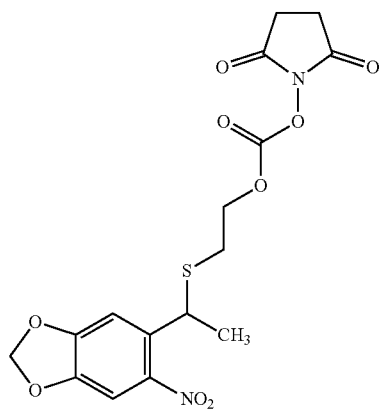

6b

Chemical Formula: $C_{16}H_{16}N_2O_9S$
Exact Mass: 412.05765
Molecular Weight: 412.36900

Intermediate 6b used for the subsequent reaction for the synthesis of DAP derivatives 6c and 6d was synthesised in situ starting from the alcohol 6a. A 3-necked 500 mL round-bottomed flask was dried in vacuo using a heat gun and purged with argon gas; this procedure was repeated three times prior to use. The dry flask was charged with 2-{[1-(6-nitrobenzo[d][1,3]dioxol-5-yl)ethyl]thio}ethan-1-ol 6a (4.883 g, 18.0 mmol, 1.0 eq.) dissolved in dry $CH_3CN$ (90 mL). Dry DIPEA (9.41 mL, 54.0 mmol, 3.0 eq.), followed by N,N'-disuccinimidyl carbonate (6.796 g of 95% purity, 25.2 mmol, 1.4 eq.), was added to the reaction mixture at r.t. in the dark under an argon atmosphere. The reaction mixture turned to turbid yellow and a white precipitate began to form, and after 1 h, the reaction mixture became a homogeneous yellow-brown solution. The reaction was left stirring at r.t. for 12 h and was judged to be complete by TLC analysis ($SiO_2$ plate, EtOAc/n-hexane=3:7) after this time. The 2,5-dioxopyrrolidin-1-yl-(2-{[1-(6-nitrobenzo[d][1,3]dioxol-5-yl)ethyl]thio}ethyl) carbonate 6b was immediately carried to the next step without further purification: $R_f$=0.12 ($SiO_2$ plate, EtOAc/n-hexane=3:7).

tert-Butyl (2S)-2-[(tert-Butoxycarbonyl)amino]-3-{[(2-{[i-(6-nitrobenzo-[d][1,3]dioxol-5-yl)ethyl]thio}ethoxy)carbonyl]amino}propanoate (6c)

(2S)-2-[(tert-Butoxycarbonyl)amino]-3-{[(2-{[i-(6-nitrobenzo[d][1,3]-dioxol-5-yl)ethyl]thio}ethoxy)carbonyl]amino}propanoic acid (6d)

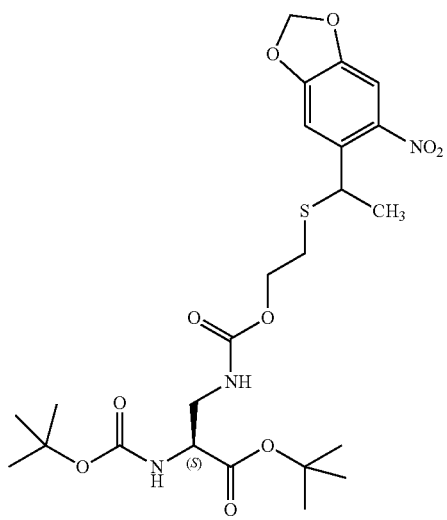

6c

Chemical Formula: $C_{24}H_{35}N_3O_{10}S$
Exact Mass: 557.20432
Molecular Weight: 557.61500

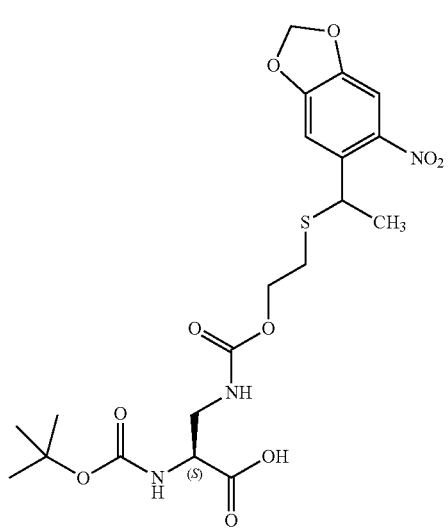

6d

Chemical Formula: $C_{20}H_{27}N_3O_{10}S$
Exact Mass: 501.14171
Molecular Weight: 501.50700

Boc-L-Dap-O'Bu·HCl (8.548 g, 28.8 mmol, 1.6 eq.) was added in one portion to a solution of 6b, prepared as described above. The yellow reaction mixture turned homogeneous in few minutes and the contents were stirred in dark under an argon atmosphere at After 10 h the reaction was judged to be complete by both TLC (SiO₂ plate, $R_f$=0.39, EtOAc/n-hexane=3:7) and LC-MS analysis (C18 reverse phase column, H₂O—CH₃CN as mobile phase), confirming consumption of 6b. The reaction mixture was then adsorbed onto Biotage® Isolute HM-N sorbent and dried under reduced pressure. This was then subjected to flash chromatography on SiO₂ [eluent: EtOAc/n-hexane=3:7] in the dark to obtain the desired tert-butyl (2S)-2-[(tert-butoxycarbonyl)amino]-3-{[(2-{[1-(6-nitrobenzo[d][1,3]dioxol-5-yl)ethyl]thio}-ethoxy)carbonyl]amino}propanoate 6c as a thick yellow gum (9.405 g, 94%) and a mixture of ~1:1 epimers: $R_f$=0.39 (EtOAc/n-hexane=3:7); ¹H NMR (400.13 MHz, CDCl₃) δ (Mixture of epimers) 1.44 (s, 9H), 1.46 (s, 9H), 1.54 (d, J=6.8 Hz, 3H), 2.36-2.61 (m, 2H), 3.41-3.68 (m, 2H), 4.00-4.18 (m, 2H), 4.24 (broad s, 1H), 4.85 (q, J=6.8 Hz, 1H), 5.15 (broad s, 1H), 5.41 (broad s, 1H), 6.10 (d, J=6.8, 2H), 7.27 (s, 1H), 7.29 (s, 1H); ¹³C NMR (100.61 MHz, CDCl₃) δ 23.1 (CH₃), 28.1 (CH₃), 28.4 (CH₃), 30.5 (CH₂), 39.0 (CH), 43.2 (CH₂), 54.6 (CH), 65.2 (CH₂), 80.1 (C), 82.9 (C), 103.0 (CH₂), 104.7 (CH), 108.2 (CH), 136.3 (C), 143.5 (C), 146.9 (C), 152.1 (C), 155.6 (C), 156.4 (C), 169.7 (C); m/z (ESI+, LC-MS) 558.2 [(M+H)⁺, 100%]

Boc-L-Dap-OH (13.479 g, 66.0 mmol, 1.082 eq.) was added in one portion to a solution of 6b (26.70 g, prepared as described above) in dry CH₃CN (305 mL) under argon and stirred for 12 h at r.t. After this time the reaction was judged to be complete by LC-MS (C18 reverse phase column, H₂O—CH₃CN as mobile phase) and the contents were adsorbed on to Biotage® Isolute HM-N sorbent and dried under reduced pressure. This was then subjected to flash chromatography on spherical SiO₂ [Supelco®, procured from Sigma Aldrich Ltd., 40-75 μm particle size; gradient; eluent: EtOAc/n-hexane=1:1→7:3→1:0] in the dark to obtain the desired (2S)-2-[(tert-butoxycarbonyl)amino]-3-{[(2-{[1-(6-nitrobenzo[d][1,3]dioxol-5-yl)ethyl]thio}-ethoxy)-carbonyl]amino}propanoic acid 6d as a thick yellow gum (28.995 g, 95%) and a mixture of ~1:1 epimers: ¹H NMR [400.13 MHz, CDCl₃ with 0.1% v/v TMS as internal standard] δ (Mixture of epimers) 1.43 (s, 9H), 1.52 (d, J=6.8 Hz, 3H), 2.30-2.95 (m, 2H), 3.33-3.82 (broad m, 2H), 3.86-4.18 (m, 2H), 4.20-4.48 (m, 1H), 4.64-4.97 (m, 1H), 5.34-5.58 (broad s, 1H), 5.60-5.84 (broad s, 1H), 6.20 (d, J=8.3 Hz, 2H), 7.10-7.39 (m, 2H), 8.47 (broad s, 1H); ¹³C NMR [100.61 MHz, CDCl₃ with 0.1% v/v TMS as internal standard] δ 23.1 (CH₃), 28.4 (3×CH₃), 30.5 (CH₂), 39.0 (CH), 42.7 (CH₂), 54.4 (CH), 65.3 (CH₂), 80.8 (C), 103.1 (CH₂), 104.7 (CH), 108.1 (CH), 136.2 (C), 143.4 (C), 146.9 (C), 152.1 (C), 156.3 (C), 157.2 (C), 173.5 (C); m/z (ESI-, LC-MS) 500.1 [(M-H)⁻, 100%]

(2S)-2-Amino-3-{[(2-{[i-(6-nitrobenzo[d][1,3]di-oxol-5-yl)ethyl]thio}ethoxy)carbonyl]amino}propanoic acid (6)

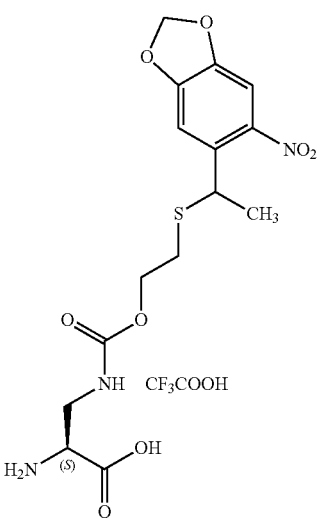

TFA (mixture of ~1:1 epimers)
Chemical Formula: C$_{15}$H$_{19}$N$_3$O$_8$S·CF$_3$COOH
Exact Mass: 401.08929 (without TFA)
Molecular Weight: 515.41321 (with TFA)

Method I (Prepared from 6c):

A dry sample of (2S)-2-[(tert-butoxycarbonyl)amino]-3-{[(2-{[1-(6-nitrobenzo[d][1,3]-dioxol-5-yl)ethyl]thio}-ethoxy)carbonyl]amino}propanoate 6c (6.728 g, 12.066 mmol, 1.0 eq.) was loaded to a dry 250 mL single-necked round-bottomed flask and dissolved in dry CH$_2$Cl$_2$ (50 mL), the flask was wrapped in foil to exclude light. Dry Et$_3$SiH (20 mL, 125.215 mmol, 10.378 eq.) was added to the solution followed by the drop-wise addition of freshly distilled CF$_3$COOH (20 mL, 261.182 mmol, 21.647 eq.) using a syringe over 15 min at r.t. The reaction mixture turned from yellow to a brown-green colour and was left stirring at r.t. in the dark. After 24 h, the reaction was judged to be complete by TLC (SiO$_2$ plate, EtOAc/n-hexane=3:7) and LC-MS analysis (C18 reverse phase column, H$_2$O—CH$_3$CN as mobile phase). The reaction mixture was concentrated under reduced pressure in the dark to obtain a yellow-brown gum. This was dissolved in anhydrous CH$_3$OH (20 mL) and evaporated to dryness under reduced pressure; this was repeated three times and dried in high vacuum (<0.1 mbar) to remove any residual CF$_3$COOH, Et$_3$SiH and H$_2$O. The yellow-brown gum was then dissolved in dry CH$_3$OH (40 mL) and transferred to a dry 2 L round-bottomed flask under an argon atmosphere and cooled to 0° C. Dry Et$_2$O (2 L) was added to the solution via cannula under a positive pressure of argon gas in the dark and the contents were vigorously stirred. A yellow precipitate formed and the contents stirred vigorously at 0° C. for 15 min, then at r.t. for a further 2 h. The pale yellow precipitate was filtered and washed with dry Et$_2$O (3×250 mL) and finally with dry n-hexane (50 mL). The product was dried in vacuum (<0.1 mbar) overnight for 14 h in the dark to obtain (2S)-2-amino-3-{[(2-{[1-(6-nitrobenzo[d][1,3]di-oxol-5-yl)ethyl]thio}ethoxy)carbonyl]amino}-propanoic acid TFA salt 6 as a pale yellow powder (3.940 g, 63%) and a 1:1 mixture of epimers: $^1$H NMR [400.13 MHz, CD$_3$OD/CF$_3$COOD (5:1) with 1% v/v TMS as internal standard] δ (Mixture of epimers) 1.55 (d, J=7.0 Hz, 3H), 2.49-2.73 (m, 2H), 3.63 (dd, J=15.0, 6.4 Hz, 1H), 3.78 (ddd, J=15.0, 3.6, 2.3 Hz, 1H), 4.0-4.24 (m, 3H), 4.81 (q, J=7.0 Hz, 1H), 6.11 and 6.13 (2×s, 1H), 6.40 (s, 1H), 7.29 and 7.33 (2×s, 1H); $^{13}$C NMR [100.61 MHz, CD$_3$OD/CF$_3$COOD (5:1) with 1% v/v TMS as internal standard] δ 23.2 (CH$_3$), 31.4 (CH$_2$), 40.0 (CH), 42.1 (CH$_2$), 55.1 (CH), 65.8 (CH$_2$), 104.8 (CH$_2$), 105.6 (CH), 109.0 (CH), 117.0 (C, $^1J_{C-F}$=286.5 Hz), 137.1 (C), 144.9 (C), 148.7 (C), 153.7 (C), 160.7 (C), 160.8 (C, $^1J_{C-F}$=38.1 Hz), 170.2 (C); MS (ESI+) m/z (rel intensity) 402 [(M+H)$^+$, 100%], 386 (20), 224 (9), 208 (11), 151 (11); HRMS (ESI+) m/z calc'd for C$_{15}$H$_{20}$N$_3$O$_8$S [M+H]$^+$: 402.0971. found 402.0974 (Δ=0.7 ppm).

Storage: The dry sample of DAP amino acid 6-TFA was stored in air-tight dark glass vials in a cold, dry and dark environment and was stable for over 3 years without decomposition.

Handling: DAP amino acid 6-TFA is light sensitive and slightly hygroscopic upon exposure to moist air, hence the sample of it in a vial was always handled in a dark and dry atmosphere. It is noteworthy that the vial containing 6-TFA taken out from the fridge or freezer was always allowed to warm to r.t. prior to opening and handling.

Method II (Prepared from 6d):

A dry sample of (2S)-2-[(tert-butoxycarbonyl)amino]-3-{[(2-{[1-(6-nitrobenzo[d][1,3]dioxol-5-yl)ethyl]thio}ethoxy)carbonyl]amino}propanoic acid 6d (26.70 g, 53.2395 mmol, 1.0 eq.) was loaded on to a dry 1 litre single-necked round-bottomed flask and dissolved in dry CH$_2$Cl$_2$ (300 mL). The flask was wrapped with aluminium foil to exclude light, and dry Et$_3$SiH (84.69 mL, 530.24 mmol, 10.0 eq.) was added to the solution. After 5 min, freshly distilled CF$_3$COOH (81.54 mL, 1.0648 mol, 20.0 eq.) was added to the solution drop-wise for 15 min. The solution turned yellow-brown and was left stirring at r.t. in the dark. After 5 h, the reaction was judged to be complete by TLC (SiO2 plate, EtOAc/CH$_3$COOH=98:2) and LC-MS analysis (C18 reverse phase column, H$_2$O—CH$_3$CN as mobile phase) and the solution was concentrated to dryness under reduced pressure to obtain a yellow-brown gum. This was dissolved in dry CH$_3$OH (40 mL) and evaporated to dryness under reduced pressure; this was repeated three times and product dried in high vacuum (<0.1 mbar) to remove any residual CF$_3$COOH, Et$_3$SiH and H$_2$O. The yellow-brown gum was dissolved in dry CH$_3$OH (40 mL), transferred to a dry 3 L round-bottomed flask under an argon atmosphere and cooled to 0° C. Dry Et$_2$O (2.5 L) was added to the flask via cannula under a positive pressure of argon gas while the contents were vigorously stirred. A pale yellow precipitate was formed and the contents stirred vigorously at 0° C. for 15 min and then at r.t. for 2 h. The precipitate was then filtered and washed with dry Et$_2$O (3×500 mL), followed by dry n-hexane (150 mL). The product was dried in high vacuum (<0.1 mbar) overnight for 14 h in the dark to obtain (2S)-2-amino-3-{[(2-{[1-(6-nitrobenzo[d][1,3]di-oxol-5-yl)ethyl]thio}ethoxy)carbonyl]amino}propanoic acid TFA salt 6 as a pale-yellow powder (20.465 g, 75%) and a mixture of ~1:1 epimers.

VlmTE Substrate Syntheses

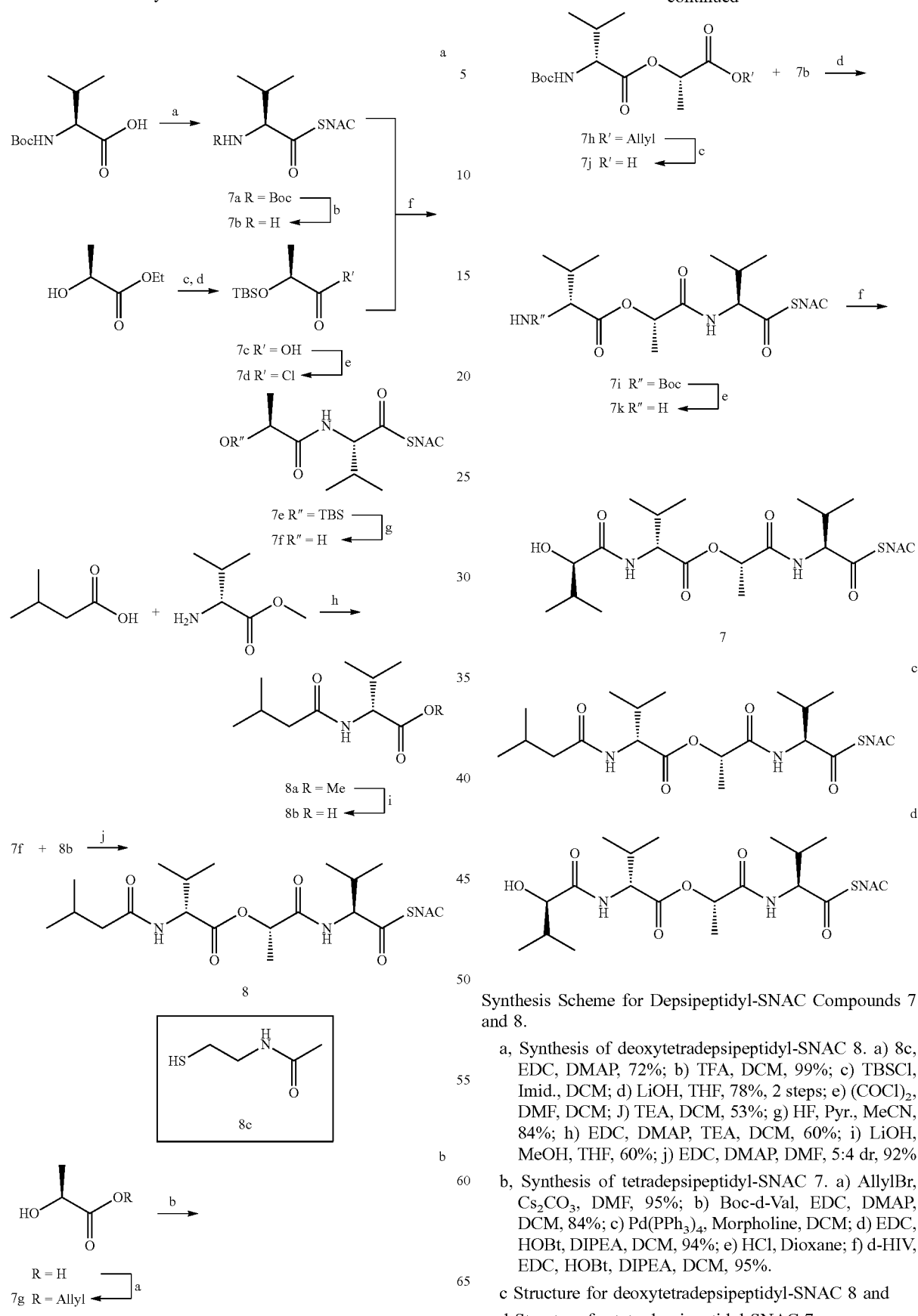

Synthesis Scheme for Depsipeptidyl-SNAC Compounds 7 and 8.

a, Synthesis of deoxytetradepsipeptidyl-SNAC 8. a) 8c, EDC, DMAP, 72%; b) TFA, DCM, 99%; c) TBSCl, Imid., DCM; d) LiOH, THF, 78%, 2 steps; e) (COCl)$_2$, DMF, DCM; J) TEA, DCM, 53%; g) HF, Pyr., MeCN, 84%; h) EDC, DMAP, TEA, DCM, 60%; i) LiOH, MeOH, THF, 60%; j) EDC, DMAP, DMF, 5:4 dr, 92% b, Synthesis of tetradepsipeptidyl-SNAC 7. a) AllylBr, Cs$_2$CO$_3$, DMF, 95%; b) Boc-d-Val, EDC, DMAP, DCM, 84%; c) Pd(PPh$_3$)$_4$, Morpholine, DCM; d) EDC, HOBt, DIPEA, DCM, 94%; e) HCl, Dioxane; f) d-HIV, EDC, HOBt, DIPEA, DCM, 95%.

c Structure for deoxytetradepsipeptidyl-SNAC 8 and d Structure for tetradepsipeptidyl-SNAC 7.

(S)-S-(2-acetamidoethyl) 2-((tert-butoxycarbonyl)amino)-3-methylbutanethioate (7a)

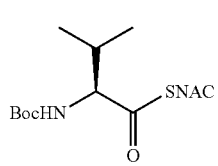

Boc-L-Valine (7.29 g, 33-56 mmol, 1.0 equiv.) was dissolved in CH$_2$Cl$_2$. N-Acetyl-cysteamine (4.00 g, 33-56 mmol, 1.0 equiv.). N-(3-dimethylaminopropyl)-N'-ethylcarbodiimide hydrochloride (EDC, 7.72 g, 40.27 mmol, 1.2 equiv.) and 4-(dimethyl-amino)pyridine (DMAP, 410 mg, 3.36 mmol, 0.1 equiv.) were added to the mixture. The reaction was stirred for 16 h at ambient temperature. The reaction was quenched with NH$_4$Cl(aq) and extracted 3× with EtOAc. The organic fractions were combined, washed with brine, dried over Na$_2$SO$_4$ and concentrated. The desired product (7.69 g, 24.16 mmol, 72% yield) was purified with silica column chromatography (5% MeOH in CH$_2$Cl$_2$). R$_f$=0.37 (2:3 acetone:hexanes). $^1$H NMR (400 MHz, CDCl$_3$) δ 5.95 (s, 1H), 4.97 (d, J=8.8 Hz, 1H), 4.21 (dd, J=8.9, 4.8 Hz, 1H), 3.48-3.30 (m, 2H), 3.08-2.94 (m, 2H), 2.22 (td, J=13.4, 6.7 Hz, 1H), 1.43 (s, 9H), 0.96 (d, J=6.9 Hz, 3H), 0.85 (d, J=6.9 Hz, 3H). $^{13}$C NMR (100 MHz, CDCl$_3$) δ 201.74, 170.35, 155.66, 80.42, 65.68, 39.38, 30.77, 28.38, 28.33, 23.16, 19.40, 17.01. HRMS (ESI+) Calculated Mass (C$_{14}$H$_{26}$N$_2$O$_4$SNa) 341.1511. found 341.1512.

(S)-S-(2-acetamidoethyl) 2-amino-3-methylbutanethioate (7b)

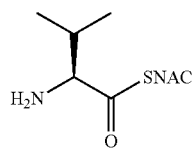

In a round-bottom flask, 7a (0.5 g, 1.57 mmol, 1.0 equiv.) was dissolved in CH$_2$Cl$_2$ (3 mL). The solution was cooled to 0° C. using an ice bath and trifluoroacetic acid (3 mL) was added. The reaction was allowed to proceed at ambient temperature for 45 min. The reaction mixture was concentrated and the desired product (341 mg, 1.56 mmol, >99% yield) was purified by silica column chromatography (5% to 10% MeOH in CH$_2$Cl$_2$). $^1$H NMR (300 MHz, DMSO) δ 8.45 (s, 157 2H), 8.10 (t, J=5.5 Hz, 1H), 4.15 (d, J=4.8 Hz, 1H), 3.27-3.17 (m, 2H), 3.13-2.98 (m, 2H), 2.28-2.09 (m, 1H), 0.99 (d, J=6.9 Hz, 3H), 0.95 (d, J=7.0 Hz, 3H). $^{13}$C NMR (75 MHz, DMSO) δ 196.18, 169-35, 63-48, 37-78, 30.10, 28.40, 22-50, 18.03, 17.26.

(S)-2-((tert-butyldimethylsilyl)oxy)propanoic acid (7c)

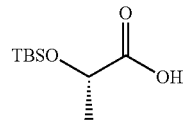

In a round-bottom flask, ethyl L-lactate (5.08 g, 43.0 mmol, 1.0 equiv.) was dissolved in CH$_2$Cl$_2$ (55 mL) and the solution was cooled to 0° C. using an ice bath. tert-Butyldimethylsilyl chloride (6.48 g, 45.15 mmol, 1.05 equiv.) and imidazole (3.51 g, 51.6 mmol, 1.2 equiv.) was added to this mixture, after which the reaction was allowed to proceed at ambient temperature for 2 h. The reaction mixture was then diluted with H$_2$O and extracted 3× with CH$_2$Cl$_2$. The organic fractions were combined, washed with ice cold 5% HCl(aq), washed with brine, dried over Na$_2$SO$_4$ and concentrated. The crude intermediate (S)-ethyl 2-(tert-butyldimethylsilyloxy)propanoate was dissolved in THF (215 mL). The mixture was cooled to 0° C. using an ice bath, and a cooled solution of LiOH (0.4 M, 215 mL) was added dropwise over 20 min. The reaction mixture was stirred for 4 h at ambient temperature. The resulting reaction mixture was concentrated to half its original volume, and the resulting aqueous solution was extracted 3× with Et$_2$O. The organic fractions were combined and extracted 3× with a saturated solution of NaHCO$_3$(aq). The aqueous fractions were combined, acidified to pH 4 with 1 M KHSO$_4$(aq) and extracted 3× with Et$_2$O. The organic fractions were combined, dried over Na$_2$SO$_4$ and concentrated. The desired product (6.88 g, 33.7 mmol, 78% yield over two steps) was obtained and used without further purification. The NMR data were consistent with literature values[45]. $^1$H NMR (300 MHz, CDCl$_3$) δ 4.36 (q, J=6.8 Hz, 1H), 1.45 (d, J=6.8 Hz, 3H), 0.92 (s, 9H), 0.13 (s, 6H).

(S)-2-((tert-butyldimethylsilyl)oxy)propanoyl chloride (7d)

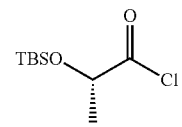

In a round-bottom flask, 7c (3.7 g, 18 mmol, 1.0 equiv.) was dissolved in DMF (45 mL) and the solution was cooled to 0° C. using an ice bath. Oxalyl chloride (13.6 mL of a 2.0 M solution in DCM, 10.0 equiv.) and a catalytic amount of DMF were added. The reaction proceeded for 2 h from 0° C. to ambient temperature. The reaction mixture was concentrated and the crude oil was used in subsequent reactions without purification.

TBSO-L-Lac-L-Val-SNAC (7e)

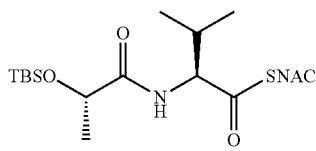

In a round-bottom flask, 7b (1.95 g, 9 mmol, 1.0 equiv.) was dissolved in CH$_2$Cl$_2$ (40 mL). The crude oil 7d (18 mmol, 2.0 equiv.) was dissolved in CH$_2$Cl$_2$ (5 mL) and added to the mixture. Et$_3$N (2.5 mL, 18 mmol, 2.0 equiv.) was added and the reaction was allowed to proceed for 4 h. The reaction mixture was quenched with NH$_4$Cl(aq), extracted 3× with EtOAc, washed with brine and concentrated. The desired product (1.93 g, 4-77 mmol, 53% yield) was purified from the crude mixture by silica column chromatography (50% to 90% EtOAc in hexanes). $^1$H NMR (300 MHz, CDCl$_3$) δ 7.22 (d, J=9.3 Hz, 1H), 6.03 (s, 1H), 4.53 (dd, J=9.3, 4.5 Hz, 1H), 4.25 (q, J=6.7 Hz, 1H), 3.38 (q, J=6.2 Hz, 2H), 3.07-2.98 (m, 2H), 2.40-2.21 (m, 1H), 1.93 (s, 3H), 1.38 (d, J=159 6.7 Hz, 3H), 1.01-0.82 (m, 15H), 0.13 (s, 3H), 0.12 (s, 3H). $^{13}$C NMR (75 MHz, CDCl$_3$) δ 200.34, 174.90, 170.47, 70.03, 63.48, 39.47, 31.04, 28.51, 25.82, 23.23, 22.04, 19.47, 18.00, 16.83, −4.54, −5.03.

HO-L-Lac-L-Val-SNAC (7f)

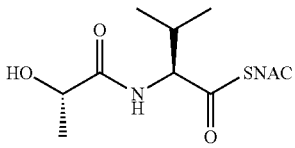

Compound 7e (250 mg, 0.617 mmol, 1.0 equiv.) was dissolved in acetonitrile (20 mL) in a 50 mL polypropylene Falcon tube. Pyridine (249 μL, 3.09 mmol, 5 equiv.) and HF (48 wt. % aq. 533 μL, 30.9 mmol, 50 equiv.) were added. The reaction was stirred at ambient temperature for 16 h. The reaction mixture was quenched with NH$_4$Cl(aq), extracted 3× with EtOAc, washed with brine, dried over Na$_2$SO$_4$ and concentrated. The desired product (150.1 mg, 0.517 mmol, 84% yield) was purified with silica column chromatography (2% to 8% MeOH in CH$_2$Cl$_2$). $^1$H NMR (400 MHz, CDCl$_3$) δ 7.21 (d, J=9.2 Hz, 1H), 6.20 (s, 1H), 4.54 (dd, J=9.2, 5.4 Hz, 1H), 4.30 (q, J=6.8 Hz, 1H), 4.15 (s, 1H), 3.52-3.32 (m, 2H), 3.12-2.94 (m, 2H), 2.36-2.21 (m, 1H), 1.95 (s, 3H), 1.44 (t, J=6.3 Hz, 3H), 0.97 (d, J=6.8 Hz, 3H), 0.91 (d, J=6.8 Hz, 3H). $^{13}$C NMR (100 MHz, CDCl$_3$) δ 200.20, 175-47, 170-94, 68.66, 63.77, 39.24, 30.90, 28.71, 23.25, 21.28, 19.45, 17.27.

(S)-allyl 2-hydroxypropanoate (7g)

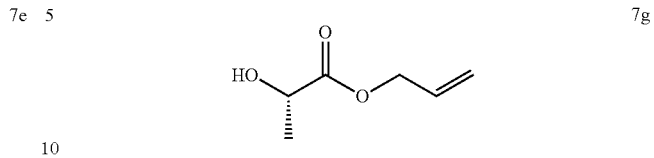

In a round bottom flask, 1 g L-lactic acid (11.11 mmol, 1 equiv.), and 3.8 g caesium carbonate (11.67 mmol, 1.05 equiv.) were dissolved in 13 mL DMF. Allyl bromide (3.75 mL, 5.37 g, 44.44 mmol, 4 equiv.) was added dropwise at ambient temperature. Upon complete addition the reaction was stirred at ambient temperature for 48 h. At completion the excess allyl bromide was removed by rotary evaporation and the remaining solution diluted with water then extracted 3× with Et$_2$O. The combined organic fractions were washed twice with water, once with brine, dried over Na$_2$SO$_4$ and concentrated to the title compound (1.47 g, 95%) as a pale yellow oil. Characterization data is consistent with reported values[46]. $^1$H NMR (400 MHz, CDCl$_3$) δ 5.99-5.82 (m, 1H), 5.40-5.18 (m, 2H), 4.71-4.59 (m, 2H), 4.29 (q, J=6.9 Hz, 1H), 2.75 (s, 1H), 1.42 (d, J=6.9 Hz, 3H).

(R)-(S)-1-(allyloxy)-1-oxopropan-2-yl 2-((tert-butoxycarbonyl)amino)-3-methyl-butanoate (7h)

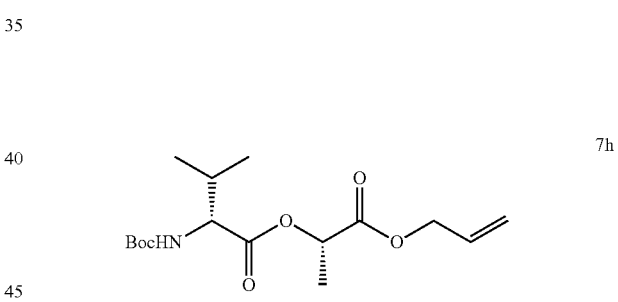

In a round bottom flask, 1 g of 7g (7.69 mmol, 1 equiv.) and 1.67 g of Boc-D-Val (8.46 mmol, 1.1 equiv.) were dissolved in 39 mL of CH$_2$Cl$_2$. To this solution 2.21 g EDC (11.54 mmol, 1.5 equiv.) and 1.03 g DMAP (8.46 mmol, 1 equiv.) were added at ambient temperature. The resulting solution was stirred for 20 h at ambient temperature. The reaction was quenched with NH$_4$Cl(aq), extracted 3× with CH$_2$Cl$_2$, washed with NaHCO$_3$(aq), washed with brine, dried over Na$_2$SO$_4$, and concentrated. The title compound (2.12 g, 84%) was purified by silica column chromatography (20% EtOAc in hexanes). R$_f$=0.41 (1:3 EtOAc:Hexanes) $^1$H NMR (400 MHz, CDCl$_3$) δ 5.95-5.81 (m, 1H), 5.29 (dddd, J=21.3, 11.7, 6.6, 1.3 Hz, 2H), 5.13 (q, J=7.0 Hz, 1H), 4.97 (d, J=8.9 Hz, 1H), 4.67-4.59 (m, 2H), 4.28 (dd, J=8.9, 4.8 Hz, 1H), 2.25-2.11 (m, 1H), 1.50 (d, J=7.1 Hz, 3H), 1.43 (s, 9H), 0.97 (d, J=6.9 Hz, 3H), 0.91 (d, J=6.9 Hz, 3H). $^{13}$C NMR (100 MHz, CDCl$_3$) δ 171-50, 169.95, 155-56, 131-43, 118.83, 79-77, 69.17, 65-93, 58.60, 31.28, 28.32, 18.99, 17.49, 17.00. HRMS (ESI+): Exact mass calculated for C$_{16}$H$_{27}$NNaO$_6$: 352.1736. Found: 352.1721.

Boc-D-Val-L-Lac-L-Val-SNAC (7i)

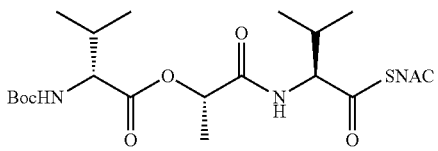

In a round bottom flask, 250 mg of 7h (0.76 mmol, 1 equiv.) was dissolved in 4 mL of $CH_2Cl_2$ under a nitrogen atmosphere. To this solution 86 μL of morpholine (87 mg, 0.99 mmol, 1.3 equiv.) and 62 mg of $Pd(PPh_3)_4$ was added in a single portion. The reaction was stirred at ambient temperature and monitored by TLC. At completion the reaction was quenched by the addition of 10% aq. HCl, the organic layer was removed and the remaining aqueous fraction was extracted 3× with $CH_2Cl_2$. The combined organic fractions were washed with brine, dried over $Na_2SO_4$ and concentrated, this intermediate, 7j, was used immediately in the subsequent reaction. To a flame dried round bottom flask was added 194 mg of 7b (as HCl salt, 0.76 mmol, 1 equiv.) and the crude 7j (0.76 mmol, 1 equiv.) in 4 mL of $CH_2Cl_2$. To the resulting solution was added 400 μL of Hunig's base (295 mg, 2.28 mmol, 3 equiv.), 154 mg HOBt (1.14 mmol, 1.5 equiv.) and 220 mg EDC (1.14 mmol, 1.5 equiv.). The reaction was stirred under argon at ambient temperature for 20 h. The reaction was quenched with $NH_4Cl(aq)$, extracted 3× with $CH_2Cl_2$, washed with $NaHCO_3(aq)$, then with brine, dried over $Na_2SO_4$, and concentrated. The title compound (350 mg, 94% over 2 steps) was purified by silica column chromatography (40% acetone in hexanes). $R_f$=0.35 (2:3 acetone:hexanes) $^1$H NMR (400 MHz, $CDCl_3$) δ 7.08 (d, J=8.2 Hz, 1H), 6.07 (s, 1H), 5.38 (q, J=6.8 Hz, 1H), 5.02 (d, J=7.0 Hz, 1H), 4.46-4.39 (m, 1H), 3.99 (t, J=6.9 Hz, 1H), 3.45-3.30 (m, 2H), 3.11-2.89 (m, 2H), 2.30 (dq, J=13.4, 6.7 Hz, 1H), 2.11-2.01 (m, 1H), 1.92 (s, 3H), 1.49 (d, J=6.9 Hz, 3H), 1.39 (s, 9H), 1.01-0.91 (m, 12H). $^{13}$C NMR (100 MHz, $CDCl_3$) δ 200.14, 171.72, 170.89, 170.48, 155.92, 80.45, 70.58, 64.74, 59.74, 39.30, 30.47, 30.27, 28.46, 28.26, 23.10, 19.33, 18.90, 18.49, 17.85, 17.53. HRMS (ESI+): Exact mass calculated for $C_{22}H_{39}N_3NaO_7S$: 512.2406. Found: 512.2391

HO-D-Hiv-D-Val-L-Lac-L-Val-SNAC (7)

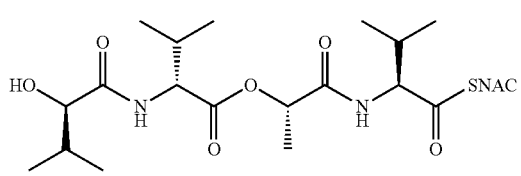

To a round bottom flask was added 118 mg 7i (0.24 mmol, 1 equiv.) in a minimal amount of THF and this was cooled to 0° C. To this was added 1 mL of 4M HCl in dioxane (Sigma), and the reaction allowed to warm to ambient temperature. The reaction was monitored by TLC and at completion all solvent was removed by rotary evaporation. The unpurified intermediate 7k was used immediately in the subsequent reaction. Intermediate 7k was dissolved in 2 mL of $CH_2Cl_2$ and to this was added sequentially 125 μL of Hunig's base (93 mg, 0.72 mmol, 3 equiv.), 32 mg of D-α-hydroxyisovaleric acid (0.27 mmol, 1.1 equiv.), 49 mg HOBt (0.36 mmol, 1.5 equiv.), and 70 mg EDC (0.36 mmol, 1.5 equiv.). The reaction was stirred at ambient temperature for 24 h and at completion was quenched with $NH_4Cl(aq)$, extracted 5× with $CH_2Cl_2$, washed with $NaHCO_3(aq)$, then with brine, dried over $Na_2SO_4$, and concentrated. The title compound (111 mg, 95%) was purified by silica column chromatography (50% Acetone in hexanes). $^1$H NMR (300 MHz, $CDCl_3$) δ 7.29 (s, 1H), 6.20 (t, J=5.7 Hz, 1H), 5.26 (q, J=7.0 Hz, 1H), 4.55 (br, 1H), 4.47 (dd, J=9.0, 6.5 Hz, 1H), 4.26 (t, J=7.7 Hz, 1H), 3.99 (d, J=2.9 Hz, 1H), 3.52-3.25 (m, 2H), 2.99 (ddt, J=20.4, 13.3, 6.5 Hz, 2H), 2.39-2.25 (m, 1H), 2.20-2.06 (m, 2H), 1.97 (s, 3H), 1.54 (d, J=7.0 Hz, 3H), 1.06-0.93 (m, 15H), 0.88 (d, J=6.9 Hz, 3H). $^{13}$C NMR (75 MHz, $CDCl_3$) δ 200.05, 175.25, 171.69, 171.43 (2C), 76.33, 71.14, 64.55, 58.39, 38.95, 31.95, 30.25, 30.12, 28.64, 23.22, 19.49, 19.17, 19.13, 18.83, 18.18, 18.04, 16.15. HRMS (ESI+): Exact mass calculated for $C_{22}H_{39}N_3NaO_7S$: 512.2401. Found: 512.2406

(R)-methyl 3-methyl-2-(3-methylbutanamido)butanoate (8a)

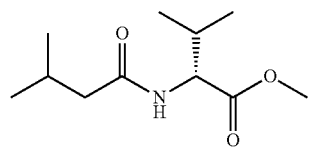

In a round-bottom flask, D-valine methyl ester hydrochloride (250 mg, 1.5 mmol, 1.0 equiv.) was dissolved in $CH_2Cl_2$ (15 mL). Isovaleric acid (230 mg, 2.25 mmol, 1.5 equiv.), EDC (430 mg, 2.25 mmol, 1.5 equiv.), DMAP (276 mg, 2.25 mmol, 1.5 equiv.), and $Et_3N$ (420 μL, 3.00 mmol, 2.0 equiv.) were added and the reaction was allowed to mix at ambient temperature for 16 h. The reaction was quenched with $NH_4Cl(aq)$, extracted 3× with $CH_2Cl_2$, washed with $NaHCO_3(aq)$, washed with brine, dried over $Na_2SO_4$, and concentrated. The desired compound (193.7 mg, 0.90 mmol, 60% yield) was purified by silica column chromatography (20 to 50% EtOAc in hexanes). $^1$H NMR (400 MHz, $CDCl_3$) δ 5.96 (d, J=8.0 Hz, 1H), 4.57 (dd, J=8.8, 4.9 Hz, 1H), 3.71 (s, 3H), 2.19-2.04 (m, 4H), 0.97-0.86 (m, 12H). $^{13}$C NMR (100 MHz, $CDCl_3$) δ 172.85, 172.49, 56.91, 52.19, 46.14, 31-35, 26.29, 22.56, 22.53, 19.07, 17.93

(R)-3-methyl-2-(3-methylbutanamido)butanoic acid (8b)

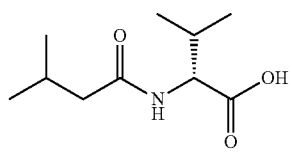

In a round-bottom flask, 8a (180 mg, 1.2 mmol, 1.0 equiv.) was dissolved in MeOH (24 mL) and THF (24 mL) and the solution was cooled to 0° C. using an ice bath. LiOH (1 M, 24 mL) was added dropwise and the solution was allowed to proceed from 0° C. to ambient temperature over 4 h. The solution was concentrated to one-third volume and the resulting aqueous solution was acidified to pH 3 with 10% HCl. The solution was extracted 3× with $CH_2Cl_2$, dried over $Na_2SO_4$ and concentrated. The desired product (145 mg, 0.72 mmol, 60% yield) was purified by silica column chromatography (5% MeOH in $CH_2Cl_2$+0.5% acetic acid). $^1$H NMR (300 MHz, MeOD) δ 4.32 (d, J=5.8 Hz, 1H), 2.23-2.01 (m, 4H), 1.01-0.92 (m, 12H). $^{13}$C NMR (75 MHz, MeOD) δ 175.84, 174.93, 59.00, 45.90, 31.53, 27.50, 22.76, 22.72, 19.65, 18.41.
8(A) and 8c (B)

(R)-(S)-1-(((S)-1-((2-acetamidoethyl)thio)-3-methyl-1-oxobutan-2-yl)amino)-1-oxopropan-2-yl 3-methyl-2-(3-methylbutanamido)butanoate (8)

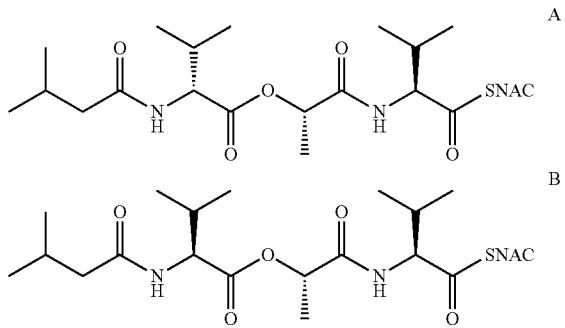

In a round bottom flask, the alcohol 7f (25.2 mg, 0.087 mmol, 1.0 equiv.) and carboxylic acid 8b (35 mg, 0.174 mmol, 2.0 equiv.) were dissolved in DMF (1 mL). The solution was cooled to −20° C. using a dry ice/acetone bath and EDC (67 mg, 0.35 mmol, 4.0 equiv.) and DMAP (21 mg, 0.174 mmol, 2.0 equiv.) were added. The mixture was allowed to warm to ambient temperature and the reaction proceeded for 16 h. The reaction was quenched with $NH_4Cl$ (aq) and extracted 3× with EtOAc. The organic fractions were combined, washed with brine, dried over $Na_2SO_4$ and concentrated. A mixture of C-2.2 diastereomers (37.9 mg, 0.08 mmol, 92% yield) in a 5:4 ratio (A:B) was purified from the crude residue by silica column chromatography (1% to 5% MeOH in CH2Cl2). The diastereomers were separated with preparatory-TLC. 8 (A) $^1$H NMR (400 MHz, CDCl$_3$) δ 7.21 (d, J=8.2 Hz, 1H), 6.15 (s, 1H), 5.93 (d, J=6.8 Hz, 1H), 5.35 (q, J=7.0 Hz, 1H), 4.44 167 (dd, J=8.3, 6.4 Hz, 1H), 4.29 (t, J=7.0 Hz, 1H), 3.50-3.32 (m, 2H), 3.08-2.95 (m, 2H), 2.41-2.29 (m, 1H), 2.19-2.00 (m, 4H), 1.96 (s, 3H), 1.53 (d, J=6.9 Hz, 3H), 1.05-0.92 (m, 18H). $^{13}$C NMR (100 MHz, CDCl$_3$) δ 200.14, 173-48, 171.62, 171.04, 170.65, 71.03, 64-93, 58.71, 45.66, 39-33, 30-37, 30-35, 28.75, 26-31, 23.27, 22.63, 22.57, 19.48, 19.07, 18.79, 18.11, 17.91. 8c (B) $^1$H NMR (400 MHz, CDCl$_3$) δ 6.95 (d, J=8.7 Hz, 1H), 6.04 (s, 1H), 5.81 (d, J=7.2 Hz, 1H), 5.25 (q, J=6.8 Hz, 1H), 4.54 (dd, J=8.8, 5.9 Hz, 1H), 4.49 (dd, J=7.3, 4.7 Hz, 1H), 3.47-3.36 (m, 2H), 3.11-2.98 (m, 2H), 2.38-2.26 (m, 2H), 2.20-2.09 (m, 3H), 1.95 (s, 3H), 1.51 (d, J=6.9 Hz, 3H), 1.04 (d, J=6.9 Hz, 3H), 0.99 (dd, J=6.7, 2.5 Hz, 12H), 0.94 (d, J=6.8 Hz, 3H). $^{13}$C NMR (100 MHz, CDCl$_3$) δ 199-74, 173.66, 170.84, 170.68, 170.49, 71.63, 64.29, 57-90, 46.06, 39.32, 30-72, 30-55, 28.91, 26.35, 23.30, 22.64, 22.57, 19.42 (2C), 18.16, 17.94, 17.70. HRMS (ESI+): Exact mass calculated for $C_{22}H_{39}N_3NaO_6S$: 496.2452. Found: 496.2457

Summary of Examples 1-8

We describe a strategy for genetically encoding DAP in recombinant proteins. We show that genetically encoding DAP in place of catalytic cysteines or serines enables the capture of unstable thioester or ester intermediates as their stable amide analogues. We have exemplified the utility of this approach for a cysteine protease and a thioesterase, and provided unique insight into intermediates in the synthesis of valinomycin by Vlm TE. Our results reveal the massive lid rearrangement associated with the dodecapeptidyl-bound Vlm TE. Importantly, the DAP system allows use of both widely-used, reaction competent, substrates (e.g. native proteins containing protease sites), substrate analogues (in this case SNACs), and commercially available natural products (here valinomycin, and likely other cyclic products[28]) to form near-native acyl-enzyme complexes.

The PCP domain, a key player in the TE domain catalytic cycle, is absent from these structures, but its binding site can be inferred from the informative dead-end inhibitor trapped PCP-TE structure of EntF[46] (FIG. 7). The PCP domain docks at αE of the TE, and the PPE extends the ~15 Å to position the thiol near Ser/DAP2463 (FIG. 7a, c-iii). The position of the PPE in the EntF structure is compatible with the dodecapeptide-bound conformation of the lid, but not with the apo/tetrapeptide-bound conformation in our Vlm TE structures. (The lid in the EntF structure is partially disordered.) This EntF structure showed how the PCP and TE domains can position the thioester of the depsipeptidyl-PPE near Ser/DAP2463, but in Vlm, these domains must also be able to position the terminal hydroxyl of tetradepsipeptidyl-PPE near Ser/DAP2463 for the oligomerization step. To do so, another ~15 Å of length of tetradepsipeptide (between terminal hydroxyl and PPE sulphur) must be accommodated in the TE domain (compare FIGS. 7c-ii and 7c-iii). The lid likely facilities this, perhaps using a pocket similar to the one we observe in the dodecapeptidyl-TE$_{DAP}$ structures.

One can thus assemble the known structures into a hypothetical pathway for oligomerization and cyclization (FIG. 7). When in the observed apo/tetradepsipeptide-bound conformation, Lα1 of Vlm TE could inhibit any attached depsipeptide from curling around for cyclization (FIG. 7). PCP binding could induce a TE conformation similar to those we observe for the dodecadepsipeptide-bound TE, which could accommodate the ~30 Å tetradepsipeptidyl-PPE bound to the PCP domain and guide it towards the active site (FIG. 7b). A transition to an open/largely disordered lid (as seen in EntF PCP-TE) could allow the PCP to present the thioester for transfer back to the Ser2463. Finally, the lid conformation observed in the dodecadepsipeptide-TE$_{DAP}$ structures, with its semi-sphere-like pocket, helps curl the dodecadepsipeptide back towards Ser2463 for cyclization. (FIG. 7b, c-iv).

The lid conformation and the semi-sphere-like pocket seen in the structures of dodecadepsipeptide-TE$_{DAP}$ are likely to be very important during the cyclization step in the thioesterase cycle. This pocket is mainly made up of hydrophobic residues, and it provides a steric barrier that prevents a dodecadepsipeptide attached to Ser/DAP2463 from extending out in a linear fashion (FIG. 7b). Rather, this lid conformation favours curling back of the substrate's free end towards the acyl linkage between TE and the substrate.

Thus, cyclization of the dodecadepsipeptide to valinomycin may be thought of as entropically controlled by the pocket, with the dodecapeptide conformations dictated by partial confinement in the pocket and TE domain active site.

The mobility of the lid seen in other studies and seen dramatically here, even when the TE domain is covalently bound with bona fide substrates, and the paucity of specific interactions between the lid and the rest of the TE domain make it unlikely that there is a single, fully defined conformation at any of these steps of the synthetic cycle. Formation of a pre-defined/templated conformation of the cyclization substrate has been proposed to facilitate cyclization in tyrocidine synthetase[40, 47], while specific interaction between the lid and the polyketide substrate was proposed to do this in pikromycin synthase, but there is no evidence for these mechanisms in Vlm TE. Indeed, specific and strong binding interactions could slow the synthetic cycle, as the tetradepsipeptide must transition back and forth between being ligated to the PCP domain and to the TE domain, and the same tetradepsipeptide must assume multiple different positions in the course of a cycle. Rather, the lid conformation likely fluctuates rapidly through the cycle, "breathing" and transiently visiting reaction-competent conformations. Interestingly, a novel inhibitor to a *Mycobacterium tuberculosis* polyketide synthase TE domain binds between the cluster of lid helices[48]. It is proposed to compete with substrate binding, but such an inhibitor could also act by preventing structural rearrangements in the lid similar to those we observe here.

While we have focussed on utilizing encoded DAP to provide insight into the thioesterase acyl-enzyme intermediates in the synthesis of valinomycin, the DAP system holds great promise for the study of the large variety of enzymes that feature cysteine- or serine-bound acyl-enzyme intermediates[1], including natural product megaenzyme domains like other cyclizing TE domains, transglutaminase homologue condensation domains and PKS ketosynthase domains. Extensions of the approaches reported herein will facilitate the structural and biochemical characterization of diverse acyl-enzyme intermediates. In addition, by genetically encoding DAP in enzymes that proceed through acyl-enzyme intermediates[49] but have unknown substrate specificity, it may be possible to covalently capture and identify native substrates.

Example 9—Expression, Purification and Activity Tests of UBE2L3-DAP

Purification of UBE2L3(C86DAP5) by GST-tag affinity purification, followed by GST-tag cleavage by TEV protease and Strep-tag affinity purification was also tested. This strategy led to a clean product.

The mass of purified UBE2L3(C86DAP5)-Strep was determined by LC-ESI-MS: LC-ESI-MS of UBE2L3 (C86DAP5)-Strep before UV light irradiation: UBE2L3 (C86DAP5)-Strep [1]: Expected: 19050.57 Da, Observed: 19048.79 Da; UBE2L3(C86INT); Strep [2]: Expected: 18857.53 Da, Observed: 18853.15 Da.

The deprotection of DAP5 occurs in two distinct steps. First, the photocaging group is removed under the action of UV-light, leading to a semi-deprotected intermediate. A second intramolecular reaction finally results in the completely deprotected DAP. After the purification of UBE2L3 (C86DAP5), it was found that most of the protein contained the semi-deprotected intermediate (UBE2L3[C86INT]), although some of it was present in the complete photocaged form. After UV light irradiation, the protein mass was assessed again by LC-ESI-MS:
  LC-ESI-MS of UBE2L3(C86DAP5)-Strep after UV light irradiation: UBE2L3(C86INT)-Strep [2]: Expected: 18857.53 Da, Observed: 18853.15 Da.

As expected UBE2L3(C86DAP5)-Strep could not be detected anymore after UV light irradiation. Indeed, only UBE2L3(C86INT)-Strep could be detected. The protein was subsequently incubated at 37° C. for 3 h and its mass assessed by LC-ESI-MS. As expected, UBE2L3(C86DAP)-Strep was detected together with UBE2L3(C86INT)-Strep.
  LC-ESI-MS of UBE2L3(C86DAP5)-Strep after UV light irradiation and 3 h incubation at 37° C.: UBE2L3(C86INT)-Strep [2]: Expected: 18857.53 Da, Observed: 18853.15 Da; UBE2L3(C86DAP)-Strep [3]: Expected: 18753.59 Da, Observed: 18753.13 Da.

Unfortunately, longer incubation times at 37° C. (6 h and 16 h) did not lead to an improvement in the deprotection of UBE2L3(C86INT)-Strep. Indeed, the fraction of protein containing DAP did not appear to vary, representing about 30% of the total protein LC-ESI-MS of UBE2L3 (C86DAP5)-Strep after UV light irradiation and longer incubation times. UBE2L3(C86INT)-Strep was incubated for 6 h or 16 h at 37° C. No improvement in deprotection was noticed, the fraction of protein containing DAP (approximately 30%) remained largely unchanged.

In order to test whether UBE2L3(C86DAP5), which had been irradiated with UV light and incubated overnight at 37° C., could be charged with Ub, a reaction containing 0.2 µM E1 and HA-tagged Ub in E2 loading buffer was set up. Each reaction (positive control [wt], negative control [C86A] and [C86DAP]) was performed with and without Ub (see FIG. 23).

As expected, a higher molecular weight band could be observed for UBE2L3(wt), corresponding to the thioester-linked E2-Ub complex. In addition, a higher molecular weight band could also be detected for UBE2L3[C86DAP], corresponding to the isopeptide-linked E2-Ub complex. The incomplete conversion of UBE2L3 into a complex with Ub (FIG. 23), is consistent with the incomplete deprotection of DAP5 in UBE2L3.

The newly formed isopeptide bond between UBE2L3 (C86DAP) and Ub is redox insensitive and cannot be reduced in the presence of ß-mercaptoethanol. This is in contrast with the complex formed of UBE2L3(wt) and Ub which is redox sensitive (FIG. 23).

To further characterise the identity of the different bands, both an anti-HA and anti-UBE2L3 blot were performed (FIGS. 23 B and C), clearly showing that the higher molecular weight band formed in the presence of both HAUb and UBE2L3(C86DAP) contains UBE2L3 and Ub.

Finally, to characterise the chemical nature of the newly formed bond, the band corresponding to the UBE2L3 (C86DAP)-Ub complex was excised and analysed by tandem mass spectrometry after tryptic digestion (performed by the Proteomics Facility, University of Bristol) Tandem mass spectrometry of isopeptide-linked UBE2L3(C86DAP)-Ub complex.

Tandem mass spectrometry unambiguously identifies the DAP modification at the desired site and the expected Gly-Gly modification on the residue which is consistent with Ub loading on DAP.

The analysis unambiguously confirmed the formation of a stable amide bond between UBE2L3(C86DAP) and Ub.

Example 10—Application in Live Cells

In this example, we demonstrate the technique in live cells.

In this example we show the invention in *E. coli* cells (BL21) and in mammalian cells (HEK293T).

We refer to TEV-GFP WB data provided in FIGS. 24 and 25.

In particular we refer to FIG. 24, which shows Dap-mediated substrate trapping in live *E. coli* cells. GFPs (GFP bearing a TEV cleavage site at C-terminus) and different variants of C-terminal Strep-tagged TEV protease (WT/Ala/TAG (with or without Dappc; (in this example compound 'DAP5' is referred to as 'Dappc')) were co-expressed in *E. coli* BL21 cells at 20° C. 20 h after expression, cells were directly irradiated by UV light (35 mW/cm$^2$) for 2 minutes and shaken at 37° C. Equal volumes of cells were collected at the indicated time points and analysed by western blot (anti-Strep for TEV and anti-GFP). Only TEV(Dap) showed UV dependent generation of TEV-GFP conjugate. The conjugate can be detected within 10 min after UV irradiation and the reaction went to completion within 2 h inside *E. coli* BL21 cells.

Moreover we refer to FIG. 25, which shows Dap-mediated substrate trapping in mammalian HEK293T cells. GFPs (GFP bearing a TEV cleavage site at C-terminus) and different variants of C-terminal Strep-tagged TEV protease (WT/Ala/TAG (with or without Dappc (DAP5))) were co-transfected into HEK293T cells. 48 h after transfection, cells were directly irradiated by UV light (8 mW/cm$^2$) for 2 minutes. Then cells were incubated at 37° C. and collected at indicated time points. Cells were lysed and TEV was pulled down by StrepTactinXT. The pulldown results were analysed by western blot (anti-Strep for TEV and anti-GFP). Only TEV(Dap) showed UV dependent generation of TEV-GFP conjugate. The conjugate started to form within 30 min after UV irradiation and enriched with increasing incubation time in HEK293T cells.

Additional Methods for Example 10

TEV(Dap)-GFP$_{sub}$ trapping in *E. coli*

BL21 (DE3) cells co-transformed with GFPs containing plasmid and TEV containing plasmid were induced to express proteins at 20° C. 0.1 mM Dappc (DAP5) was added to media to incorporated Dappc (DAP5). After 20 h, cells were transferred to a falcon 50 mL conical centrifuge tube and irradiated by UV light (365 nm, 35 mW/cm$^2$) for 2 min with gentle stirring. Then cells were centrifuged at 5,000 g for 5 min. The supernatant was discarded and the pellet was resuspended in fresh media containing freshly added antibiotics. Cell culture was shaken at 37° C. At each indicated time point, 5 mL of cell culture was collected and lysed in BugBuster (Merck). The total lysate was analyzed by WB (anti-Strep (ab76949, abcam) and anti-GFP (ab13970, abcam)).

TEV-GFP$_{sub}$ Trapping in HEK2Q3T Cells

HEK293T Cells were co-transfected with GFPs containing plasmid, TEV containing plasmid. 1 mM Dappc (DAP5) was added 30 min after transfection for amber suppression. 48 h after transfection, cells in 6-well plate were irradiated by UV light (365 nm, 10 mW/cm$^2$) for 2 min. Then, the media was replaced with fresh media and incubated at 37° C. At each indicated time point, cells were collected and lysed in NP lysis buffer (Cat. No. 87787, Thermo). The total lysate was used for StrepTactinXT pulldown. Elutes from beads were analyzed by WB (anti-Strep (ab76949, abcam) and anti-GFP (ab13970, abcam)).

Supplementary Methods

List of primers used in this study. Mutated residues are depicted in uppercase.

| Primer name | Primer sequence | SEQ ID NO |
|---|---|---|
| MbY271f | ggaaaggtctcgaccctgNNKaactatctgc gtaaactggatcgtattc | SEQ ID NO: 21 |
| MbY271r | ggaaaggtctcagggtcggggccagcatcgg acgcag | SEQ ID NO: 22 |
| MbN311f | ggaaaggtctccatggIINNKttttgccaaa tgggcagcggctgcacc | SEQ ID NO: 23 |
| MbN311r | ggaaaggtctcaccatggtgaattcttcca ggtgttc | SEQ ID NO: 24 |
| MbY349f | ggaaaggtctccatggtgNNKggcgatacc ctggatattatgcatgg | SEQ ID NO: 25 |
| MbY349r | ggaaaggtctcaccatgcagctatcgccca caatttcgaagtc | SEQ ID NO: 26 |
| MbV366f | ggaaaggtctccagcgcgNNKgtgggtccg gttagcctggatcgtg | SEQ ID NO: 27 |
| MbV366r | ggaaaggtctcgcgctgctcagttccagat cgccatgc | SEQ ID NO: 28 |
| MbW382f | ggaaaggtctctaaaccgNNKattggcgcg ggttttggcctggaacg | SEQ ID NO: 29 |
| MbW382r | ggaaaggtctcggtttatcaatgccccatt cacgatcc | SEQ ID NO: 30 |
| TEV_Amb_ fw | ggaaaggtctcgTAGggcagtccattagta tcaactagagatgg | SEQ ID NO: 31 |
| TEV_Amb_ rev | ggaaaggtctcccCTActgcccatccttgg tttgaatccaatgc | SEQ ID NO: 32 |

-continued

| Primer name | Primer sequence | SEQ ID NO |
|---|---|---|
| TEV_Ala_fw | ggaaaggtctcgGCTggcagtccattagta tcaactagagatgg | SEQ ID NO: 33 |
| TEV_Ala_rev | ggaaaggtctcccAGCctgcccatccttgg tttgaatccaatgc | SEQ ID NO: 34 |
| TE_for_pNHD_fw | ttattacatatgcatcatcatcaccacca tc | SEQ ID NO: 35 |
| TE_for_pNHD_rev | ataataactcgagttagccacgcg | SEQ ID NO: 36 |
| Vlm2_TE_Amb_Fw | gtgtatatcggtggtcacTAGctgggtggc catat | SEQ ID NO: 37 |
| Vlm2_TE_Amb_Rev | atatggccacccagCTAgtgaccaccgata tacac | SEQ ID NO: 38 |

Creation of DAPRSlib Library by Inverse PCR

Using the plasmid pBK-pylS as a template[39], the library (DAPRSlib) for amino acid 6 was generated by five consecutive rounds of inverse PCR reactions using the PrimeSTAR HS DNA Polymerase (Takara Bio) following manufacturer's guidelines. Primers randomised the codons for positions Y271, N311, Y349, V366 and W382 of the pylS gene to the codons for all 20 natural amino acids (All primer are listed in Supplementary Table 1). The resulting PCR products were digested with BsaI-HF and DpnI, and circularised with T4 DNA ligase. DNA was transformed into Eletrocompetent MegaX DH10B™ T1R Electrocomp™ E. coli cells (Invitrogen) following the manufacturer's instructions and inoculated into overnight culture with appropriate antibiotic to prepare plasmid DNA. Diversity was estimated by plating serial dilutions of the transformation rescue culture on LB-agar plates with appropriate antibiotic. A library of $10^8$ transformants that was isolated covered the theoretical diversity of the library with 97% confidence.

Selections of Active aaRS with DAP Derivatives

Selections of synthetase mutants specific for amino acids 2-6 were carried out as previously reported[39] using the following libraries: DAPRSlib (Y271, N311, Y349, V366, W382), D3 (L270, Y271, L274, N311, $C_3$13), PylS fwd (A267, Y271, L274, C313, M315), Susan 1(A267, Y271, Y349, V366, W382), Susan 2 (N311, C313, V366, W382, G386), Susan 4 (A267, Y349, S364, V366, G386). Briefly, MbPylRS libraries in pBK vectors were subjected to five rounds of alternating positive and negative selection. The positive selections were performed in the presence of the desired ncAA (1 mM) using a chloramphenicol acetyl transferase reporter with an amber codon at a permissive position (codon 112) and expressing the cognate tRNA. Cells that survived the positive selection on chloramphenicol (typically 50 [g/mL) LB agar are predicted to use either a natural amino acid that is constitutively present in the cell or the ncAA added to the cell. The negative selection used a barnase reporter containing amber codons and providing the cognate tRNA, in the absence of ncAA, to remove synthetase variants that use natural amino acids.

GFP(150TAG)His6 Expression and Purification

Superfolder green fluorescent protein (sfGFP) with 6 incorporated at position 150 was expressed from pSF-sfGFP150TAG in MegaX DH10B T1R cells containing pBK_DAPRS or pBK_PylRS vector. LB broth supplemented with 12.5 µg/mL tetracycline, 25 µg/mL kanamycin and 1 mM of 6 or $N^\varepsilon$-tert-butyloxycarbonyl-lysine (BocK) was inoculated with the transformed cells. Expression was induced with 0.2% (w/v) L-(+)-arabinose (Sigma) for 16 h at 37° C. whilst shaking at 220 rpm. Bacteria were then harvested and the protein purified by polyhistidine affinity chromatography.

His6-Lipoyl-TEV-Strep Expression and Purification

BL21 (DE3) cells were transformed with pNHD-His6-lipoyl-TEV$_{wt}$-Strep, pNHD-His6-lipoyl-TEV$_{Ala}$-Strep (gene is a gift from Mark Allen)[40] or co-transformed with pSF-DAPRS-PylT[41] pNHD-His6-lipoyl-TEV$_{Amber}$-Strep and grown on TB-agar plates containing 25 µg/mL tetracycline and (and 50 µg/mL kanamycin for co-transformed cells) overnight at 37° C. (TB media containing 25 µg/mL tetracycline (and 50 µg/mL kanamycin for co-transformed cells) was inoculated with some transformed colonies. The cultures were diluted 1:100 into TB media containing 12.5 µg/mL tetracycline (and 25 µg/mL kanamycin and 100 µM of 6 for co-transformed cells) and incubated at 37° C.; once the OD$_{600}$ reached 0.5-0.7, the cultures were moved to 20° C. After 30 min of further incubation, the cultures were induced using 250 µM isopropyl β-D-1-thiogalactopyranoside (IPTG) and protein expression was carried out at 20° C. for 16 h. Cells were harvested by centrifugation and resuspended in 50 mM tris-HCl pH 7.5, 150 mM NaCl, 2 mM β-Mercaptoethanol, 1 Roche Inhibitor Cocktail tablet/50 mL, 0.5 mg/mL lysozyme (Sigma), 50 µg/mL DNase (Sigma) and lysed by sonication. The lysate was clarified by centrifugation at 39,000×g for 30 min and filtered through a 0.4 µm polyethersulfone (PES) membrane. His6-lipoyl-TEV-Strep was purified using nickel affinity chromatography (HisTrap HP column, GE Healthcare) with a linear gradient of imidazole (o mM to 500 mM). Fractions containing the protein were further purified by Strep-tag affinity purification using a 5 mL StrepTrap HP column (GE Healthcare). After sample loading, the column was washed with strep binding buffer (50 mM 4-(2-hydroxyethyl)-1-piperazineethanesulfonic acid [HEPES] pH 8.0, 150 mM NaCl, 1 mM ethylenediaminetetraacetic acid [EDTA], 5 mM dithiothreitol [DTT]). The protein was eluted using a linear gradient of desthiobiotin (0 mM to 1.25 mM). For His6-lipoyl-TEV$_{Amber}$-Strep, the protein was irradiated with UV light (365 nm, 35 mWcm$^{-2}$, 1 min) at the end of the purification.

Ub$_{tev}$ Expression and Purification

BL21 (DE3) cells were transformed with pNHD-Ub-tev-His6 and grown on LB-agar plates containing 25 µg/mL tetracycline overnight at 37° C. LB media containing 25

μg/mL tetracycline was inoculated with the some colonies resulting from the transformation. The culture was diluted 1:100 into fresh LB media containing 12.5 μg/mL tetracycline; once the $OD_{600}$ reached 0.5, the cultures were induced using 1 mM IPTG and protein expression was carried out at 37° C. for 6 h. Cells were harvested by centrifugation and resuspended 50 mM tris-HCl pH 7.5, 150 mM NaCl, 2 mM β-Mercaptoethanol, 1 Roche Inhibitor Cocktail tablet/50 mL, 0.5 mg/mL lysozyme (Sigma), 50 μg/mL DNase (Sigma) and lysed by sonication. The lysate was clarified by centrifugation at 39,000× g for 30 min and filtration through a 0.4 μm PES membrane. Ub was purified using nickel affinity chromatography (HisTrap HP column, GE Healthcare) with a linear gradient of imidazole (30 mM to 500 mM). The protein was dialysed overnight against 10 mM tris-HCl at 4° C. and Ub was further purified by ion exchange chromatography (HiTrapS 5 mL column, GE Healthcare) using a NaCl gradient (0-1 M mM) in 50 mM ammonium acetate, pH 4.5. Pure fractions were pooled before overnight dialysis against 20 mM tris-HCl pH 7.4. The sample was then concentrated to ~15 mg/mL using an Amicon Ultra-15 (3 kDa MWCO) centrifugal filter device (Millipore).

Reactions of TEV with $Ub_{tev}$

15 μg of His6-lipoyl-TEV-Strep were incubated at 30° C. with 60 μg of $Ub_{tev}$ and allowed to react overnight in 150 μL of 50 mM HEPES pH 8.0, 150 mM NaCl, 1 mM EDTA, 5 mM DTT. 20 μL of the reaction were loaded on a 4-12% NuPAGE Bis-Tris gel (Invitrogen) and allowed to run for 45 min in 2-(n-morpholino)-ethanesulfonic acid (MES) buffer. Protein was transferred on a polyvinylidene fluoride (PVSF) membrane (Roche) using 25 mM Tris pH 8.2, 192 mM glycine, 10% (v/v) methanol. Membranes were subsequently blocked for 1 h in TBST buffer (25 mM Tris pH pH 7.4, 150 mM NaCl, 0.05% [v/v] Tween 20) containing 5% (w/v) milk powder at room temperature. Antibodies (Strep-Tactin-HRP conjugate (α Strep) [IBA Lifesciences] or P4D1 antibody (α Ub) [Enzo Life Sciences]) were added in 5% TBST-Milk and incubated at 4° C. overnight. Secondary antibody (for α Ub antibody) was added in 5% TBST-Milk and incubated at room temperature for 1 h. Blots were developed using Amersham enhanced chemiluminescence (ECL) (GE Healthcare) and a ChemiDoc XRS+ gel imaging system (Bio-Rad).

Analysis of Intracellular Concentration of DAP Derivatives

The analysis of intracellular concentration of DAP derivatives was performed as previously described[41]. In short, DAP derivatives were added to a 5 mL solution of LB media to a final concentration of 1 mM. A control sample was also prepared with 5 mL of unsupplemented LB media. Each solution was inoculated with DH10B cells. The cultures were agitated at 220 rpm in the dark at 37° C. for 12 h. The $OD_{600}$ of each sample was determined, and the cells from each culture were harvested. The cell pellets were washed three times with 1 mL of fresh ice-cold LB media by cycles of resuspension and centrifugation. The washed cell pellets were resuspended in a methanol:water solution (60:40). Zirconium beads (0.1 mm) were added to each suspension. The suspensions were vortexed for 12 min to lyse the cells. The lysate was centrifuged at 21000×g for 30 min at 4° C. The supernatant was carefully removed, and placed into a fresh 1.5 mL Eppendorf tube. The solutions were centrifuged again at 21000×g for 2 h at 4° C. A 100 μl aliquot of the supernatant from the resulting sample was analyzed by LC-ESI-MS. A gradient of 0.5% to 95% acetonitrile in water was applied to elute the clarified lysates from a Zorbax C18 (4.6×150 mm) column. The concentrations were estimated using an estimate of $8\times10^8$ cells per 1 $OD_{600}$ unit and a cell volume of $0.6\times10^{-15}$ L.

Cloning, Expression and Purification of Vlm TE Constructs

A codon-optimized construct containing $vlm2_{PCP4-TE}$ (encoding residues 2290-2655 of Vlm2 from *Streptomyces tsusimaensis*, GenBank: ABA59548.1) was synthesized by ATUM (formerly DNA 2.0) in a pJExpress411 vector, with an N-terminal hexahistidine tag followed by a tobacco etch virus protease (TEV) cleavage recognition sequence (pJExpress411-vlm2-PCP4-$TE_{wt}$). Two BamHI recognition sequences were included in pJExpress411-vlm2-PCP4-$TE_{wt}$ at nucleotide positions 2024-2025 and 2267-2268. Digestion with BamHI followed by ligation with T4 DNA ligase (New England Biolabs) excised the PCP4 domain sequence, yielding the plasmid pJExpress411-vlm2-$TE_{wt}$ which encodes residues 2368-2655 of Vlm2. To generate an expression vector for $TE_{DAP}$, the $TE_{wt}$ coding sequence was PCR-amplified from pJExpress411-vlm2-$TE_{wt}$ with primers TE_for_pNHD_fw and TE_for_pNHD_rev. The PCR product was digested with NdeI and XhoI and ligated into similarly digested pNHD plasmid using T4 DNA ligase, generating plasmid pNHD-vlm2-$TE_{wt}$. Next, an amber stop codon was introduced in place of the codon for serine 2463 by site-directed mutagenesis using primers Vlm2_TE_Amb_Fw and Vlm2_TE_Amb_Rev, generating pNHD-vlm2-$TE_{amber2463}$.

TE domains were heterologously expressed in *E. coli* BL21(DE3) cells transformed with pJExpress411-vlm2-$TE_{wt}$ ($TE_{wt}$) or co-transformed with pNHD-Vlm2-$TE_{amber2463}$ and pSF-DAPRS-PylT ($TE_{DAP}$). Cultures expressing $TE_{wt}$ were grown in LB media supplemented with 17 mg $L^{-1}$ of kanamycin. Those expressing $TE_{DAP}$ were grown in TB media supplemented with 25 mg $L^{-1}$ of kanamycin, 12.5 mg $L^{-1}$ of tetracycline, 0.1 mM of 6 (a 100 mM stock solution of 6 was prepared in 0.4 M NaOH, added to the culture and neutralised using 5 M HCl). Cultures were incubated at 37° C., with agitation at 220 r.p.m, until they reached an $OD_{600\ nm}=0.6$, after which they were incubated at 16° C. for 30 min, and then expression was induced with 100 μM IPTG. Cultures were incubated for an additional 16 hours at 16° C. before harvesting by centrifugation at 5000 g for 20 min. Cell pellets were stored at −80° C.

For protein purification, cell pellets of $TE_{wt}$ were resuspended in 5 mL of buffer wt-A (50 mM TRIS pH 7.4, 150 mM NaCl, 50 mM imidazole, 2 mM β-mercaptoethanol [βME]) plus DNAseI (Bioshop) per g of wet cells, and lysed by sonication. Lysate was clarified by centrifugation at 40 000 g for 20 min. Clarified lysate was applied to two 5 mL HiTrap IMAC FF (GE Healthcare Life Sciences) columns connected in series on an AKTA Prime system (GE Healthcare Life Sciences). Bound protein was eluted with buffer wt-B (buffer wt-A plus 150 mM imidazole). Fractions containing $TE_{wt}$ (as determined by SDS-PAGE analysis) were pooled and incubated with TEV protease in a 1:100 (Te:TEV) mass/mass ratio and dialyzed against buffer wt-C(50 mM TRIS pH 7.4, 10 mM NaCl, 2 mM βME) for 16 hours at 4° C. The dialyzed sample was applied to two 5 mL HiTrap IMAC FF columns connected in series, pre-equilibrated in buffer wt-A. Cleaved protein was recovered from the flow through and applied to two 5 mL HiTrap Q HP columns connected in series, pre-equilibrated in buffer Q-A (50 mM TRIS pH 7.4, 10 mM NaCl, 2 mM βME). Protein was eluted by a gradient of 0 to 100% buffer Q-B (50 mM TRIS pH 7.4, 500 mM NaCl, 2 mM βME) over 240 mL. $TE_{wt}$-containing fractions were concentrated in a 10 kDa molecular weight cut off Amicon® Ultra centrifugal filter (Millipore) and injected onto a Superdex S-200 16/60 PG column (GE-Healthcare) pre-equilibrated in SEC buffer (25 mM HEPES pH 7.4 or pH 8.0, 100 mM NaCl, 0.2 mM tris(2-carboxyethyl)phosphine [TCEP]). Fractions containing purified $TE_{wt}$ were pooled, concentrated and flash frozen.

Cell resuspension, lysis, clarification and Ni-IMAC purification for $TE_{DAP}$ were performed as described for $Te_{wt}$, except that prolonged exposure to light was avoided. After elution from the Ni-IMAC column, the sample was irradiated with UV light (365 nm, 35 mWcm$^{-2}$, 1 min). TEV cleavage and the subsequent IMAC column were performed as described for $TE_{wt}$, except that a 1:1 TE:TEV ratio was used. Anion exchange was performed as described for $Te_{wt}$, except that 25 mM HEPES replaced TRIS as the buffer and 0.2 mM TCEP replaced βME as the reducing agent in the mobile phases. Relevant fractions were concentrated and injected onto a Superdex S-75 10/300 column pre-equilibrated in buffer T (25 mM HEPES pH 8.0, 100 mM NaCl, 0.2 mM TCEP). Fractions containing purified $TE_{DAP}$ were pooled, concentrated, and immediately used for further experiments. The yield of purified $TE_{wt}$ was 30-60 mg per L, the yield of purified $TE_{DAP}$ was 0.1-0.5 mg per L.

Crystallography

Crystallization conditions for $TE_{wt}$ structure 1 were found in vapour diffusion crystallization trials using commercially available screens (Qiagen) and a protein concentration of 10 mg mL$^{-1}$. Optimization of an initial crystallization hit in 24-well plates led to a final crystallization condition where 3.2 μL of 10 mg mL-1 $TE_{wt}$, 4.0 μL 1.65 M DL-malic acid pH 9.5, and 0.8 μL of 17% m/v IPTG were incubated against a reservoir solution of 500 μL of 1.65 M DL-malic acid pH 9.5. $TE_{wt}$ structure 2 crystals were grown in similar conditions, where 0.5 μL of purified $TE_{wt}$ at 22.4 mg mL$^{-1}$ and 0.5 μL of 1.65 M DL-malic acid pH 8.1 were incubated against a reservoir solution of 500 μL of DL-malic acid pH 8.1. Crystals appeared between 24 and 48 hours and reached their maximum size in approximately one week.

Crystals of unliganded $TE_{DAP}$ were grown in similar conditions to $TE_{wt}$, with a reservoir solution of 1.65 M DL-malic acid pH 8.0. In order to obtain the tetradepsipeptidyl-$TE_{DAP}$ complex structure, $TE_{DAP}$ crystals were incubated with deoxytetradepsipeptidyl-SNAC 8 once they achieved their maximum size. The reservoir solution was exchanged to 2.66 M DL-malic acid, pH 9.5, and 32 μL of a solution of 1 mM deoxytetradepsipeptidyl-SNAC, 2.66 M DL-malic acid pH 9.5, 100 mM NaCl, 25 mM HEPES pH 9.2, 10% DMSO was added to the drop. Crystals were incubated in this condition for 9 days at room temperature.

For dodecadepsipeptidyl-$TE_{DAP}$ complex crystals, $TE_{DAP}$ (0.1 mg mL-1) was incubated in a 1.1 mg mL-1 suspension of valinomycin in buffer T for 16 hours at room temperature. The sample was centrifuged at 20 000 g and applied to a Superdex S-75 10/300 column preequilibrated in buffer T to remove excess valinomycin. Relevant fractions were pooled and complex formation was evaluated by LC-ESI-MS (see below). The sample was concentrated to 13.4 mg mL-1 and diffraction-quality crystals, with a different morphology from the $TE_{wt}$ crystals, were obtained in sitting drops consisting of 1 μL of dodecadepsipeptidyl-$TE_{DAP}$ complex plus 1 μL reservoir solution (1.30 to 1.45 M DL-malic acid pH 8.1) equilibrated against 500 μL reservoir solution. In an attempt to improve the occupancy of the ligand, a subset of these crystals were further incubated with valinomycin, by addition of 20 μL of a solution containing 555 μM valinomycin, 2 M DL-malic acid pH 8.1, 11 mM HEPES pH 8.0, 44 mM NaCl, 0.088 mM TCEP for 24 hours.

$TE_{wt}$ and dodecadepsipeptidyl-$TE_{DAP}$ crystals were cryoprotected by addition of 10 μL ($TE_{wt}$ structure 1 and dodecadepsipeptidyl-$TE_{DAP}$) or 20 μL ($TE_{wt}$ structure 2) 3.6 M DL-malic acid pH 8.1 to the crystallization drop. For dodecadepsipeptidyl-$TE_{DAP}$ crystals that had been incubated with valinomycin, the drop solution was removed and replaced by 10 μL of 3.6 M DL-malic acid. Crystals were equilibrated for at least two minutes and then flash cooled in liquid nitrogen. Tetradepsipeptidyl-$TE_{DAP}$ complex crystals were looped and flash cooled directly from the incubating solution. $TE_{wt}$ data were first collected at the Centre for Structural Biology at McGill University, Montreal, Canada, on a Rigaku RUH3R generator and a R-AXIS IV++ detector. Higher resolution data for $TE_{wt}$ and depsipeptidyl-$TE_{DAP}$ complexes were collected at the Canadian Light Source (CLS) 08ID-1 beamline or at the Advanced Photon Source (APS) NE-CAT 24-ID-C beamline using a Pilatus detector (Extended Data Table 1).

$TE_{wt}$ Structure Determination

Diffraction data from $TE_{wt}$ structure 1 crystals were indexed and integrated in the space group P432 using iMosflm[47] or DIALS[48]. Further space group determination and scaling were performed using the programs POINTLESS and SCALA[49]. The structure was solved by molecular replacement using PHASER[50], with a SCULPTOR[51] modified version of the TE domain of srfA-C (PDB ID 2VSQ)[52] as a search model. The structure was iteratively refined and built with the programs Phenix[53] and AUTOBUILD[54]. Coot[55] was used for iterative model building. Topology diagrams were generated using TopDraw[56] based on results from PDBsum generate (European Bioinformatics Institute) using the $TE_{wt}$ structure as input.

Diffraction data sets collected from dodecadepsipeptidyl-$TE_{DAP}$ complex crystals were indexed into either P1 or H3 space groups using iMosflm[47] or DIALS[48]. Most crystals belonging to the H3 group showed evidence of twinning, and only non-twinned diffraction data were used for structure determination. Structures in both the P1 and H3 space groups were solved by molecular replacement using PHASER[50], with the $TE_{wt}$ structure lacking residues 2500-2647 used as a search model. The Pt structure had six molecules in the asymmetric unit whereas the H3 structure contained 2 molecules in the asymmetric unit. All depsipeptidyl-$TE_{DAP}$ models were refined, and $mF_o$-$F_c$ maps were generated before depsipeptide residues were built in the model (FIG. 4c,d and Extended Data FIG. 8). Depsipeptides were built from individual monomers of the PDB Chemical Component Dictionary (DPP, VAL, 2OP, DVA, VAD). Monomer libraries and restraints for the links between the monomers (namely DPP→VAL, VAL→2OP, 2OP→DVA, DVA→VAD and VAD→VAL) were calculated using AceDRG57 and merged using LIBCHECK[58]. The resulting merged dictionary was then used for substrate building in Coot[55] and refinement in REFMAC5[59] and phenix.refine[53]. Final statistics are shown in Extended Data Table 1.

Depsipeptidyl-TE Complex Formation $TE_{DAP}$ or $TE_{wt}$ at a final concentration of 0.2 mg mL-1 was incubated with tetradepsipeptidyl-SNAC 7 (1.7 mM), or valinomycin (50 μM) in buffer T containing 1.7% or 1% v/v DMSO for 16 hours. Reactions were concentrated in a 10 kDa molecular weight cut off Amicon® Ultra centrifugal filter (Millipore), clarified by centrifugation at 20 000 g and applied to a Superdex S-75 10/300 column pre-equilibrated in buffer T to remove excess depsipeptidyl-SNACs or valinomycin before final LC-ESI-MS analysis. To form the deoxytetradepsipeptidyl-$TE_{DAP}$ complex, $TE_{DAP}$ at a final concentration of 8.7 mg mL-1 was incubated with deoxytetradepsipeptidyl-SNAC 8 (2.6 mM) in 25 mM HEPES pH 8.6, 100 mM NaCl, 3.8% v/v DMSO for 40 hours. The sample was diluted in 100 mM ammonium bicarbonate pH 8.0 before final LC-ESI-MS analysis. All incubations were performed at room temperature.

LC-ESI-MS Analysis of Intact Proteins

For experiments shown in FIG. 2c, Extended Data FIG. 3b, 7c, protein samples were subjected to a liquid chromatography (LC) system (Agilent 1200 series) followed by in-line electrospray ionization mass spectrometry (ESI-MS) on a 6130 Quadrupole spectrometer. Using a Jupiter 5µ C4 300 A column, 150 mm×2.00 mm (Phenomenex), proteins were run through the LC system using water with 0.1% (v/v) formic acid (solvent A) and a gradient (10% to 75% in 6 min and 75% to 95% in 1.5 min) of acetonitrile with 0.1% (v/v) formic acid (solvent B). Proteins were detected by monitoring UV absorbance at 200 and 280 nm. Protein masses were calculated by deconvolution from the MS acquisition in positive ion mode, using the OpenLAB CDS software (Agilent Technologies).

For experiments shown in FIG. 4a,b, Extended Data FIG. 6d-f, 7d,e, protein concentration was adjusted to 0.1 mg mL-1 in buffer T, and 16 µL was injected onto an Agilent PLRP-S (1000 A 5 µM, 50×2.1 mm ID) column pre-equilibrated in 95% mobile phase A (0.1% formic acid in water) and 5% mobile phase B (0.1% formic acid in 100% acetonitrile) on an Agilent Technologies 1260 Infinity HPLC system coupled to a Bruker Amazon Speed ETD ion trap mass spectrometer. MS data was collected with ExtremeScan mass range mode in positive ion polarity, scan range from 50 to 3000 m/z, accumulation time of 1586 ps, RF level of 96%, trap drive 69.8, PSP target Mass 922 m/z, and averaging over 5 spectra. External instrument calibration was performed using the Agilent ESI tune mix. The column compartment temperature was set up at 80° C. throughout the run. After injection, the column was washed for 5 minutes in initial HPLC conditions with the sample compartment diversion valve in the waste position. Next, a 5-minute gradient from 5% to 100% mobile phase B was performed, followed by an isocratic step of 100% mobile phase B for 8 minutes. Proteins were detected by monitoring UV absorbance at 280 nm. Data was analyzed using the Bruker DataAnalysis software (Bruker). Mass spectra were integrated from 10.5 to 13 minutes, and deconvoluted using a window between 10 000 to 40 000 m/z.

Tandem MS/MS Analysis

Proteins were run on 4-12% NuPAGE Bis-Tris gel (Invitrogen) with MES buffer and briefly stained using InstantBlue (Expedeon). The bands were excised and stored in 20 mM Tris pH 7.4. Tryptic digestion and tandem MS/MS analyses were performed by Kate Heesom (Proteomics Facility, University of Bristol).

LC-ESI-MS Analysis of Vlm TE Reaction Products

Purified $TE_{wt}$ or $TE_{DAP}$ at 0.2 mg mL-1 (6.5 µM) was incubated with tetradepsipeptidyl-SNAC 7 (1.7 mM), or a mix of tetradepsipeptidyl-SNAC 7 and deoxytetradepsipeptidyl-SNAC 8 (1.7 mM each) in buffer T. Samples were incubated at room temperature for 24 hours, and then quenched with one volume of 0.1% formic acid in acetonitrile. Next, samples were centrifuged at 20,000 g, flash frozen in liquid nitrogen and stored at −80° C. before HPLC analysis. For HPLC-MS analysis, frozen samples were thawed at room temperature, vortexed and clarified by centrifugation at 20,000 g before injection. HR-LC-ESI-MS was performed at the Mass Spectroscopy Facility (Department of Chemistry, McGill University) with an Agilent XDB-C8 (5 µm, 4.6×150 mm) column in a Dionex Ultimate 3000 UHPLC system coupled to a Bruker maXis impact QTOF mass spectrometer in positive ESI mode. Ion-trap LC-ESI-MS analysis was performed in an Agilent Technologies 1260 Infinity HPLC system coupled to a Bruker Amazon Speed ETD ion trap mass spectrometer in positive ESI mode. The column compartment was set up at 40° C. throughout the runs. Starting HPLC conditions were 50% mobile phase A (0.1% formic acid in $H_2O$), 50% mobile phase B (0.1% formic acid in acetonitrile). After injection (1 µL for HR-LC-ESI-MS and 5 µL for ion-trap LC-ESI-MS), a gradient from 50% to 98% mobile phase B in 5 minutes was performed, followed by an isocratic step of 98% mobile phase B, run for 20 minutes. For HR-LC-ESI-MS, internal calibration was performed with an intra-run infusion at the beginning of the first analysis using $Na^+$ formate, and the resulting calibration was used as an external calibration for subsequent analysis. Ion trap external calibration was performed using the Agilent ESI tune mix. Data was analyzed using the Bruker DataAnalysis software and the SmartFormula tool (Bruker).

REFERENCES TO EXAMPLES 1-9

1. Holliday, G. L., Mitchell, J. B. O. & Thornton, J. M. Understanding the Functional Roles of Amino Acid Residues in Enzyme Catalysis. *Journal of molecular biology* 390, 560-577 (2009).
2. Di Cera, E. Serine proteases. *IUBMB Life* 61, 510-515 (2009).
3. Hedstrom, L. Serine protease mechanism and specificity. *Chem Rev* 102, 4501-4523 (2002).
4. Long, J. Z. & Cravatt, B. F. The Metabolic Serine Hydrolases and Their Functions in Mammalian Physiology and Disease. *Chem Rev* 111, 6022-6063 (2011).
5. Verma, S., Dixit, R. & Pandey, K. C. Cysteine Proteases: Modes of Activation and Future Prospects as Pharmacological Targets. *Front Pharmacol* 7 (2016).
6. Otto, H. H. & Schirmeister, T. Cysteine proteases and their inhibitors. *Chem Rev* 97, 133-171 (1997).
7. Swatek, K. N. & Komander, D. Ubiquitin modifications. *Cell Res* 26, 399-422 (2016).
8. Yang, W. & Drueckhammer, D. G. Understanding the relative acyl-transfer reactivity of oxoesters and thioesters: computational analysis of transition state delocalization effects. *Journal of the American Chemical Society* 123, 11004-11009 (2001).
9. Liu, B., Schofield, C. J. & Wilmouth, R. C. Structural analyses on intermediates in serine protease catalysis. *Journal of Biological Chemistry* 281, 24024-24035 (2006).
10. Ngo, P. D., Mansoorabadi, S. O. & Frey, P. A. Serine Protease Catalysis: A Computational Study of Tetrahedral Intermediates and Inhibitory Adducts. *J Phys Chem B* 120, 7353-7359 (2016).
11. Cleary, J. A., Doherty, W., Evans, P. & Malthouse, J. P. G. Quantifying tetrahedral adduct formation and stabilization in the cysteine and the serine proteases. *Bba-Proteins Proteom* 1854, 1382-1391 (2015).
12. Scaglione, J. B. et al. Biochemical and structural characterization of the tautomycetin thioesterase: analysis of a stereoselective polyketide hydrolase. *Angew Chem Int Ed Engl* 49, 5726-5730 (2010).
13. Cappadocia, L. & Lima, C. D. Ubiquitin-like Protein Conjugation: Structures, Chemistry, and Mechanism. *Chem Rev* 118, 889-918 (2018).

14. Plechanovova, A., Jaffray, E. G., Tatham, M. H., Naismith, J. H. & Hay, R. T. Structure of a RING E3 ligase and ubiquitin-loaded E2 primed for catalysis. *Nature* 489, 115-U135 (2012).
15. Hay, R. W. & Morris, P. J. Interaction of Dl-2,3-Diaminopropionic Acid and Its Methyl Ester with Metal Ions 0.1. Formation Constants. *J Chem Soc A*, 3562-& (1971).
16. Lan, Y. et al. Incorporation of 2,3-Diaminopropionic Acid into Linear Cationic Amphipathic Peptides Produces pH-Sensitive Vectors. *Chembiochem* 11, 1266-1272 (2010).
17. Radzicka, A. & Wolfenden, R. Rates of uncatalyzed peptide bond hydrolysis in neutral solution and the transition state affinities of proteases. *Journal of the American Chemical Society* 118, 6105-6109 (1996).
18. Hoyer, K. M., Mahlert, C. & Marahiel, M. A. The iterative gramicidin s thioesterase catalyzes peptide ligation and cyclization. *Chemistry & biology* 14, 13-22 (2007).
19. Alonzo, D. A., Magarvey, N. A. & Schmeing, T. M. Characterization of cereulide synthetase, a toxin-producing macromolecular machine. *PloS one* 10, e0128569 (2015).
20. Magarvey, N. A., Ehling-Schulz, M. & Walsh, C. T. Characterization of the cereulide NRPS alpha-hydroxy acid specifying modules: activation of alpha-keto acids and chiral reduction on the assembly line. *Journal of the American Chemical Society* 128, 10698-10699 (2006).
21. Shaw-Reid, C. A. et al. Assembly line enzymology by multimodular nonribosomal peptide synthetases: the thioesterase domain of *E. coli* EntF catalyzes both elongation and cyclolactonization. *Chemistry & biology* 6, 385-400 (1999).
22. May, J. J., Wendrich, T. M. & Marahiel, M. A. The dhb operon of *Bacillus subtilis* encodes the biosynthetic template for the catecholic siderophore 2,3-dihydroxybenzoate-glycine-threonine trimeric ester bacillibactin. *J Biol Chem* 276, 7209-7217 (2001).
23. Zhou, Y. et al. Iterative Mechanism of Macrodiolide Formation in the Anticancer Compound Conglobatin. *Chemistry & biology* 22, 745-754 (2015).
24. Robbel, L., Hoyer, K. M. & Marahiel, M. A. TioS T-TE—a prototypical thioesterase responsible for cyclodimerization of the quinoline- and quinoxaline-type class of chromodepsipeptides. *FEBS J* 276, 1641-1653 (2009).
25. Jaitzig, J., Li, J., Sussmuth, R. D. & Neubauer, P. Reconstituted biosynthesis of the nonribosomal macrolactone antibiotic valinomycin in *Escherichia coli*. *ACS Synth Biol* 3, 432-438 (2014).
26. Akey, D. L. et al. Structural basis for macrolactonization by the pikromycin thioesterase. *Nat Chem Biol* 2, 537-542 (2006).
27. Samel, S. A., Wagner, B., Marahiel, M. A. & Essen, L. O. The thioesterase domain of the fengycin biosynthesis cluster: a structural base for the macrocyclization of a non-ribosomal lipopeptide. *Journal of molecular biology* 359, 876-889 (2006).
28. Tseng, C. C. et al. Characterization of the surfactin synthetase C-terminal thioesterase domain as a cyclic depsipeptide synthase. *Biochemistry* 41, 13350-13359 (2002).
29. Bruner, S. D. et al. Structural basis for the cyclization of the lipopeptide antibiotic surfactin by the thioesterase domain SrfTE. *Structure* 10, 301-310 (2002).
30. Li, J. et al. Palladium-triggered deprotection chemistry for protein activation in living cells. *Nat Chem* 6, 352-361 (2014).
31. Baker, A. S. & Deiters, A. Optical Control of Protein Function through Unnatural Amino Acid Mutagenesis and Other Optogenetic Approaches. *Acs Chemical Biology* 9, 1398-1407 (2014).
32. Nguyen, D. P. et al. Genetic Encoding of Photocaged Cysteine Allows Photoactivation of TEV Protease in Live Mammalian Cells. *Journal of the American Chemical Society* 136, 2240-2243 (2014).
33. Nguyen, D. P., Elliott, T., Holt, M., Muir, T. W. & Chin, J. W. Genetically Encoded 1,2-Aminothiols Facilitate Rapid and Site-Specific Protein Labeling via a Bio-orthogonal Cyanobenzothiazole Condensation. *Journal of the American Chemical Society* 133, 11418-11421 (2011).
34. Neumann, H., Peak-Chew, S. Y. & Chin, J. W. Genetically encoding N-epsilon-acetyllysine in recombinant proteins. *Nature Chemical Biology* 4, 232-234 (2008).
35. Chin, J. W. Expanding and Reprogramming the Genetic Code of Cells and Animals. *Annu Rev Biochem* 83, 379-408 (2014).
36. Liu, C. C. & Schultz, P. G. Adding New Chemistries to the Genetic Code. *Annual Review of Biochemistry, Vol 79* 79, 413-444 (2010).
37. Zhang, M. S. et al. Biosynthesis and genetic encoding of phosphothreonine through parallel selection and deep sequencing. *Nat Methods* 14, 729-736 (2017).
38. Virdee, S., Ye, Y., Nguyen, D. P., Komander, D. & Chin, J. W. Engineered diubiquitin synthesis reveals Lys29-isopeptide specificity of an OTU deubiquitinase. *Nature Chemical Biology* 6, 750-757 (2010).
39. Phan, J. et al. Structural basis for the substrate specificity of tobacco etch virus protease. *Journal of Biological Chemistry* 277, 50564-50572 (2002).
40. Trauger, J. W., Kohli, R. M., Mootz, H. D., Marahiel, M. A. & Walsh, C. T. Peptide cyclization catalysed by the thioesterase domain of tyrocidine synthetase. *Nature* 407, 215-218 (2000).
41. Zhou, Y., Prediger, P., Dias, L. C., Murphy, A. C. & Leadlay, P. F. Macrodiolide formation by the thioesterase of a modular polyketide synthase. *Angew Chem Int Ed Engl* 54, 5232-5235 (2015).
42. Horsman, M. E., Hari, T. P. A. & Boddy, C. N. Polyketide synthase and non-ribosomal peptide synthetase thioesterase selectivity: Logic gate or a victim of fate? *Natrual Products Reports* (2015).
43. Frueh, D. P. et al. Dynamic thiolation-thioesterase structure of a non-ribosomal peptide synthetase. *Nature* 454, 903-906 (2008).
44. Whicher, J. R. et al. Structure and function of the RedJ protein, a thioesterase from the prodiginine biosynthetic pathway in *Streptomyces coelicolor*. *J Biol Chem* 286, 22558-22569 (2011).
45. Ekici, O. D., Paetzel, M. & Dalbey, R. E. Unconventional serine proteases: variations on the catalytic Ser/His/Asp triad configuration. *Protein Sci* 17, 2023-2037 (2008).
46. Liu, Y., Zheng, T. & Bruner, S. D. Structural basis for phosphopantetheinyl carrier domain interactions in the terminal module of nonribosomal peptide synthetases. *Chemistry & biology* 18, 1482-1488 (2011).
47. Trauger, J. W., Kohli, R. M. & Walsh, C. T. Cyclization of backbone-substituted peptides catalyzed by the thioesterase domain from the tyrocidine nonribosomal peptide synthetase. *Biochemistry* 40, 7092-7098 (2001).

48. Aggarwal, A. et al. Development of a Novel Lead that Targets *M. tuberculosis* Polyketide Synthase 13. *Cell* 170, 249-259 e225 (2017).
49. Cravatt, B. F., Wright, A. T. & Kozarich, J. W. Activity-based protein profiling: from enzyme chemistry to proteomic chemistry. *Annu Rev Biochem* 77, 383-414 (2008).
50. McGall, G. H. et al. The efficiency of light-directed synthesis of DNA arrays on glass substrates. *Journal of the American Chemical Society* 119, 5081-5090, doi:DOI 10.1021/ja964427a (1997).
51. Pendrak, I., Wittrock, R. & Kingsbury, W. D. Synthesis and Anti-Hsv Activity of Methylenedioxy Mappicine Ketone Analogs. *J Org Chem* 60, 2912-2915, doi:DOI 10.1021/jo00114a050 (1995).

REFERENCES TO SUPPLEMENTARY METHODS

31 Alonzo, D. A., Magarvey, N. A. & Schmeing, T. M. Characterization of cereulide synthetase, a toxin-producing macromolecular machine. *PloS one* 10, e0128569, doi:10.1371/journal.pone.0128569 (2015).
32 Shaw-Reid, C. A. et al. Assembly line enzymology by multimodular nonribosomal peptide synthetases: the thioesterase domain of *E. coli* EntF catalyzes both elongation and cyclolactonization. *Chemistry & biology* 6, 385-400, doi:10.1016/S1074-5521(99)80050-7 (1999).
33 May, J. J., Wendrich, T. M. & Marahiel, M. A. The dhb operon of *Bacillus subtilis* encodes the biosynthetic template for the catecholic siderophore 2,3-dihydroxybenzoate-glycine-threonine trimeric ester bacillibactin. *J Biol Chem* 276, 7209-7217, doi:10.1074/jbc.M009140200 (2001).
34 Zhou, Y. et al. Iterative Mechanism of Macrodiolide Formation in the Anticancer Compound Conglobatin. *Chemistry & biology* 22, 745-754, doi:10.1016/j.chembiol.2015.05.010 (2015).
35 Robbel, L., Hoyer, K. M. & Marahiel, M. A. TioS T-TE—a prototypical thioesterase responsible for cyclodimerization of the quinoline- and quinoxaline-type class of chromodepsipeptides. *FEBS J* 276, 1641-1653, doi:10.1111/j.1742-4658.2009.06897.x (2009).
36 Liu, Y., Zheng, T. & Bruner, S. D. Structural basis for phosphopantetheinyl carrier domain interactions in the terminal module of nonribosomal peptide synthetases. *Chemistry & biology* 18, 1482-1488, doi:10.1016/j.chembiol.2011.09.018 (2011).
37 Trauger, J. W., Kohli, R. M. & Walsh, C. T. Cyclization of backbone-substituted peptides catalyzed by the thioesterase domain from the tyrocidine nonribosomal peptide synthetase. *Biochemistry* 40, 7092-7098 (2001).
38 Aggarwal, A. et al. Development of a Novel Lead that Targets *M. tuberculosis* Polyketide Synthase 13. *Cell* 170, 249-259 e225, doi:10.1016/j.cell.2017.06.025 (2017).
39 Neumann, H., Peak-Chew, S. Y. & Chin, J. W. Genetically encoding N(epsilon)-acetyllysine in recombinant proteins. *Nat Chem Biol* 4, 232-234, doi:10.1038/nchembio.73 (2008).
40 Rogerson, D. T. et al. Efficient genetic encoding of phosphoserine and its nonhydrolyzable analog. *Nat Chem Biol* 11, 496-503, doi:10.1038/nchembio.1823 (2015).
41 Zhang, M. S. et al. Biosynthesis and genetic encoding of phosphothreonine through parallel selection and deep sequencing. *Nat Methods* 14, 729-736, doi:10.1038/nmeth.4302 (2017).
42 McGall, G. H. et al. The efficiency of light-directed synthesis of DNA arrays on glass substrates. *Journal of the American Chemical Society* 119, 5081-5090, doi:DOI 10.1021/ja964427a (1997).
43 Nguyen, D. P. et al. Genetic encoding of photocaged cysteine allows photoactivation of TEV protease in live mammalian cells. *Journal of the American Chemical Society* 136, 2240-2243, doi:10.1021/ja412191m (2014).
44 Pendrak, I., Wittrock, R. & Kingsbury, W. D. Synthesis and Anti-Hsv Activity of Methylenedioxy Mappicine Ketone Analogs. *J Org Chem* 60, 2912-2915, doi:DOI 10.1021/jo00114a050 (1995).
45 Mayer, S. C., Ramanjulu, J., Vera, M. D., Pfizenmayer, A. J. & Joullie, M. M. Synthesis of New Didemnin B Analogs for Investigations of Structure/Biological Activity Relationships. *J Org Chem* 59, 5192-5205, doi: 10.1021/jo00097a022 (1994).
46 Faure, S. et al. Asymmetric intramolecular [2+2] photocycloadditions: alpha- and beta-hydroxy acids as chiral tether groups. *J Org Chem* 67, 1061-1070, doi:10.1021/jo001631e (2002).
47 Battye, T. G., Kontogiannis, L., Johnson, O., Powell, H. R. & Leslie, A. G. iMOSFLM: a new graphical interface for diffraction-image processing with MOSFLM. *Acta crystallographica. Section D, Biological crystallography* 67, 271-281, doi:10.1107/S0907444910048675 (2011).
48 Winter, G. et al. DIALS: implementation and evaluation of a new integration package. *Acta crystallographica. Section D, Structural biology* 74, 85-97, doi:10.1107/52059798317017235 (2018).
49 Evans, P. Scaling and assessment of data quality. *Acta crystallographica. Section D, Biological crystallography* 62, 72-82, doi:10.1107/S0907444905036693 (2006).
50 McCoy, A. J. et al. Phaser crystallographic software. *Journal of applied crystallography* 40, 658-674, doi: 10.1107/S0021889807021206 (2007).
51 Bunkoczi, G. & Read, R. J. Improvement of molecular-replacement models with Sculptor. *Acta crystallographica. Section D, Biological crystallography* 67, 303-312, doi:10.1107/S0907444910051218 (2011).
52 Tanovic, A., Samel, S. A., Essen, L. O. & Marahiel, M. A. Crystal structure of the termination module of a nonribosomal peptide synthetase. *Science* 321, 659-663, doi:10.1126/science.1159850 (2008).
53 Adams, P. D. et al. PHENIX: a comprehensive Python-based system for macromolecular structure solution. *Acta crystallographica. Section D, Biological crystallography* 66, 213-221, doi:10.1107/S0907444909052925 (2010).
54 Terwilliger, T. C. et al. Iterative model building, structure refinement and density modification with the PHENIX AutoBuild wizard. *Acta crystallographica. Section D, Biological crystallography* 64, 61-69, doi:10.1107/5090744490705024X (2008).
55 Emsley, P., Lohkamp, B., Scott, W. G. & Cowtan, K. Features and development of Coot. *Acta crystallographica. Section D, Biological crystallography* 66, 486-501, doi:10.1107/S0907444910007493 (2010).
56 Bond, C. S. TopDraw: a sketchpad for protein structure topology cartoons. *Bioinformatics* 19, 311-312 (2003).
57 Long, F. et al. AceDRG: a stereochemical description generator for ligands. *Acta crystallographica. Section D, Structural biology* 73, 112-122, doi:10.1107/S2059798317000067 (2017).
58 Vagin, A. A. et al. REFMAC5 dictionary: organization of prior chemical knowledge and guidelines for its use. *Acta crystallographica. Section D, Biological crystallography* 60, 2184-2195, doi:10.1107/S0907444904023510 (2004).

59 Murshudov, G. N. et al. REFMAC5 for the refinement of macromolecular crystal structures. *Acta crystallographica. Section D, Biological crystallography* 67, 355-367, doi:10.1107/50907444911001314 (2011).
60 Korman, T. P. et al. Structure and function of an iterative polyketide synthase thioesterase domain catalyzing Claisen cyclization in aflatoxin biosynthesis. *Proceedings of the National Academy of Sciences of the United States of America* 107, 6246-6251, doi:10.1073/pnas.0913531107 (2010).
61 Gehret, J. J. et al. Terminal alkene formation by the thioesterase of curacin A biosynthesis: structure of a decarboxylating thioesterase. *J Biol Chem* 286, 14445-14454, doi:10.1074/jbc.M110.214635 (2011).
62 Tsai, S. C. et al. Crystal structure of the macrocycle-forming thioesterase domain of the erythromycin polyketide synthase: versatility from a unique substrate channel. *Proceedings of the National Academy of Sciences of the United States of America* 98, 14808-14813, doi:10.1073/pnas.011399198 (2001).
63 Tsai, S. C., Lu, H., Cane, D. E., Khosla, C. & Stroud, R. M. Insights into channel architecture and substrate specificity from crystal structures of two macrocycle-forming thioesterases of modular polyketide synthases. *Biochemistry* 41, 12598-12606 (2002).
64 Argyropoulos, P. et al. Towards a characterization of the structural determinants of specificity in the macrocyclizing thioesterase for deoxyerythronolide B biosynthesis. *Biochim Biophys Acta* 1860, 486-497, doi:10.1016/j.bbagen.2015.11.007 (2016).
65 Giraldes, J. W. et al. Structural and mechanistic insights into polyketide macrolactonization from polyketide-based affinity labels. *Nat Chem Biol* 2, 531-536, doi:10.1038/nchembio822 (2006).
66 Koglin, A. et al. Structural basis for the selectivity of the external thioesterase of the surfactin synthetase. *Nature* 454, 907-911, doi:10.1038/nature07161 (2008).
67 Drake, E. J. et al. Structures of two distinct conformations of holo-non-ribosomal peptide synthetases. *Nature* 529, 235-238, doi:10.1038/nature16163 (2016).
68 Gavalda, S. et al. The polyketide synthase Pks13 catalyzes a novel mechanism of lipid transfer in mycobacteria. *Chemistry & biology* 21, 1660-1669, doi:10.1016/j.chembiol.2014.10.011 (2014).
69 Guntaka, N. S., Healy, A. R., Crawford, J. M., Herzon, S. B. & Bruner, S. D. Structure and Functional Analysis of ClbQ, an Unusual Intermediate-Releasing Thioesterase from the Colibactin Biosynthetic Pathway. *ACS Chem Biol* 12, 2598-2608, doi:10.1021/acschembio.7b00479 (2017).

Although illustrative embodiments of the invention have been disclosed in detail herein, with reference to the accompanying drawings, the reader should note that the invention is not limited to those precise embodiments and that various changes and modifications can be effected therein by one skilled in the art without departing from the scope of the invention as defined by the appended claims and their equivalents.

The invention claimed is:

1. A method of producing a polypeptide comprising 2,3-diamino propionic acid (DAP), said method comprising genetically incorporating an unnatural amino acid into a polypeptide, wherein the unnatural amino acid is of formula (I) or (II):

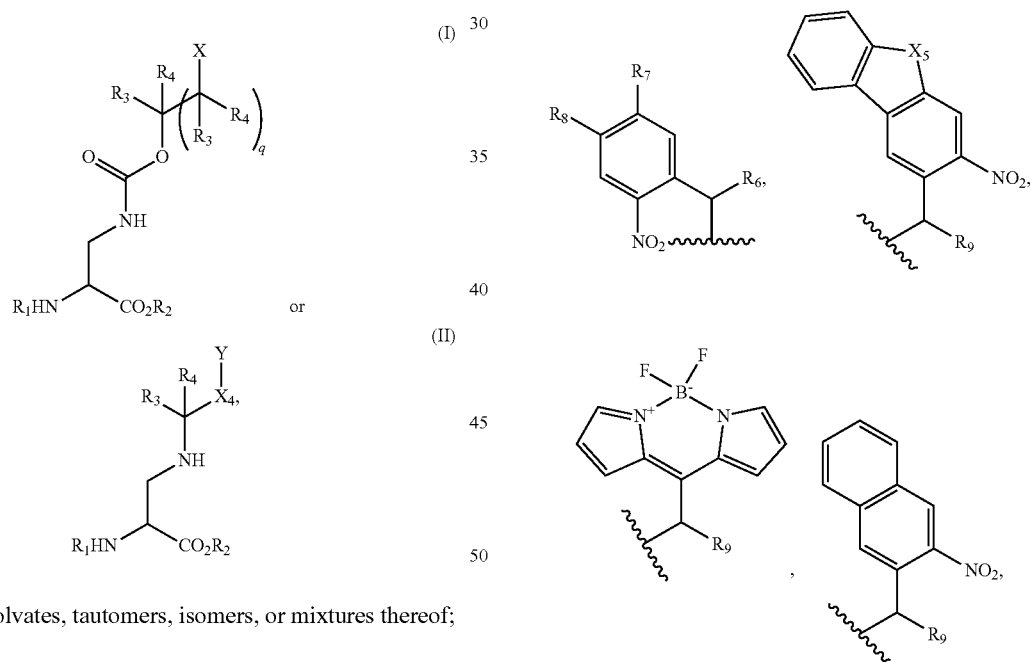

or salts, solvates, tautomers, isomers, or mixtures thereof; wherein:

$R_1$ is H, an amino acid residue, or a peptide;
$R_2$ is H, $C_{1-6}$ alkyl, $C_{1-6}$ haloalkyl, or $C_{5-20}$ aryl;
q is 1, 2, or 3;
each $R_3$ or $R_4$ is independently selected from H, halo, $C_{1-6}$ alkyl, $C_{1-6}$ haloalkyl, $C_{5-20}$ aryl, $C_{3-20}$ heteroaryl, $OC_{1-6}$ alkyl, $SC_{1-6}$ alkyl, $NH(C_{1-6}$ alkyl), and $N(C_{1-6}$ alkyl$)_2$;
X is $X_1$—Y, S—S—$R_5$, Se—Se—$R_5$, O—NH—$R_5$, S—NH—$R_5$, Se—NH—$R_5$, $X_2$—$Y_1$, $X_3$—$Y_2$, $N_3$, or NH—S(O)$_2$—$Y_3$;
$X_1$ is S, Se, O, NH, or N($C_{1-6}$ alkyl);
$X_2$ is S, Se, or O;
$X_3$ is NH—C(O)—O;
$X_4$ is NH—C(O)—O, O, S, or NH;

$R_5$ is selected from H, halo, $C_{1-6}$ alkyl, $C_{1-6}$ haloalkyl, $C_{5-20}$ aryl, $C_{3-20}$ heteroaryl, $OC_{1-6}$ alkyl, $NH(C_{1-6}$ alkyl), $N(C_{1-6}$ alkyl$)_2$, peptides, sugars, $C_{3-20}$ heterocyclyl, and nucleic acids;

Y is a protecting group selected from:

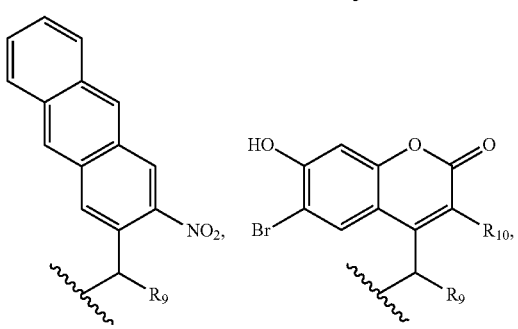

-continued

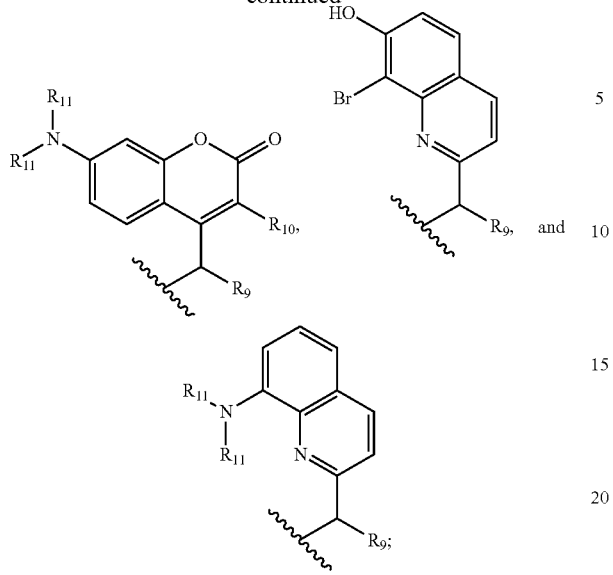

$R_6$ is selected from H, $C_{1-6}$ alkyl, $C_{1-6}$ haloalkyl, $CO_2H$, $CO_2R'$, $SO_3H$, $SO_2R'$, $C_{5-20}$ aryl, $C_{3-20}$ heteroaryl, NHC(O)R', and NHR';

$R_7$ and $R_8$ are independently selected from H, OH, O($C_{1-6}$ alkyl), O($C_{5-20}$ aryl), and O($C_{3-20}$ heteroaryl); or $R_7$ and $R_8$ are linked together to form an O—$CH_2$—O group;

each R' is independently selected from $C_{1-6}$ alkyl, $C_{1-6}$ haloalkyl, and $C_{5-20}$ aryl;

$R_9$ is selected from H, $C_{1-6}$ alkyl, $C_{1-6}$ haloalkyl, $CO_2H$, $CO_2R'$, $SO_3H$, $SO_2R'$, and $C_{5-20}$ aryl;

$R_{10}$ is selected from H, $C_{1-6}$ alkyl, and $C_{1-6}$ haloalkyl;

$R_{11}$ is selected from H, $C_{1-6}$ alkyl, and $C_{1-6}$ haloalkyl;

$X_5$ is S, O, NH, N—C(O)—O—R', N—S(O)$_2$H, N—S(O)$_2$R', or NR';

$Y_1$ is a protecting group selected from:

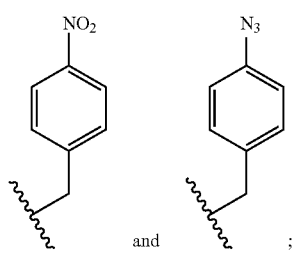 [SMILES: *Cc1ccc([N+](=O)[O-])cc1 ; *Cc1ccc(N=[N+]=[N-])cc1]

$Y_2$ is a protecting group selected from:

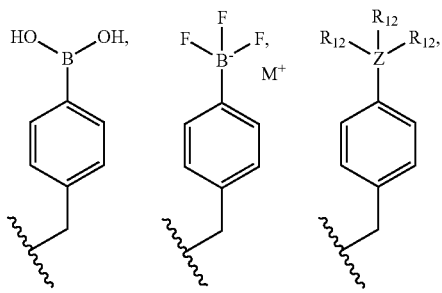

t-Bu, and $CH_2Ph$;

$M^+$ is $Li^+$, $Na^+$, $K^+$, or $N(R_{13})_4^+$;

Z is Si or Ge;

$R_{12}$ is $C_{1-6}$ alkyl or C(O)—($C_{5-20}$ aryl);

$R_{13}$ is H, $C_{1-6}$ alkyl, allyl, or $C_{5-20}$ aryl; and $Y_3$ is a protecting group

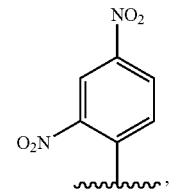 [SMILES: *c1ccc([N+](=O)[O-])cc1[N+](=O)[O-]]

wherein the method comprises:
(i) providing a nucleic acid encoding the polypeptide, wherein said nucleic acid comprises an orthogonal codon encoding the unnatural amino acid; and
(ii) translating said nucleic acid in the presence of an orthogonal tRNA synthetase/tRNA pair capable of recognising said orthogonal codon and incorporating said unnatural amino acid into the polypeptide chain, wherein said orthogonal codon comprises an amber codon (TAG), said tRNA comprises *Methanosarcina barkeri* tRNA$_{CUA}$ (MbtRNA$_{CUA}$), and said tRNA synthetase comprises the *Methanosarcina barkeri* pyrrolysyl-tRNA synthetase (MbPylRS synthetase) of SEQ ID NO: 3.

2. The method of claim 1, wherein said unnatural amino acid comprises

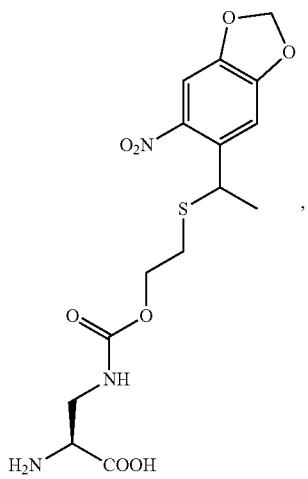 [SMILES: CC(SCCOC(=O)NC[C@H](N)C(=O)O)c1cc2c(cc1[N+](=O)[O-])OCO2]

or salts, solvates, tautomers, isomers, or mixtures thereof.

3. The method of claim 1, wherein said method is carried out inside a live cell.

4. The method of claim 3, wherein said live cell is an *E. coli* cell.

5. The method of claim 3, wherein said live cell is a mammalian cell.

6. The method of claim 1, wherein said unnatural amino acid is of the formula:

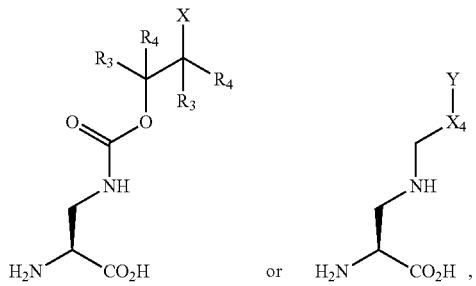

or salts, solvates, tautomers, isomers, or mixtures thereof.

7. The method of claim 1, wherein said unnatural amino acid is of formula (I), or salts, solvates, tautomers, isomers, or mixtures thereof, and wherein said unnatural amino acid is of the formula:

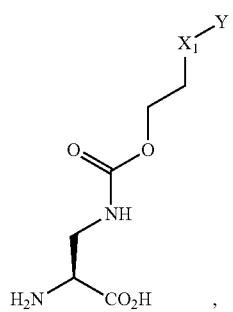

or salts, solvates, tautomers, isomers, or mixtures thereof.

8. The method of claim 1, wherein said unnatural amino acid is of formula (I), or salts, solvates, tautomers, isomers, or mixtures thereof, and wherein Y is:

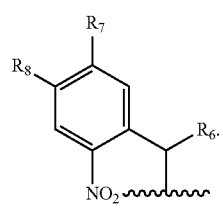

9. The method of claim 1, wherein said unnatural amino acid is of formula (I), or salts, solvates, tautomers, isomers, or mixtures thereof, and wherein said unnatural amino acid is of the formula:

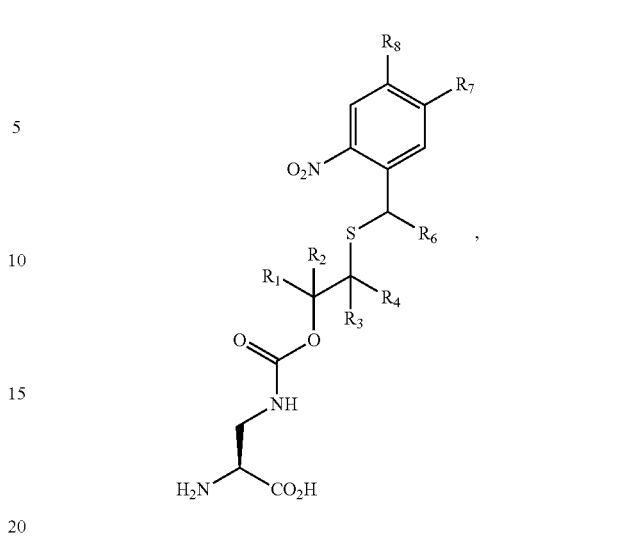

or salts, solvates, tautomers, isomers, or mixtures thereof.

10. The method of claim 1, wherein said unnatural amino acid is of formula (I), or salts, solvates, tautomers, isomers, or mixtures thereof, and wherein Y is selected from the group consisting of:

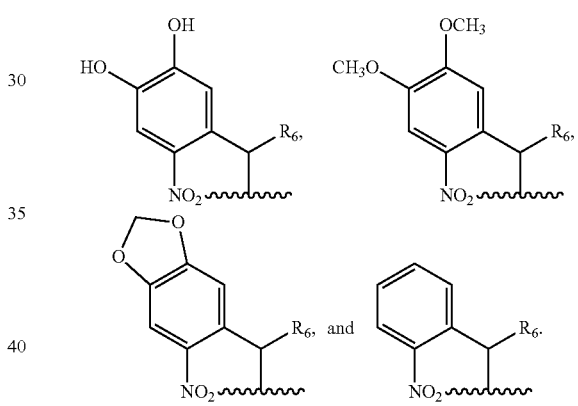

11. The method of claim 1, wherein said unnatural amino acid is of formula (I), or salts, solvates, tautomers, isomers, or mixtures thereof, and wherein $R_6$ is selected from the group consisting of H, $CH_3$, $CH_2CH_3$, $CF_3$, $CO_2H$, $CO_2CH_3$, $CO_2CH_2CH_3$, and Ph.

12. The method of claim 1, wherein said unnatural amino acid is of formula (I), or salts, solvates, tautomers, isomers, or mixtures thereof, and wherein $R_6$ is $CH_3$.

13. The method of claim 1, wherein said unnatural amino acid is of formula (I), or salts, solvates, tautomers, isomers, or mixtures thereof, wherein Y is:

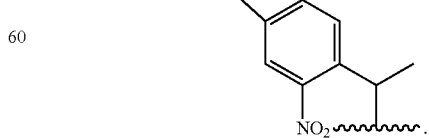

14. The method of claim 4, wherein the *E. coli* cell is a BL21 DE3 cell.

15. The method of claim 5, wherein the mammalian cell is a HEK293T cell.

16. The method of claim 1, further comprising deprotecting said unnatural amino acid to 2,3-diamino propionic acid (DAP).

* * * * *

SEQUENCE LISTING

```
<160> NUMBER OF SEQ ID NOS: 38

<210> SEQ ID NO 1
<211> LENGTH: 72
<212> TYPE: DNA
<213> ORGANISM: Methanosarcina barkeri

<400> SEQUENCE: 1
gggaacctga tcatgtagat cgaatggact ctaaatccgt tcagccgggt tagattcccg      60
gggtttccgc ca                                                          72

<210> SEQ ID NO 2
<211> LENGTH: 72
<212> TYPE: DNA
<213> ORGANISM: Methanosarcina barkeri

<400> SEQUENCE: 2
ggaaacctga tcatgtagat cgaatggact ctaaatccgt tcagccgggt tagattcccg      60
gggtttccgc ca                                                          72

<210> SEQ ID NO 3
<211> LENGTH: 419
<212> TYPE: PRT
<213> ORGANISM: Artificial Sequence
<220> FEATURE:
<223> OTHER INFORMATION: DAPRS synthetase

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30
```

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
 50                  55                  60

Tyr Arg Lys Thr Cys Lys Arg Cys Arg Val Ser Asp Glu Asp Ile Asn
 65                  70                  75                  80

Asn Phe Leu Thr Arg Ser Thr Glu Ser Lys Asn Ser Val Lys Val Arg
                 85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
            210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Cys Asn
            260                 265                 270

Tyr Leu Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
            290                 295                 300

Glu Glu Phe Thr Met Val Gln Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Phe Gly Asp Thr
            340                 345                 350

Leu Asp Ile Met His Gly Asp Leu Glu Leu Ser Ser Ala Cys Val Gly
            355                 360                 365

Pro Val Ser Leu Asp Arg Glu Trp Gly Ile Asp Lys Pro Trp Ile Gly
370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 4
<211> LENGTH: 419
<212> TYPE: PRT
<213> ORGANISM: Methanosarcina barkeri

```
<400> SEQUENCE: 4

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
```

Thr Asn Leu

<210> SEQ ID NO 5
<211> LENGTH: 419
<212> TYPE: PRT
<213> ORGANISM: Methanosarcina barkeri

<400> SEQUENCE: 5

```
Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Ala Met Pro Lys Ser Val Ser
                100                 105                 110

Arg Ala Pro Lys Pro Leu Glu Asn Pro Val Ser Ala Lys Ala Ser Thr
            115                 120                 125

Asp Thr Ser Arg Ser Val Pro Ser Pro Ala Lys Ser Thr Pro Asn Ser
        130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
```

```
            355                 360                 365
Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 6
<211> LENGTH: 454
<212> TYPE: PRT
<213> ORGANISM: Methanosarcina mazeii

<400> SEQUENCE: 6

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
```

```
                305                 310                 315                 320
Lys Ile Phe Glu Ile Gly Pro Cys Tyr Arg Lys Glu Ser Asp Gly Lys
                    325                 330                 335

Glu His Leu Glu Glu Phe Thr Met Leu Asn Phe Cys Gln Met Gly Ser
                    340                 345                 350

Gly Cys Thr Arg Glu Asn Leu Glu Ser Ile Ile Thr Asp Phe Leu Asn
                    355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
                420                 425                 430

Asp Phe Lys Asn Ile Lys Arg Ala Ala Arg Ser Glu Ser Tyr Tyr Asn
                435                 440                 445

Gly Ile Ser Thr Asn Leu
    450

<210> SEQ ID NO 7
<211> LENGTH: 443
<212> TYPE: PRT
<213> ORGANISM: Methanosarcina acetivorans

<400> SEQUENCE: 7

Met Asp Lys Lys Pro Leu Asp Thr Leu Ile Ser Ala Thr Gly Leu Trp
1               5                   10                  15

Met Ser Arg Thr Gly Met Ile His Lys Ile Lys His His Glu Val Ser
                20                  25                  30

Arg Ser Lys Ile Tyr Ile Glu Met Ala Cys Gly Glu Arg Leu Val Val
            35                  40                  45

Asn Asn Ser Arg Ser Ser Arg Thr Ala Arg Ala Leu Arg His His Lys
    50                  55                  60

Tyr Arg Lys Thr Cys Arg His Cys Arg Val Ser Asp Glu Asp Ile Asn
65                  70                  75                  80

Asn Phe Leu Thr Lys Thr Ser Glu Glu Lys Thr Thr Val Lys Val Lys
                85                  90                  95

Val Val Ser Ala Pro Arg Val Arg Lys Ala Met Pro Lys Ser Val Ala
                100                 105                 110

Arg Ala Pro Lys Pro Leu Glu Ala Thr Ala Gln Val Pro Leu Ser Gly
            115                 120                 125

Ser Lys Pro Ala Pro Ala Thr Pro Val Ser Ala Pro Ala Gln Ala Pro
    130                 135                 140

Ala Pro Ser Thr Gly Ser Ala Ser Ala Thr Ser Ala Ser Ala Gln Arg
145                 150                 155                 160

Met Ala Asn Ser Ala Ala Ala Pro Ala Ala Pro Val Pro Thr Ser Ala
                165                 170                 175

Pro Ala Leu Thr Lys Gly Gln Leu Asp Arg Leu Glu Gly Leu Leu Ser
                180                 185                 190

Pro Lys Asp Glu Ile Ser Leu Asp Ser Glu Lys Pro Phe Arg Glu Leu
            195                 200                 205

Glu Ser Glu Leu Leu Ser Arg Arg Lys Lys Asp Leu Lys Arg Ile Tyr
    210                 215                 220
```

-continued

```
Ala Glu Glu Arg Glu Asn Tyr Leu Gly Lys Leu Arg Glu Ile Thr
225                 230                 235                 240

Lys Phe Phe Val Asp Arg Gly Phe Leu Glu Ile Lys Ser Pro Ile Leu
            245                 250                 255

Ile Pro Ala Glu Tyr Val Glu Arg Met Gly Ile Asn Ser Asp Thr Glu
        260                 265                 270

Leu Ser Lys Gln Val Phe Arg Ile Asp Lys Asn Phe Cys Leu Arg Pro
    275                 280                 285

Met Leu Ala Pro Asn Leu Tyr Asn Tyr Leu Arg Lys Leu Asp Arg Ala
290                 295                 300

Leu Pro Asp Pro Ile Lys Ile Phe Glu Ile Gly Pro Cys Tyr Arg Lys
305                 310                 315                 320

Glu Ser Asp Gly Lys Glu His Leu Glu Glu Phe Thr Met Leu Asn Phe
            325                 330                 335

Cys Gln Met Gly Ser Gly Cys Thr Arg Glu Asn Leu Glu Ala Ile Ile
        340                 345                 350

Thr Glu Phe Leu Asn His Leu Gly Ile Asp Phe Glu Ile Ile Gly Asp
    355                 360                 365

Ser Cys Met Val Tyr Gly Asn Thr Leu Asp Val Met His Asp Asp Leu
370                 375                 380

Glu Leu Ser Ser Ala Val Val Gly Pro Val Pro Leu Asp Arg Glu Trp
385                 390                 395                 400

Gly Ile Asp Lys Pro Trp Ile Gly Ala Gly Phe Gly Leu Glu Arg Leu
            405                 410                 415

Leu Lys Val Met His Gly Phe Lys Asn Ile Lys Arg Ala Ala Arg Ser
        420                 425                 430

Glu Ser Tyr Tyr Asn Gly Ile Ser Thr Asn Leu
    435                 440

<210> SEQ ID NO 8
<211> LENGTH: 478
<212> TYPE: PRT
<213> ORGANISM: Methanosarcina thermophila

<400> SEQUENCE: 8

Met Asp Lys Lys Pro Leu Asn Thr Leu Ile Ser Ala Thr Gly Leu Trp
1               5                   10                  15

Met Ser Arg Thr Gly Lys Leu His Lys Ile Arg His His Glu Val Ser
            20                  25                  30

Lys Arg Lys Ile Tyr Ile Glu Met Glu Cys Gly Glu Arg Leu Val Val
        35                  40                  45

Asn Asn Ser Arg Ser Cys Arg Ala Ala Arg Ala Leu Arg His His Lys
    50                  55                  60

Tyr Arg Lys Ile Cys Lys His Cys Arg Val Ser Asp Glu Asp Leu Asn
65                  70                  75                  80

Lys Phe Leu Thr Arg Thr Asn Glu Asp Lys Ser Asn Ala Lys Val Thr
            85                  90                  95

Val Val Ser Ala Pro Lys Ile Arg Lys Val Met Pro Lys Ser Val Ala
        100                 105                 110

Arg Thr Pro Lys Pro Leu Glu Asn Thr Ala Pro Val Gln Thr Leu Pro
    115                 120                 125

Ser Glu Ser Gln Pro Ala Pro Thr Thr Pro Ile Ser Ala Ser Thr Thr
130                 135                 140

Ala Pro Ala Ser Thr Ser Thr Thr Ala Pro Ala Pro Ala Ser Thr Thr
145                 150                 155                 160
```

Ala Pro Ala Pro Ala Ser Thr Thr Ala Pro Ala Ser Ala Ser Thr Thr
              165                 170                 175

Ile Ser Thr Ser Ala Met Pro Ala Ser Thr Ser Ala Gln Gly Thr Thr
          180                 185                 190

Lys Phe Asn Tyr Ile Ser Gly Gly Phe Pro Arg Pro Ile Pro Val Gln
          195                 200                 205

Ala Ser Ala Pro Ala Leu Thr Lys Ser Gln Ile Asp Arg Leu Gln Gly
      210                 215                 220

Leu Leu Ser Pro Lys Asp Glu Ile Ser Leu Asp Ser Gly Thr Pro Phe
225                 230                 235                 240

Arg Lys Leu Glu Ser Glu Leu Leu Ser Arg Arg Lys Asp Leu Lys
              245                 250                 255

Gln Ile Tyr Ala Glu Glu Arg Glu His Tyr Leu Gly Lys Leu Glu Arg
              260                 265                 270

Glu Ile Thr Lys Phe Phe Val Asp Arg Gly Phe Leu Glu Ile Lys Ser
          275                 280                 285

Pro Ile Leu Ile Pro Met Glu Tyr Ile Glu Arg Met Gly Ile Asp Asn
290                 295                 300

Asp Lys Glu Leu Ser Lys Gln Ile Phe Arg Val Asp Asn Asn Phe Cys
305                 310                 315                 320

Leu Arg Pro Met Leu Ala Pro Asn Leu Tyr Asn Tyr Leu Arg Lys Leu
              325                 330                 335

Asn Arg Ala Leu Pro Asp Pro Ile Lys Ile Phe Glu Ile Gly Pro Cys
              340                 345                 350

Tyr Arg Lys Glu Ser Asp Gly Lys Glu His Leu Glu Glu Phe Thr Met
              355                 360                 365

Leu Asn Phe Cys Gln Met Gly Ser Gly Cys Thr Arg Glu Asn Leu Glu
          370                 375                 380

Ala Ile Ile Lys Asp Phe Leu Asp Tyr Leu Gly Ile Asp Phe Glu Ile
385                 390                 395                 400

Val Gly Asp Ser Cys Met Val Tyr Gly Asp Thr Leu Asp Val Met His
              405                 410                 415

Gly Asp Leu Glu Leu Ser Ser Ala Val Val Gly Pro Val Pro Met Asp
              420                 425                 430

Arg Asp Trp Gly Ile Asn Lys Pro Trp Ile Gly Ala Gly Phe Gly Leu
          435                 440                 445

Glu Arg Leu Leu Lys Val Met His Asn Phe Lys Asn Ile Lys Arg Ala
450                 455                 460

Ser Arg Ser Glu Ser Tyr Tyr Asn Gly Ile Ser Thr Asn Leu
465                 470                 475

<210> SEQ ID NO 9
<211> LENGTH: 416
<212> TYPE: PRT
<213> ORGANISM: Methanococcoides burtonii

<400> SEQUENCE: 9

Met Glu Lys Gln Leu Leu Asp Val Leu Val Glu Leu Asn Gly Val Trp
1               5                   10                  15

Leu Ser Arg Ser Gly Leu Leu His Gly Ile Arg Asn Phe Glu Ile Thr
              20                  25                  30

Thr Lys His Ile His Ile Glu Thr Asp Cys Gly Ala Arg Phe Thr Val
          35                  40                  45

Arg Asn Ser Arg Ser Ser Arg Ser Ala Arg Ser Leu Arg His Asn Lys

```
                50                  55                  60
Tyr Arg Lys Pro Cys Lys Arg Cys Arg Pro Ala Asp Glu Gln Ile Asp
 65                  70                  75                  80

Arg Phe Val Lys Lys Thr Phe Lys Glu Lys Arg Gln Thr Val Ser Val
                 85                  90                  95

Phe Ser Ser Pro Lys Lys His Val Pro Lys Pro Lys Val Ala Val
                100                 105                 110

Ile Lys Ser Phe Ser Ile Ser Thr Pro Ser Pro Lys Glu Ala Ser Val
                115                 120                 125

Ser Asn Ser Ile Pro Thr Pro Ser Ile Ser Val Val Lys Asp Glu Val
                130                 135                 140

Lys Val Pro Glu Val Lys Tyr Thr Pro Ser Gln Ile Glu Arg Leu Lys
145                 150                 155                 160

Thr Leu Met Ser Pro Asp Asp Lys Ile Pro Ile Gln Asp Glu Leu Pro
                165                 170                 175

Glu Phe Lys Val Leu Glu Lys Glu Leu Ile Gln Arg Arg Asp Asp
                180                 185                 190

Leu Lys Lys Met Tyr Glu Glu Asp Arg Glu Asp Arg Leu Gly Lys Leu
                195                 200                 205

Glu Arg Asp Ile Thr Glu Phe Phe Val Asp Arg Gly Phe Leu Glu Ile
                210                 215                 220

Lys Ser Pro Ile Met Ile Pro Phe Glu Tyr Ile Glu Arg Met Gly Ile
225                 230                 235                 240

Asp Lys Asp Asp His Leu Asn Lys Gln Ile Phe Arg Val Asp Glu Ser
                245                 250                 255

Met Cys Leu Arg Pro Met Leu Ala Pro Cys Leu Tyr Asn Tyr Leu Arg
                260                 265                 270

Lys Leu Asp Lys Val Leu Pro Asp Pro Ile Arg Ile Phe Glu Ile Gly
                275                 280                 285

Pro Cys Tyr Arg Lys Glu Ser Asp Gly Ser Ser His Leu Glu Glu Phe
                290                 295                 300

Thr Met Val Asn Phe Cys Gln Met Gly Ser Gly Cys Thr Arg Glu Asn
305                 310                 315                 320

Met Glu Ala Leu Ile Asp Glu Phe Leu Glu His Leu Gly Ile Glu Tyr
                325                 330                 335

Glu Ile Glu Ala Asp Asn Cys Met Val Tyr Gly Asp Thr Ile Asp Ile
                340                 345                 350

Met His Gly Asp Leu Glu Leu Ser Ser Ala Val Val Gly Pro Ile Pro
                355                 360                 365

Leu Asp Arg Glu Trp Gly Val Asn Lys Pro Trp Met Gly Ala Gly Phe
                370                 375                 380

Gly Leu Glu Arg Leu Leu Lys Val Arg His Asn Tyr Thr Asn Ile Arg
385                 390                 395                 400

Arg Ala Ser Arg Ser Glu Leu Tyr Tyr Asn Gly Ile Asn Thr Asn Leu
                405                 410                 415

<210> SEQ ID NO 10
<211> LENGTH: 279
<212> TYPE: PRT
<213> ORGANISM: Desulfitobacterium hafniense

<400> SEQUENCE: 10

Met Ser Ser Phe Trp Thr Lys Val Gln Tyr Gln Arg Leu Lys Glu Leu
 1               5                  10                  15
```

```
Asn Ala Ser Gly Glu Gln Leu Glu Met Gly Phe Ser Asp Ala Leu Ser
            20                  25                  30

Arg Asp Arg Ala Phe Gln Gly Ile Glu His Gln Leu Met Ser Gln Gly
        35                  40                  45

Lys Arg His Leu Glu Gln Leu Arg Thr Val Lys His Arg Pro Ala Leu
    50                  55                  60

Leu Glu Leu Glu Glu Gly Leu Ala Lys Ala Leu His Gln Gln Gly Phe
65                  70                  75                  80

Val Gln Val Val Thr Pro Thr Ile Ile Thr Lys Ser Ala Leu Ala Lys
                85                  90                  95

Met Thr Ile Gly Glu Asp His Pro Leu Phe Ser Gln Val Phe Trp Leu
            100                 105                 110

Asp Gly Lys Lys Cys Leu Arg Pro Met Leu Ala Pro Asn Leu Tyr Thr
        115                 120                 125

Leu Trp Arg Glu Leu Glu Arg Leu Trp Asp Lys Pro Ile Arg Ile Phe
130                 135                 140

Glu Ile Gly Thr Cys Tyr Arg Lys Glu Ser Gln Gly Ala Gln His Leu
145                 150                 155                 160

Asn Glu Phe Thr Met Leu Asn Leu Thr Glu Leu Gly Thr Pro Leu Glu
                165                 170                 175

Glu Arg His Gln Arg Leu Glu Asp Met Ala Arg Trp Val Leu Glu Ala
            180                 185                 190

Ala Gly Ile Arg Glu Phe Glu Leu Val Thr Glu Ser Ser Val Val Tyr
        195                 200                 205

Gly Asp Thr Val Asp Val Met Lys Gly Asp Leu Glu Leu Ala Ser Gly
210                 215                 220

Ala Met Gly Pro His Phe Leu Asp Glu Lys Trp Glu Ile Val Asp Pro
225                 230                 235                 240

Trp Val Gly Leu Gly Phe Gly Leu Glu Arg Leu Leu Met Ile Arg Glu
                245                 250                 255

Gly Thr Gln His Val Gln Ser Met Ala Arg Ser Leu Ser Tyr Leu Asp
            260                 265                 270

Gly Val Arg Leu Asn Ile Asn
        275

<210> SEQ ID NO 11
<211> LENGTH: 312
<212> TYPE: PRT
<213> ORGANISM: Desulfitobacterium hafniense

<400> SEQUENCE: 11

Met Asp Arg Ile Asp His Thr Asp Ser Lys Phe Val Gln Ala Gly Glu
1               5                   10                  15

Thr Pro Val Leu Pro Ala Thr Phe Met Phe Leu Thr Arg Arg Asp Pro
            20                  25                  30

Pro Leu Ser Ser Phe Trp Thr Lys Val Gln Tyr Gln Arg Leu Lys Glu
        35                  40                  45

Leu Asn Ala Ser Gly Glu Gln Leu Glu Met Gly Phe Ser Asp Ala Leu
    50                  55                  60

Ser Arg Asp Arg Ala Phe Gln Gly Ile Glu His Gln Leu Met Ser Gln
65                  70                  75                  80

Gly Lys Arg His Leu Glu Gln Leu Arg Thr Val Lys His Arg Pro Ala
                85                  90                  95

Leu Leu Glu Leu Glu Glu Gly Leu Ala Lys Ala Leu His Gln Gln Gly
            100                 105                 110
```

```
Phe Val Gln Val Val Thr Pro Thr Ile Ile Thr Lys Ser Ala Leu Ala
            115                 120                 125

Lys Met Thr Ile Gly Glu Asp His Pro Leu Phe Ser Gln Val Phe Trp
        130                 135                 140

Leu Asp Gly Lys Lys Cys Leu Arg Pro Met Leu Ala Pro Asn Leu Tyr
145                 150                 155                 160

Thr Leu Trp Arg Glu Leu Glu Arg Leu Trp Asp Lys Pro Ile Arg Ile
                165                 170                 175

Phe Glu Ile Gly Thr Cys Tyr Arg Lys Glu Ser Gln Gly Ala Gln His
            180                 185                 190

Leu Asn Glu Phe Thr Met Leu Asn Leu Thr Glu Leu Gly Thr Pro Leu
        195                 200                 205

Glu Glu Arg His Gln Arg Leu Glu Asp Met Ala Arg Trp Val Leu Glu
210                 215                 220

Ala Ala Gly Ile Arg Glu Phe Glu Leu Val Thr Glu Ser Ser Val Val
225                 230                 235                 240

Tyr Gly Asp Thr Val Asp Val Met Lys Gly Asp Leu Glu Leu Ala Ser
                245                 250                 255

Gly Ala Met Gly Pro His Phe Leu Asp Glu Lys Trp Glu Ile Val Asp
            260                 265                 270

Pro Trp Val Gly Leu Gly Phe Gly Leu Glu Arg Leu Leu Met Ile Arg
        275                 280                 285

Glu Gly Thr Gln His Val Gln Ser Met Ala Arg Ser Leu Ser Tyr Leu
290                 295                 300

Asp Gly Val Arg Leu Asn Ile Asn
305                 310

<210> SEQ ID NO 12
<211> LENGTH: 288
<212> TYPE: PRT
<213> ORGANISM: Desulfitobacterium hafniense

<400> SEQUENCE: 12

Met Phe Leu Thr Arg Arg Asp Pro Pro Leu Ser Ser Phe Trp Thr Lys
1               5                   10                  15

Val Gln Tyr Gln Arg Leu Lys Glu Leu Asn Ala Ser Gly Glu Gln Leu
            20                  25                  30

Glu Met Gly Phe Ser Asp Ala Leu Ser Arg Asp Arg Ala Phe Gln Gly
        35                  40                  45

Ile Glu His Gln Leu Met Ser Gln Gly Lys Arg His Leu Glu Gln Leu
    50                  55                  60

Arg Thr Val Lys His Arg Pro Ala Leu Leu Glu Leu Glu Glu Lys Leu
65                  70                  75                  80

Ala Lys Ala Leu His Gln Gln Gly Phe Val Gln Val Thr Pro Thr
            85                  90                  95

Ile Ile Thr Lys Ser Ala Leu Ala Lys Met Thr Ile Gly Glu Asp His
            100                 105                 110

Pro Leu Phe Ser Gln Val Phe Trp Leu Asp Gly Lys Lys Cys Leu Arg
        115                 120                 125

Pro Met Leu Ala Pro Asn Leu Tyr Thr Leu Trp Arg Glu Leu Glu Arg
    130                 135                 140

Leu Trp Asp Lys Pro Ile Arg Ile Phe Glu Ile Gly Thr Cys Tyr Arg
145                 150                 155                 160

Lys Glu Ser Gln Gly Ala Gln His Leu Asn Glu Phe Thr Met Leu Asn
```

```
                   165                 170                 175
Leu Thr Glu Leu Gly Thr Pro Leu Glu Glu Arg His Gln Arg Leu Glu
            180                 185                 190

Asp Met Ala Arg Trp Val Leu Glu Ala Ala Gly Ile Arg Glu Phe Glu
            195                 200                 205

Leu Val Thr Glu Ser Ser Val Val Tyr Gly Asp Thr Val Asp Val Met
210                 215                 220

Lys Gly Asp Leu Glu Leu Ala Ser Gly Ala Met Gly Pro His Phe Leu
225                 230                 235                 240

Asp Glu Lys Trp Glu Ile Phe Asp Pro Trp Val Gly Leu Gly Phe Gly
            245                 250                 255

Leu Glu Arg Leu Leu Met Ile Arg Glu Gly Thr Gln His Val Gln Ser
            260                 265                 270

Met Ala Arg Ser Leu Ser Tyr Leu Asp Gly Val Arg Leu Asn Ile Asn
            275                 280                 285

<210> SEQ ID NO 13
<211> LENGTH: 277
<212> TYPE: PRT
<213> ORGANISM: Desulfotomaculum acetoxidans

<400> SEQUENCE: 13

Met Ser Phe Leu Trp Thr Val Ser Gln Gln Lys Arg Leu Ser Glu Leu
1               5                   10                  15

Asn Ala Ser Glu Glu Lys Asn Met Ser Phe Ser Ser Thr Ser Asp
            20                  25                  30

Arg Glu Ala Ala Tyr Lys Arg Val Glu Met Arg Leu Ile Asn Glu Ser
            35                  40                  45

Lys Gln Arg Leu Asn Lys Leu Arg His Glu Thr Arg Pro Ala Ile Cys
        50                  55                  60

Ala Leu Glu Asn Arg Leu Ala Ala Ala Leu Arg Gly Ala Gly Phe Val
65                  70                  75                  80

Gln Val Ala Thr Pro Val Ile Leu Ser Lys Lys Leu Leu Gly Lys Met
                85                  90                  95

Thr Ile Thr Asp Glu His Ala Leu Phe Ser Gln Val Phe Trp Ile Glu
            100                 105                 110

Glu Asn Lys Cys Leu Arg Pro Met Leu Ala Pro Asn Leu Tyr Tyr Ile
        115                 120                 125

Leu Lys Asp Leu Leu Arg Leu Trp Glu Lys Pro Val Arg Ile Phe Glu
130                 135                 140

Ile Gly Ser Cys Phe Arg Lys Glu Ser Gln Gly Ser Asn His Leu Asn
145                 150                 155                 160

Glu Phe Thr Met Leu Asn Leu Val Glu Trp Gly Leu Pro Glu Glu Gln
                165                 170                 175

Arg Gln Lys Arg Ile Ser Glu Leu Ala Lys Leu Val Met Asp Glu Thr
            180                 185                 190

Gly Ile Asp Glu Tyr His Leu Glu His Ala Glu Ser Val Tyr Gly
        195                 200                 205

Glu Thr Val Asp Val Met His Arg Asp Ile Glu Leu Gly Ser Gly Ala
        210                 215                 220

Leu Gly Pro His Phe Leu Asp Gly Arg Trp Gly Val Gly Pro Trp
225                 230                 235                 240

Val Gly Ile Gly Phe Gly Leu Glu Arg Leu Leu Met Val Glu Gln Gly
                245                 250                 255
```

```
Gly Gln Asn Val Arg Ser Met Gly Lys Ser Leu Thr Tyr Leu Asp Gly
            260                 265                 270

Val Arg Leu Asn Ile
        275

<210> SEQ ID NO 14
<211> LENGTH: 419
<212> TYPE: PRT
<213> ORGANISM: Methanosarcina barkeri

<400> SEQUENCE: 14

Met Asp Lys Lys Pro Leu Asp Val Leu Ile Ser Ala Thr Gly Leu Trp
1               5                   10                  15

Met Ser Arg Thr Gly Thr Leu His Lys Ile Lys His Tyr Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Gly Lys Thr Ser Val Lys Val Lys
                85                  90                  95

Val Val Ser Ala Pro Lys Val Lys Lys Ala Met Pro Lys Ser Val Ser
            100                 105                 110

Arg Ala Pro Lys Pro Leu Glu Asn Pro Val Ser Ala Lys Ala Ser Thr
        115                 120                 125

Asp Thr Ser Arg Ser Val Pro Ser Pro Ala Lys Ser Thr Pro Asn Ser
    130                 135                 140

Pro Val Pro Thr Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Ile Ala Lys Pro Phe Arg Glu Leu Glu Ser Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Asp Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Asp Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ser Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350
```

```
Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 15
<211> LENGTH: 419
<212> TYPE: PRT
<213> ORGANISM: Artificial Sequence
<220> FEATURE:
<223> OTHER INFORMATION: artificial synthetase

<400> SEQUENCE: 15

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Cys Arg Thr Ala Arg Ala Phe Arg His His Lys
        50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
                100                 105                 110

Arg Ala Pro Lys Pro Leu Glu Asn Ser Val Ser Ala Lys Ala Ser Thr
            115                 120                 125

Asn Thr Ser Arg Ser Val Pro Ser Pro Ala Lys Ser Thr Pro Asn Ser
        130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
                180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
        210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Leu Arg Lys Leu Asp Arg Ile Leu Pro Gly Pro Ile Lys Ile Phe
        275                 280                 285
```

```
Glu Val Gly Pro Cys Tyr Arg Lys Glu Ser Asp Gly Lys Glu His Leu
    290                 295                 300
Glu Glu Phe Thr Met Val Asn Phe Cys Gln Met Gly Ser Gly Cys Thr
305                 310                 315                 320
Arg Glu Asn Leu Glu Ala Leu Ile Lys Glu Phe Leu Asp Tyr Leu Glu
                325                 330                 335
Ile Asp Phe Glu Ile Val Gly Asp Ser Cys Met Val Tyr Gly Asp Thr
                340                 345                 350
Leu Asp Ile Met His Gly Asp Leu Glu Leu Ser Ser Ala Val Val Gly
            355                 360                 365
Pro Val Ser Leu Asp Arg Glu Trp Gly Ile Asp Lys Pro Trp Ile Gly
370                 375                 380
Ala Gly Phe Gly Leu Glu Arg Leu Leu Lys Val Met His Gly Phe Lys
385                 390                 395                 400
Asn Ile Lys Arg Ala Ser Arg Ser Glu Ser Tyr Tyr Asn Gly Ile Ser
                405                 410                 415
Thr Asn Leu

<210> SEQ ID NO 16
<211> LENGTH: 419
<212> TYPE: PRT
<213> ORGANISM: Artificial Sequence
<220> FEATURE:
<223> OTHER INFORMATION: AcKRS synthetase

<400> SEQUENCE: 16

Met Asp Lys Lys Pro Leu Asp Val Leu Ile Ser Ala Thr Gly Leu Trp
1               5                   10                  15
Met Ser Arg Thr Gly Thr Leu His Lys Ile Lys His His Glu Val Ser
                20                  25                  30
Arg Ser Lys Ile Tyr Ile Glu Met Ala Cys Gly Asp His Leu Val Val
            35                  40                  45
Asn Asn Ser Arg Ser Cys Arg Thr Ala Arg Ala Phe Arg His His Lys
        50                  55                  60
Tyr Arg Lys Thr Cys Lys Arg Cys Arg Val Ser Gly Glu Asp Ile Asn
65                  70                  75                  80
Asn Phe Leu Thr Arg Ser Thr Glu Ser Lys Asn Ser Val Lys Val Arg
                85                  90                  95
Val Val Ser Ala Pro Lys Val Lys Lys Ala Met Pro Lys Ser Val Ser
                100                 105                 110
Arg Ala Pro Lys Pro Leu Glu Asn Ser Val Ser Ala Lys Ala Ser Thr
            115                 120                 125
Asn Thr Ser Arg Ser Val Pro Ser Pro Ala Lys Ser Thr Pro Asn Ser
        130                 135                 140
Ser Val Pro Ala Ser Ala Pro Ala Pro Ser Leu Thr Arg Ser Gln Leu
145                 150                 155                 160
Asp Arg Val Glu Ala Leu Leu Ser Pro Glu Asp Lys Ile Ser Leu Asn
                165                 170                 175
Met Ala Lys Pro Phe Arg Glu Leu Glu Pro Glu Leu Val Thr Arg Arg
            180                 185                 190
Lys Asn Asp Phe Gln Arg Leu Tyr Thr Asn Asp Arg Glu Asp Tyr Leu
        195                 200                 205
Gly Lys Leu Glu Arg Asp Ile Thr Lys Phe Phe Val Asp Arg Gly Phe
    210                 215                 220
Leu Glu Ile Lys Ser Pro Ile Leu Ile Pro Ala Glu Tyr Val Glu Arg
```

```
                225                 230                 235                 240
Met Gly Ile Asn Asn Asp Thr Glu Leu Ser Lys Gln Ile Phe Arg Val
                    245                 250                 255
Asp Lys Asn Leu Cys Leu Arg Pro Met Val Ala Pro Thr Ile Phe Asn
                260                 265                 270
Tyr Ala Arg Lys Leu Asp Arg Ile Leu Pro Gly Pro Ile Lys Ile Phe
                275                 280                 285
Glu Val Gly Pro Cys Tyr Arg Lys Glu Ser Asp Gly Lys Glu His Leu
            290                 295                 300
Glu Glu Phe Thr Met Val Asn Phe Phe Gln Met Gly Ser Gly Cys Thr
305                 310                 315                 320
Arg Glu Asn Leu Glu Ala Leu Ile Lys Glu Phe Leu Asp Tyr Leu Glu
                325                 330                 335
Ile Asp Phe Glu Ile Val Gly Asp Ser Cys Met Val Tyr Gly Asp Thr
                340                 345                 350
Leu Asp Ile Met His Gly Asp Leu Glu Leu Ser Ser Ala Val Val Gly
            355                 360                 365
Pro Val Ser Leu Asp Arg Glu Trp Gly Ile Asp Lys Pro Trp Ile Gly
        370                 375                 380
Ala Gly Phe Gly Leu Glu Arg Leu Leu Lys Val Met His Gly Phe Lys
385                 390                 395                 400
Asn Ile Lys Arg Ala Ser Arg Ser Glu Ser Tyr Tyr Asn Gly Ile Ser
                405                 410                 415
Thr Asn Leu

<210> SEQ ID NO 17
<211> LENGTH: 419
<212> TYPE: PRT
<213> ORGANISM: Artificial Sequence
<220> FEATURE:
<223> OTHER INFORMATION: PCKRS synthetase

<400> SEQUENCE: 17

Met Asp Lys Lys Pro Leu Asp Val Leu Ile Ser Ala Thr Gly Leu Trp
1               5                   10                  15
Met Ser Arg Thr Gly Thr Leu His Lys Ile Lys His His Glu Val Ser
                20                  25                  30
Arg Ser Lys Ile Tyr Ile Glu Met Ala Cys Gly Asp His Leu Val Val
            35                  40                  45
Asn Asn Ser Arg Ser Cys Arg Thr Ala Arg Ala Phe Arg His His Lys
        50                  55                  60
Tyr Arg Lys Thr Cys Lys Arg Cys Arg Val Ser Asp Glu Asp Ile Asn
65                  70                  75                  80
Asn Phe Leu Thr Arg Ser Thr Glu Ser Lys Asn Ser Val Lys Val Arg
                85                  90                  95
Val Val Ser Ala Pro Lys Val Lys Lys Ala Met Pro Lys Ser Val Ser
                100                 105                 110
Arg Ala Pro Lys Pro Leu Glu Asn Ser Val Ser Ala Lys Ala Ser Thr
            115                 120                 125
Asn Thr Ser Arg Ser Val Pro Ser Pro Ala Lys Ser Thr Pro Asn Ser
        130                 135                 140
Ser Val Pro Ala Ser Ala Pro Ala Pro Ser Leu Thr Arg Ser Gln Leu
145                 150                 155                 160
Asp Arg Val Glu Ala Leu Leu Ser Pro Glu Asp Lys Ile Ser Leu Asn
                165                 170                 175
```

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
            195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Phe Gly Ile Asn Asn Asp Thr Glu Leu Ser Lys Gln Ile Phe Arg Val
                245                 250                 255

Asp Lys Asn Leu Cys Leu Arg Pro Met Leu Ser Pro Thr Leu Cys Asn
            260                 265                 270

Tyr Met Arg Lys Leu Asp Arg Ile Leu Pro Gly Pro Ile Lys Ile Phe
            275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
            355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 18
<211> LENGTH: 454
<212> TYPE: PRT
<213> ORGANISM: Artificial Sequence
<220> FEATURE:
<223> OTHER INFORMATION: artificial synthetase

<400> SEQUENCE: 18

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

```
Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 19
<211> LENGTH: 454
<212> TYPE: PRT
<213> ORGANISM: Artificial Sequence
<220> FEATURE:
<223> OTHER INFORMATION: Mm-ACKRS synthetase

<400> SEQUENCE: 19

Met Asp Lys Lys Pro Leu Asn Thr Leu Ile Ser Ala Thr Gly Leu Trp
1               5                   10                  15
```

```
Met Ser Arg Thr Gly Thr Ile His Lys Ile His His Glu Val Ser
             20                  25                  30

Arg Ser Lys Ile Tyr Ile Glu Met Ala Cys Gly Asp His Leu Val Val
         35                  40                  45

Asn Asn Ser Arg Ser Ser Arg Thr Ala Arg Ala Leu Arg His His Lys
50                   55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                 85                  90                  95

Val Val Ser Ala Pro Thr Arg Thr Lys Lys Ala Met Pro Lys Ser Val
                100                 105                 110

Ala Arg Ala Pro Lys Pro Leu Glu Asn Thr Glu Ala Ala Gln Ala Gln
             115                 120                 125

Pro Ser Gly Ser Lys Phe Ser Pro Ala Ile Pro Val Ser Thr Gln Glu
             130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
             180                 185                 190

Ser Gln Thr Asp Arg Leu Glu Val Leu Leu Asn Pro Lys Asp Glu Ile
             195                 200                 205

Ser Leu Asn Ser Gly Lys Pro Phe Arg Glu Leu Glu Ser Glu Leu Leu
             210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
             260                 265                 270

Ile Glu Arg Met Gly Ile Asp Asn Asp Thr Glu Leu Ser Lys Gln Ile
             275                 280                 285

Phe Arg Val Asp Lys Asn Phe Cys Leu Arg Pro Met Val Ala Pro Asn
             290                 295                 300

Ile Phe Asn Tyr Ala Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Phe Gln Met Gly Ser
             340                 345                 350

Gly Cys Thr Arg Glu Asn Leu Glu Ser Ile Ile Thr Asp Phe Leu Asn
             355                 360                 365

His Leu Gly Ile Asp Phe Lys Ile Val Gly Asp Ser Cys Met Val Tyr
             370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
             420                 425                 430

Asp Phe Lys Asn Ile Lys Arg Ala Ala Arg Ser Glu Ser Tyr Tyr Asn
```

```
                435                 440                 445
Gly Ile Ser Thr Asn Leu
    450

<210> SEQ ID NO 20
<211> LENGTH: 454
<212> TYPE: PRT
<213> ORGANISM: Artificial Sequence
<220> FEATURE:
<223> OTHER INFORMATION: Mm-PCKRS synthetase

<400> SEQUENCE: 20

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Phe Gly Ile Asp Asn Asp Thr Glu Leu Ser Lys Gln Ile
        275                 280                 285

Phe Arg Val Asp Lys Asn Phe Cys Leu Arg Pro Met Leu Ser Pro Asn
    290                 295                 300

Leu Cys Asn Tyr Met Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
```

```
                340               345               350
Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 21
<211> LENGTH: 49
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 21
ggaaaggtct cgaccctgnn kaactatctg cgtaaactgg atcgtattc          49

<210> SEQ ID NO 22
<211> LENGTH: 37
<212> TYPE: DNA
<213> ORGANISM: Artificial Sequence
<220> FEATURE:
<223> OTHER INFORMATION: primer

<400> SEQUENCE: 22
ggaaaggtct cagggtcggg gccagcatcg gacgcag                      37

<210> SEQ ID NO 23
<211> LENGTH: 48
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 23
ggaaaggtct ccatggttnn kttttgccaa atgggcagcg gctgcacc          48

<210> SEQ ID NO 24
<211> LENGTH: 42
<212> TYPE: DNA
<213> ORGANISM: Artificial Sequence
<220> FEATURE:
<223> OTHER INFORMATION: primer

<400> SEQUENCE: 24
ggaaaggtct caccatggtg aattcttcca ggtgttcttt gc                42
```

<210> SEQ ID NO 25
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 25
ggaaaggtct ccatggtgnn kggcgatacc ctggatatta tgcatgg         47

<210> SEQ ID NO 26
<211> LENGTH: 43
<212> TYPE: DNA
<213> ORGANISM: Artificial Sequence
<220> FEATURE:
<223> OTHER INFORMATION: primer

<400> SEQUENCE: 26
ggaaaggtct caccatgcag ctatcgccca caatttcgaa gtc             43

<210> SEQ ID NO 27
<211> LENGTH: 46
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 27
ggaaaggtct ccagcgcgnn kgtgggtccg gttagcctgg atcgtg          46

<210> SEQ ID NO 28
<211> LENGTH: 38
<212> TYPE: DNA
<213> ORGANISM: Artificial Sequence
<220> FEATURE:
<223> OTHER INFORMATION: primer

<400> SEQUENCE: 28
ggaaaggtct cgcgctgctc agttccagat cgccatgc                   38

<210> SEQ ID NO 29
<211> LENGTH: 47
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (19)..(20)
<223> OTHER INFORMATION: n is a, c, g, or t

<400> SEQUENCE: 29
ggaaaggtct ctaaaccgnn kattggcgcg ggttttggcc tggaacg         47

<210> SEQ ID NO 30
<211> LENGTH: 38
<212> TYPE: DNA
<213> ORGANISM: Artificial Sequence
<220> FEATURE:
<223> OTHER INFORMATION: primer

```
<400> SEQUENCE: 30
ggaaaggtct cggtttatca atgccccatt cacgatcc                              38

<210> SEQ ID NO 31
<211> LENGTH: 44
<212> TYPE: DNA
<213> ORGANISM: Artificial Sequence
<220> FEATURE:
<223> OTHER INFORMATION: primer

<400> SEQUENCE: 31
ggaaaggtct cgtagggcag tccattagta tcaactagag atgg                       44

<210> SEQ ID NO 32
<211> LENGTH: 44
<212> TYPE: DNA
<213> ORGANISM: Artificial Sequence
<220> FEATURE:
<223> OTHER INFORMATION: primer

<400> SEQUENCE: 32
ggaaaggtct cccctactgc ccatccttgg tttgaatcca atgc                       44

<210> SEQ ID NO 33
<211> LENGTH: 44
<212> TYPE: DNA
<213> ORGANISM: Artificial Sequence
<220> FEATURE:
<223> OTHER INFORMATION: primer

<400> SEQUENCE: 33
ggaaaggtct cggctggcag tccattagta tcaactagag atgg                       44

<210> SEQ ID NO 34
<211> LENGTH: 44
<212> TYPE: DNA
<213> ORGANISM: Artificial Sequence
<220> FEATURE:
<223> OTHER INFORMATION: primer

<400> SEQUENCE: 34
ggaaaggtct cccagcctgc ccatccttgg tttgaatcca atgc                       44

<210> SEQ ID NO 35
<211> LENGTH: 31
<212> TYPE: DNA
<213> ORGANISM: Artificial Sequence
<220> FEATURE:
<223> OTHER INFORMATION: primer

<400> SEQUENCE: 35
ttattacata tgcatcatca tcaccaccat c                                     31

<210> SEQ ID NO 36
<211> LENGTH: 24
<212> TYPE: DNA
<213> ORGANISM: Artificial Sequence
<220> FEATURE:
<223> OTHER INFORMATION: primer

<400> SEQUENCE: 36
ataataactc gagttagcca cgcg                                             24

<210> SEQ ID NO 37
```

```
<211> LENGTH: 35
<212> TYPE: DNA
<213> ORGANISM: Artificial Sequence
<220> FEATURE:
<223> OTHER INFORMATION: primer

<400> SEQUENCE: 37
gtgtatatcg gtggtcacta gctgggtggc catat                           35

<210> SEQ ID NO 38
<211> LENGTH: 35
<212> TYPE: DNA
<213> ORGANISM: Artificial Sequence
<220> FEATURE:
<223> OTHER INFORMATION: primer

<400> SEQUENCE: 38
atatggccac ccagctagtg accaccgata tacac                           35
```